United States Patent
Haketa et al.

(10) Patent No.: US 10,547,007 B2
(45) Date of Patent: Jan. 28, 2020

(54) COMPOUND, ORGANIC ELECTROLUMINESCENT MATERIAL, ORGANIC ELECTROLUMINESCENT ELEMENT, AND ELECTRONIC APPARATUS

(71) Applicant: IDEMITSU KOSAN CO., LTD., Chiyoda-ku (JP)

(72) Inventors: Tasuku Haketa, Chiba (JP); Hirokatsu Ito, Ichihara (JP); Yu Kudo, Chiba (JP); Masahiro Kawamura, Chiba (JP); Ryota Takahashi, Ichihara (JP)

(73) Assignee: IDEMITSU KOSAN CO., LTD., Chiyoda-ku (JP)

( * ) Notice: Subject to any disclaimer, the term of this patent is extended or adjusted under 35 U.S.C. 154(b) by 369 days.

(21) Appl. No.: 15/502,401

(22) PCT Filed: Oct. 8, 2015

(86) PCT No.: PCT/JP2015/078692
§ 371 (c)(1),
(2) Date: Feb. 7, 2017

(87) PCT Pub. No.: WO2016/056640
PCT Pub. Date: Apr. 14, 2016

(65) Prior Publication Data
US 2017/0222144 A1    Aug. 3, 2017

(30) Foreign Application Priority Data
Oct. 9, 2014  (JP) .................................. 2014-208414

(51) Int. Cl.
*H01L 51/00* (2006.01)
*C07C 211/61* (2006.01)
(Continued)

(52) U.S. Cl.
CPC .......... *H01L 51/006* (2013.01); *C07C 211/61* (2013.01); *C09K 11/06* (2013.01);
(Continued)

(58) Field of Classification Search
CPC ............... C07C 211/61; C07C 2603/52; C07C 2603/94; C07D 307/77; C07D 333/50;
(Continued)

(56) References Cited

U.S. PATENT DOCUMENTS

2003/0118866 A1* 6/2003 Oh ...................... H01L 51/0058
428/690
2008/0145708 A1* 6/2008 Heil ........................ C07C 17/12
428/704

(Continued)

FOREIGN PATENT DOCUMENTS

JP    2008-115093 A    5/2008
KR    10-2012-0112257 A    10/2012
(Continued)

OTHER PUBLICATIONS

International Search Report dated Dec. 22, 2015 in PCT/JP2015/078692 filed Oct. 8, 2015.

*Primary Examiner* — Dawn L Garrett
(74) *Attorney, Agent, or Firm* — Oblon, McClelland, Maier & Neustadt, L.L.P.

(57) ABSTRACT

A compound represented by formula (1):

(Continued)

wherein Ar is a substituted or unsubstituted alkyl group having 1 to 20 carbon atoms, a substituted or unsubstituted aryl group having 6 to 30 ring carbon atoms, or a substituted or unsubstituted nitrogen-comprising heteroaryl group having 5 to 30 ring atoms; each of $L_1$ and $L_2$ is independently a single bond, a substituted or unsubstituted arylene group having 6 to 30 ring carbon atoms, a substituted or unsubstituted heteroarylene group having 5 to 30 ring atoms, or a substituted or unsubstituted divalent linking group wherein 2 to 4 groups selected from an arylene group having 6 to 30 ring carbon atoms and a heteroarylene group having 5 to 30 ring atoms are bonded to each other via a single bond; A is a monovalent group represented by formula (2); and B is a monovalent group represented by formula (5):

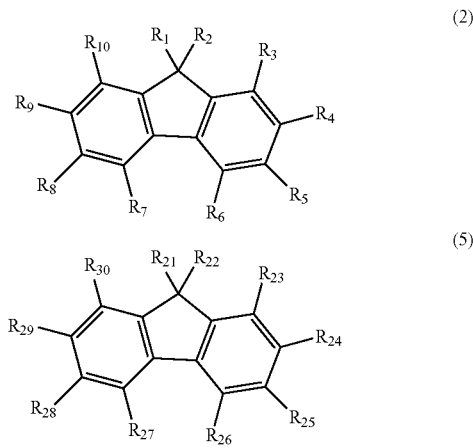

wherein $R_1$ to $R_{10}$ and $R_{21}$ to $R_{30}$ are as defined in the description, enables the emission of light of a purer blue (shorter wavelength), a narrower half width (higher color purity), and a single peak with no second peak.

20 Claims, 7 Drawing Sheets

(51) Int. Cl.
  *C09K 11/06* (2006.01)
  *H01L 51/50* (2006.01)
(52) U.S. Cl.
  CPC .. *C07C 2603/52* (2017.05); *C09K 2211/1007* (2013.01); *C09K 2211/1011* (2013.01); *C09K 2211/1014* (2013.01); *H01L 51/0055* (2013.01); *H01L 51/0058* (2013.01); *H01L 51/5012* (2013.01)
(58) Field of Classification Search
  CPC ............ C09K 11/06; C09K 2211/1007; C09K 2211/1011; C09K 2211/1014; H01L 51/0055; H01L 51/0058; H01L 51/006; H01L 51/50; H01L 51/5012
  See application file for complete search history.

(56) References Cited

U.S. PATENT DOCUMENTS

| | | | |
|---|---|---|---|
| 2009/0267491 A1 | 10/2009 | Takashima et al. | |
| 2014/0131681 A1* | 5/2014 | Ito ..................... | H01L 51/006 257/40 |
| 2015/0255720 A1 | 9/2015 | Heil et al. | |

FOREIGN PATENT DOCUMENTS

| | | |
|---|---|---|
| WO | 2008/006449 A1 | 1/2008 |
| WO | 2014/037077 A1 | 3/2014 |
| WO | 2014/069602 A1 | 5/2014 |
| WO | 2014/106522 A1 | 7/2014 |

* cited by examiner

COMPOUND, ORGANIC ELECTROLUMINESCENT MATERIAL, ORGANIC ELECTROLUMINESCENT ELEMENT, AND ELECTRONIC APPARATUS

TECHNICAL FIELD

The present invention relates to compounds, materials for organic electroluminescence devices, organic electroluminescence devices, and electronic devices.

BACKGROUND ART

Recently, organic electroluminescence devices (organic EL devices) have been used in wide applications, such as an emission device for mobile displays. As a blue fluorescent emitting component, i.e. a blue emitting material (blue dopant material) for use in such applications, a diamine compound of a fused aryl ring has been hitherto mainly developed. Particularly, a diaminopyrene dopant has been known to have a high color purity.

In the application to display, it has been required to further improve the color purity to obtain a high color reproducibility, this in turn requiring an emission of light with shorter wavelength. Patent Literatures 1 to 5 propose fluorene compounds as materials which realize the emission of light with a shorter wavelength.

CITATION LIST

Patent Literature

Patent Literature 1: JP 2008-115093A
Patent Literature 2: WO2014/069602
Patent Literature 3: WO2008/006449
Patent Literature 4: WO2014/037077
Patent Literature 5: WO2014/106522

SUMMARY OF INVENTION

Technical Problem

However, known fluorene compounds provide, in many cases, an emission spectrum having a broad peak with a large half width or having a peak with a second peak. In view of optical design of device, a material which provides an emission spectrum having no second peak and a small half width has been required in the application to display.

In an aspect, the present invention provides a material which enables the emission of light of a purer blue (shorter wavelength), a narrower half width (higher color purity), and more suitable spectrum (single peak without second peak), as compared with the emission of light obtained by the emitting materials described in Patent Literature 1 to 5. In another aspect, the present invention provides a material for organic EL device comprising the compound and an organic EL device comprising the compound. In still another aspect, the present invention provides an electronic device comprising the organic EL device.

Solution to Problem

The inventors have found that a compound comprising the specific fused fluorene structure represented by formula (1) as the main skeleton, wherein one monocyclic ring is fused to each of two benzene rings of the fluorene structure, enables the emission of light of a purer blue (shorter wavelength), a narrower half width (higher color purity), and more suitable spectrum (single peak with no second peak). The present invention has been made on the basis of this finding.

In an aspect of the invention, the compound represented by formula (1) is provided:

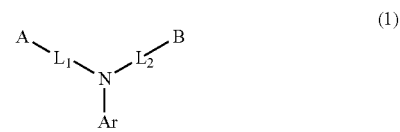

(1)

wherein:

Ar is a substituted or unsubstituted alkyl group having 1 to 20 carbon atoms, a substituted or unsubstituted aryl group having 6 to 30 ring carbon atoms, or a substituted or unsubstituted nitrogen-comprising heteroaryl group having 5 to 30 ring atoms;

each of $L_1$ and $L_2$ is independently a single bond, a substituted or unsubstituted arylene group having 6 to 30 ring carbon atoms, a substituted or unsubstituted heteroarylene group having 5 to 30 ring atoms, or a substituted or unsubstituted divalent linking group, wherein 2 to 4 groups selected from an arylene group having 6 to 30 ring carbon atoms and a heteroarylene group having 5 to 30 ring atoms are bonded to each other via a single bond;

A is a monovalent group represented by formula (2):

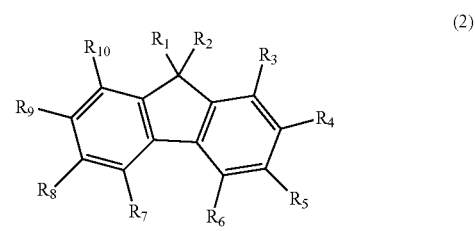

(2)

wherein:

each of $R_1$ and $R_2$ is independently a hydrogen atom, a substituted or unsubstituted alkyl group having 1 to 20 carbon atoms; a mono-, di-, or trialkylsilyl group each comprising a substituted or unsubstituted alkyl group having 1 to 20 carbon atoms; a substituted or unsubstituted aryl group having 6 to 30 ring carbon atoms; a mono-, di-, or triarylsilyl group each comprising a substituted or unsubstituted aryl group having 6 to 30 ring carbon atoms; or a substituted or unsubstituted heteroaryl group having 5 to 30 ring atoms; wherein $R_1$ and $R_2$ may be bonded to each other to form a ring;

adjacent two groups in one pair selected from $R_8$ and $R_4$, $R_4$ and $R_5$, and $R_5$ and $R_6$ are bonded to each other to form a divalent group represented by formula (3);

adjacent two groups in one pair selected from $R_7$ and $R_8$, $R_8$ and $R_9$, and $R_9$ and $R_{10}$ are bonded to each other to form a divalent group represented by formula (4);

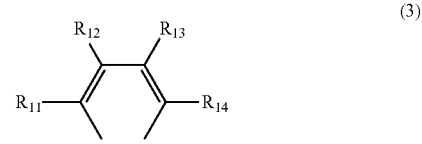

(3)

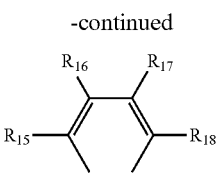

(4)

wherein:

each of $R_{11}$ to $R_{18}$ is independently a hydrogen atom; a substituted or unsubstituted alkyl group having 1 to 20 carbon atoms; a mono-, di-, or trialkylsilyl group each comprising a substituted or unsubstituted alkyl group having 1 to 20 carbon atoms; a substituted or unsubstituted aryl group having 6 to 30 ring carbon atoms; a mono-, di-, or triarylsilyl group each comprising a substituted or unsubstituted aryl group having 6 to 30 ring carbon atoms; or a substituted or unsubstituted heteroaryl group having 5 to 30 ring atoms;

provided that one selected from $R_3$ to $R_6$ which do not form the divalent group represented by formula (3), $R_7$ to $R_{10}$ which do not form the divalent group represented by formula (4), and $R_{11}$ to $R_{18}$ is a single bond bonded to $L_1$;

each selected from $R_3$ to $R_6$ which do not form the divalent group represented by formula (3) and is not a single bond bonded to $L_1$, and each selected from $R_7$ to $R_{10}$ which do not form the divalent group represented by formula (4) and is not a single bond bonded to $L_1$ is independently a hydrogen atom; a substituted or unsubstituted alkyl group having 1 to 20 carbon atoms; a mono-, di-, or trialkylsilyl group each comprising a substituted or unsubstituted alkyl group having 1 to 20 carbon atoms; a substituted or unsubstituted aryl group having 6 to 30 ring carbon atoms; a mono-, di-, or triarylsilyl group each comprising a substituted or unsubstituted aryl group having 6 to 30 ring carbon atoms; or a substituted or unsubstituted heteroaryl group having 5 to 30 ring atoms;

B is a monovalent group represented by formula (5):

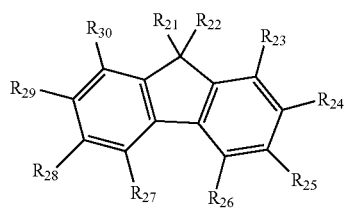

(5)

wherein:

each of $R_{21}$ and $R_{22}$ is independently a hydrogen atom, a substituted or unsubstituted alkyl group having 1 to 20 carbon atoms, a mono-, di-, or trialkylsilyl group each comprising a substituted or unsubstituted alkyl group having 1 to 20 carbon atoms, a substituted or unsubstituted aryl group having 6 to 30 ring carbon atoms, a mono-, di-, or triarylsilyl group each comprising a substituted or unsubstituted aryl group having 6 to 30 ring carbon atoms, or a substituted or unsubstituted heteroaryl group having 5 to 30 ring atoms, wherein $R_{21}$ and $R_{22}$ may be bonded to each other to form a ring;

each of $R_{23}$ to $R_{30}$ is independently a hydrogen atom, a substituted or unsubstituted alkyl group having 1 to 20 carbon atoms, a mono-, di-, or trialkylsilyl group each comprising a substituted or unsubstituted alkyl group having 1 to 20 carbon atoms, a substituted or unsubstituted aryl group having 6 to 30 ring carbon atoms, a mono-, di-, or triarylsilyl group each comprising a substituted or unsubstituted aryl group having 6 to 30 ring carbon atoms, or a substituted or unsubstituted heteroaryl group having 5 to 30 ring atoms;

adjacent groups in one or two pairs selected from $R_{23}$ and $R_{24}$, $R_{24}$ and $R_{25}$, and $R_{25}$ and $R_{26}$ may be bonded to each other to form a ring;

adjacent groups in one or two pairs selected from $R_{27}$ and $R_{28}$, $R_{28}$ and $R_{29}$, and $R_{29}$ and $R_{30}$ may be bonded to each other to form a carbon ring;

provided that one selected from $R_{27}$ to $R_{30}$ which do not form the optional carbon ring is a single bond bonded to $L_2$, or one of ring carbon atoms of the carbon ring which is optionally formed by one pair selected from $R_{27}$ and $R_{28}$, $R_{28}$ and $R_{29}$, and $R_{29}$ and $R_{30}$ is bonded to $L_2$; and an optional substituent referred to by "substituted or unsubstituted" is selected from the group consisting of a substituted or unsubstituted alkyl group having 1 to 20 carbon atoms; a mono-, di-, or trialkylsilyl group each comprising a substituted or unsubstituted alkyl group having 1 to 20 carbon atoms; a substituted or unsubstituted aryl group having 6 to 30 ring carbon atoms; a mono-, di-, or triarylsilyl group each comprising a substituted or unsubstituted aryl group having 6 to 30 ring carbon atoms; and a substituted or unsubstituted heteroaryl group having 5 to 30 ring atoms.

In another aspect of the invention, a material for organic electroluminescence device comprising the compound (1) is provided.

In still another aspect of the invention, an organic electroluminescence device is provided, which comprises a cathode, an anode, and at least one organic thin film layer provided between the cathode and the anode, wherein the at least one organic thin film layer comprises a light emitting layer and at least one layer of the at least one organic thin film layer comprises the compound (1).

In still another aspect of the invention, an electronic device comprising the organic electroluminescence device is provided.

Advantageous Effects of Invention

The compound (1) realizes the emission of light of a purer blue (shorter wavelength), a narrower half width (higher color purity), and a more suitable spectrum (single peak with no second peak). In an aspect of the invention, a material for organic EL device comprising the compound and an organic EL device comprising the compound are provided. In another aspect of the invention, an electronic device comprising the organic EL device is provided.

DESCRIPTION OF EMBODIMENTS

Figure 1:
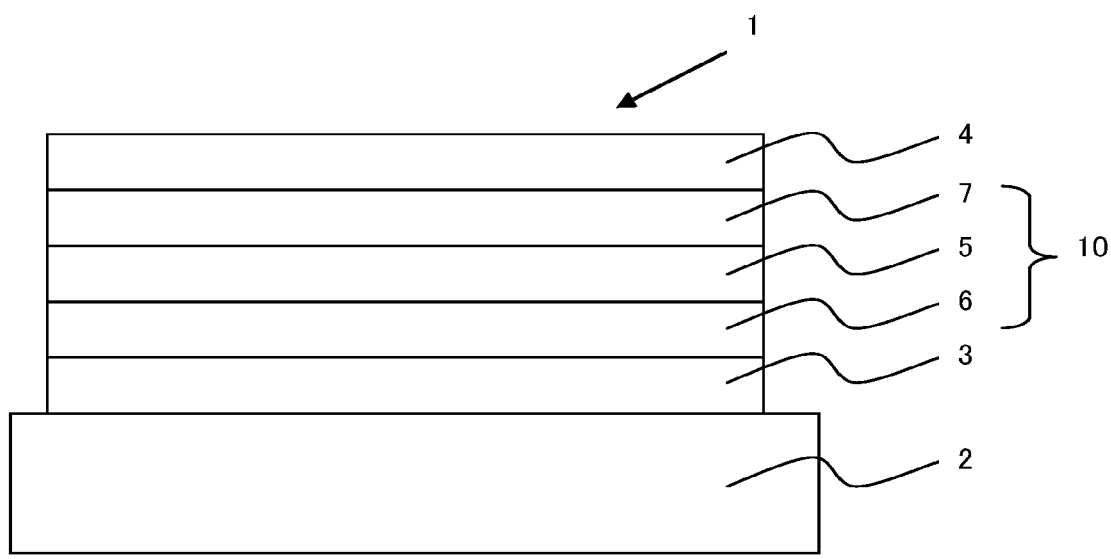
FIG. 1 is a schematic view showing the structure of the organic EL device in an aspect of the invention.

The term of "XX to YY carbon atoms" referred to by "a substituted or unsubstituted group ZZ having XX to YY carbon atoms" used herein is the number of carbon atoms of the unsubstituted group ZZ and does not include any carbon atom in the substituent of the substituted group ZZ. "YY" is larger than "XX" and each represents an integer of 1 or more.

The term of "XX to YY atoms" referred to by "a substituted or unsubstituted group ZZ having XX to YY atoms" used herein is the number of atoms of the unsubstituted group ZZ and does not include any atom in the substituent of the substituted group ZZ. "YY" is larger than "XX" and each represents an integer of 1 or more.

The term of "unsubstituted group ZZ" referred to by "substituted or unsubstituted group ZZ" used herein means that no hydrogen atom in the group ZZ is substituted by a substituent.

The definition of "hydrogen atom" used herein includes isotopes different in the neutron numbers, i.e., light hydrogen (protium), heavy hydrogen (deuterium), and tritium.

The number of "ring carbon atoms" referred to herein means the number of the carbon atoms included in the atoms which are members forming the ring itself of a compound in which a series of atoms is bonded to form a ring (for example, a monocyclic compound, a fused ring compound, a cross-linked compound, a carbocyclic compound, and a heterocyclic compound). If the ring has a substituent, the carbon atom in the substituent is not included in the ring carbon atom. The same applies to the number of "ring carbon atom" described below, unless otherwise noted. For example, a benzene ring has 6 ring carbon atoms, a naphthalene ring has 10 ring carbon atoms, a pyridinyl group has 5 ring carbon atoms, and a furanyl group has 4 ring carbon atoms. If a benzene ring or a naphthalene ring has, for example, an alkyl substituent, the carbon atom in the alkyl substituent is not counted as the ring carbon atom of the benzene or naphthalene ring. In case of a fluorene ring to which a fluorene substituent is bonded (inclusive of a spirofluorene ring), the carbon atom in the fluorene substituent is not counted as the ring carbon atom of the fluorene ring.

The number of "ring atom" referred to herein means the number of the atoms which are members forming the ring itself (for example, a monocyclic ring, a fused ring, and a ring assembly) of a compound in which a series of atoms is bonded to form the ring (for example, a monocyclic compound, a fused ring compound, a cross-linked compound, a carbocyclic compound, and a heterocyclic compound). The atom not forming the ring (for example, hydrogen atom(s) for saturating the valence of the atom which forms the ring) and the atom in a substituent, if the ring is substituted, are not counted as the ring atom. The same applies to the number of "ring atoms" described below, unless otherwise noted. For example, a pyridine ring has 6 ring atoms, a quinazoline ring has 10 ring atoms, and a furan ring has 5 ring atoms. The hydrogen atom on the ring carbon atom of a pyridine ring or a quinazoline ring and the atom in a substituent are not counted as the ring atom. In case of a fluorene ring to which a fluorene substituent is bonded (inclusive of a spirofluorene ring), the atom in the fluorene substituent is not counted as the ring atom of the fluorene ring.

The optional substituent referred to by "substituted or unsubstituted" used herein is selected from an alkyl group having 1 to 20, preferably 1 to 10, and more preferably 1 to 5 carbon atoms; a mono-, di-, or trialkylsilyl group each comprising an alkyl group having 1 to 20, preferably 1 to 10, and more preferably 1 to 5 carbon atoms; an aryl group having 6 to 30, preferably 6 to 24, and more preferably 6 to 18 ring carbon atoms; a mono-, di-, or triarylsilyl group each comprising an aryl group having 6 to 30, preferably 6 to 24, and more preferably 6 to 18 ring carbon atoms; and a heteroaryl group having 5 to 50, preferably 6 to 24, more preferably 6 to 18 ring atoms which includes 1 to 5, preferably 1 to 3, more preferably 1 or 2 heteroatoms, wherein the heteroatoms are the same or different and selected from a nitrogen atom, an oxygen atom and a sulfur atom. These optional substituents may be further substituted by the optional substituents mentioned above. The optional substituents may be bonded to each other to form a ring.

Examples, preferred examples, more preferred examples, and still more preferred examples of the above optional substituents are the same as the corresponding substituents mentioned below.

The compound in an aspect of the invention is represented by formula (1) (hereinafter also referred to as "compound (1)").

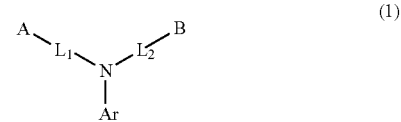

(1)

Ar is a substituted or unsubstituted alkyl group having 1 to 20 carbon atoms, a substituted or unsubstituted aryl group having 6 to 30 ring carbon atoms, or a substituted or unsubstituted nitrogen-comprising heteroaryl group having 5 to 30 ring atoms.

Examples of the alkyl group having 1 to 20, preferably 1 to 10, and more preferably 1 to 5 carbon atoms for Ar include a methyl group, an ethyl group, a n-propyl group, an isopropyl group, a n-butyl group, an isobutyl group, a s-butyl group, a t-butyl group, a pentyl group (inclusive of isomeric groups), a hexyl group (inclusive of isomeric groups), a heptyl group (inclusive of isomeric groups), an octyl group (inclusive of isomeric groups), a nonyl group (inclusive of isomeric groups), a decyl group (inclusive of isomeric groups), an undecyl group (inclusive of isomeric groups), and a dodecyl group (inclusive of isomeric groups), with a methyl group, an ethyl group, a n-propyl group, an isopropyl group, a n-butyl group, an isobutyl group, a s-butyl group, a t-butyl group, and a pentyl group (inclusive of isomeric groups) being preferred; a methyl group, an ethyl group, a n-propyl group, an isopropyl group, a n-butyl group, an isobutyl group, a s-butyl group, and a t-butyl group being more preferred, and a methyl group, an ethyl group, an isopropyl group, and a t-butyl group being still more preferred.

Examples of the aryl group having 6 to 30, preferably 6 to 24, and more preferably 6 to 18 ring carbon atoms for Ar include a phenyl group, a biphenylyl group, a terphenylyl group, a naphthyl group, an acenaphthylenyl group, an anthryl group, a benzanthryl group, an aceanthryl group, a phenanthryl group, a benzo[c]phenanthryl group, a phenalenyl group, a fluorenyl group, a picenyl group, a pentaphenyl group, a pyrenyl group, a chrysenyl group, a benzo[g]

chrysenyl group, a s-indanyl group, an as-indanyl group, a fluoranthenyl group, a benzo[k]fluoranthenyl group, a triphenylenyl group, a benzo[b]triphenylenyl group, and a perylenyl group, with a phenyl group, a biphenylyl group, a terphenylyl group, and a naphthyl group being preferred; a phenyl group, a biphenylyl group, and a terphenylyl group being more preferred; and a phenyl group being still more preferred. The aryl group mentioned above and each of the groups mentioned below include position-isomeric groups (groups different in the positions of free bonds), if any.

Examples of the substituted aryl group include a phenylnaphthyl group, a naphthylphenyl group, a tolyl group, a xylyl group, a 9,9-dimethylfluorenyl group, a 9,9-diphenylfluorenyl group, a t-butylphenyl group, a monovalent group represented by formula (2) or (5) which is mentioned below in detail.

The nitrogen-comprising heteroaryl group having 5 to 30, preferably 6 to 24, and more preferably 6 to 18 ring atoms for Ar comprises at least one, preferably 1 to 5, more preferably 1 to 3, and still more preferably 1 to 2 ring hetero atoms, which may be the same or different and selected from, for example, a nitrogen atom, a sulfur atom, and an oxygen atom. The ring hetero atom comprises at least one nitrogen atom.

Examples of the nitrogen-comprising heteroaryl group include a pyrrolyl group, a pyridyl group, a pyridazinyl group, a pyrimidinyl group, a pyrazinyl group, a triazinyl group, an imidazolyl group, an oxazolyl group, a thiazolyl group, a pyrazolyl group, an isoxazolyl group, an isothiazolyl group, an oxadiazolyl group, a thiadiazolyl group, a triazolyl group, a tetrazolyl group, an indolyl group, an isoindolyl group, an indolizinyl group, a quinolizinyl group, a quinolyl group, an isoquinolyl group, a cinnolyl group, a phthalazinyl group, a quinazolinyl group, a quinoxalinyl group, a benzimidazolyl group, a benzoxazolyl group, a benzothiazolyl group, an indazolyl group, a benzisoxazolyl group, a benzisothiazolyl group, a carbazolyl group, a phenanthridinyl group, an acridinyl group, a phenanthrolinyl group, a phenazinyl group, a phenothiazinyl group, a phenoxazinyl group, and a xanthenyl group, with a pyridyl group, a pyridazinyl group, a pyrimidinyl group, a pyrazinyl group, and a triazinyl group being preferred, and a pyridyl group, a pyrimidinyl group, and a triazinyl group being more preferred.

Ar is preferably a substituted or unsubstituted aryl group having 6 to 30 ring carbon atoms, more preferably a phenyl group, a biphenylyl group, a triphenylenyl group, a terphenyl group, a tolyl group, a xylyl group, an isopropylphenyl group, a t-butylphenyl group, a naphthyl group, or a monovalent group represented by formula (2) or (5), still more preferably a terphenyl group, a tolyl group, a xylyl group, an isopropylphenyl group, a t-butylphenyl group, a naphthyl group, or a triphenylenyl group, and particularly preferably a phenyl group, a tolyl group, a xylyl group, or a t-butylphenyl group.

Each of $L_1$ and $L_2$ is independently a single bond, a substituted or unsubstituted arylene group having 6 to 30 ring carbon atoms, a substituted or unsubstituted heteroarylene group having 5 to 30 ring atoms, or a substituted or unsubstituted divalent linking group, wherein 2 to 4 groups selected from an arylene group having 6 to 30 ring carbon atoms and a heteroarylene group having 5 to 30 ring atoms are bonded to each other via a single bond.

Examples, preferred examples, more preferred examples, and still more preferred examples of the arylene group having 6 to 30, preferably 6 to 24, and more preferably 6 to 18 ring carbon atoms for $L_1$ and $L_2$ include divalent groups obtained by removing one hydrogen atom from the aryl group having 6 to 30 ring carbon atoms mentioned above, preferred example thereof, more preferred example thereof, and still more preferred example thereof.

The heteroarylene group having 5 to 30, preferably 6 to 24, and more preferably 6 to 18 ring atoms for $L_1$ and $L_2$ comprises at least one, preferably 1 to 5, more preferably 1 to 3, and still more preferably 1 to 2 ring hetero atoms, which may be the same or different and selected from, for example, a nitrogen atom, a sulfur atom, and an oxygen atom.

Examples of the heteroarylene group include divalent residues of pyrrole, furan, thiophene, pyridine, pyridazine, pyrimidine, pyrazine, triazine, imidazole, oxazole, thiazole, pyrazole, isoxazole, isothiazole, oxadiazole, thiadiazole, triazole, tetrazole, indole, isoindole, benzofuran, isobenzofuran, benzothiophene, isobenzothiophene, indolizine, quinolizine, quinoline, isoquinoline, cinnoline, phthalazine, quinazoline, quinoxaline, benzimidazole, benzoxazole, benzothiazole, indazole, benzisoxazole, benzisothiazole, dibenzofuran, dibenzothiophene, carbazole, phenanthridine, acridine, phenanthroline, phenazine, phenothiazine, phenoxazine, and xanthene, with divalent residues of furan, thiophene, pyridine, pyridazine, pyrimidine, pyrazine, triazine, benzofuran, benzothiophene, dibenzofuran, and dibenzothiophene being preferred, and divalent residues of benzofuran, benzothiophene, dibenzofuran, and dibenzothiophene being more preferred.

Preferably each of $L_1$ and $L_2$ is independently a single bond, a substituted or unsubstituted arylene group having 6 to 30 ring carbon atoms, or a substituted or unsubstituted heteroarylene group having 5 to 30 ring atoms, more preferably a single bond, an arylene group having 6 to 30 ring carbon atoms, or a heteroarylene group having 5 to 30 ring atoms, still more preferably a single bond or an arylene group having 6 to 30 ring carbon atoms, and particularly preferably a single bond.

A is a monovalent group represented by formula (2):

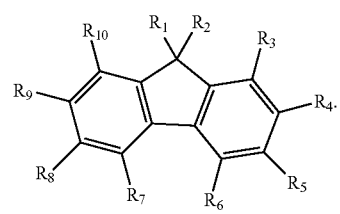

(2)

Each of $R_1$ and $R_2$ is independently a hydrogen atom, a substituted or unsubstituted alkyl group having 1 to 20 carbon atoms, a mono-, di-, or trialkylsilyl group each comprising a substituted or unsubstituted alkyl group having 1 to 20 carbon atoms, a substituted or unsubstituted aryl group having 6 to 30 ring carbon atoms, a mono-, di-, or triarylsilyl group each comprising a substituted or unsubstituted aryl group having 6 to 30 ring carbon atoms, or a substituted or unsubstituted heteroaryl group having 5 to 30 ring atoms, wherein $R_1$ and $R_2$ may be bonded to each other to form a ring.

In each of $R_1$ and $R_2$, examples, preferred examples, more preferred examples, and still more preferred examples of the alkyl group having 1 to 20, preferably 1 to 10, and more preferably 1 to 5 carbon atoms; the alkyl group having 1 to 20, preferably 1 to 10, and more preferably 1 to 5 carbon atoms in each of the mono-, di-, and trialkylsilyl groups; the aryl group having 6 to 30, preferably 6 to 24, and more preferably 6 to 18 ring carbon atoms; and the aryl group having 6 to 30, preferably 6 to 24, and more preferably 6 to 18 ring carbon atoms in each of the mono-, di-, and triarylsilyl groups are the same as the examples, the preferred examples, the more preferred examples, and the still more preferred examples of the alkyl group and the aryl group, which are mentioned above with respect to Ar.

The alkylsilyl group is preferably a trimethylsilyl group, a triethylsilyl group, a t-butyldimethylsilyl group, a pyropydimethylsilyl group, and an isopyropydimethylsilyl group, more preferably a trimethylsilyl group and a triethylsilyl group, and still more preferably a trimethylsilyl group.

The arylsilyl group is preferably a triphenylsilyl group.

The heteroaryl group having 5 to 30, preferably 6 to 24, and more preferably 6 to 18 ring atoms for $R_1$ and $R_2$ comprises at least one, preferably 1 to 5, more preferably 1 to 3, and still more preferably 1 to 2 ring hetero atoms, which may be the same or different and selected from a nitrogen atom, a sulfur atom, and an oxygen atom.

Examples of the heteroaryl group include a pyrrolyl group, a furyl group, a thienyl group, a pyridyl group, a pyridazinyl group, a pyrimidinyl group, a pyrazinyl group, a triazinyl group, an imidazolyl group, an oxazolyl group, a thiazolyl group, a pyrazolyl group, an isoxazolyl group, an isothiazolyl group, an oxadiazolyl group, a thiadiazolyl group, a triazolyl group, a tetrazolyl group, an indolyl group, an isoindolyl group, a benzofuranyl group, an isobenzofuranyl group, a benzothiophenyl group, an isobenzothiophenyl group, an indolizinyl group, a quinolizinyl group, a quinolyl group, an isoquinolyl group, a cinnolyl group, a phthalazinyl group, a quinazolinyl group, a quinoxalinyl group, a benzimidazolyl group, a benzoxazolyl group, a benzothiazolyl group, an indazolyl group, a benzisoxazolyl group, a benzisothiazolyl group, a dibenzofuranyl group, a dibenzothiophenyl group, a carbazolyl group, a phenanthridinyl group, an acridinyl group, a phenanthrolinyl group, a phenazinyl group, a phenothiazinyl group, a phenoxazinyl group, and a xanthenyl group, with a furyl group, a thienyl group, a pyridyl group, a pyridazinyl group, a pyrimidinyl group, a pyrazinyl group, a triazinyl group, a benzofuranyl group, a benzothiophenyl group, a dibenzofuranyl group, and a dibenzothiophenyl group being preferred, and a benzofuranyl group, a benzothiophenyl group, a dibenzofuranyl group, and a dibenzothiophenyl group being more preferred.

Preferably each of $R_1$ and $R_2$ is independently a hydrogen atom, a substituted or unsubstituted alkyl group having 1 to 20 carbon atoms, or a substituted or unsubstituted aryl group having 6 to 30 ring carbon atoms, more preferably an alkyl group having 1 to 20 carbon atoms or an aryl group having 6 to 30 ring carbon atoms, still more preferably a methyl group, an ethyl group, a n-propyl group, an isopropyl group, or a phenyl group, and particularly preferably a methyl group.

$R_1$ and $R_2$ may be bonded to each other to form a ring. Examples of the ring to be formed by $R_1$ and $R_2$ together with the carbon atom to which $R_1$ and $R_2$ are bonded include a cyclopentane ring, a cyclohexane ring, a fluorene ring (a 9,9-spirofluorene structure is formed together with the fluorene ring to which $R_1$ and $R_2$ are bonded).

Adjacent two groups in one pair selected from $R_3$ and $R_4$, $R_4$ and $R_5$, and $R_5$ and $R_6$ are bonded to each other to form a divalent group represented by formula (3). Adjacent two groups in one pair selected from $R_7$ and $R_8$, $R_8$ and $R_9$, and $R_9$ and $R_{10}$ are bonded to each other to form a divalent group represented by formula (4).

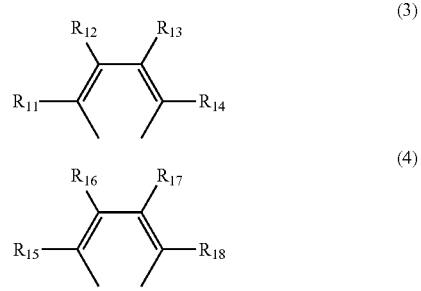

In an embodiment of the invention, formula (3) and formula (4) are the same. In another embodiment of the invention, formula (3) is different from formula (4).

Each of $R_{11}$ to $R_{18}$ is independently a hydrogen atom, a substituted or unsubstituted alkyl group having 1 to 20 carbon atoms; a mono-, di-, or trialkylsilyl group each comprising a substituted or unsubstituted alkyl group having 1 to 20 carbon atoms; a substituted or unsubstituted aryl group having 6 to 30 ring carbon atoms; a mono-, di-, or triarylsilyl group each comprising a substituted or unsubstituted aryl group having 6 to 30 ring carbon atoms, or a substituted or unsubstituted heteroaryl group having 5 to 30 ring atoms.

In $R_{11}$ to $R_{18}$, examples, preferred examples, more preferred examples, and still more preferred examples of the alkyl group having 1 to 20, preferably 1 to 10, and more preferably 1 to 5 carbon atoms; the alkyl group having 1 to 20, preferably 1 to 10, and more preferably 1 to 5 carbon atoms in each of the mono-, di-, and trialkylsilyl groups; the aryl group having 6 to 30, preferably 6 to 24, and more preferably 6 to 18 ring carbon atoms; the aryl group having 6 to 30, preferably 6 to 24, and more preferably 6 to 18 ring carbon atoms in each of the mono-, di-, and triarylsilyl groups, and the heteroaryl group having 5 to 30, preferably 6 to 24, and more preferably 6 to 18 ring atoms are the same as the examples, the preferred examples, the more preferred examples, and the still more preferred examples of the corresponding groups which are described above with respect to $R_1$ and $R_2$.

Preferably each of $R_{11}$ to $R_{18}$ is independently a hydrogen atom, a substituted or unsubstituted alkyl group having 1 to 20 carbon atoms, or a substituted or unsubstituted aryl group having 6 to 30 ring carbon atoms, more preferably a hydrogen atom, an alkyl group having 1 to 20 carbon atoms, or an aryl group having 6 to 30 ring carbon atoms, and still more preferably a hydrogen atom.

One selected from $R_3$ to $R_6$ which do not form the divalent group represented by formula (3), $R_7$ to $R_{10}$ which do not form the divalent group represented by formula (4), and $R_{11}$ to $R_{18}$ is a single bond bonded to $L_1$.

Each of $R_3$ to $R_1$ which do not form the divalent group represented by formula (3) and is not a single bond bonded to $L_1$, and each of $R_7$ to $R_{10}$ which do not form the divalent group represented by formula (4) and is not a single bond bonded to $L_1$ is independently a hydrogen atom; a substituted or unsubstituted alkyl group having 1 to 20 carbon atoms; a mono-, di-, or trialkylsilyl group each comprising a substituted or unsubstituted alkyl group having 1 to 20 carbon atoms; a substituted or unsubstituted aryl group having 6 to 30 ring carbon atoms; a mono-, di-, or triarylsilyl group each comprising a substituted or unsubstituted aryl group having 6 to 30 ring carbon atoms, or a substituted or unsubstituted heteroaryl group having 5 to 30 ring atoms.

Examples, preferred examples, more preferred examples, and still more preferred examples of the alkyl group having 1 to 20, preferably 1 to 10, and more preferably 1 to 5 carbon atoms; the alkyl group having 1 to 20, preferably 1 to 10, and more preferably 1 to 5 carbon atoms in each of the mono-, di-, and trialkylsilyl groups; the aryl group having 6 to 30, preferably 6 to 24, and more preferably 6 to 18 ring carbon atoms; the aryl group having 6 to 30, preferably 6 to 24, and more preferably 6 to 18 ring carbon atoms in each of the mono-, di-, and triarylsilyl groups; and the heteroaryl group having 5 to 30, preferably 6 to 24, and more preferably 6 to 18 ring atoms are the same as the examples, the preferred examples, the more preferred examples, and the still more preferred examples of the corresponding groups which are mentioned with respect to $R_1$ and $R_2$.

Each of $R_3$ to $R_6$ which do not form the divalent group represented by formula (3) and is not a single bond bonded to $L_1$, and each of $R_7$ to $R_{10}$ which do not form the divalent group represented by formula (4) and is not a single bond bonded to $L_1$ is independently preferably a hydrogen atom, a substituted or unsubstituted alkyl group having 1 to 20 carbon atoms, or a substituted or unsubstituted aryl group having 6 to 30 ring carbon atoms, more preferably a hydrogen atom, an alkyl group having 1 to 20 carbon atoms, or an aryl group having 6 to 30 ring carbon atoms, and still more preferably a hydrogen atom.

In formula (2), adjacent two groups selected from $R_1$; $R_2$; $R_3$ to $R_6$ not forming the divalent group represented by formula (3); $R_7$ to $R_{10}$ not forming the divalent group represented by formula (4); $R_{11}$ to $R_{14}$; and $R_{15}$ to $R_{18}$ are not bonded to each other thereby failing to form a ring, provided that a pair of $R_1$ and $R_2$ may be bonded to each other to form a ring.

Namely, only one monocyclic ring is fused to each of two benzene rings of the fluorene structure of formula (2), i.e., two or more rings do not fuse to each benzene ring of the fluorene structure of formula (2), and also, a ring comprising two or more rings does not fuse thereto.

Formula (2) (inclusive of formula (2) for Ar) is preferably represented by any of formulae (6) to (11), more preferably represented by any of formulae (6), (8), and (9), and still more preferably represented by formula (6) or (9).

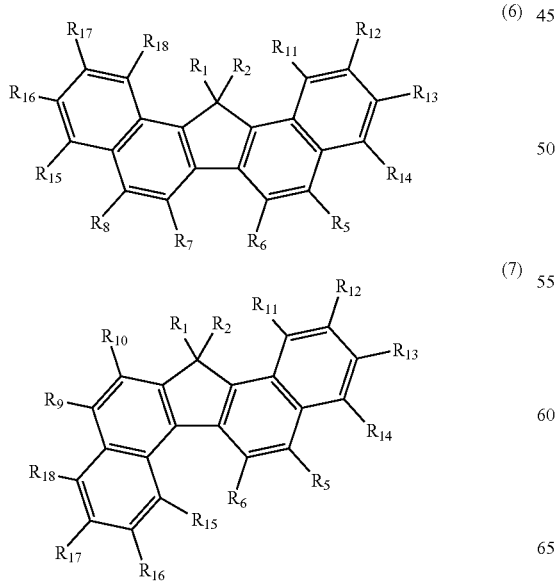

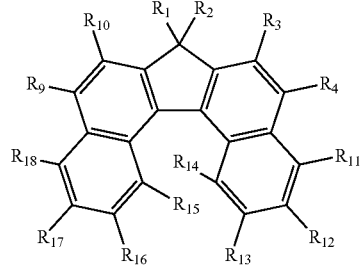

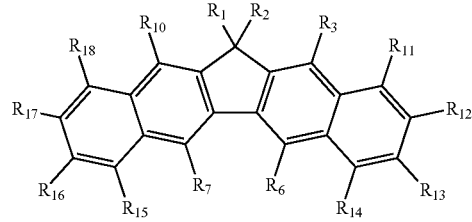

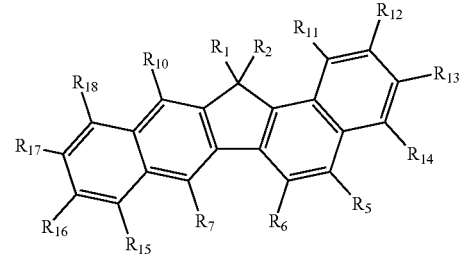

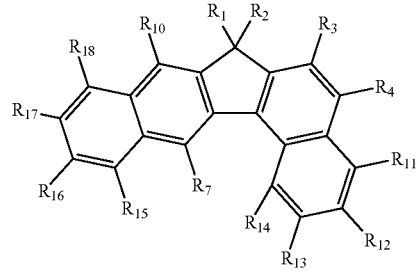

In formulae (6) to (11), $R_1$ to $R_{18}$ are as defined above.

In formula (6), one of $R_5$ to $R_8$ and $R_{11}$ to $R_{18}$, preferably $R_{13}$ or $R_{16}$ is a single bond which is bonded to $L_1$.

In formula (7), one of $R_5$, $R_6$, $R_9$, $R_{10}$, and $R_{11}$ to $R_{18}$, preferably $R_5$, $R_9$, or $R_{13}$ is a single bond which is bonded to $L_1$.

In formula (8), one of $R_3$, $R_4$, $R_9$, $R_{10}$, and $R_{11}$ to $R_{18}$, preferably $R_4$ or $R_9$ is a single bond which is bonded to $L_1$.

In formula (9), one of $R_3$, $R_6$, $R_7$, $R_{10}$, and $R_{11}$ to $R_{18}$, preferably $R_{12}$ or $R_{17}$ is a single bond which is bonded to $L_1$.

In formula (10), one of $R_5$ to $R_7$, $R_{10}$, and $R_{11}$ to $R_{18}$, preferably $R_7$, $R_{13}$, or $R_{17}$ is a single bond which is bonded to $L_1$.

In formula (11), one of $R_3$, $R_4$, $R_7$, $R_{10}$, and $R_{11}$ to $R_{18}$, preferably $R_4$ or $R_{17}$ is a single bond which is bonded to $L_1$.

B is a monovalent group represented by formula (5):

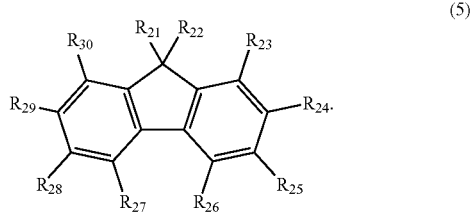

(5)

Each of $R_{21}$ and $R_{22}$ is independently a hydrogen atom, a substituted or unsubstituted alkyl group having 1 to 20 carbon atoms, a mono-, di-, or trialkylsilyl group each comprising a substituted or unsubstituted alkyl group having 1 to 20 carbon atoms, a substituted or unsubstituted aryl group having 6 to 30 ring carbon atoms, a mono-, di-, or triarylsilyl group each comprising a substituted or unsubstituted aryl group having 6 to 30 ring carbon atoms, or a substituted or unsubstituted heteroaryl group having 5 to 30 ring atoms, wherein $R_{21}$ and $R_{22}$ may be bonded to each other to form a ring.

In $R_{21}$ and $R_{22}$, examples, preferred examples, more preferred examples, and still more preferred examples of the alkyl group having 1 to 20, preferably 1 to 10, and more preferably 1 to 5 carbon atoms; the alkyl group having 1 to 20, preferably 1 to 10, and more preferably 1 to 5 carbon atoms in each of the mono-, di-, and trialkylsilyl groups; the aryl group having 6 to 30, preferably 6 to 24, and more preferably 6 to 18 ring carbon atoms; the aryl group having 6 to 30, preferably 6 to 24, and more preferably 6 to 18 ring carbon atoms in each of the mono-, di-, and triarylsilyl groups, and the heteroaryl group having 5 to 30, preferably 6 to 24, and more preferably 6 to 18 ring atoms are the same as the examples, the preferred examples, the more preferred examples, and the still more preferred examples of the corresponding groups which are described above with respect to $R_1$ and $R_2$.

Preferably each of $R_{21}$ and $R_{22}$ is independently a hydrogen atom, a substituted or unsubstituted alkyl group having 1 to 20 carbon atoms, or a substituted or unsubstituted aryl group having 6 to 30 ring carbon atoms, more preferably an alkyl group having 1 to 20 carbon atoms or an aryl group having 6 to 30 ring carbon atoms, still more preferably a methyl group, an ethyl group, a n-propyl group, an isopropyl group, or a phenyl group, and particularly preferably a methyl group.

$R_{21}$ and $R_{22}$ may be bonded to each other to form a ring. Examples of the ring to be formed by $R_{21}$ and $R_{22}$ together with the carbon atom to which $R_{21}$ and $R_{22}$ are bonded include a cyclopentane ring, a cyclohexane ring, a fluorene ring (a 9,9-spirofluorene structure is formed together with the fluorene ring to which $R_{21}$ and $R_{22}$ are bonded).

Each of $R_{23}$ to $R_{30}$ is independently a hydrogen atom, a substituted or unsubstituted alkyl group having 1 to 20 carbon atoms; a mono-, di-, or trialkylsilyl group each comprising a substituted or unsubstituted alkyl group having 1 to 20 carbon atoms; a substituted or unsubstituted aryl group having 6 to 30 ring carbon atoms; a mono-, di-, or triarylsilyl group each comprising a substituted or unsubstituted aryl group having 6 to 30 ring carbon atoms; or a substituted or unsubstituted heteroaryl group having 5 to 30 ring atoms. One selected from $R_{27}$ to $R_{30}$ may be a single bond bonded to $L_2$.

In $R_{23}$ to $R_{30}$, examples, preferred examples, more preferred examples, and still more preferred examples of the alkyl group having 1 to 20, preferably 1 to 10, and more preferably 1 to 5 carbon atoms; the alkyl group having 1 to 20, preferably 1 to 10, and more preferably 1 to 5 carbon atoms in each of the mono-, di-, and trialkylsilyl groups; the aryl group having 6 to 30, preferably 6 to 24, and more preferably 6 to 18 ring carbon atoms; the aryl group having 6 to 30, preferably 6 to 24, and more preferably 6 to 18 ring carbon atoms in each of the mono-, di-, and triarylsilyl groups, and the heteroaryl group having 5 to 30, preferably 6 to 24, and more preferably 6 to 18 ring atoms are the same as the examples, the preferred examples, the more preferred examples, and the still more preferred examples of the corresponding groups which are described above with respect to $R_1$ and $R_2$.

Preferably each of $R_{23}$ to $R_{30}$ is independently a hydrogen atom, a substituted or unsubstituted alkyl group having 1 to 20 carbon atoms, or a substituted or unsubstituted aryl group having 6 to 30 ring carbon atoms, more preferably a hydrogen atom, an alkyl group having 1 to 20 carbon atoms, or an aryl group having 6 to 30 ring carbon atoms, and still more preferably a hydrogen atom.

Adjacent groups in one or two pairs selected from $R_{23}$ and $R_{24}$, $R_{24}$ and $R_{25}$, and $R_{25}$ and $R_{26}$ may be bonded to each other to form a ring.

Adjacent groups in one or two pairs selected from $R_{27}$ and $R_{28}$, $R_{28}$ and $R_{29}$, and $R_{29}$ and $R_{30}$ may be bonded to each other to form a carbon ring.

In formula (5), one selected from $R_{27}$ to $R_{30}$ which do not form the optional carbon ring is a single bond bonded to $L_2$, or one of ring carbon atoms of the carbon ring which is optionally formed by one pair selected from $R_{27}$ and $R_{28}$, $R_{28}$ and $R_{29}$, and $R_{29}$ and $R_{30}$ is bonded to $L_2$.

The divalent group which is optionally formed by one or two pairs selected from $R_{23}$ and $R_{24}$, $R_{24}$ and $R_{25}$, and $R_{25}$ and $R_{26}$ is preferably represented by formula (12) or (13). The divalent group which is optionally formed by one or two pairs selected from $R_{27}$ and $R_{28}$, $R_{28}$ and $R_{29}$, and $R_{29}$ and $R_{30}$ is preferably represented by formula (14).

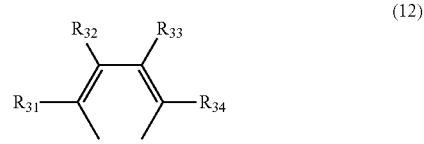

(12)

(13)

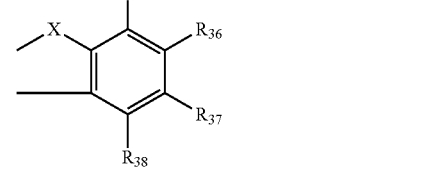

(14)

Each of $R_{31}$ to $R_{34}$, $R_{35}$ to $R_{38}$, and $R_{39}$ to $R_{42}$ is independently a hydrogen atom, a substituted or unsubstituted alkyl group having 1 to 20 carbon atoms, a mono-, di-, or trialkylsilyl group each comprising a substituted or unsubstituted alkyl group having 1 to 20 carbon atoms, a substituted or unsubstituted aryl group having 6 to 30 ring carbon atoms, a mono-, di-, or triarylsilyl group each comprising a substituted or unsubstituted aryl group having 6 to 30 ring carbon atoms, or a substituted or unsubstituted heteroaryl group having 5 to 30 ring atoms.

Adjacent two groups respectively selected from $R_{31}$ to $R_{34}$, $R_{35}$ to $R_{38}$, and $R_{39}$ to $R_{42}$ may be bonded to each other to form, together with the carbon atoms to which two groups are bonded, a ring, such as a benzene ring.

In $R_{31}$ to $R_{34}$, $R_{35}$ to $R_{38}$, and $R_{39}$ to $R_{42}$, examples, preferred examples, more preferred examples, and still more preferred examples of the alkyl group having 1 to 20, preferably 1 to 10, and more preferably 1 to 5 carbon atoms; the alkyl group having 1 to 20, preferably 1 to 10, and more preferably 1 to 5 carbon atoms in each of the mono-, di-, and trialkylsilyl groups; the aryl group having 6 to 30, preferably 6 to 24, and more preferably 6 to 18 ring carbon atoms; the aryl group having 6 to 30, preferably 6 to 24, and more preferably 6 to 18 ring carbon atoms in each of the mono-, di-, and triarylsilyl groups, and the heteroaryl group having 5 to 30, preferably 6 to 24, and more preferably 6 to 18 ring atoms are the same as the examples, the preferred examples, the more preferred examples, and the still more preferred examples of the corresponding groups which are described above with respect to $R_1$ and $R_2$.

One of $R_{39}$ to $R_{42}$ may be a single bond which is bonded to $L_2$.

Preferably each of $R_{31}$ to $R_{34}$, $R_{35}$ to $R_{38}$, and $R_{39}$ to $R_{42}$ is independently a hydrogen atom, a substituted or unsubstituted alkyl group having 1 to 20 carbon atoms, or a substituted or unsubstituted aryl group having 6 to 30 ring carbon atoms, more preferably a hydrogen atom, an alkyl group having 1 to 20 carbon atoms, or an aryl group having 6 to 30 ring carbon atoms, and still more preferably a hydrogen atom.

X is $CR_{43}R_{44}$, $NR_{45}$, O, or S.

Each of $R_{43}$ to $R_{45}$ is independently a hydrogen atom, a substituted or unsubstituted alkyl group having 1 to 20 carbon atoms; a mono-, di-, or trialkylsilyl group each comprising a substituted or unsubstituted alkyl group having 1 to 20 carbon atoms; a substituted or unsubstituted aryl group having 6 to 30 ring carbon atoms; a mono-, di-, or triarylsilyl group each comprising a substituted or unsubstituted aryl group having 6 to 30 ring carbon atoms; or a substituted or unsubstituted heteroaryl group having 5 to 30 ring atoms, wherein $R_{43}$ and $R_{44}$ may be bonded to each other to form a ring.

In $R_{43}$ to $R_{45}$, examples, preferred examples, more preferred examples, and still more preferred examples of the alkyl group having 1 to 20, preferably 1 to 10, and more preferably 1 to 5 carbon atoms; the alkyl group having 1 to 20, preferably 1 to 10, and more preferably 1 to 5 carbon atoms in each of the mono-, di-, and trialkylsilyl groups; the aryl group having 6 to 30, preferably 6 to 24, and more preferably 6 to 18 ring carbon atoms; the aryl group having 6 to 30, preferably 6 to 24, and more preferably 6 to 18 ring carbon atoms in each of the mono-, di-, and triarylsilyl groups, and the heteroaryl group having 5 to 30, preferably 6 to 24, and more preferably 6 to 18 ring atoms are the same as the examples, the preferred examples, the more preferred examples, and the still more preferred examples of the corresponding groups which are described above with respect to $R_1$ and $R_2$.

Each of $R_{43}$ and $R_{44}$ is preferably a hydrogen atom, a substituted or unsubstituted alkyl group having 1 to 20 carbon atoms, or a substituted or unsubstituted aryl group having 6 to 30 ring carbon atoms, more preferably a hydrogen atom, an alkyl group having 1 to 20 carbon atoms, or an aryl group having 6 to 30 ring carbon atoms, and still more preferably a methyl group or a phenyl group.

$R_{45}$ is preferably a hydrogen atom, a substituted or unsubstituted alkyl group having 1 to 20 carbon atoms, or a substituted or unsubstituted aryl group having 6 to 30 ring carbon atoms, more preferably a hydrogen atom, an alkyl group having 1 to 20 carbon atoms, or an aryl group having 6 to 30 ring carbon atoms, and still more preferably a phenyl group.

Formula (5) is preferably represented by any of formulae (15) to (54), more preferably any of formula (15), (18), (19), (24), (25), (26), (28) to (37), and (39) to (41), and still more preferably any of formulae (15), (19), (28), (30) to (33), (35), (36), and (37).

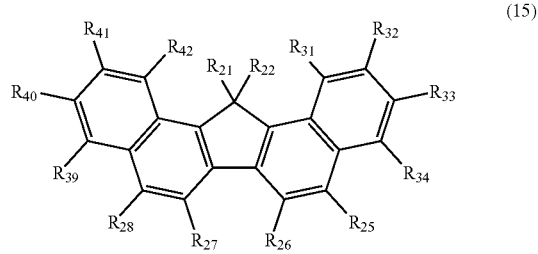

(15)

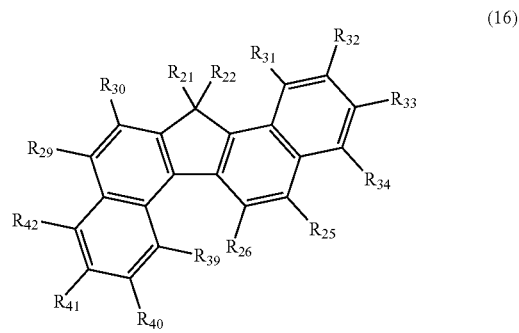

(16)

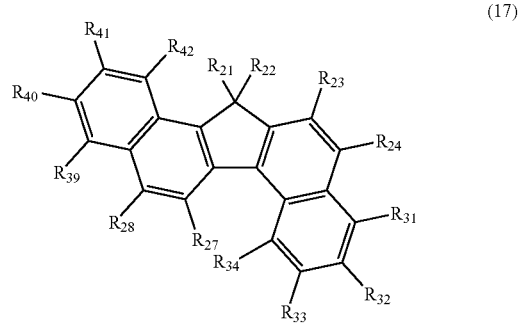

(17)

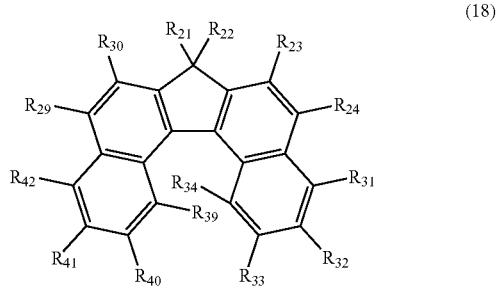

(18)

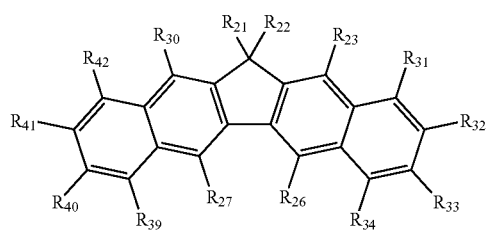
(19)
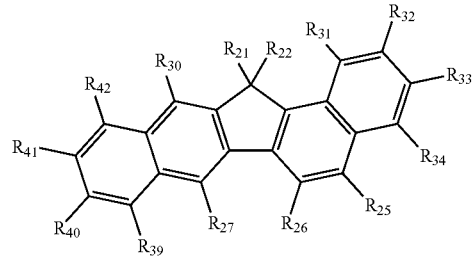
(20)
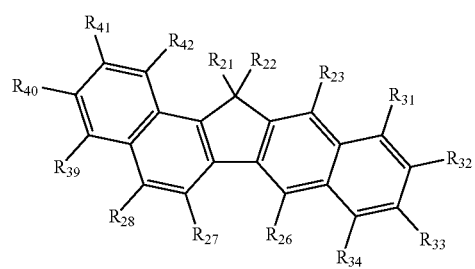
(21)
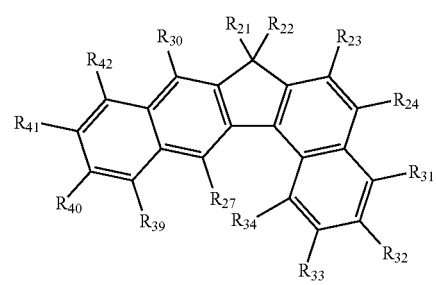
(22)
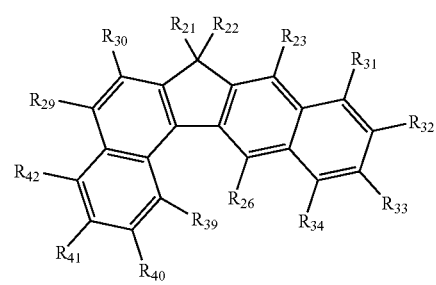
(23)
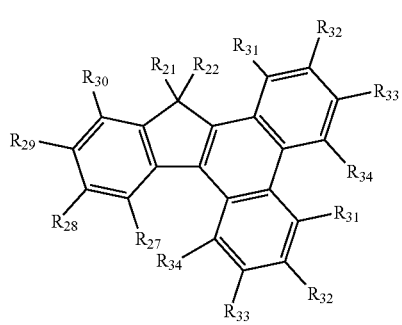
(24)
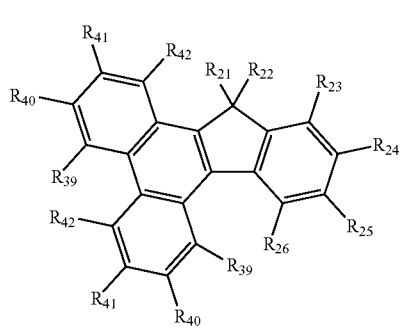
(25)
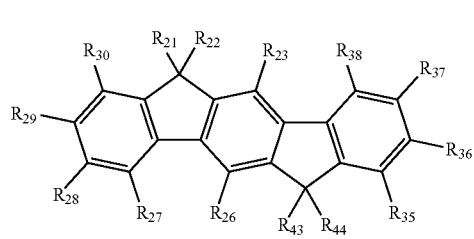
(26)
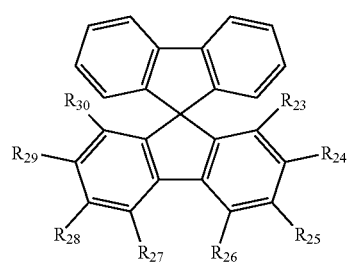
(27)
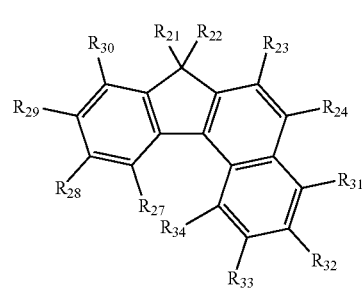
(28)

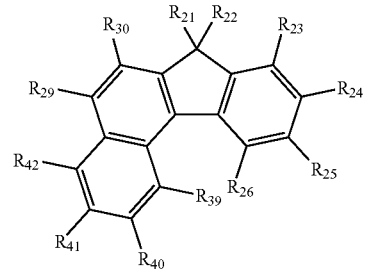
(29)
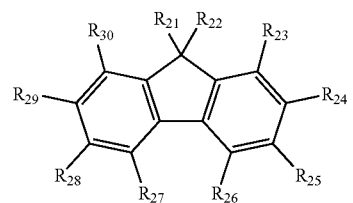
(30)
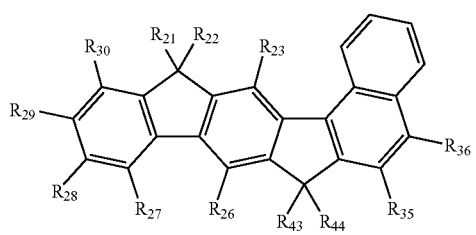
(31)
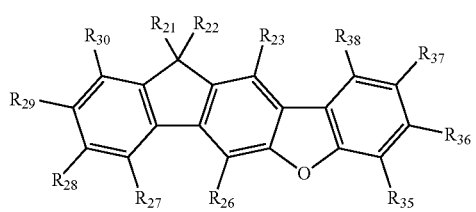
(32)
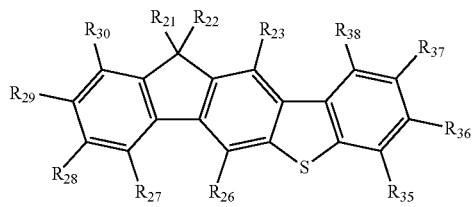
(33)
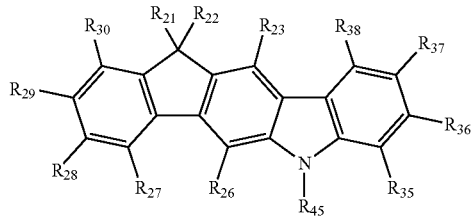
(34)
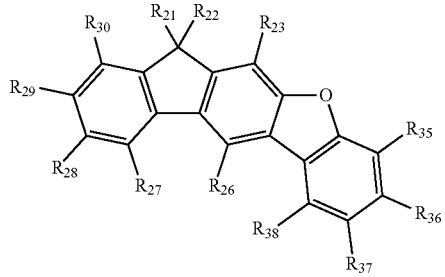
(35)
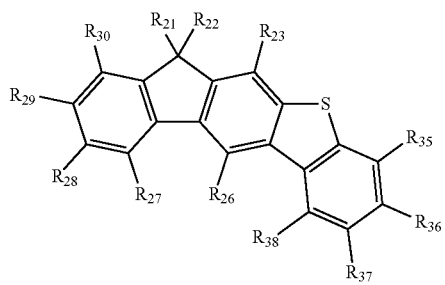
(36)
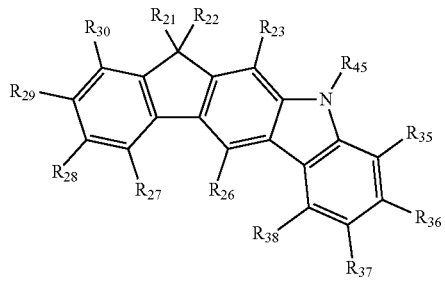
(37)
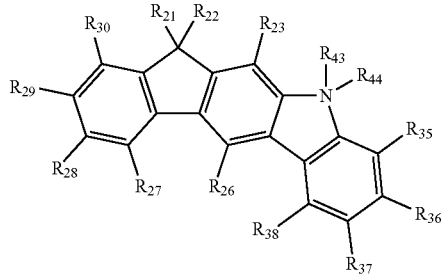
(38)
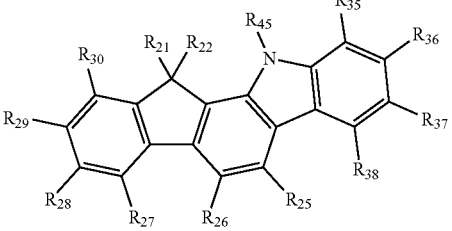
(39)
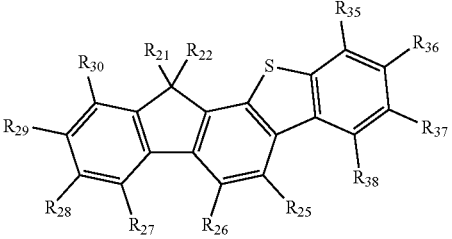
(40)

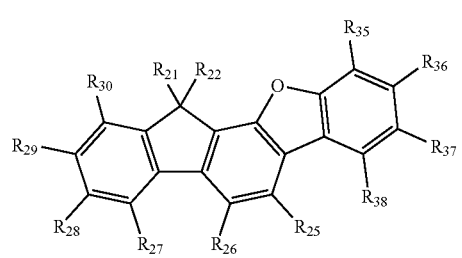
(41)
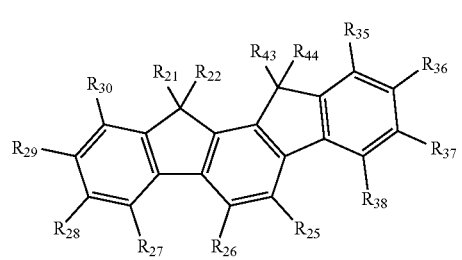
(42)
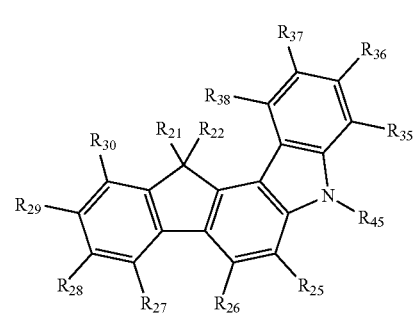
(43)
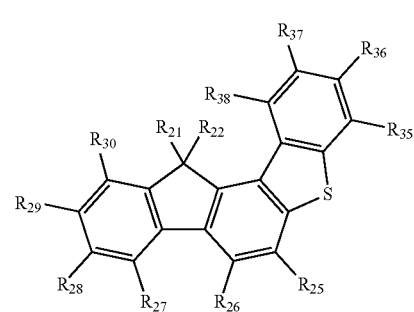
(44)
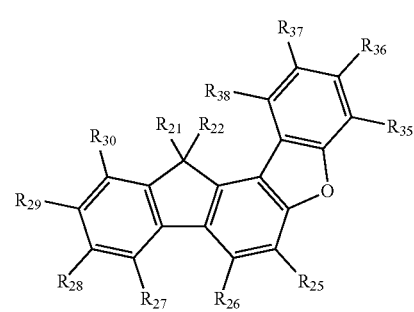
(45)
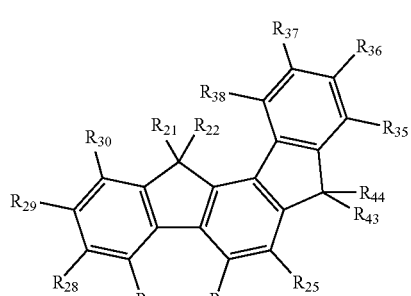
(46)
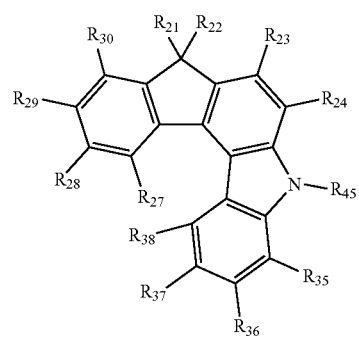
(47)
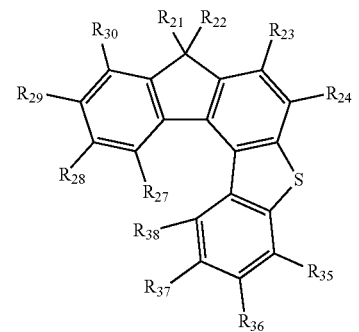
(48)
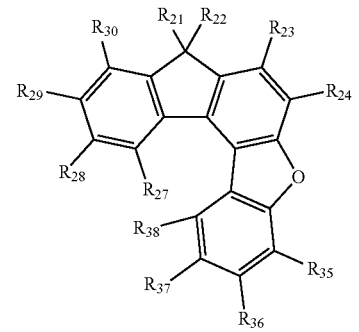
(49)
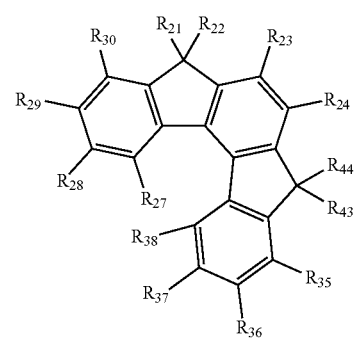
(50)

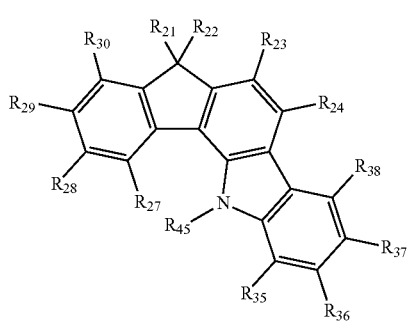

(51)

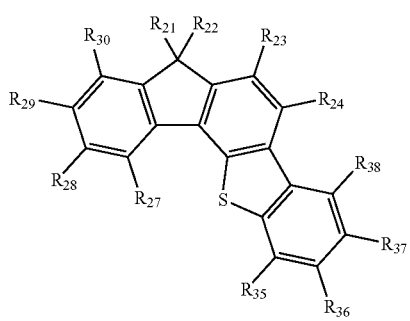

(52)

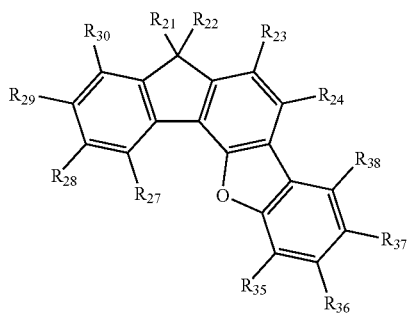

(53)

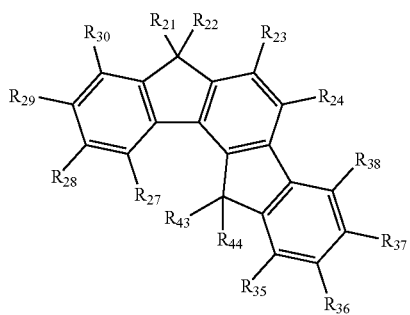

(54)

In formulae (15) to (54), $R_{21}$ to $R_{45}$ are as defined above.

In formula (15), one of $R_{27}$, $R_{28}$, and $R_{39}$ to $R_{42}$, preferably $R_{40}$ is a single bond which is bonded to $L_2$.

In formula (16), one of $R_{29}$, $R_{30}$, and $R_{39}$ to $R_{42}$, preferably $R_{29}$ is a single bond which is bonded to $L_2$.

In formula (17), one of $R_{27}$, $R_{28}$, and $R_{39}$ to $R_{42}$, preferably $R_{28}$ or $R_{40}$ is a single bond which is bonded to $L_2$.

In formula (18), one of $R_{29}$, $R_{30}$, and $R_{39}$ to $R_{42}$, preferably $R_{29}$ is a single bond which is bonded to $L_2$.

In formula (19), one of $R_{27}$, $R_{30}$, and $R_{39}$ to $R_{42}$, preferably $R_{41}$ is a single bond which is bonded to $L_2$.

In formula (20), one of $R_{27}$, $R_{30}$, and $R_{39}$ to $R_{42}$, preferably $R_{27}$ or $R_{41}$ is a single bond which is bonded to $L_2$.

In formula (21), one of $R_{27}$, $R_{28}$, and $R_{39}$ to $R_{42}$, preferably $R_{40}$ is a single bond which is bonded to $L_2$.

In formula (22), one of $R_{27}$, $R_{30}$, and $R_{39}$ to $R_{42}$, preferably $R_{41}$ is a single bond which is bonded to $L_2$.

In formula (23), one of $R_{29}$, $R_{30}$, and $R_{39}$ to $R_{42}$, preferably $R_{29}$ is a single bond which is bonded to $L_2$.

In formula (24), two groups $R_{31}$, two groups $R_{32}$, two groups $R_{33}$, and two groups $R_{34}$ may be the same or different, respectively, and one of $R_{27}$ to $R_{30}$, preferably $R_{29}$ is a single bond which is bonded to $L_2$.

In formula (25), two groups $R_{39}$, two groups $R_{40}$, two groups $R_{41}$, and two groups $R_{42}$ may be the same or different, respectively, and one of these groups, preferably $R_{40}$ on the benzene ring fused to the position 1-2 (side a) of the fluorene structure is a single bond which is bonded to $L_2$.

In formula (26), one of $R_{27}$ to $R_{30}$, preferably $R_{29}$ is a single bond which is bonded to $L_2$.

In formula (27), one of $R_{27}$ to $R_{30}$, preferably $R_{27}$ or $R_{29}$ is a single bond which is bonded to $L_2$.

In formula (28), one of $R_{27}$ to $R_{30}$, preferably $R_{29}$ is a single bond which is bonded to $L_2$.

In formula (29), one of $R_{29}$, $R_{30}$, and $R_{39}$ to $R_{42}$, preferably $R_{29}$ is a single bond which is bonded to $L_2$.

In formula (30), one of $R_{27}$ to $R_{30}$, preferably one of $R_{27}$ to $R_{29}$ is a single bond which is bonded to $L_2$.

In formulae (31) to (54), one of $R_{27}$ to $R_{30}$, preferably $R_{29}$ is a single bond which is bonded to $L_2$.

In an embodiment of the invention, the compound (1) is represented by formula (1) wherein Ar is a monovalent group represented by formula (5), and B and Ar are preferably the same.

In another embodiment of the invention, the compound (1) is represented by formula (1) wherein A and B are the same, preferably A being represented by any of formulae (6) to (11), and B being represented by any of formulae (15) to (23).

In still another embodiment of the invention, the compound (1) is represented by formula (1) wherein Ar is a monovalent group represented by formula (2), preferably, each of A and Ar is represented by any of formulae (6) to (11), B is represented by any of formulae (15) to (23), and A, B, and Ar are the same.

The compound (1) is useful as a material for organic EL device, particularly as a dopant material for a fluorescent emitting layer. The production method of the compound (1) is not limited, and one of ordinary skill in the art can easily produce the compound (1) by using or modifying the known synthesis reaction with reference to the examples described below.

Examples of the compound (1) are shown below, although not limited thereto.

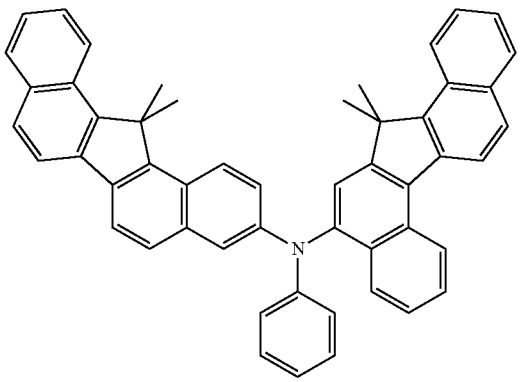

-continued
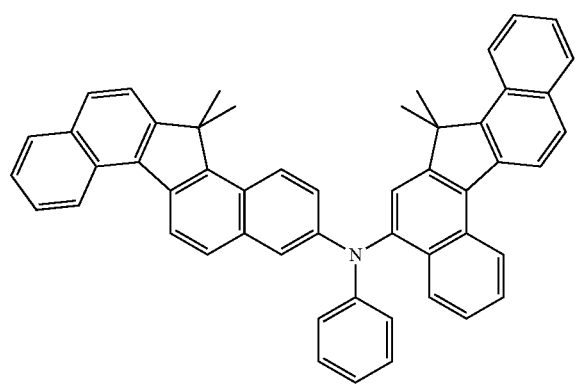
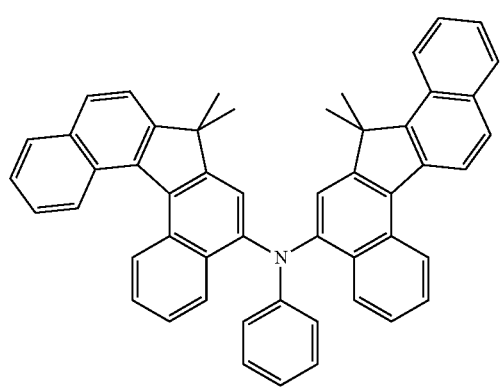
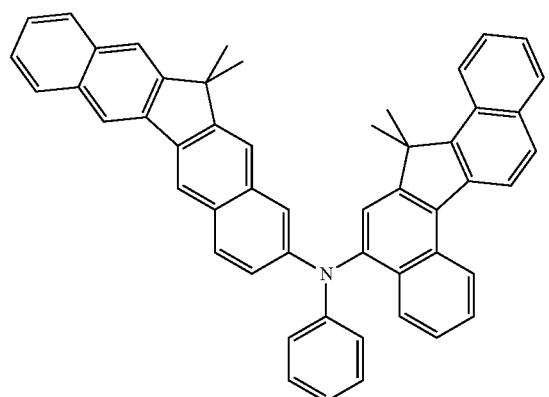
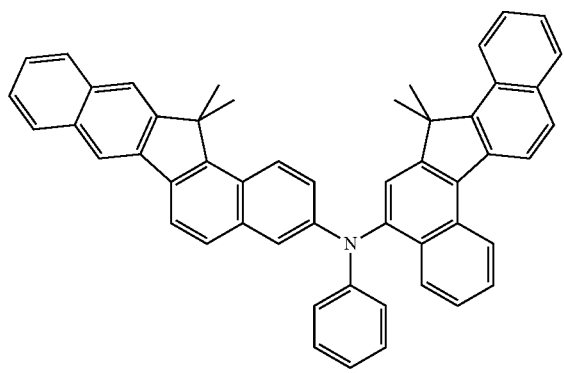
-continued
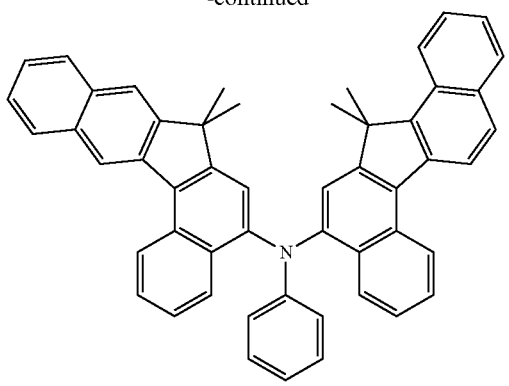
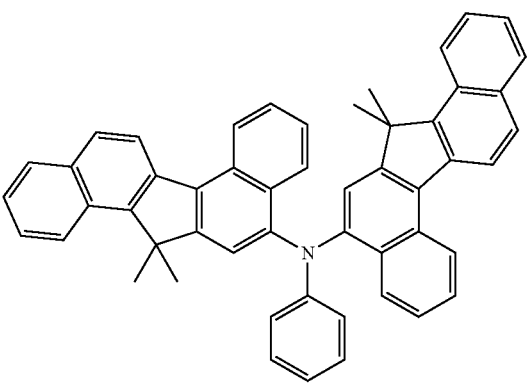
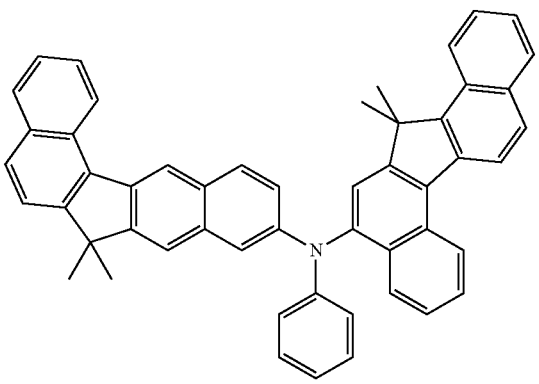
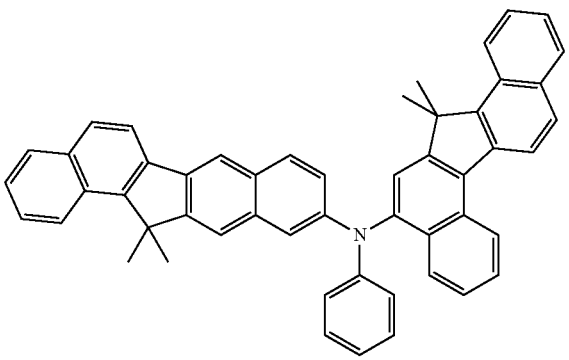

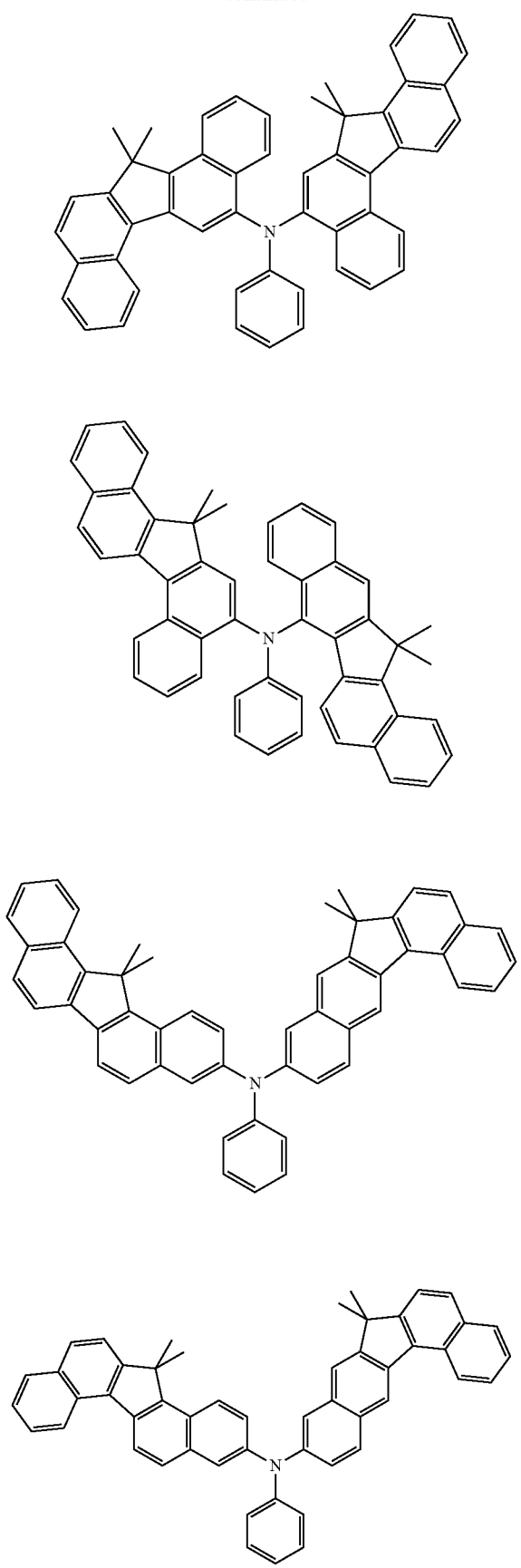
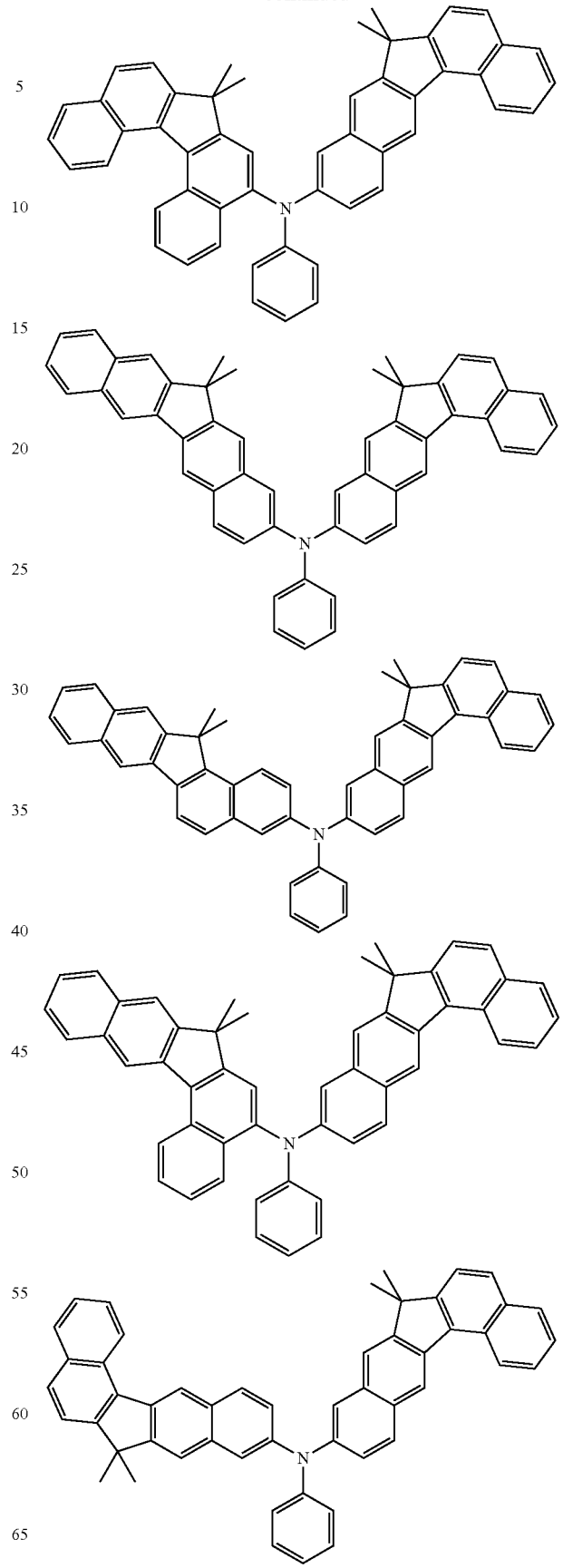

-continued
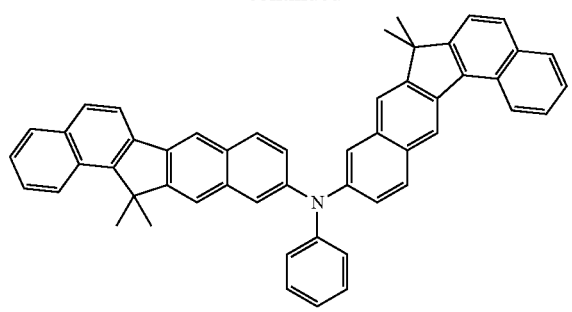
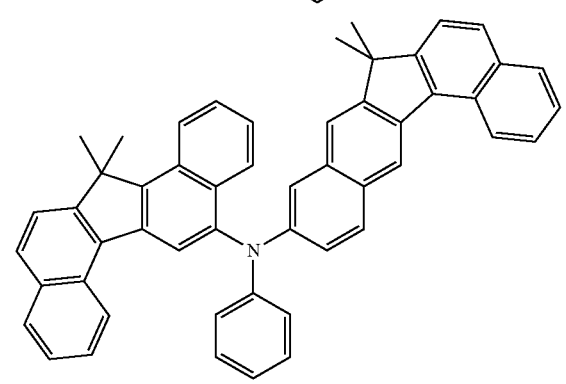
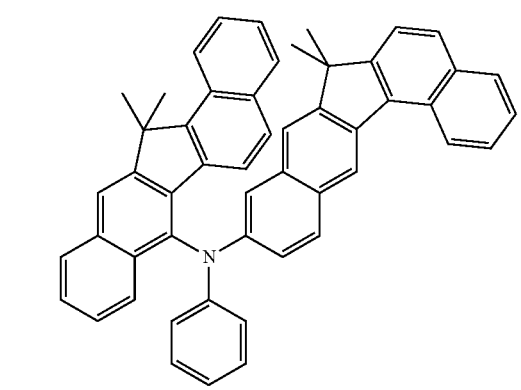
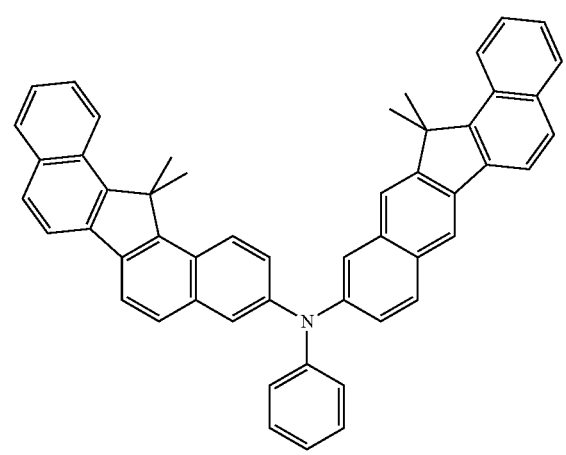
-continued
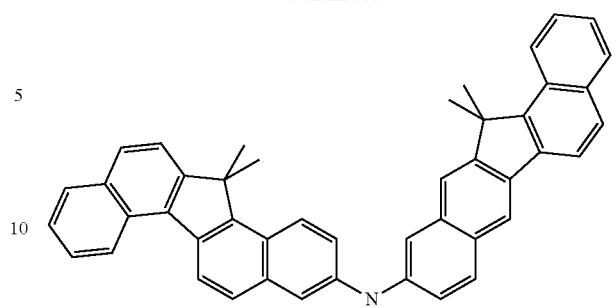
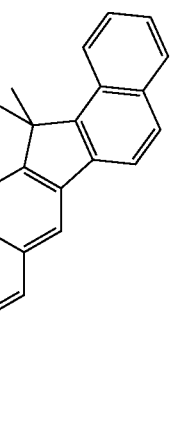
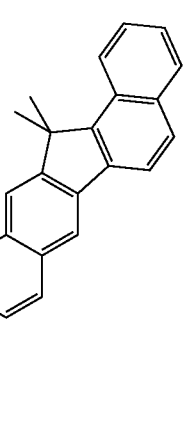
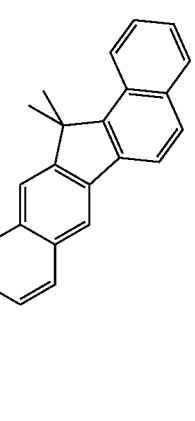

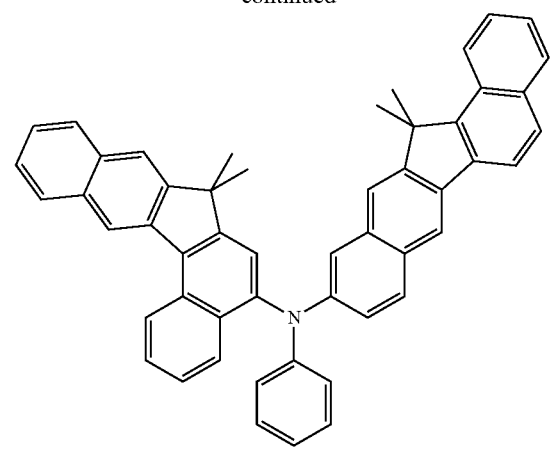
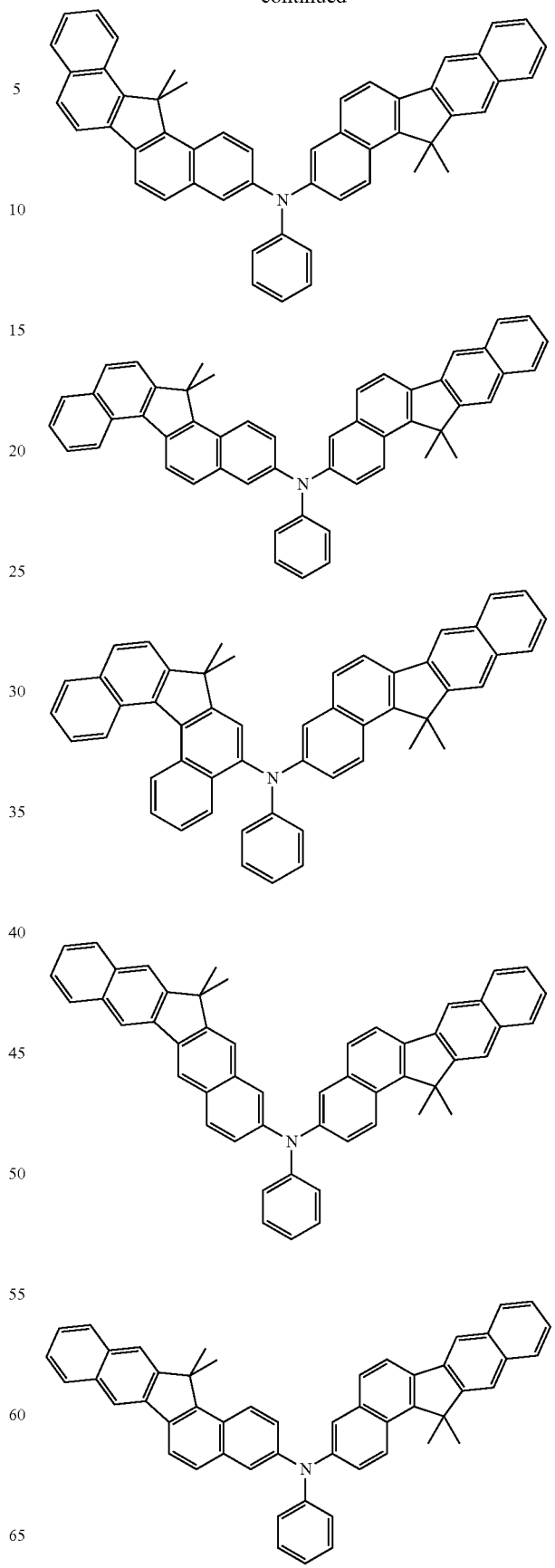

-continued
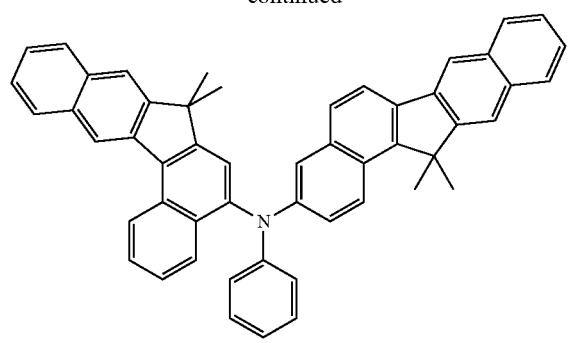
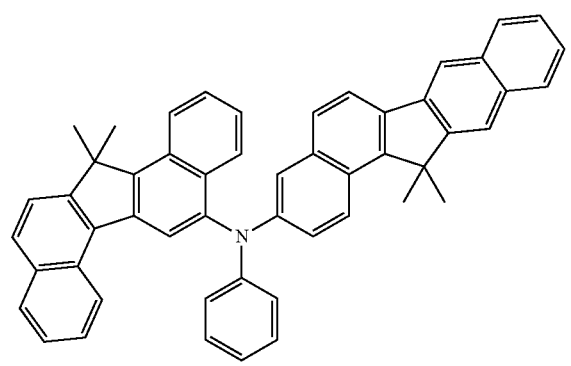
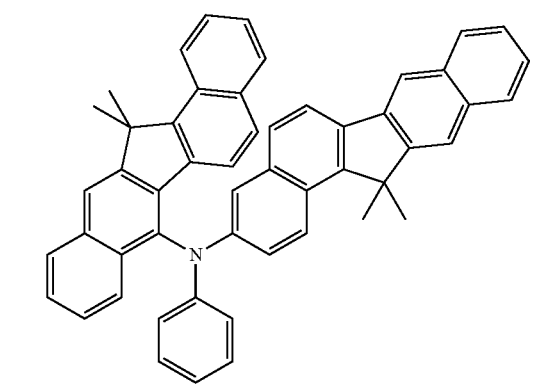
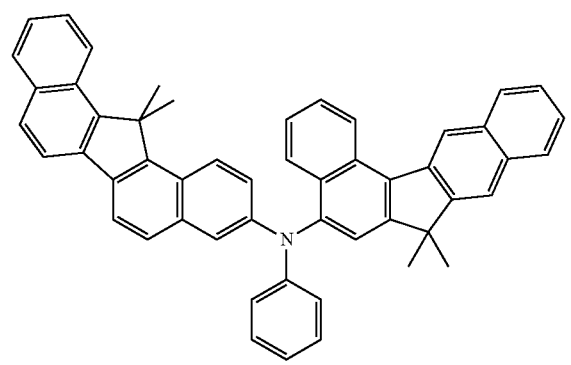
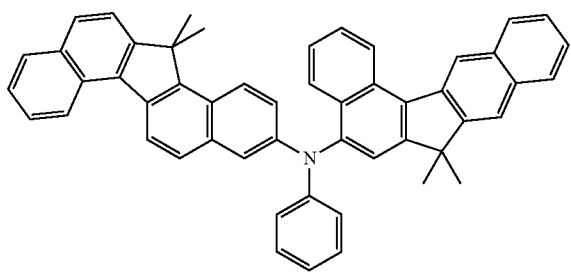
-continued
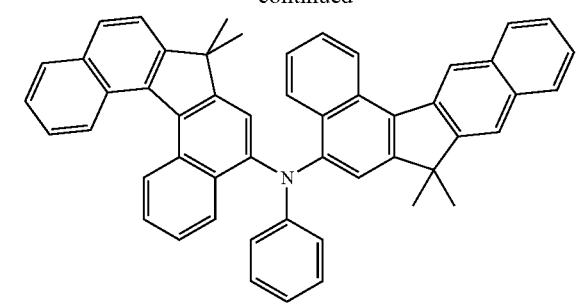
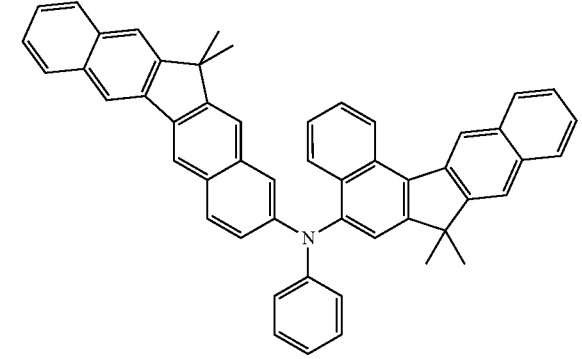
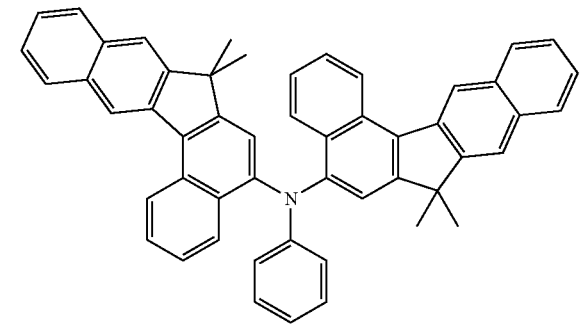
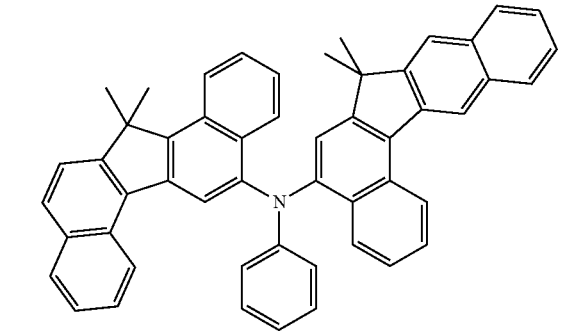
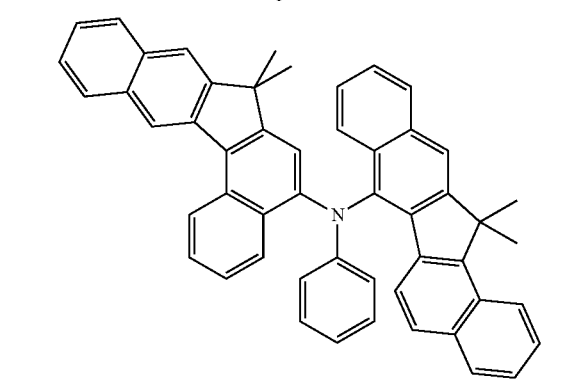

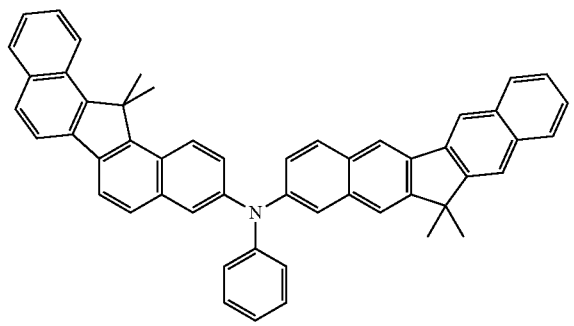
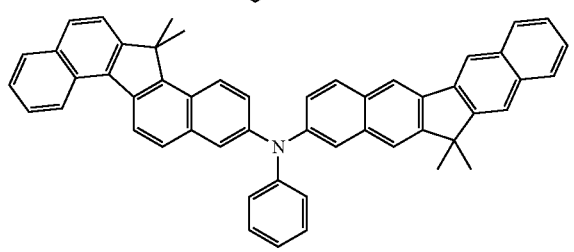
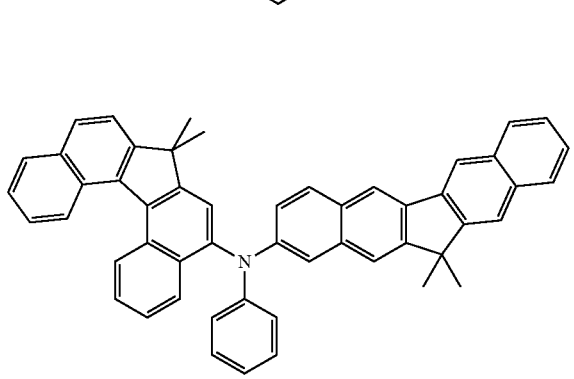
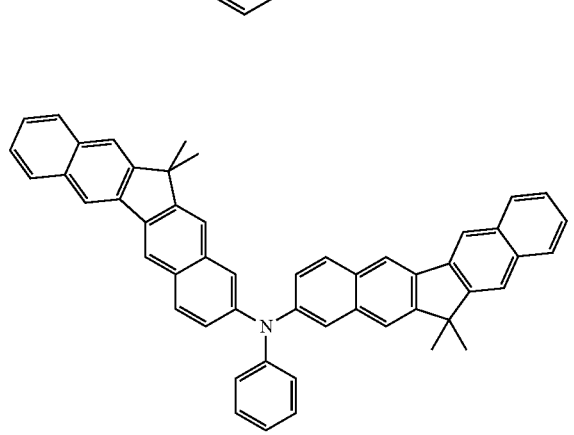
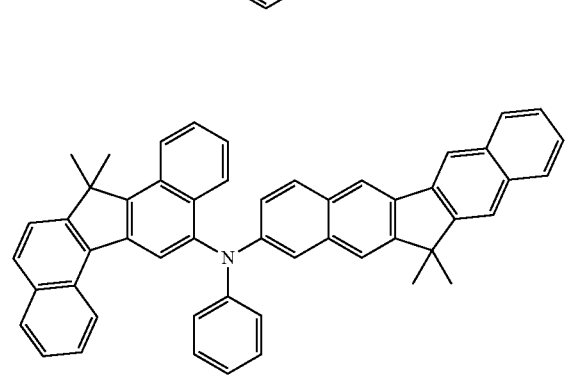
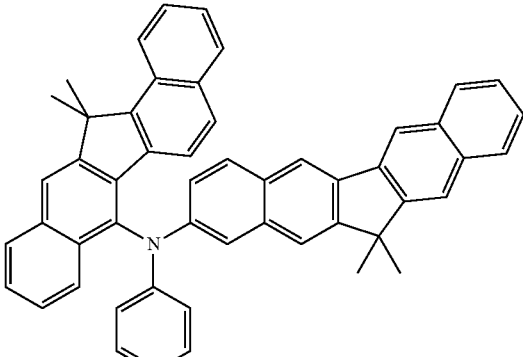
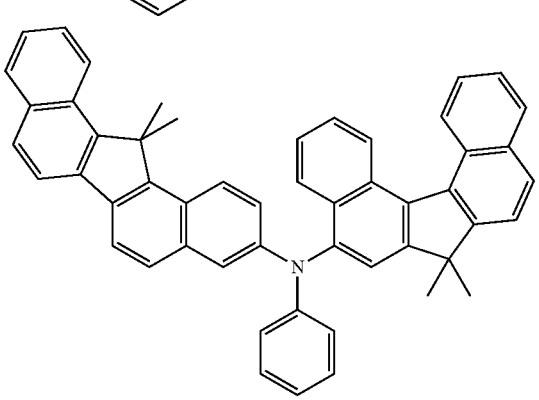
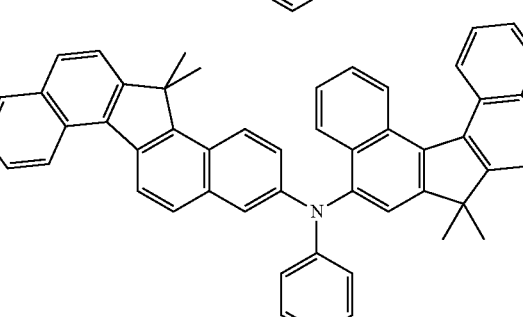
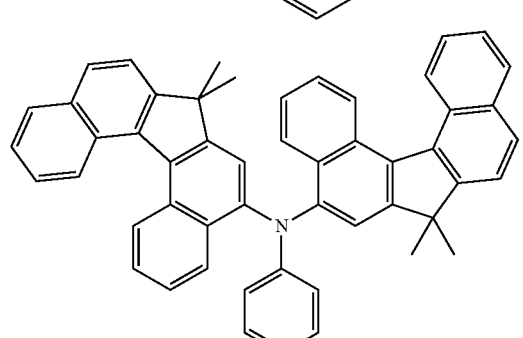
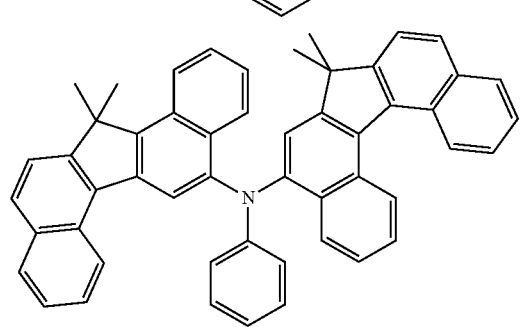

-continued
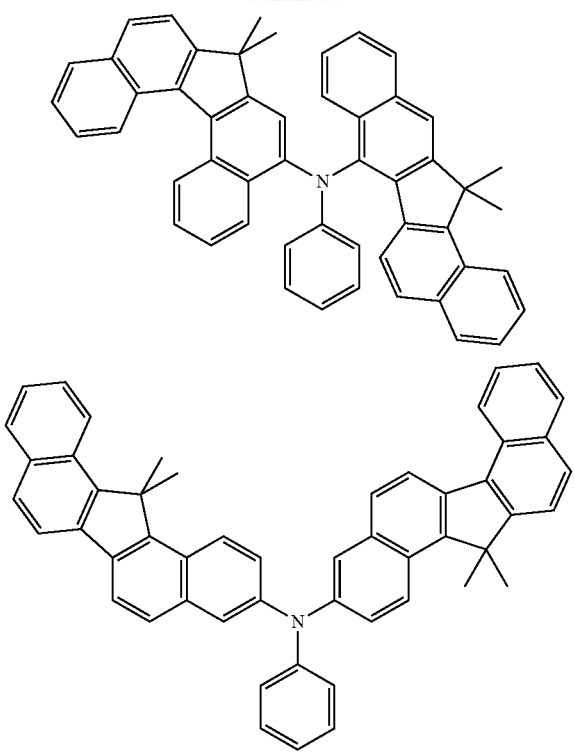
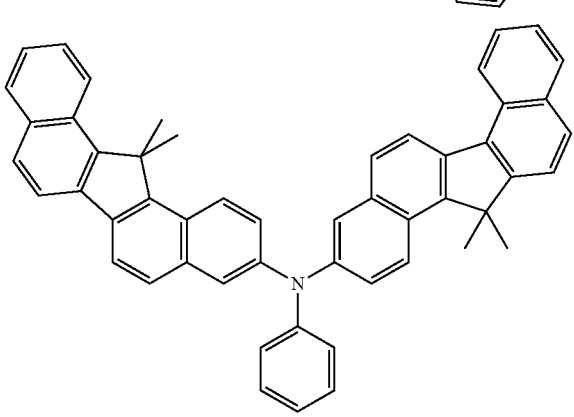
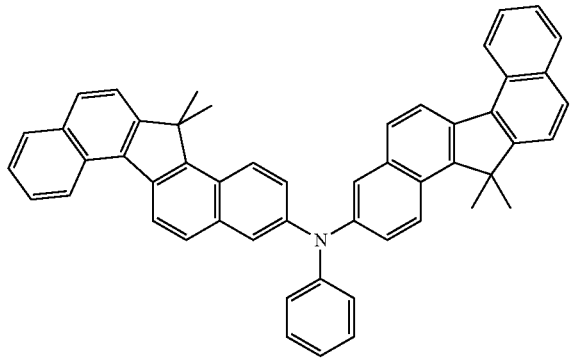
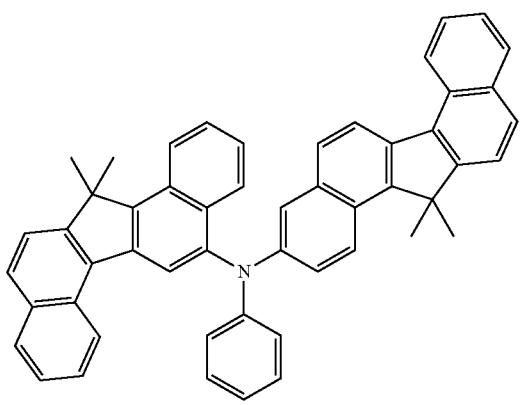
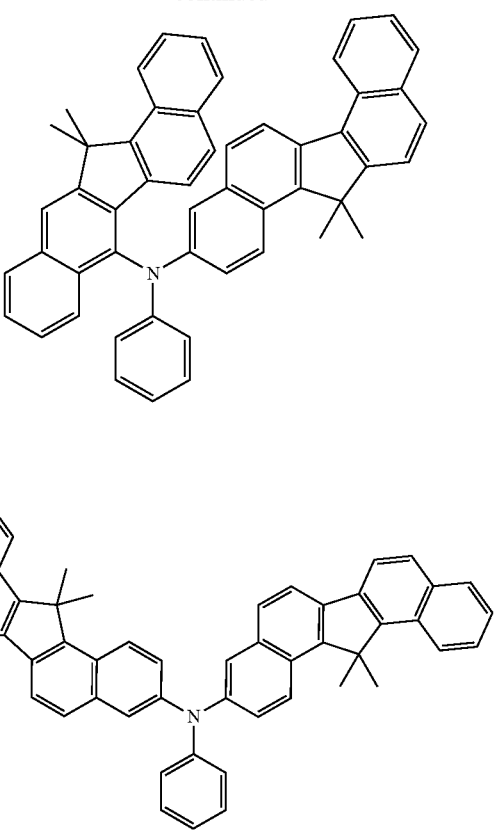

39
-continued
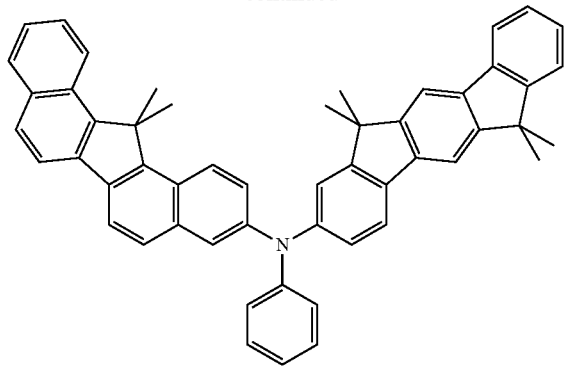
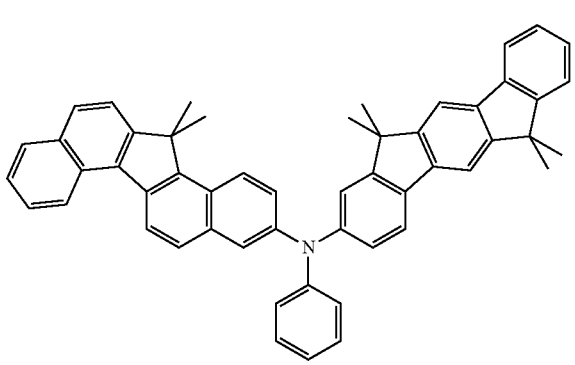
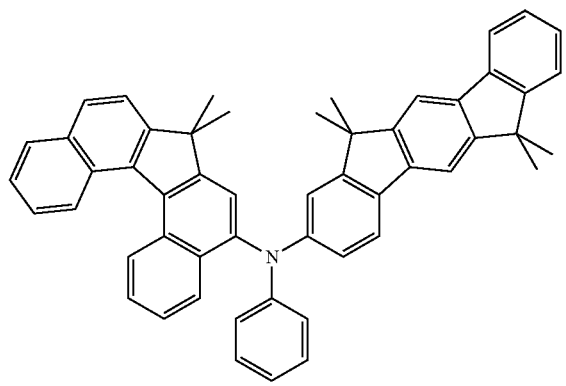
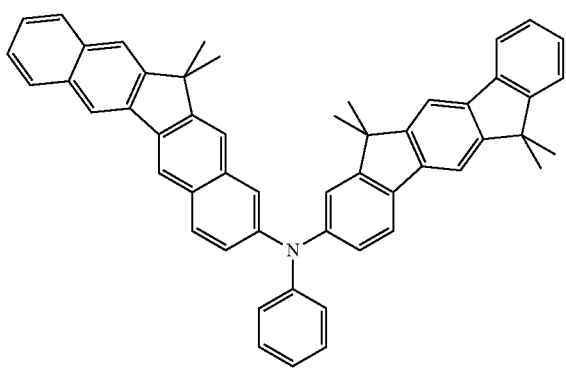
40
-continued
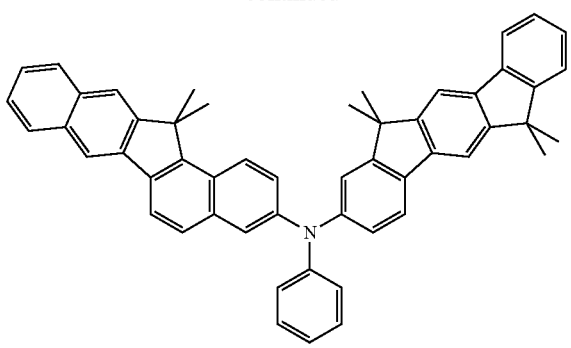
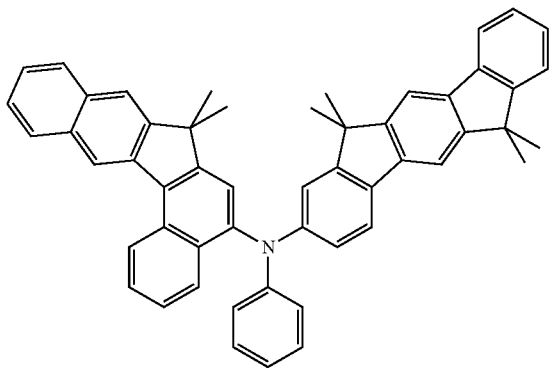
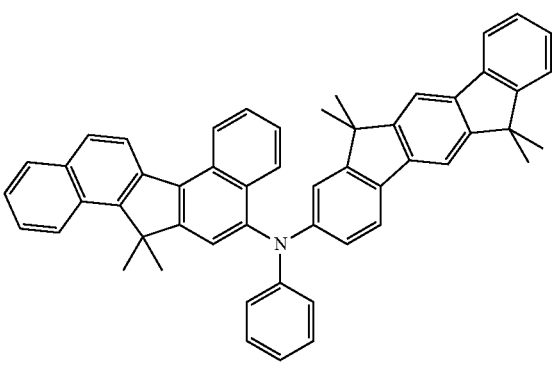
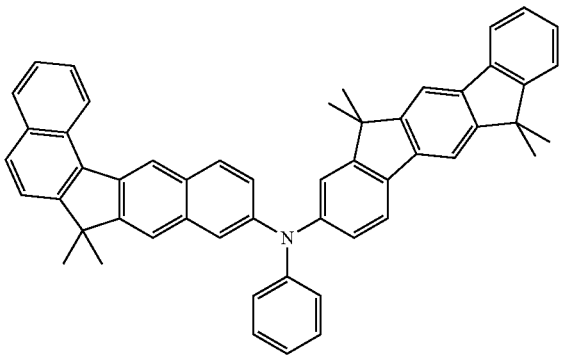

41
-continued
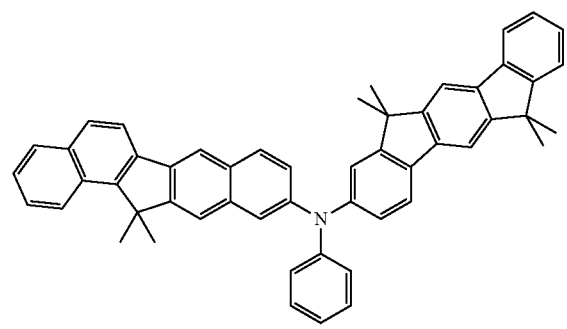
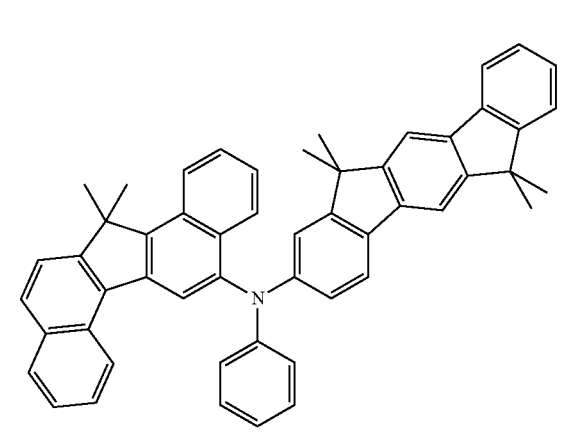
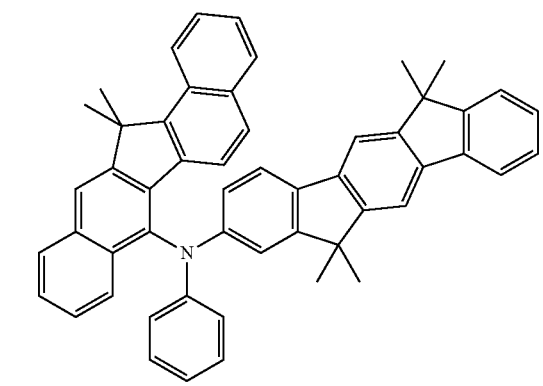
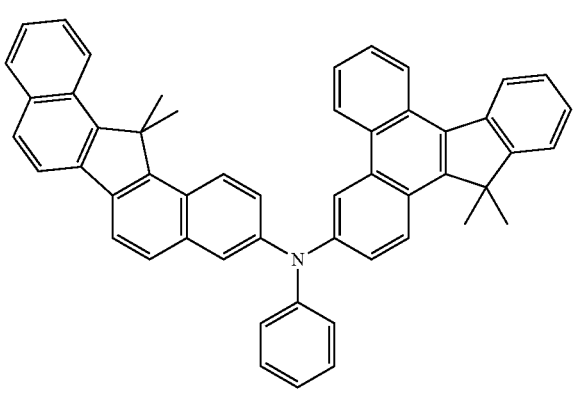
42
-continued
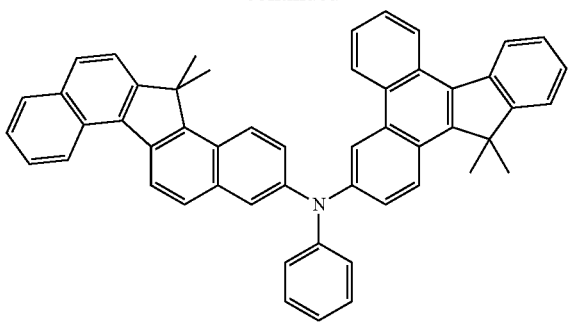
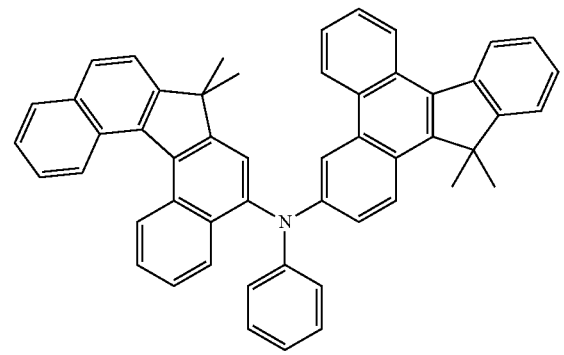
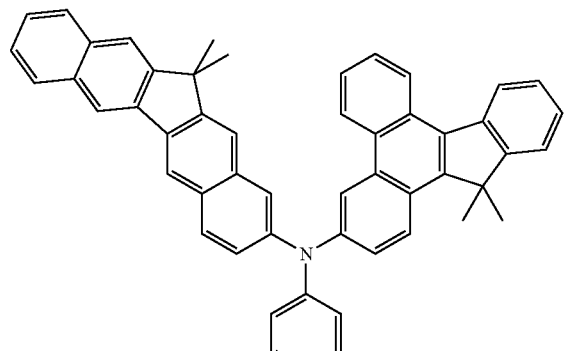
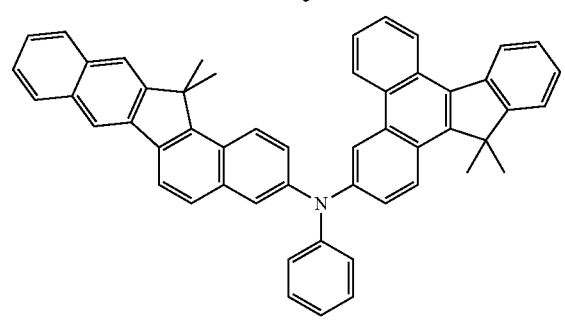
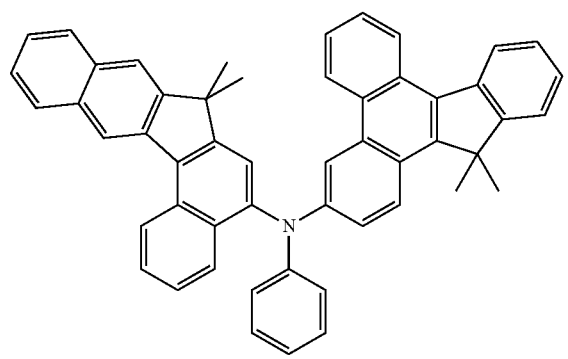

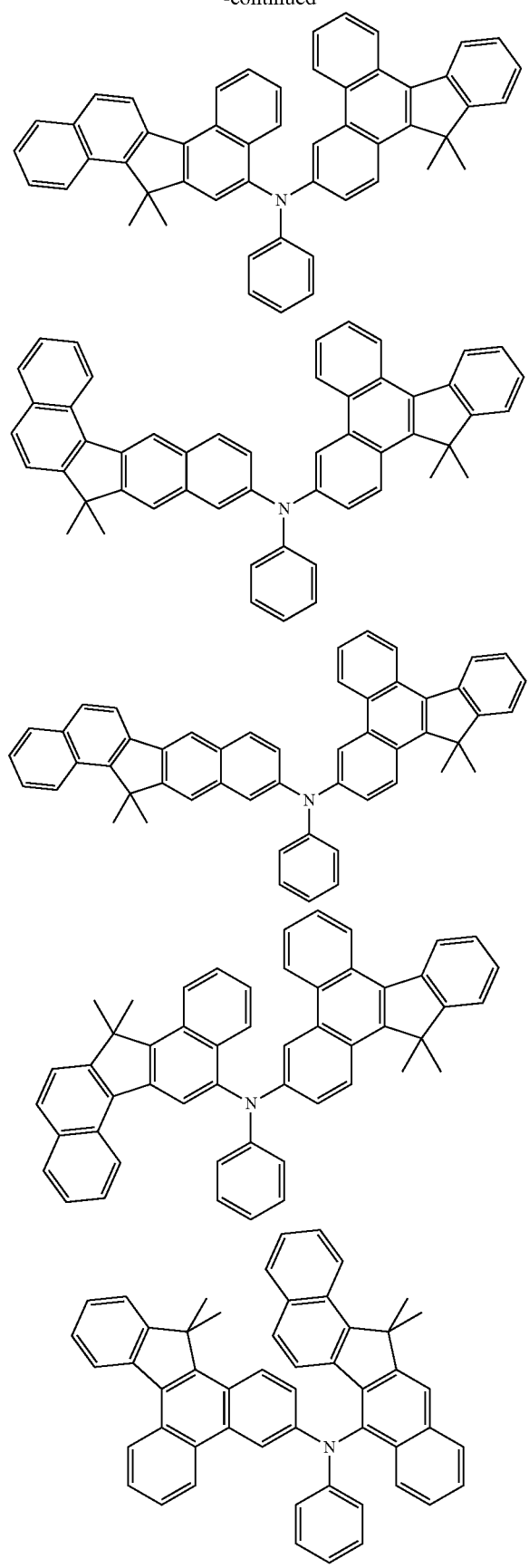
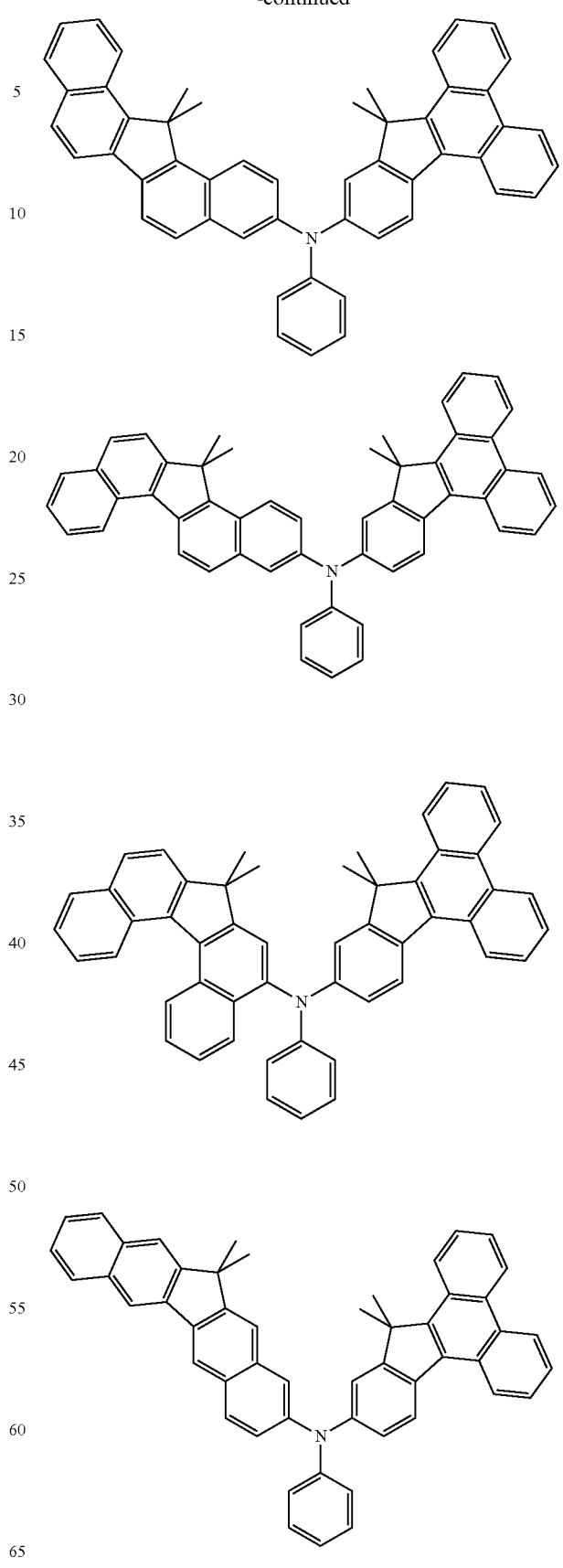

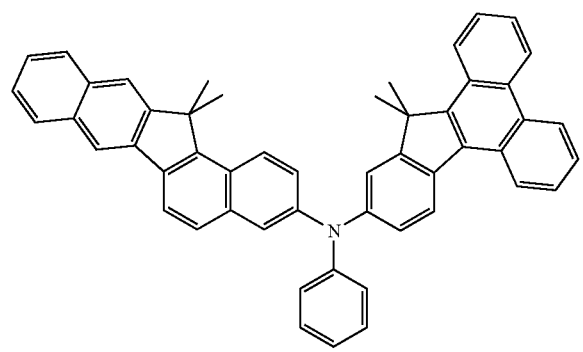
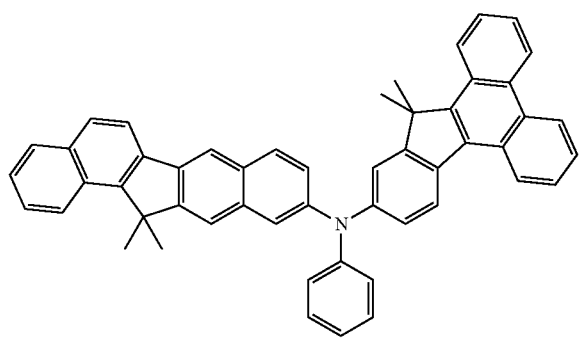
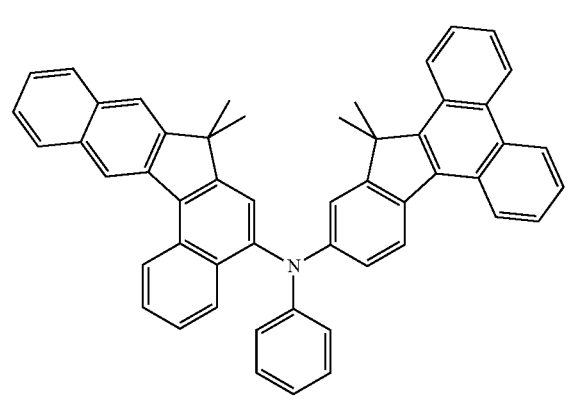
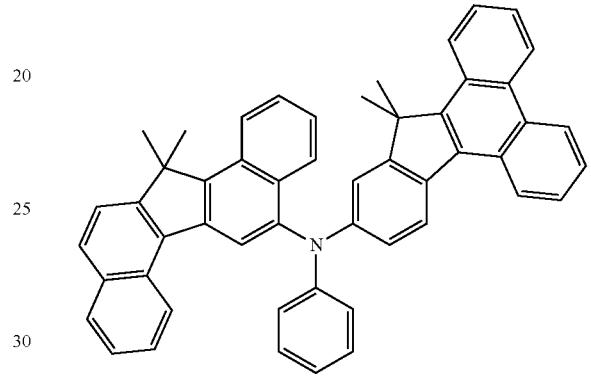
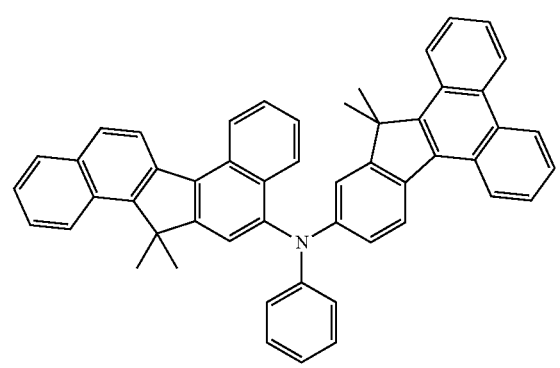
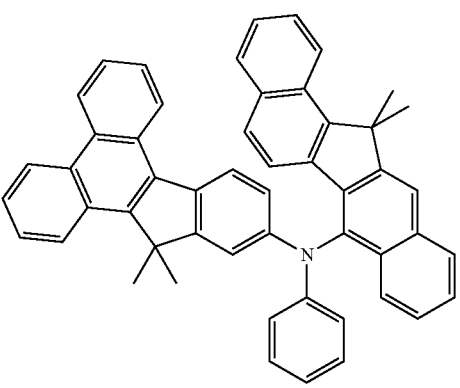
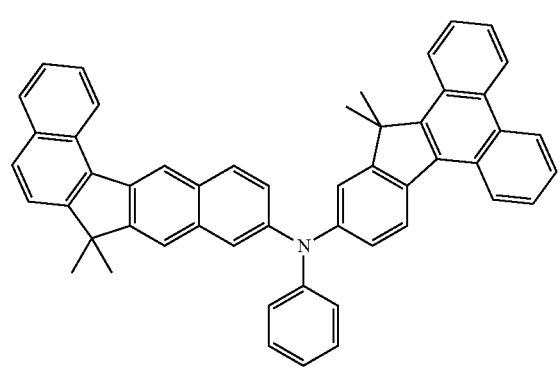
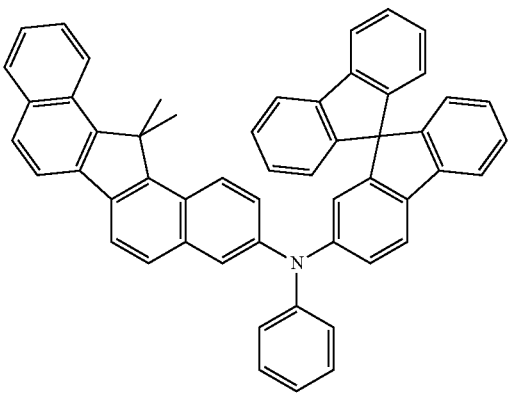

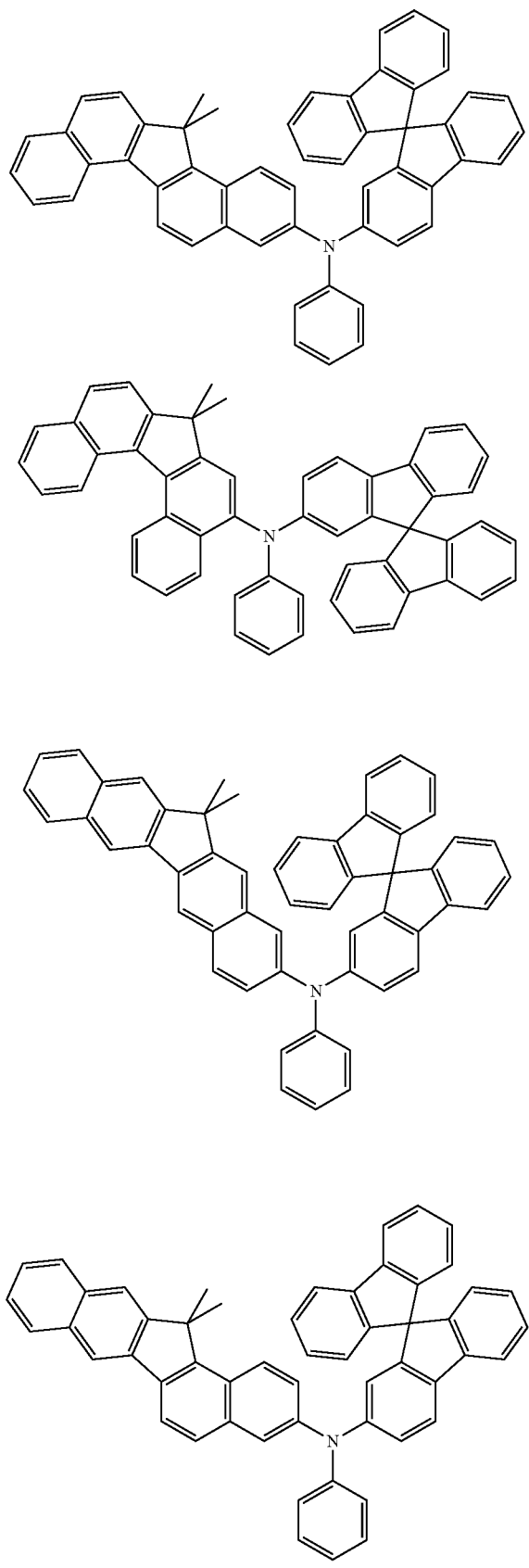
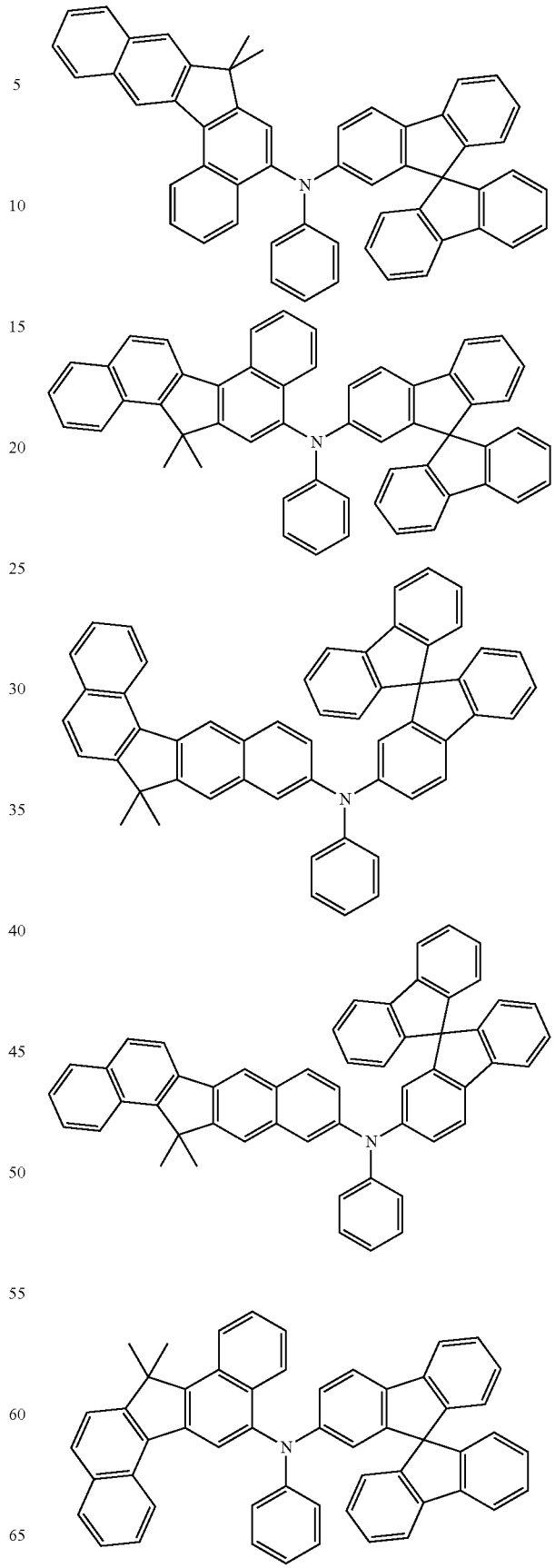

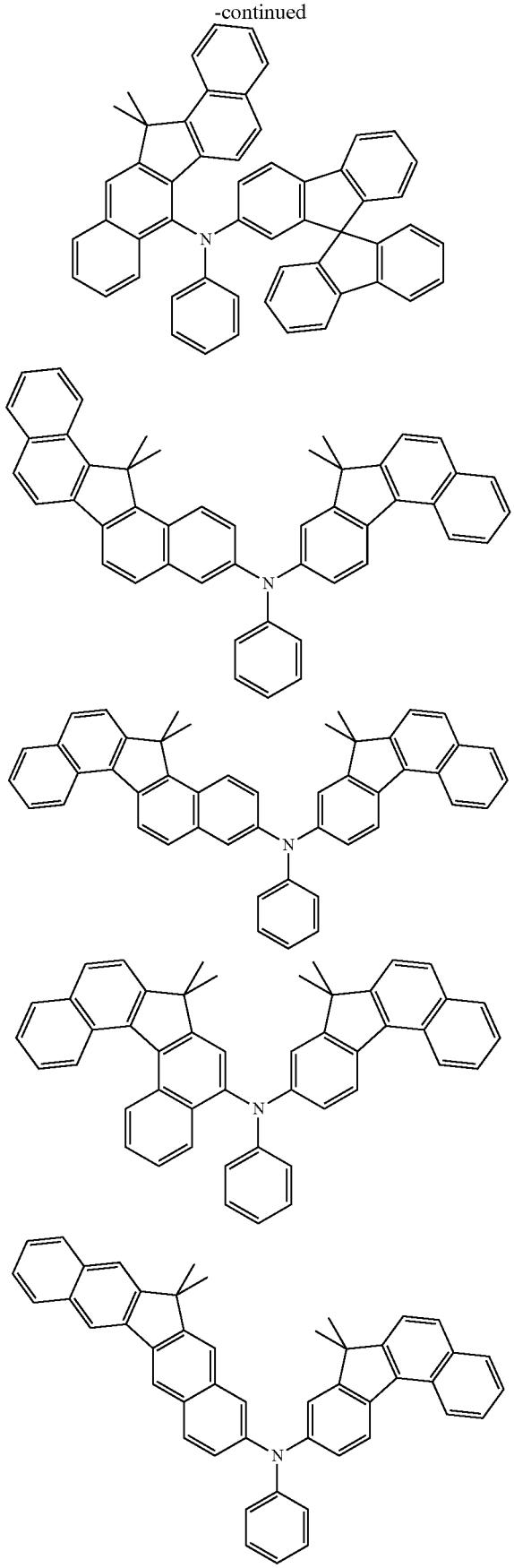
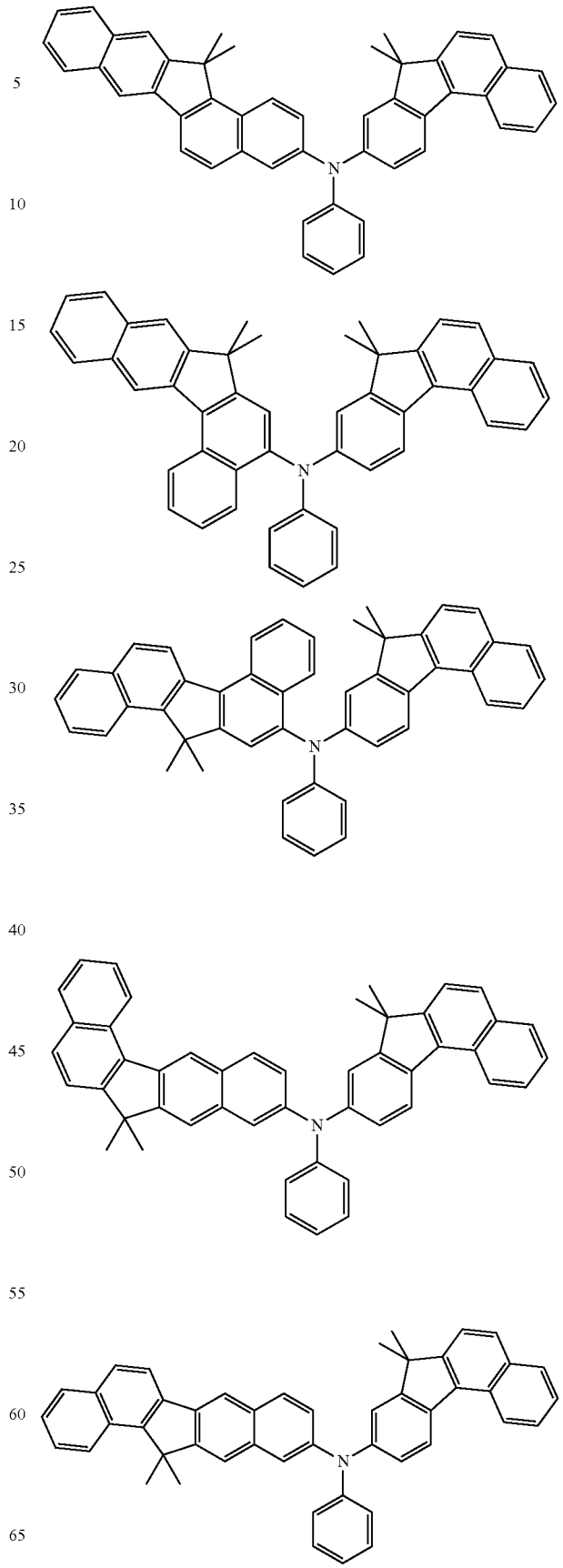

51
-continued
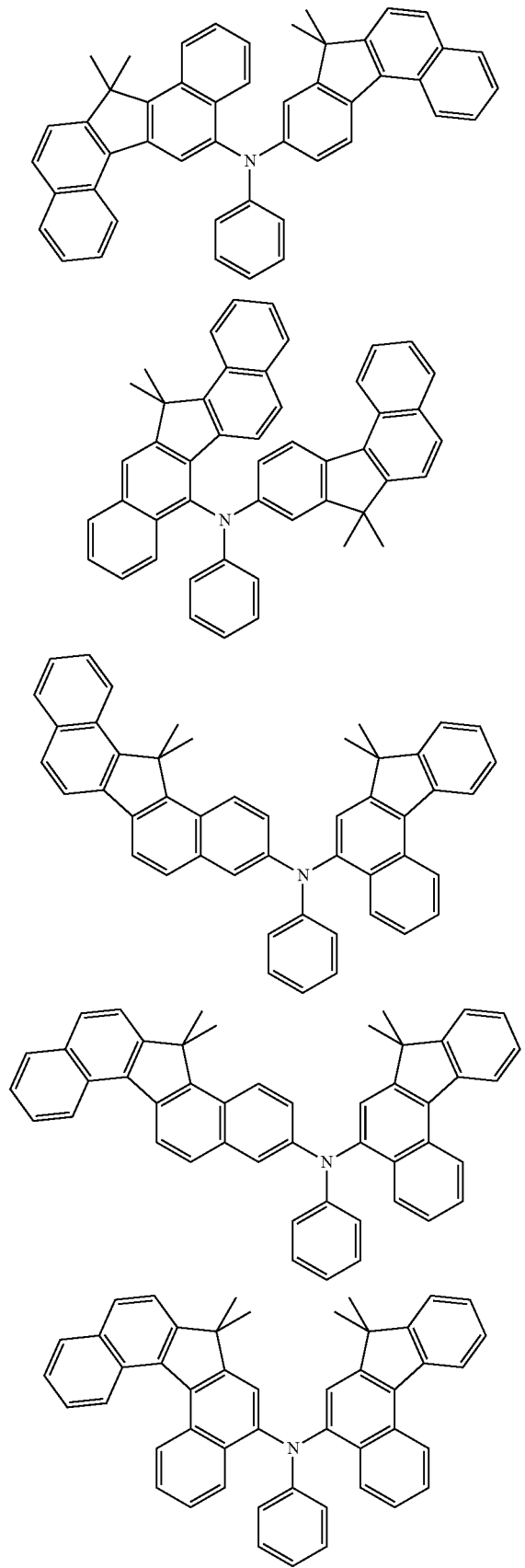
52
-continued
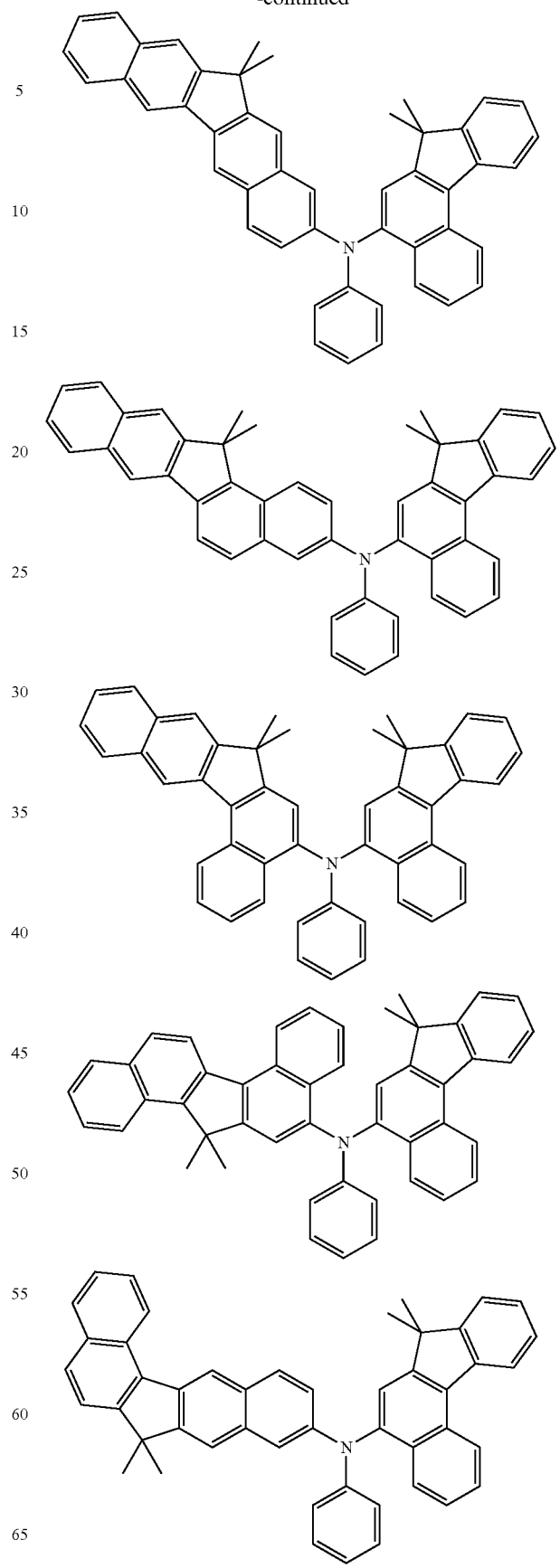

-continued
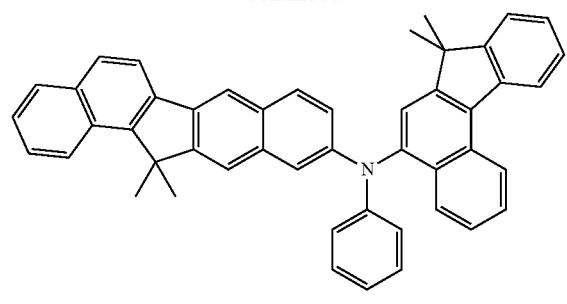
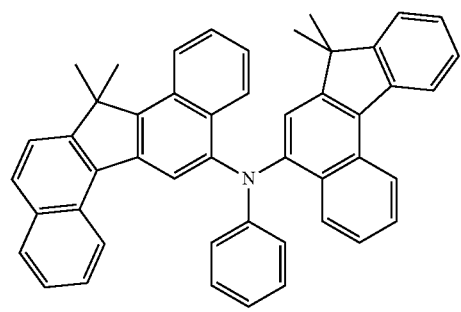
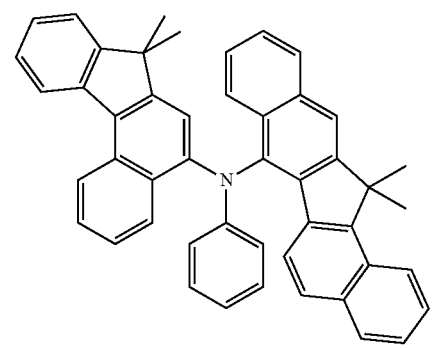
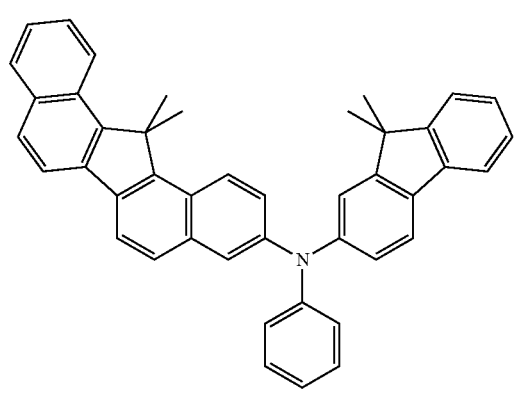
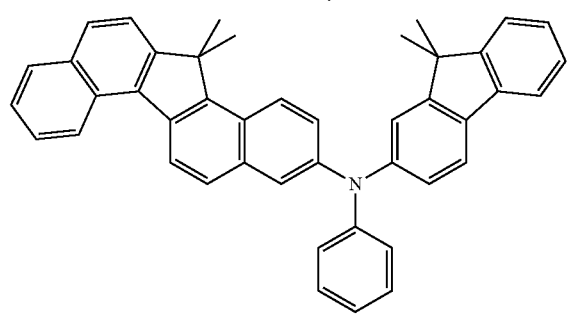
-continued
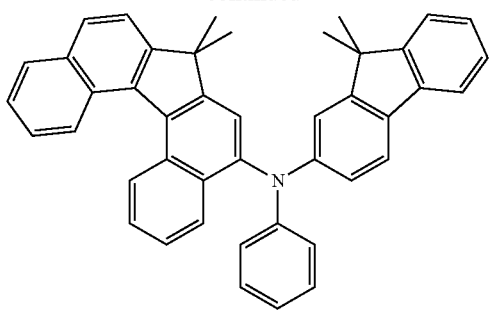
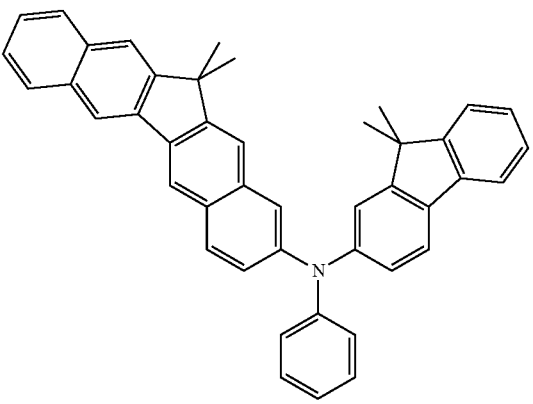
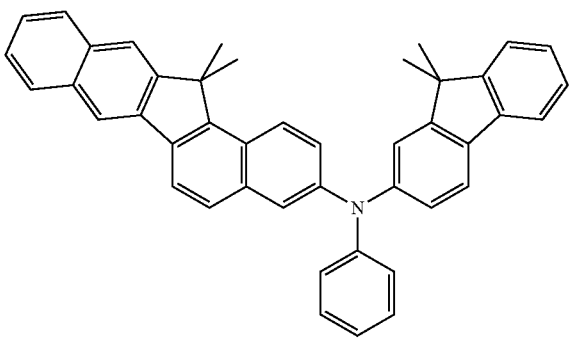
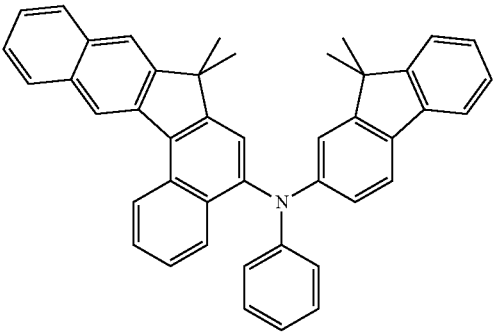
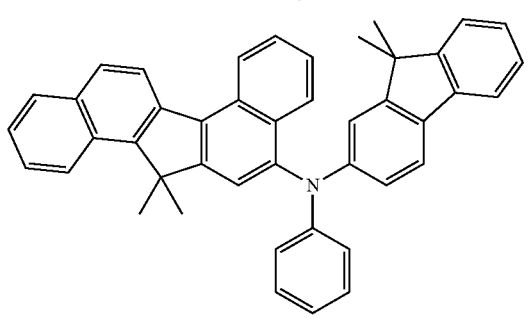

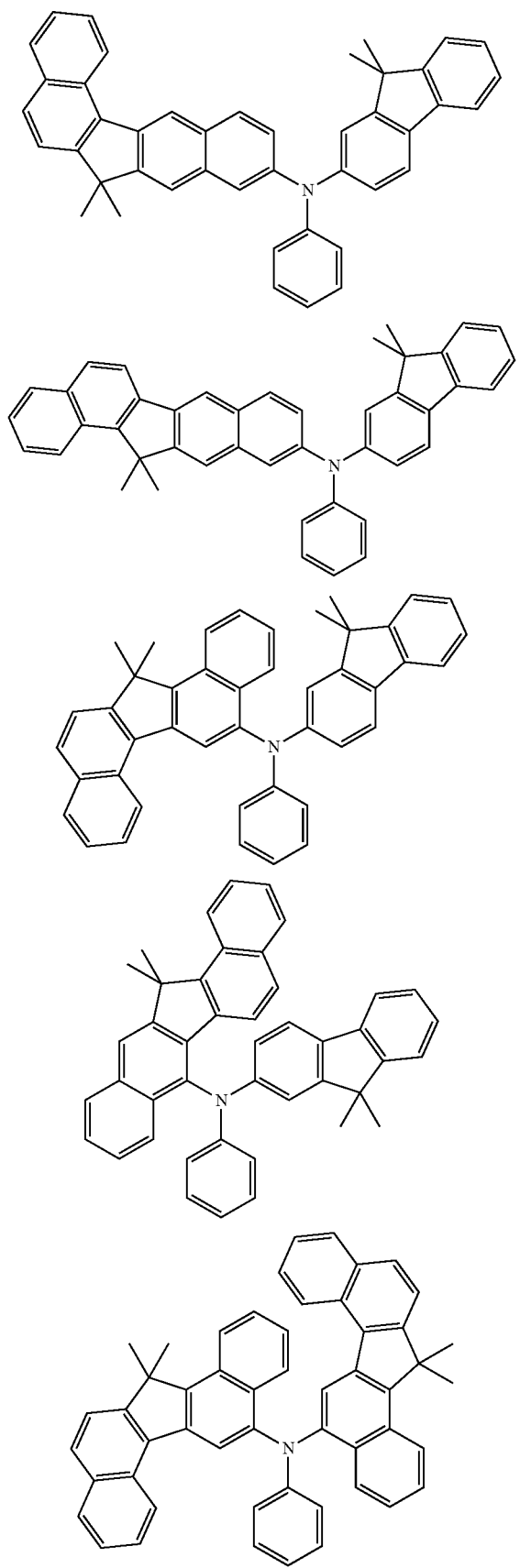
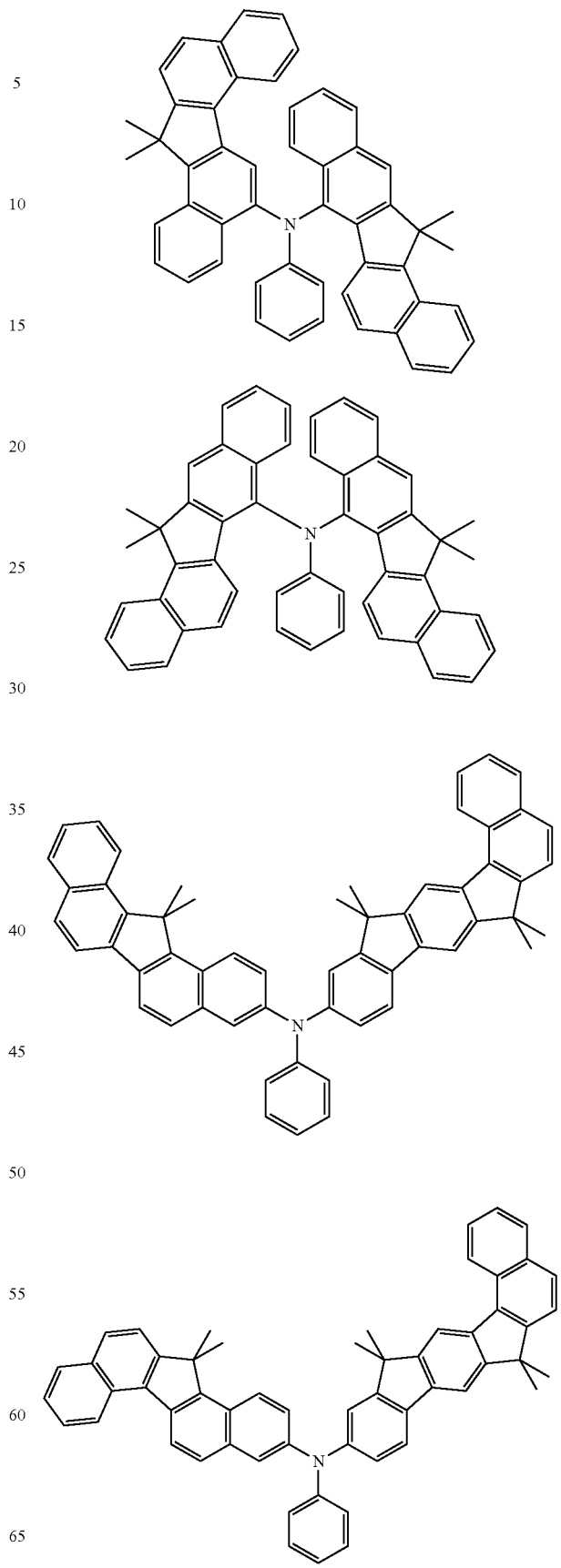

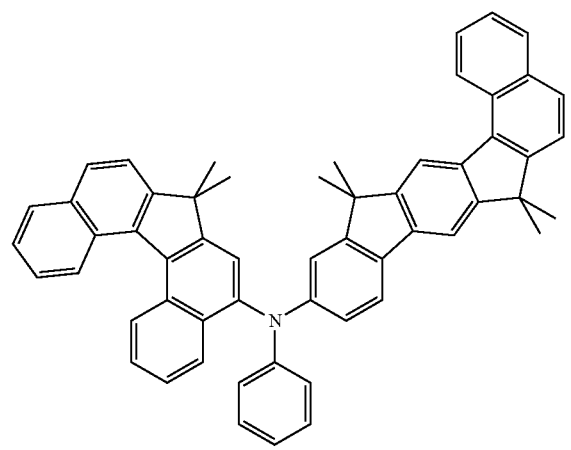
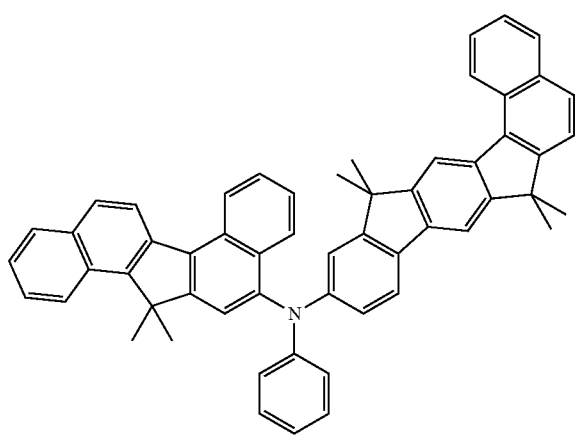
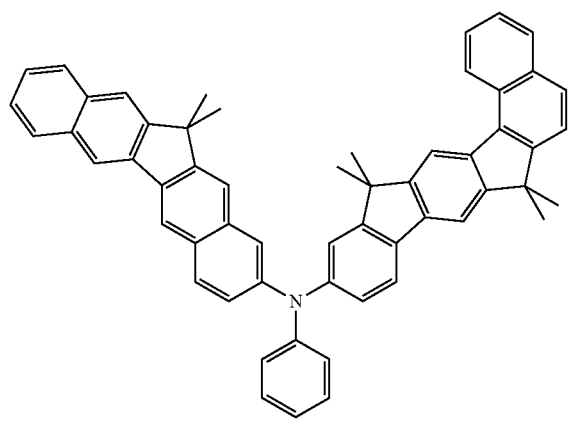
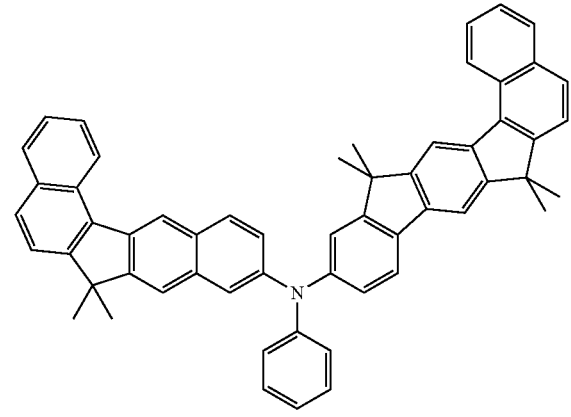
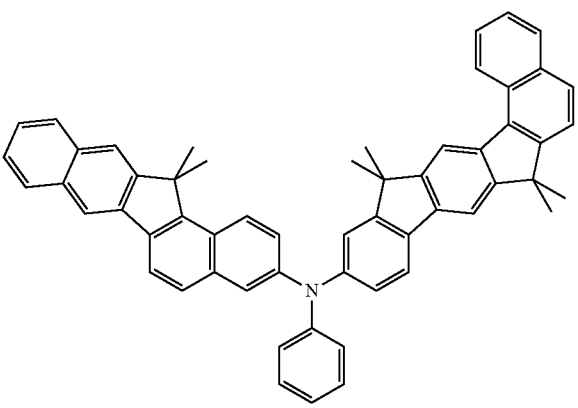
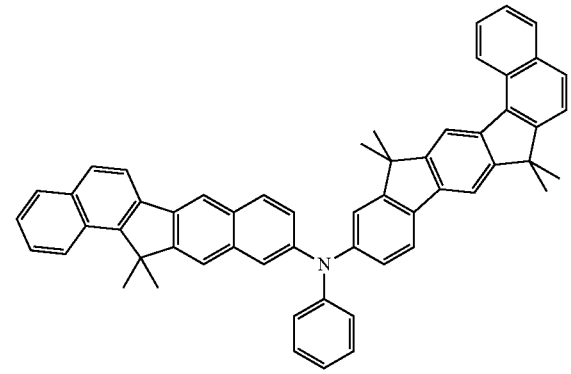
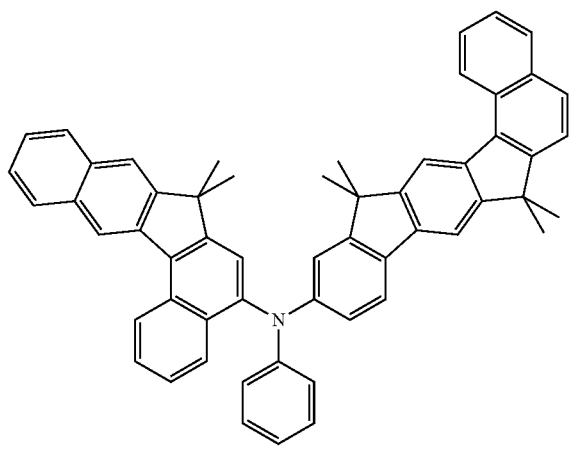
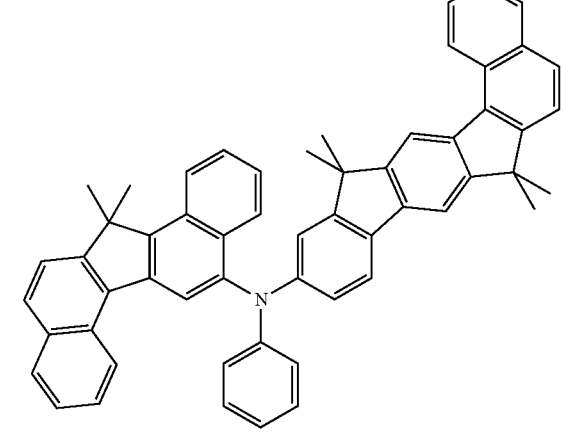

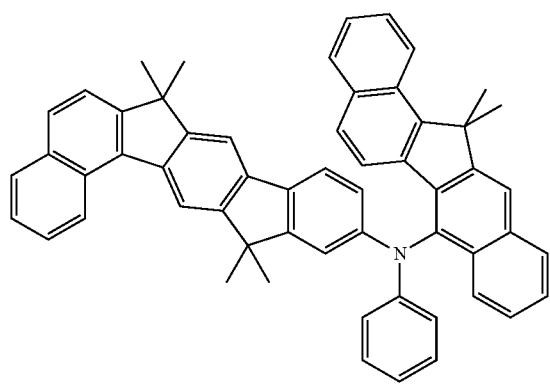
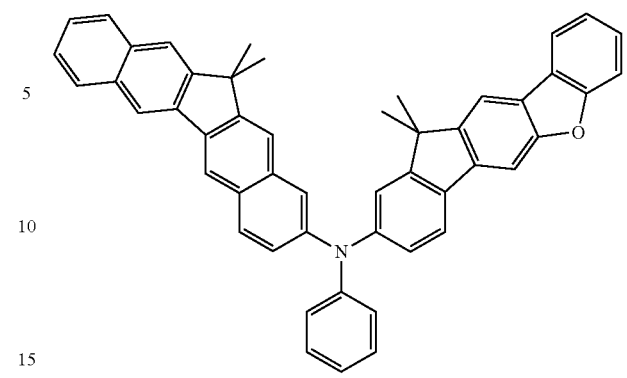
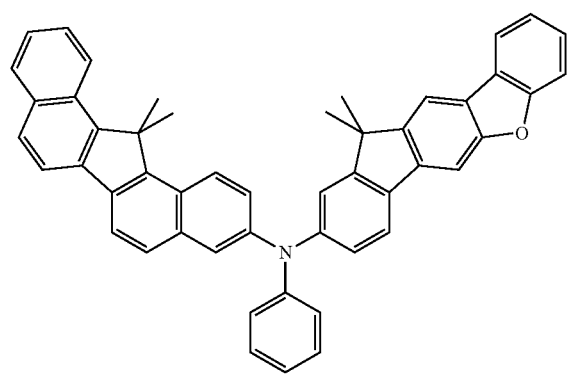
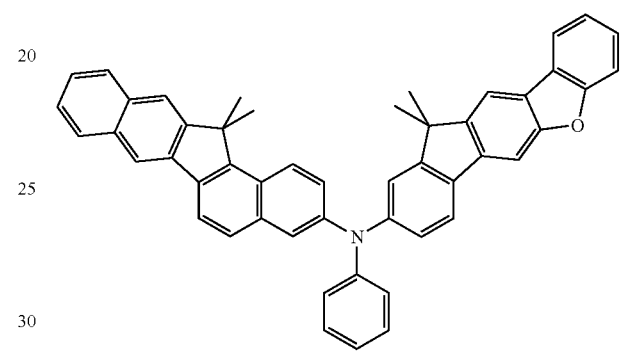
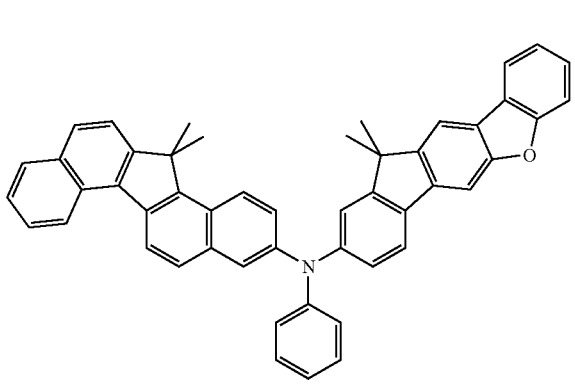
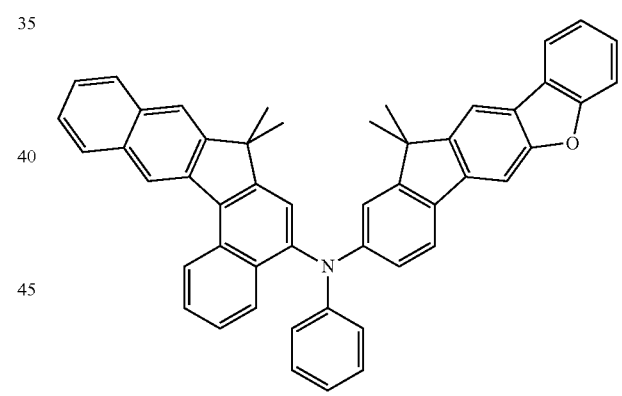
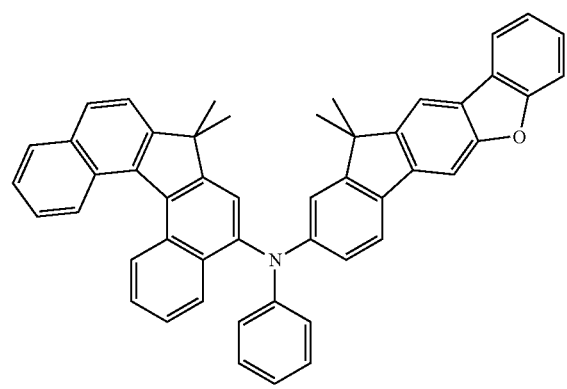
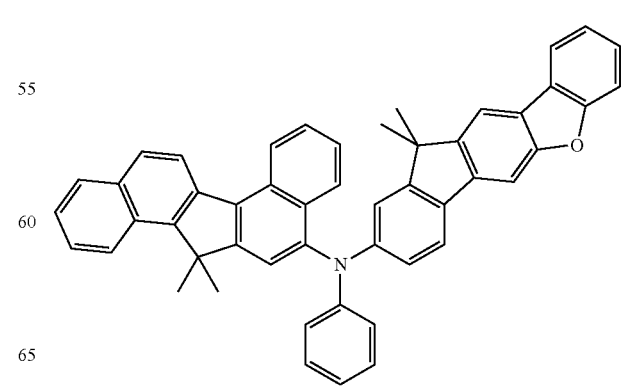

61
-continued
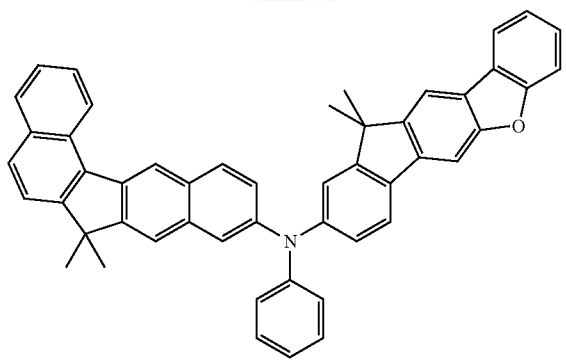
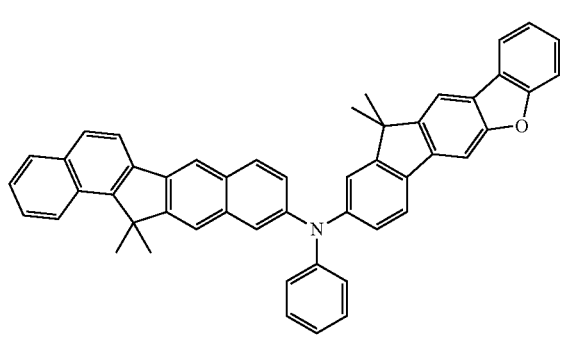
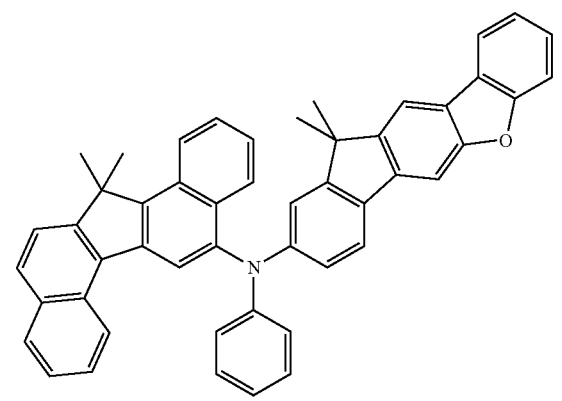
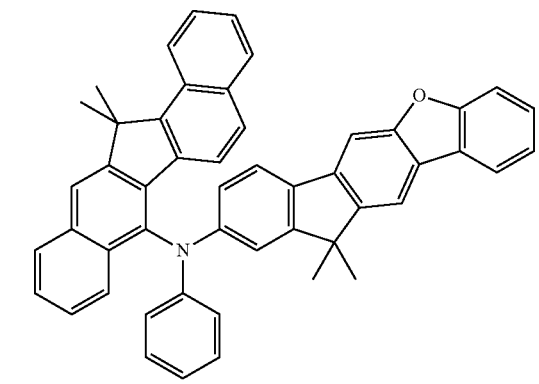
62
-continued
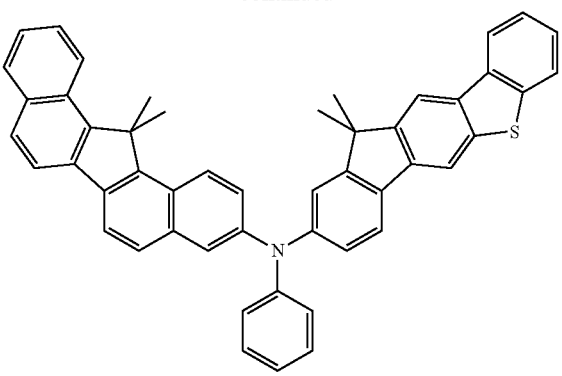
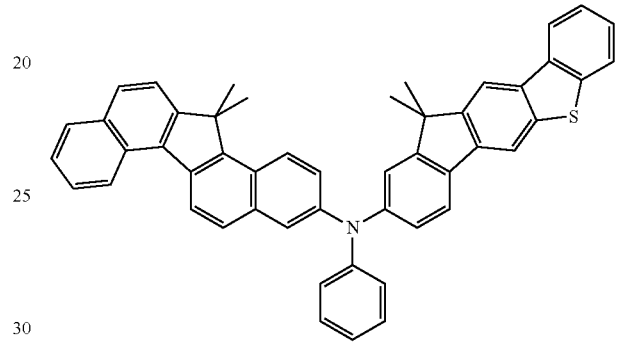
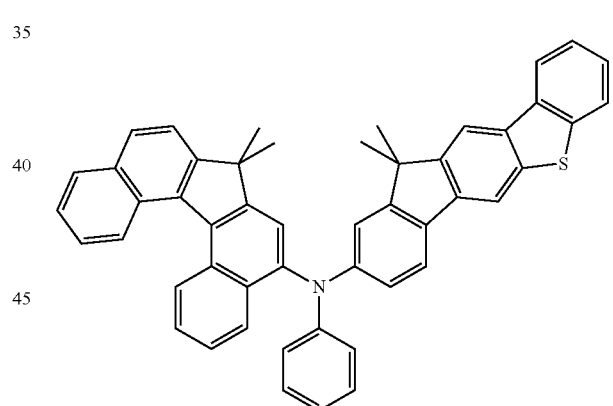
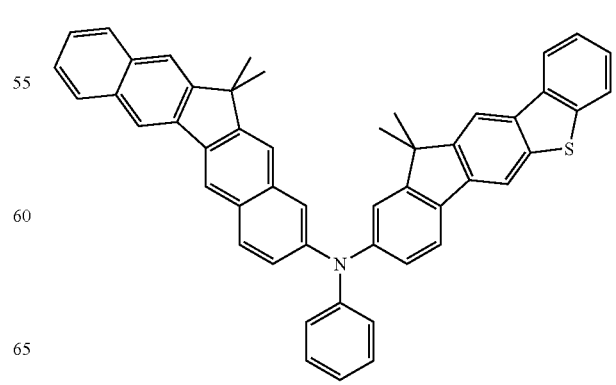

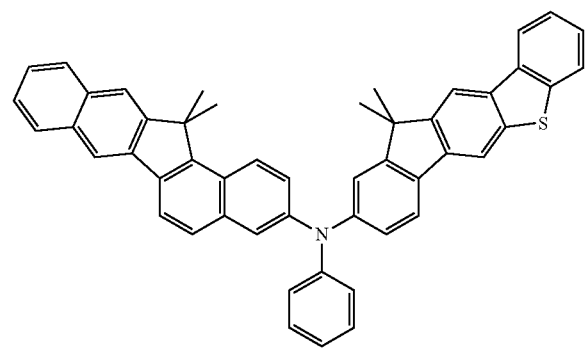
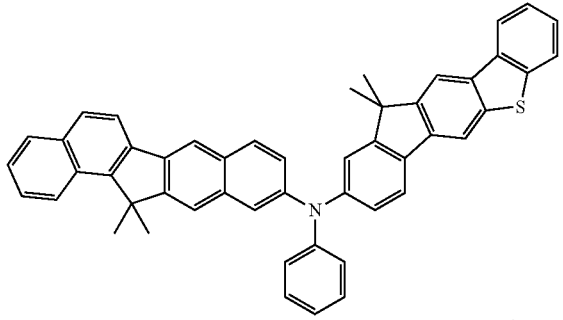
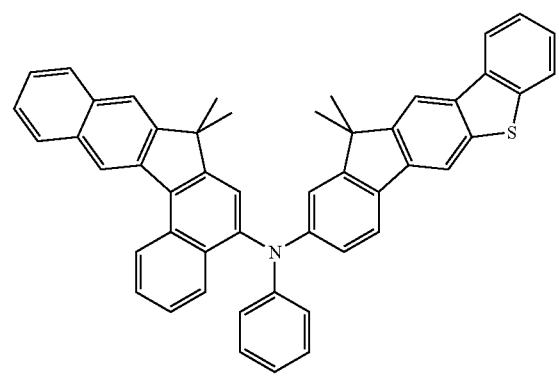
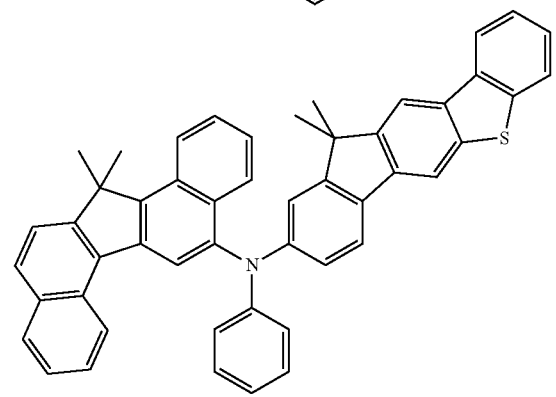
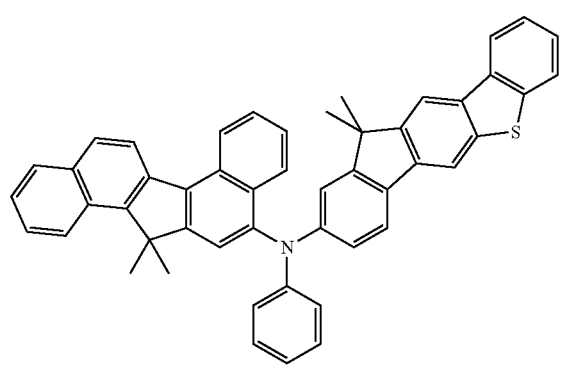
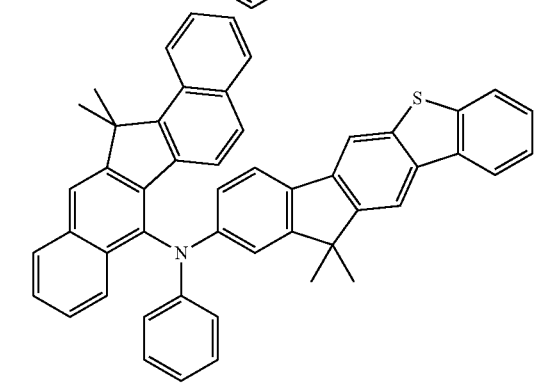
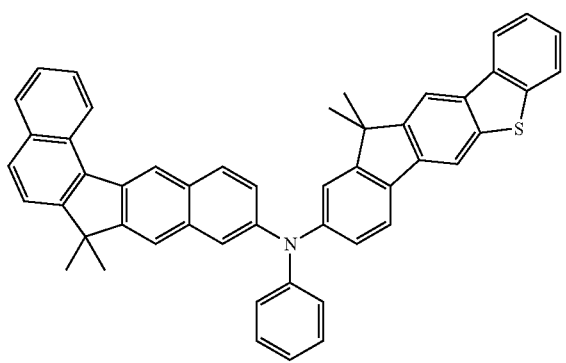
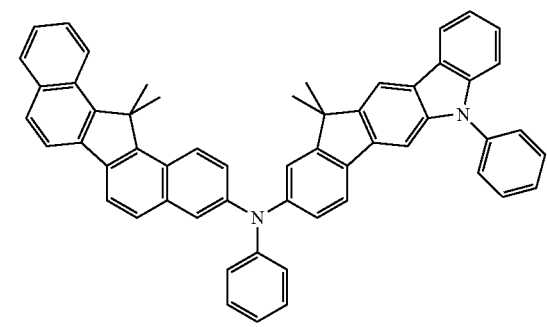

-continued
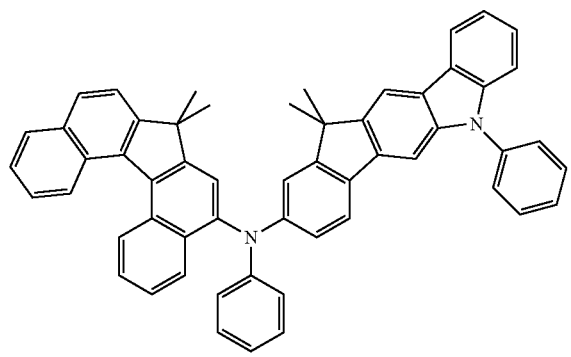
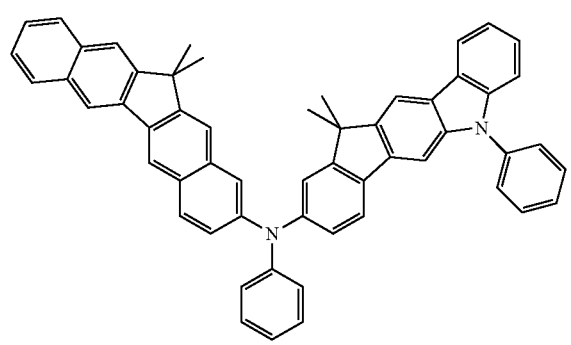
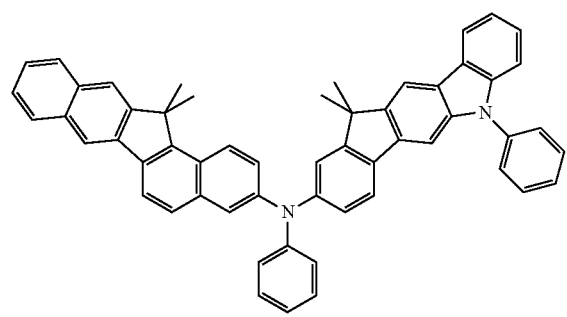
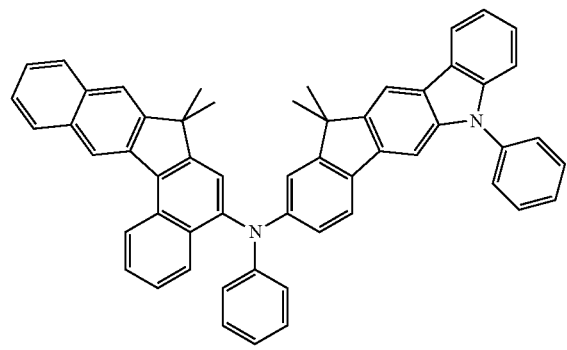
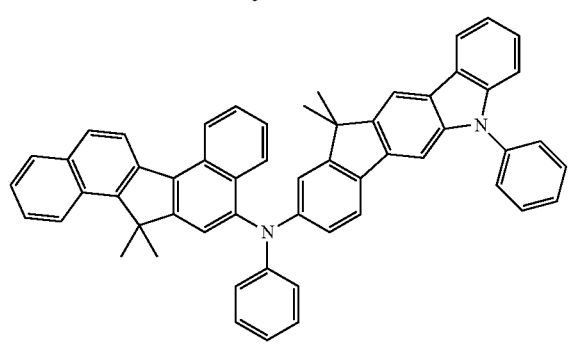
-continued
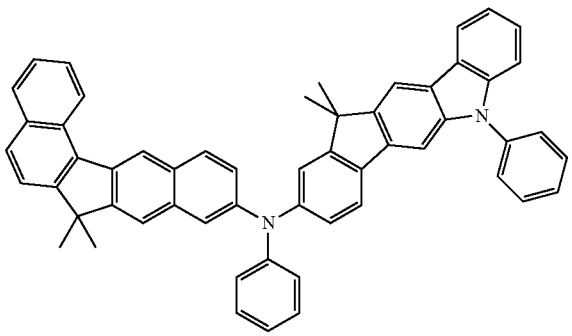
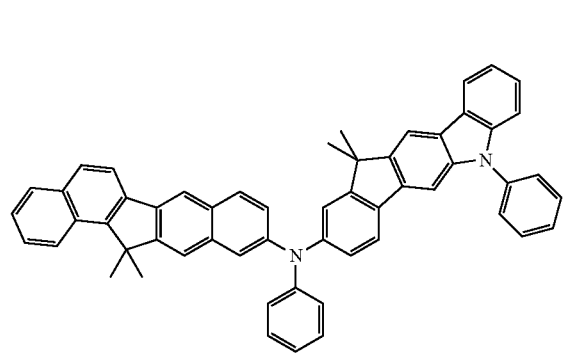
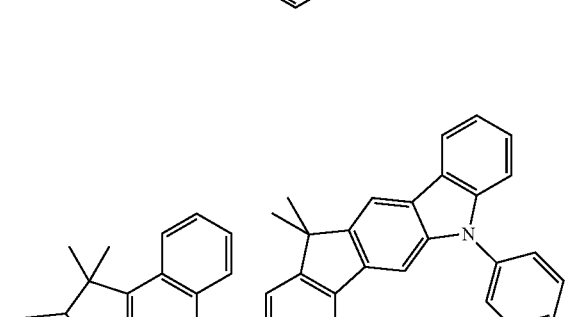
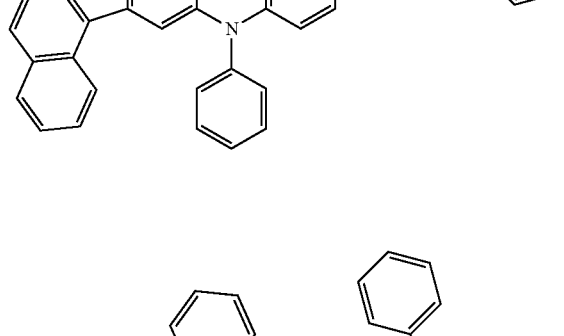

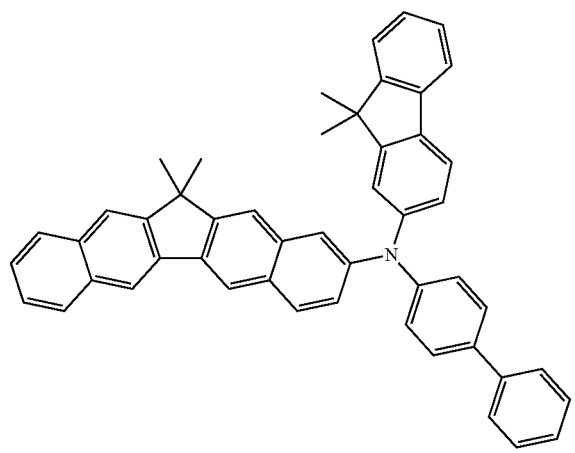
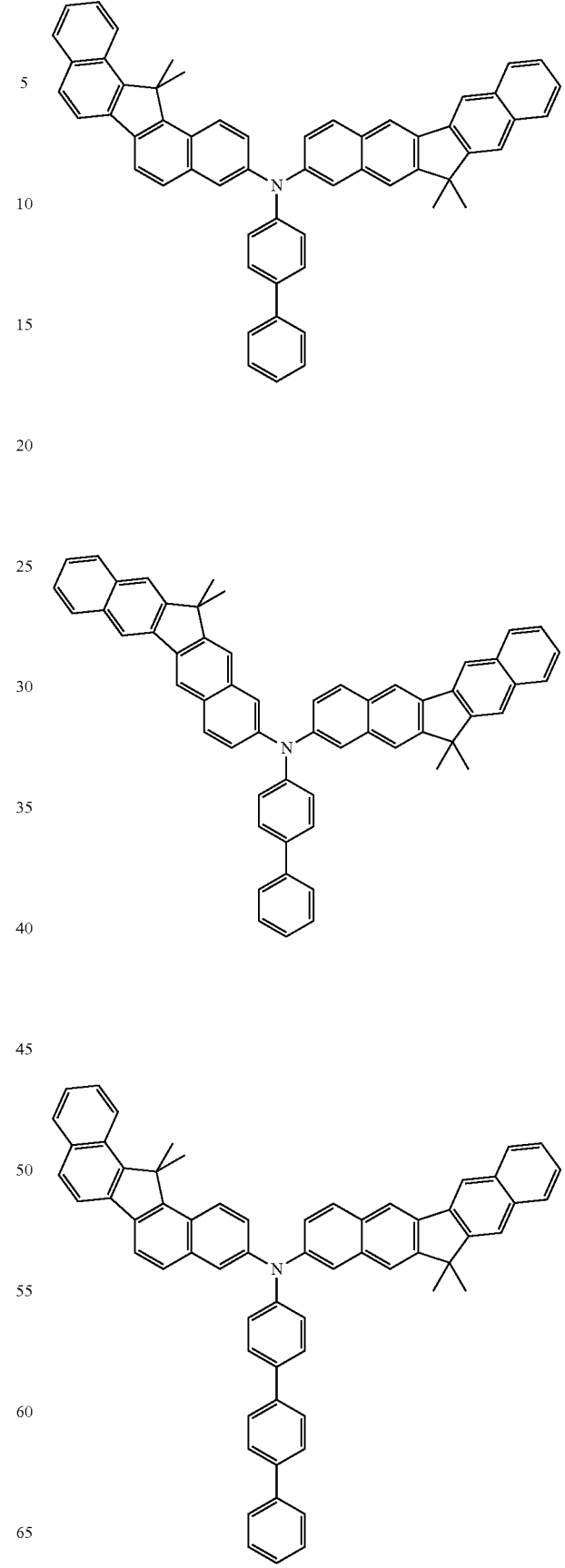

-continued
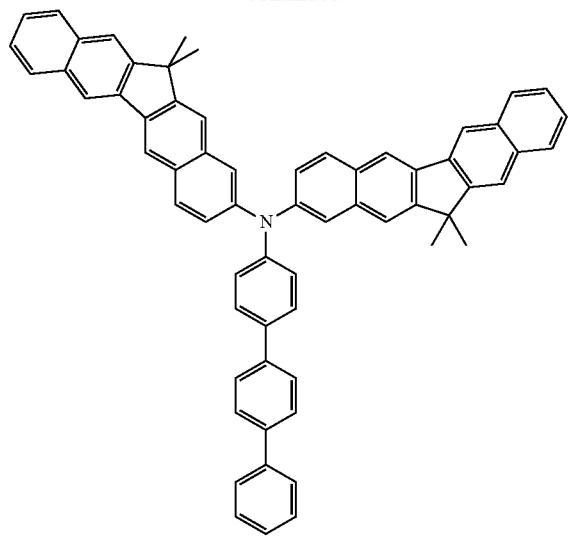
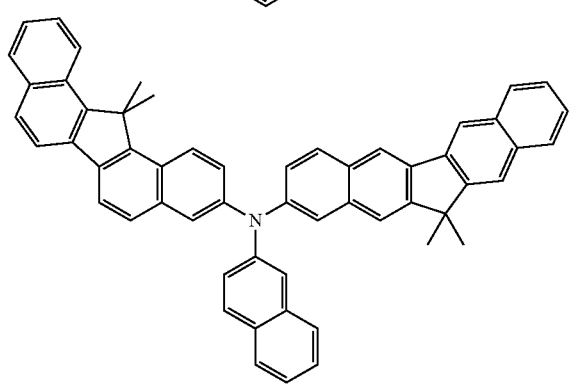
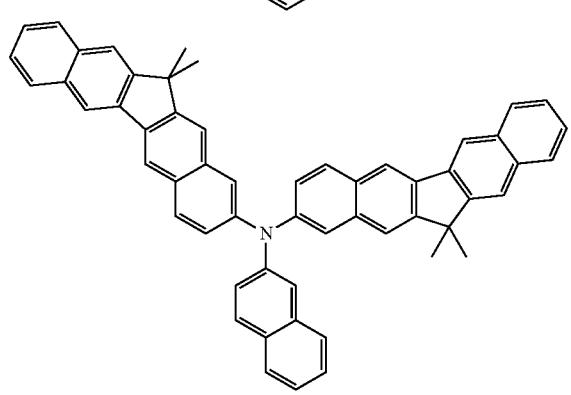
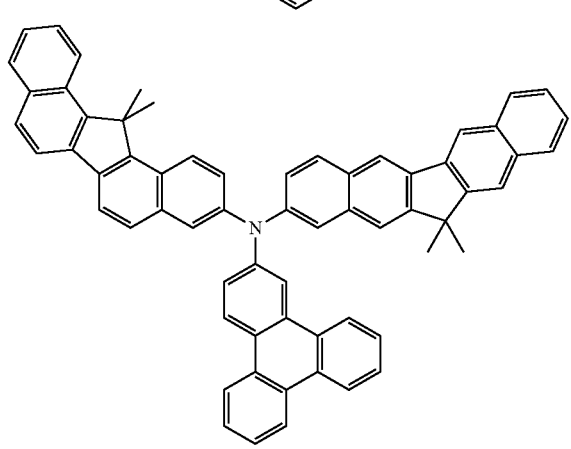
-continued
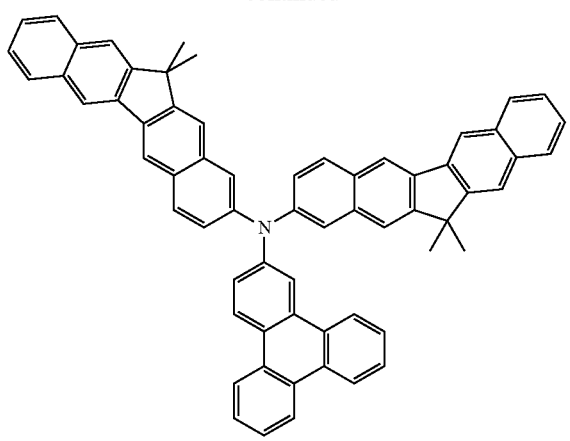
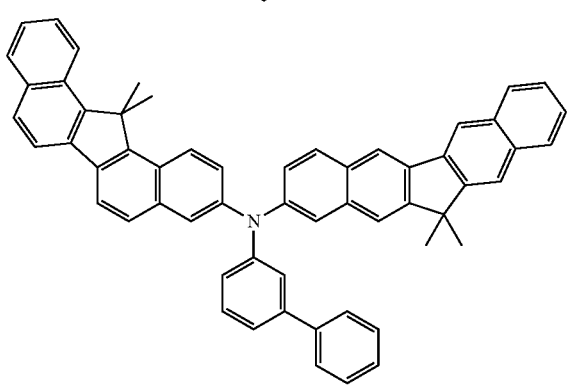
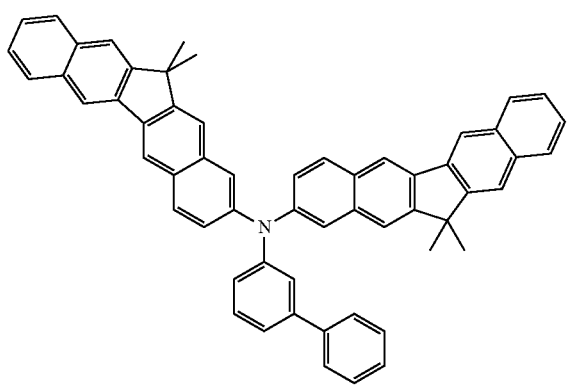
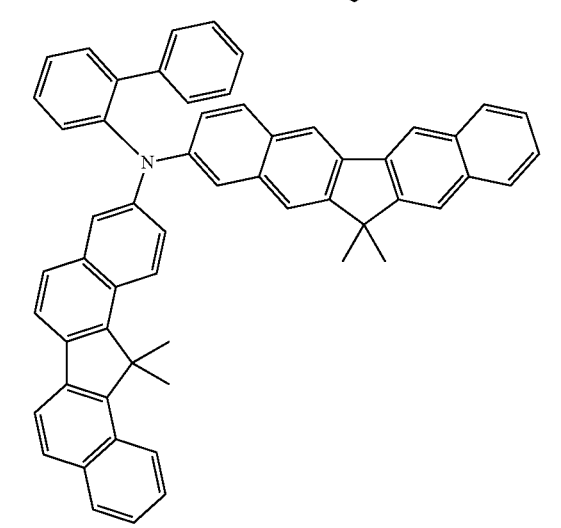

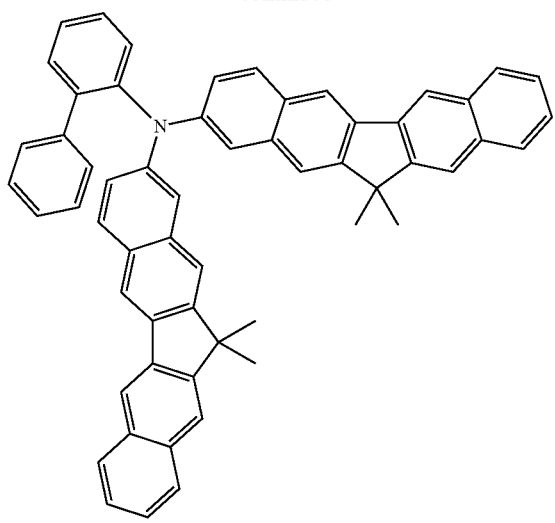
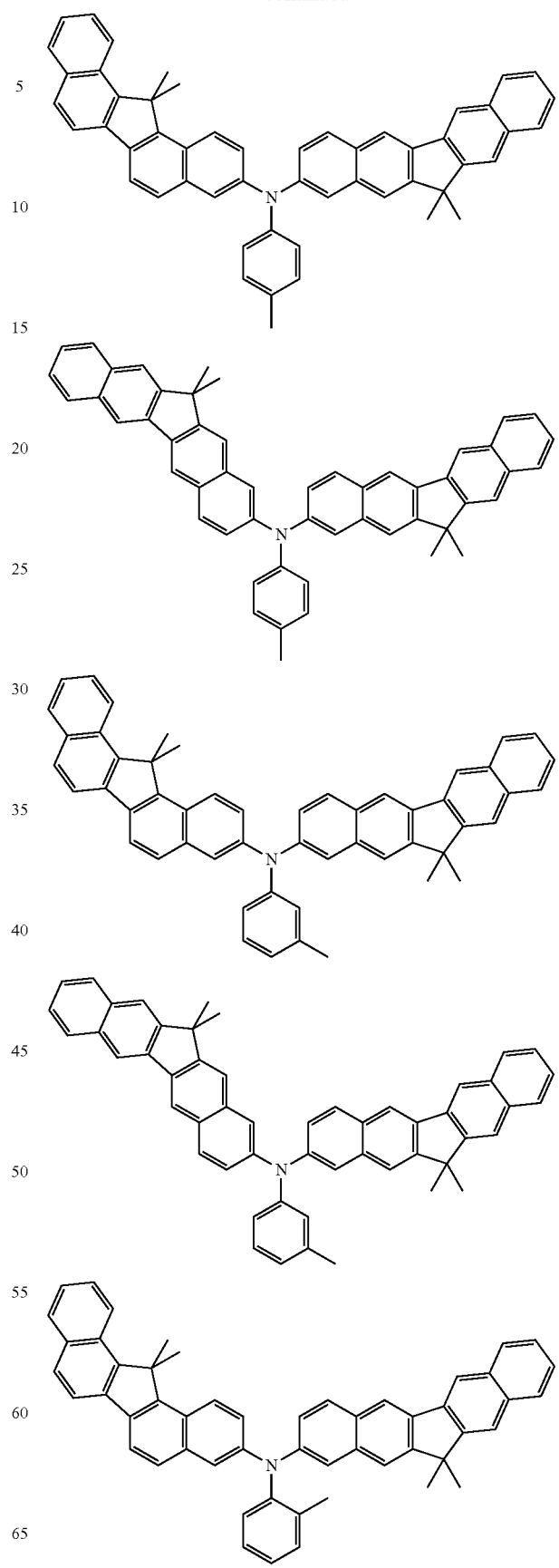

73
-continued
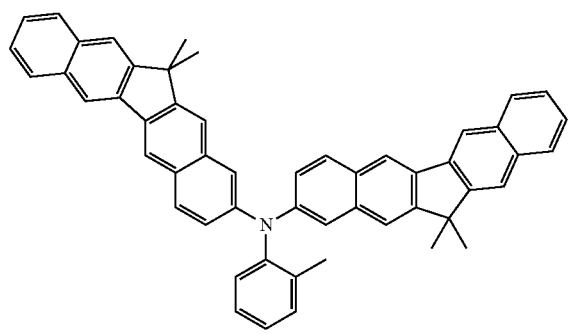
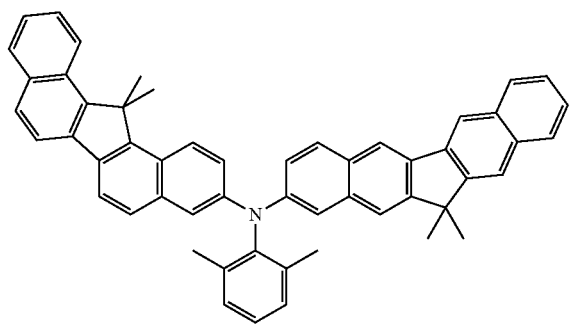
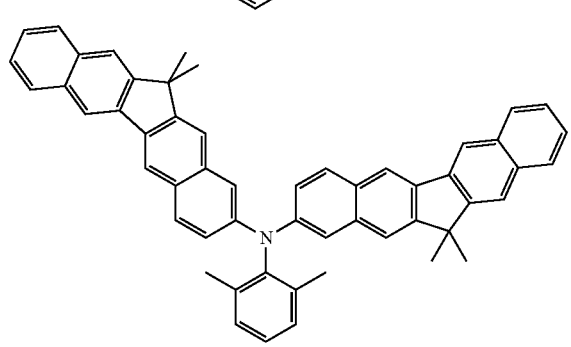
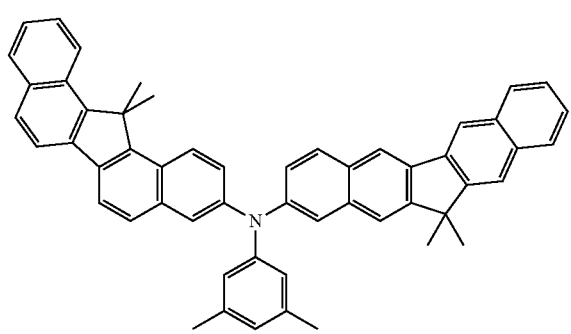
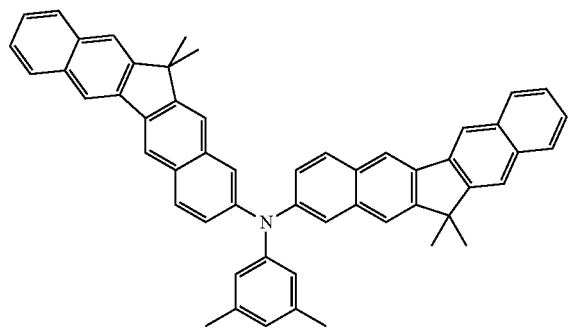
74
-continued
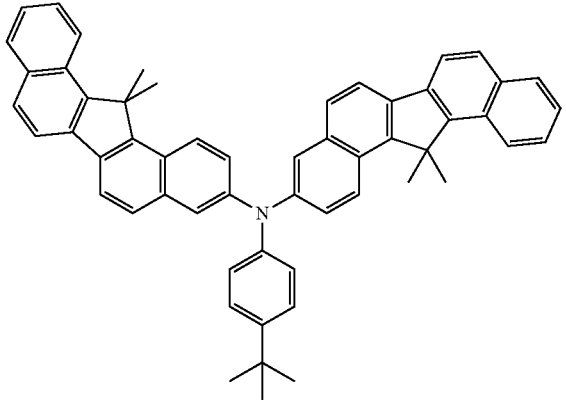
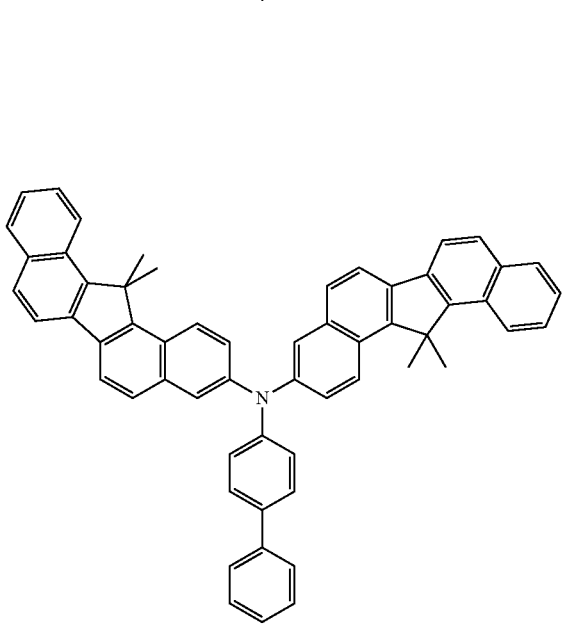
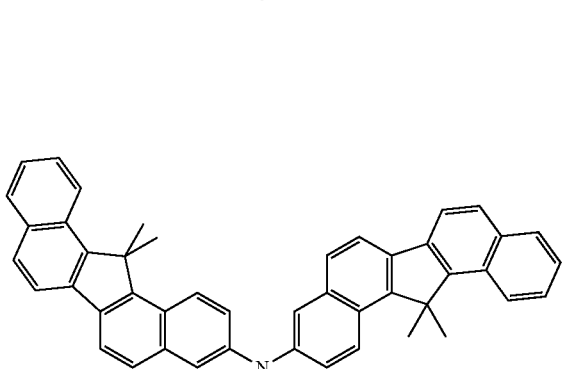
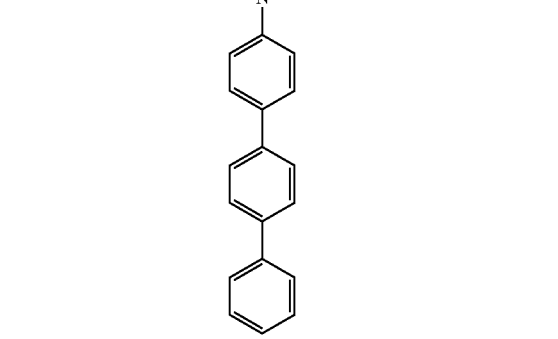

75
-continued
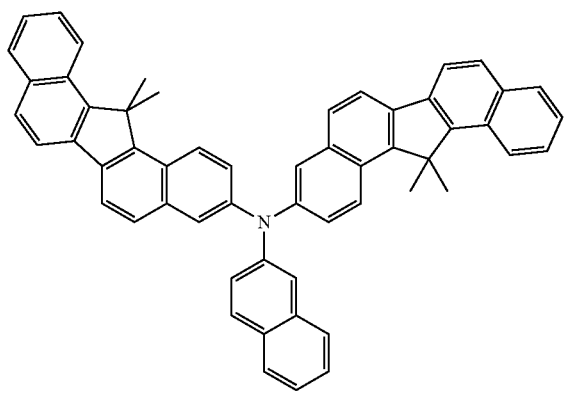
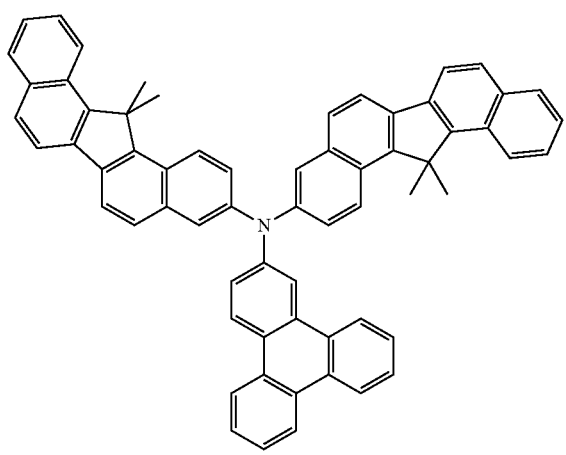
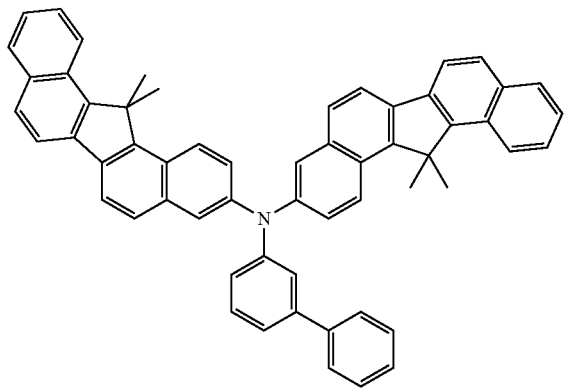
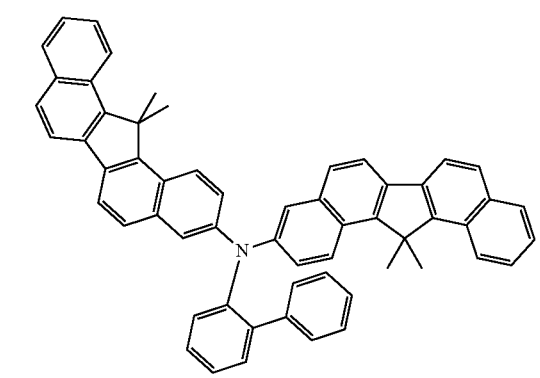
76
-continued
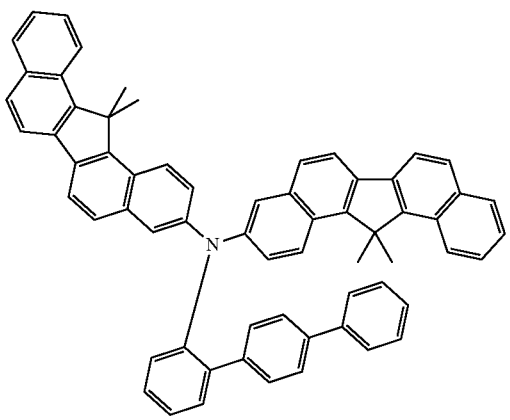
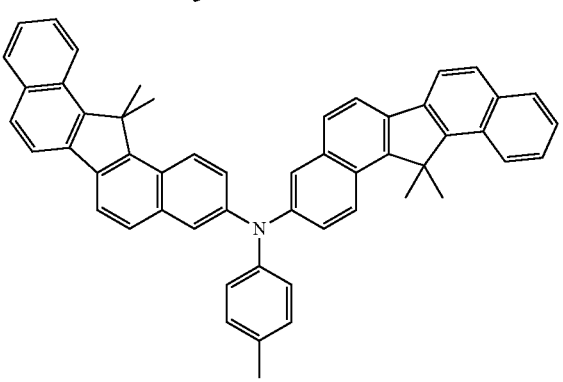
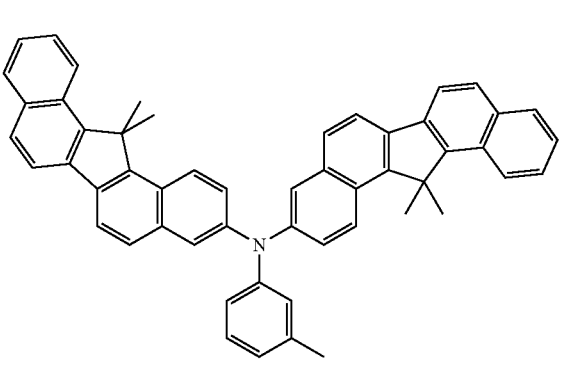
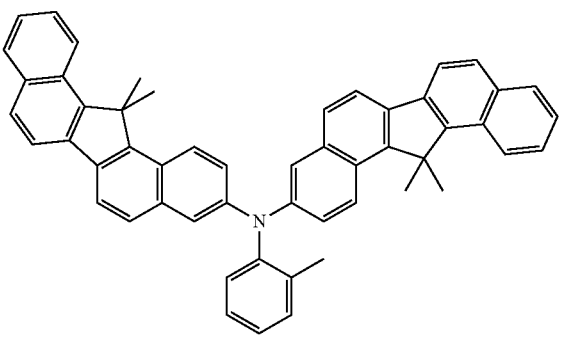

77
-continued
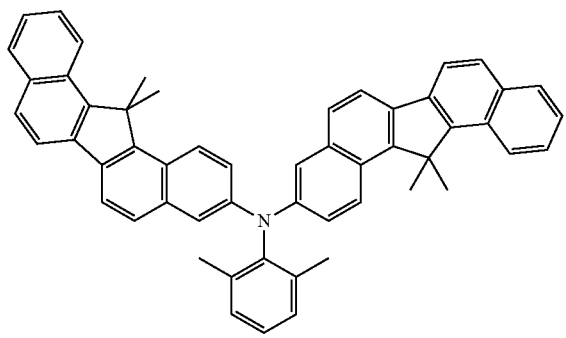
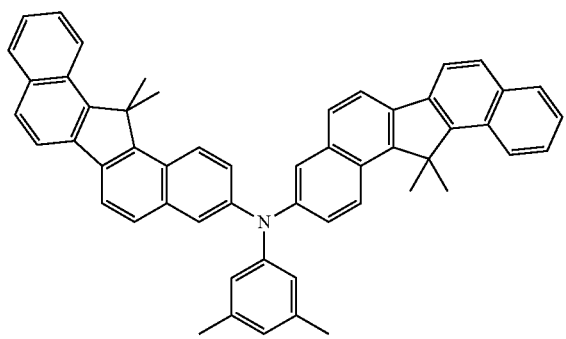
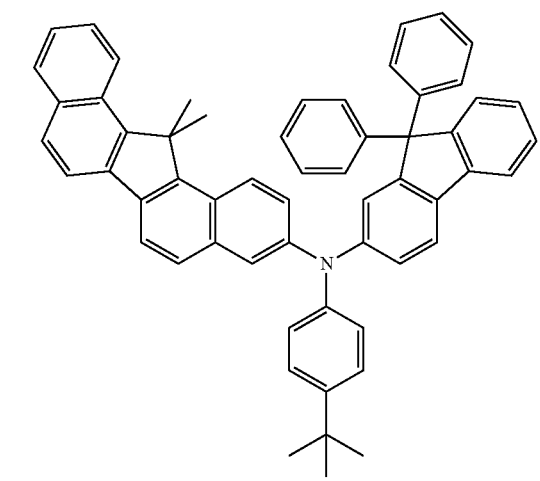
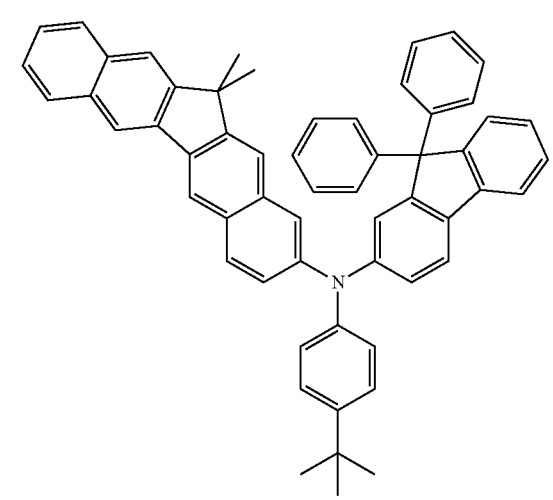
78
-continued
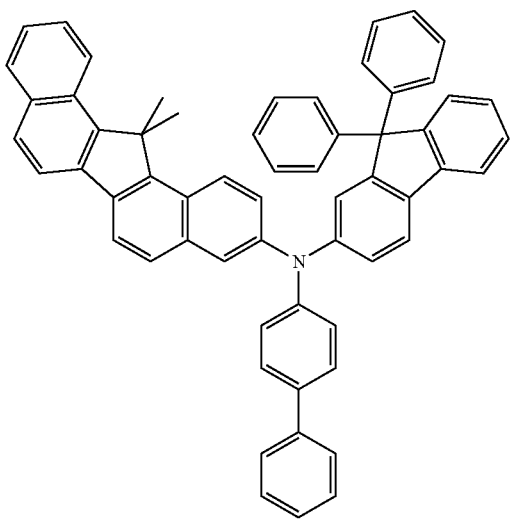
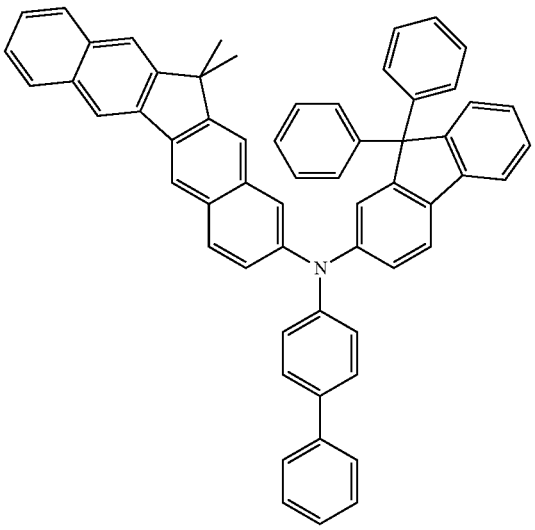
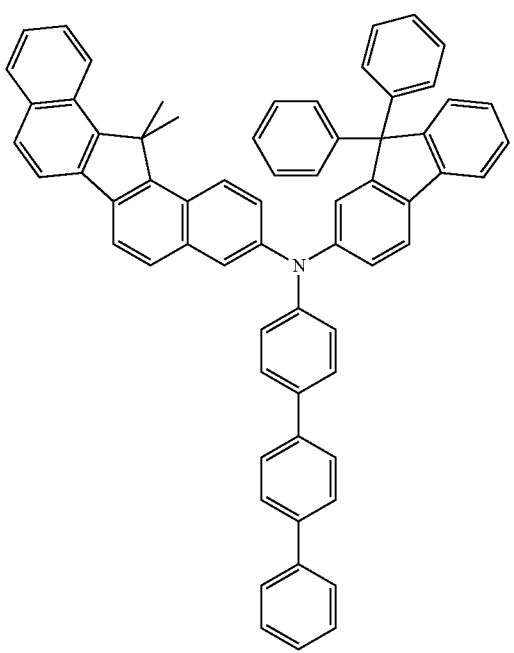

-continued
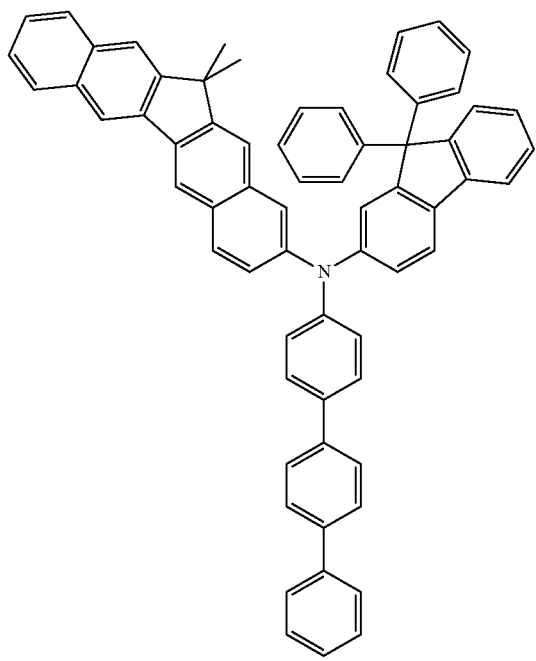
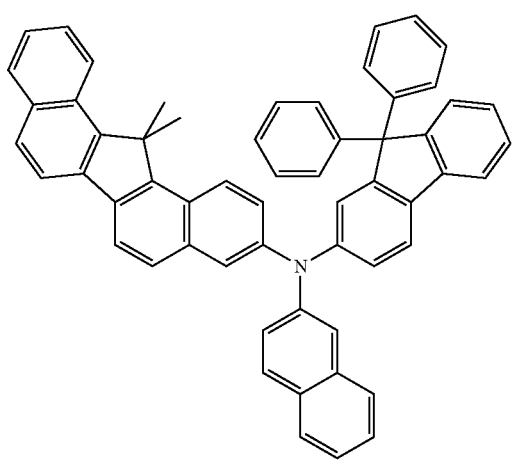
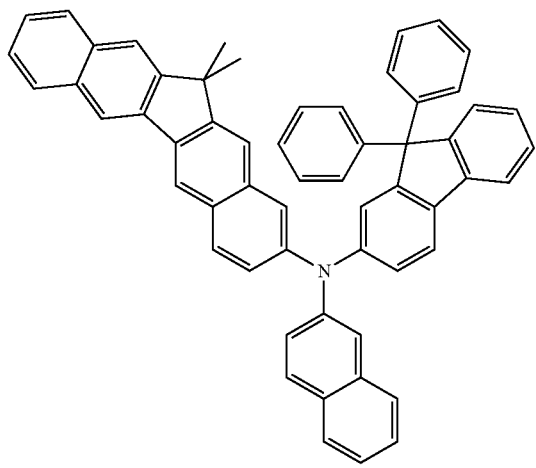
-continued
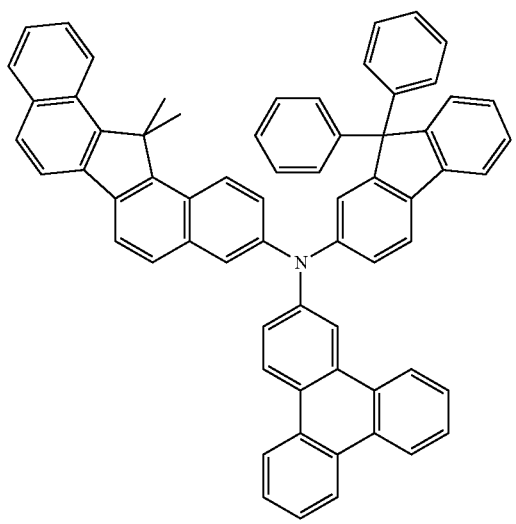
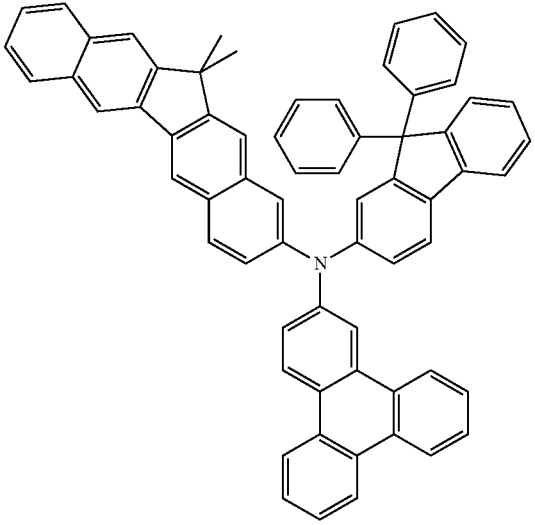
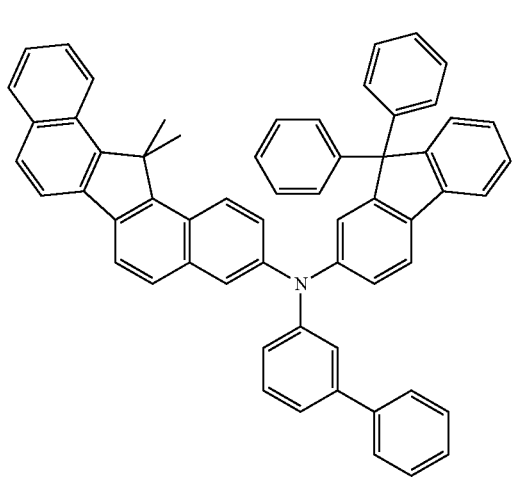

81
-continued
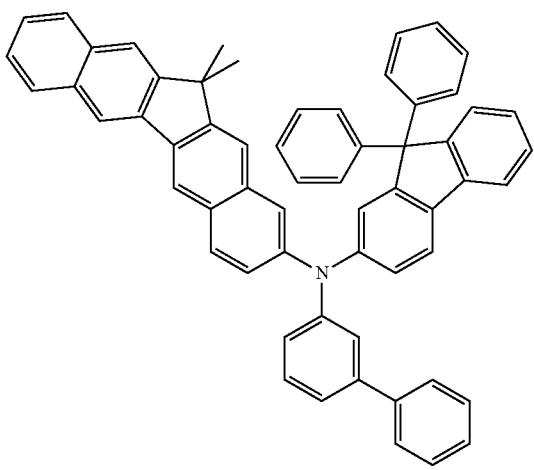
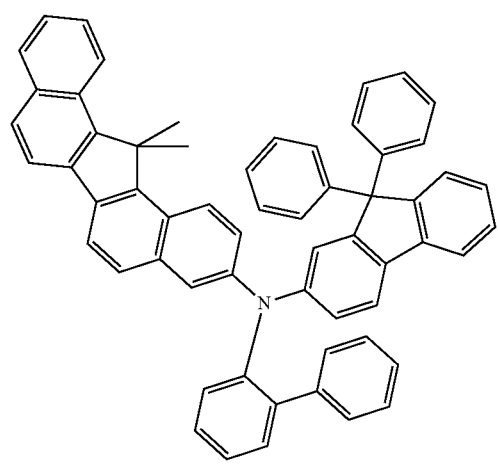
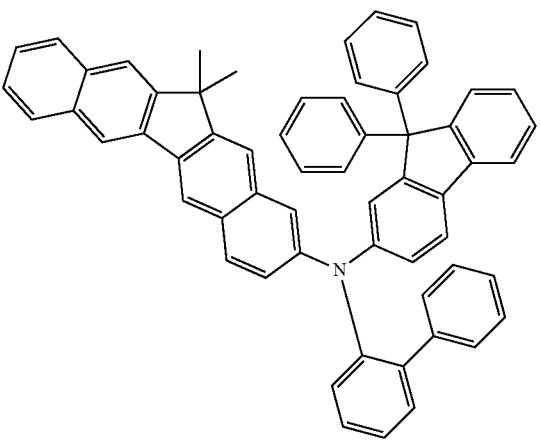
82
-continued
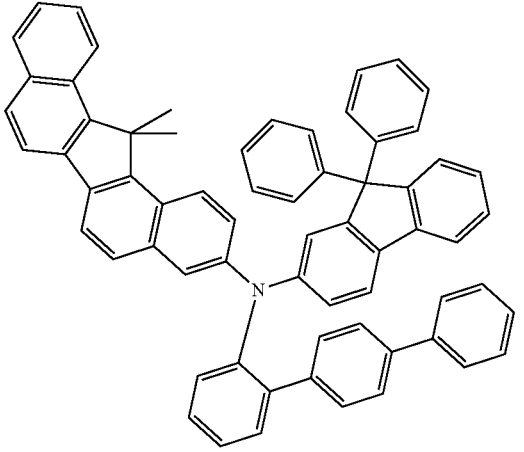
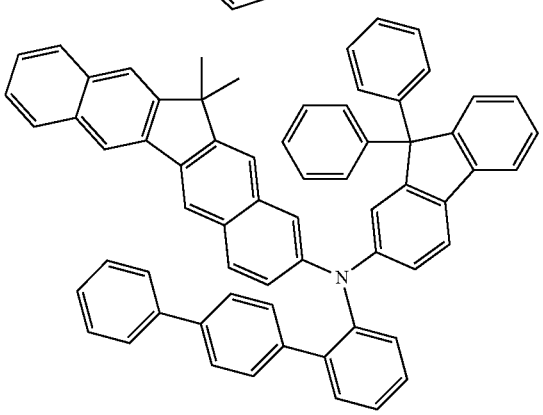
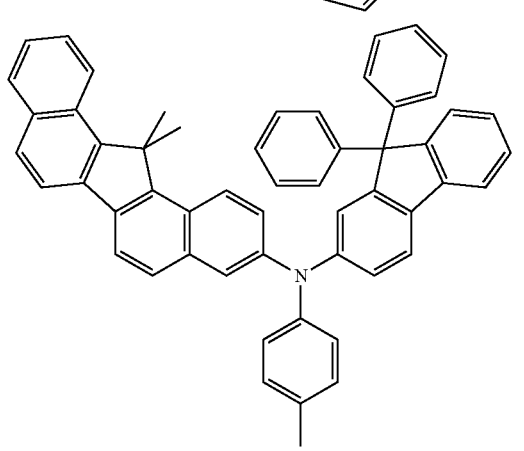
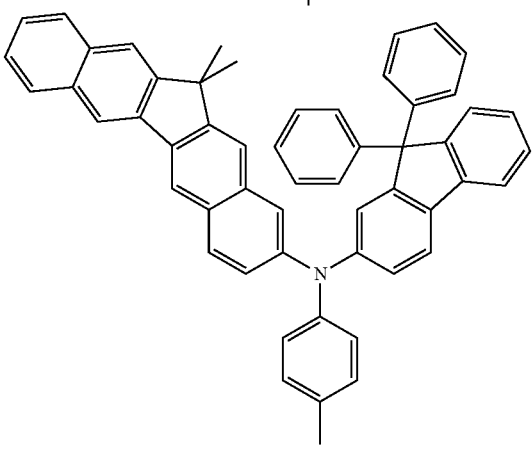

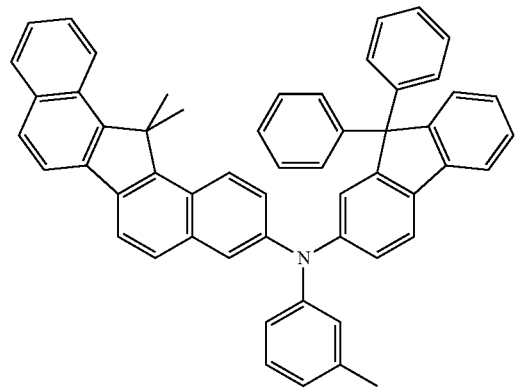
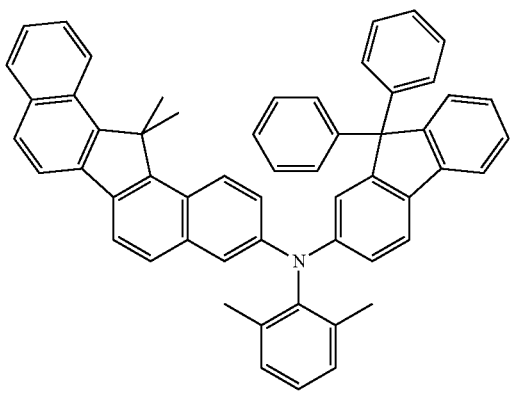
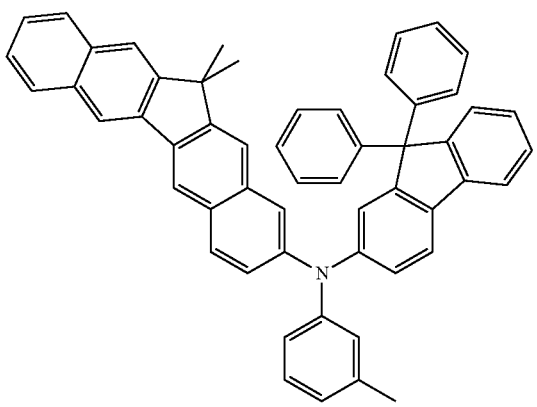
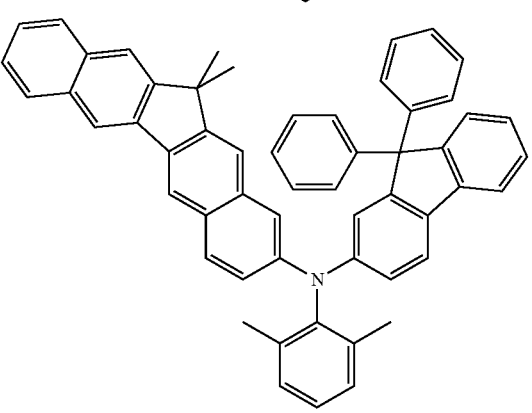
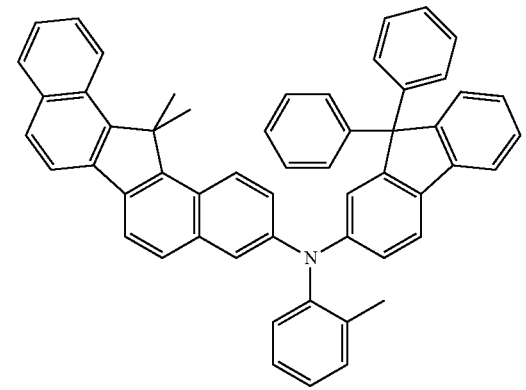
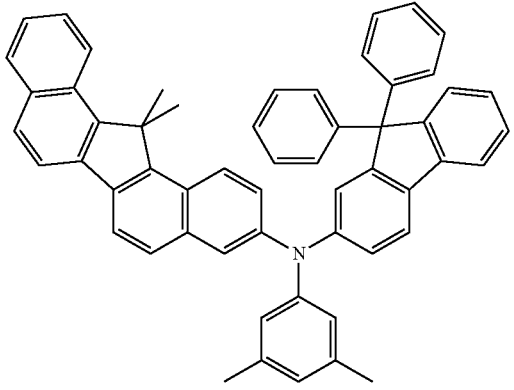
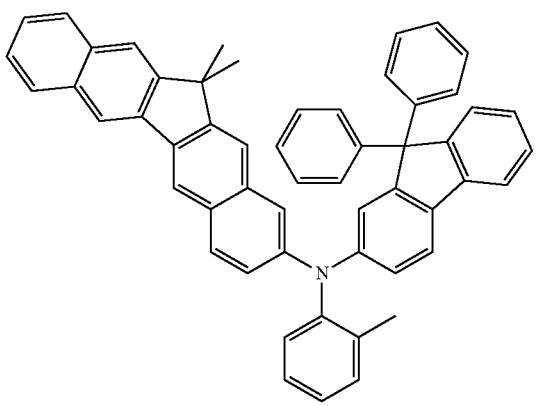
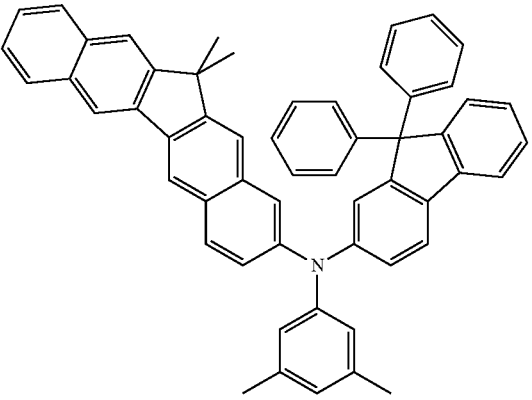

85
-continued
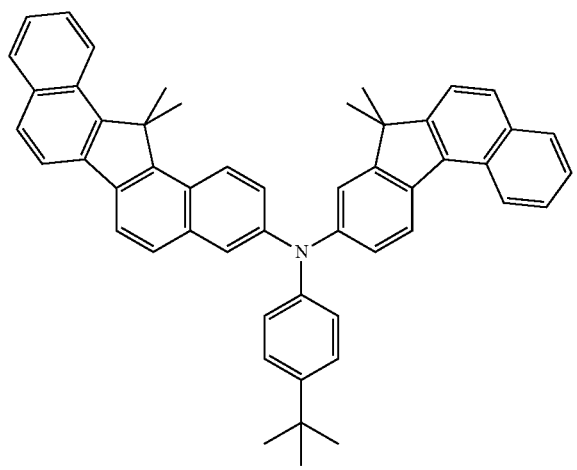
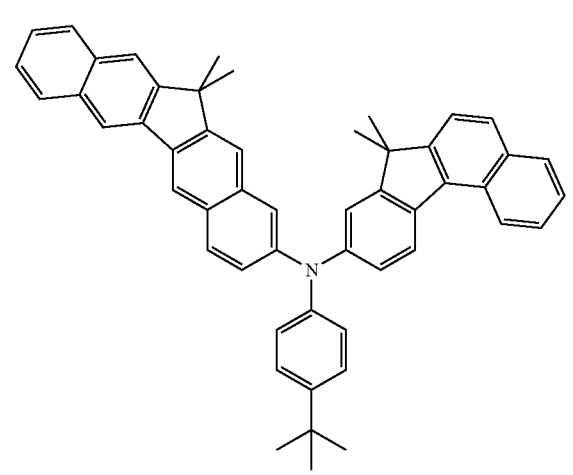
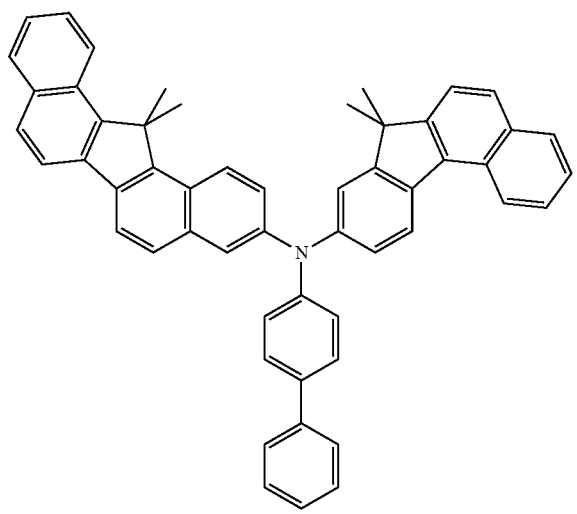
86
-continued
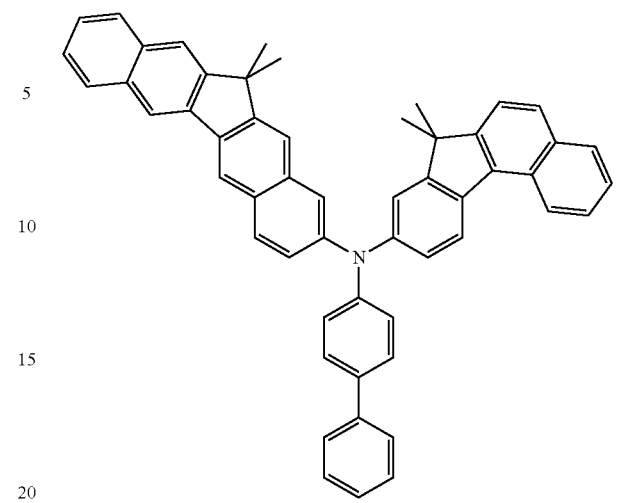
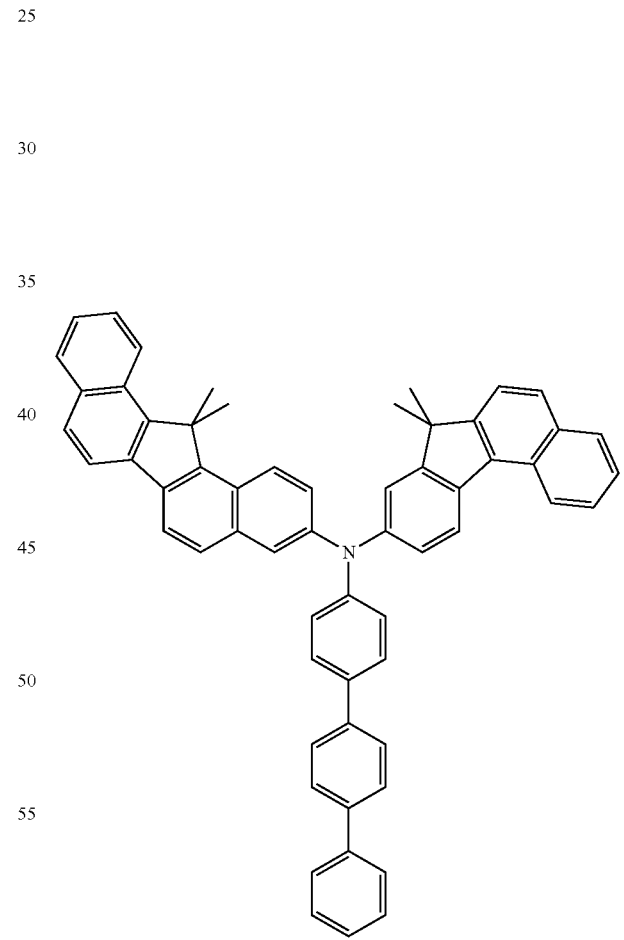

87
-continued
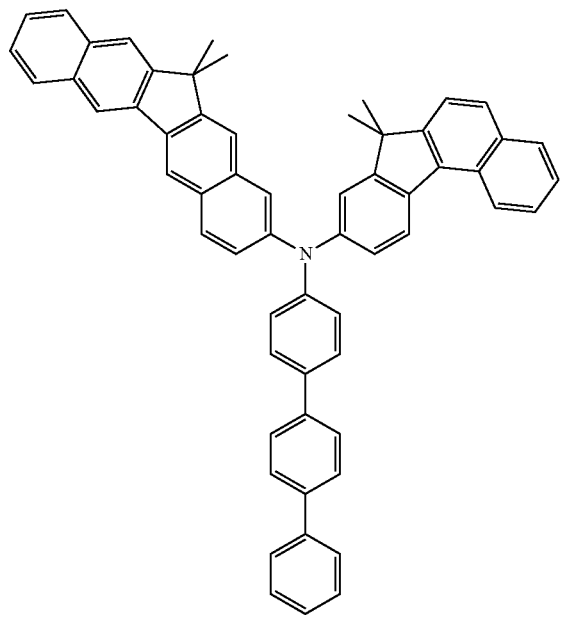
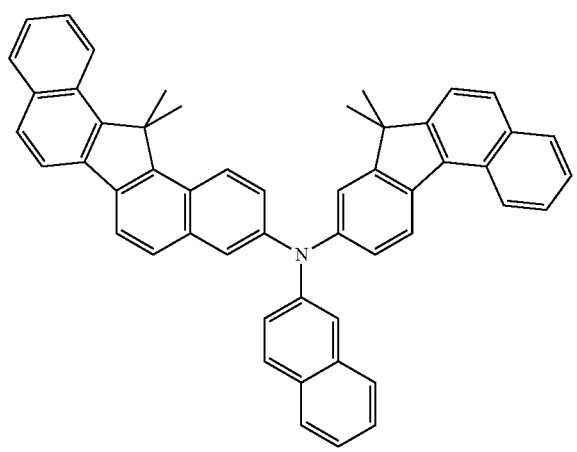
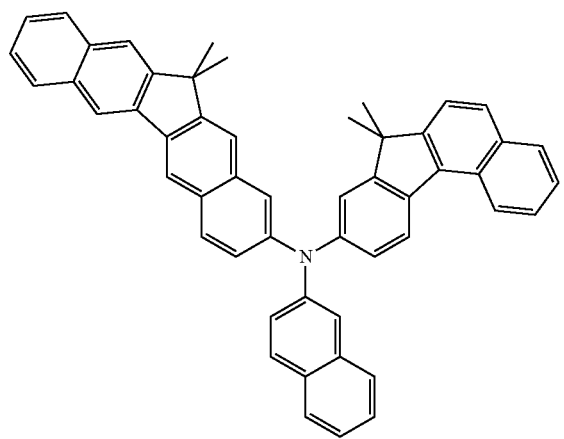
88
-continued
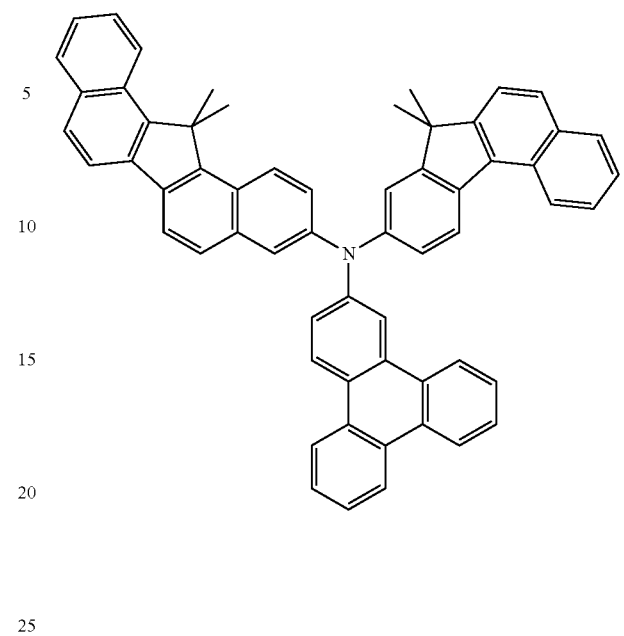
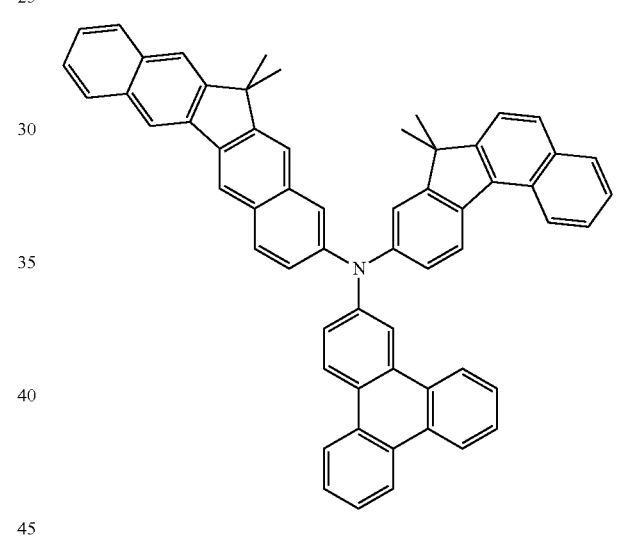
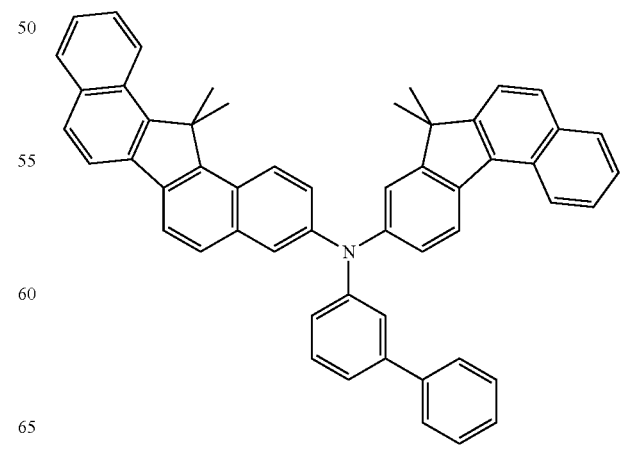

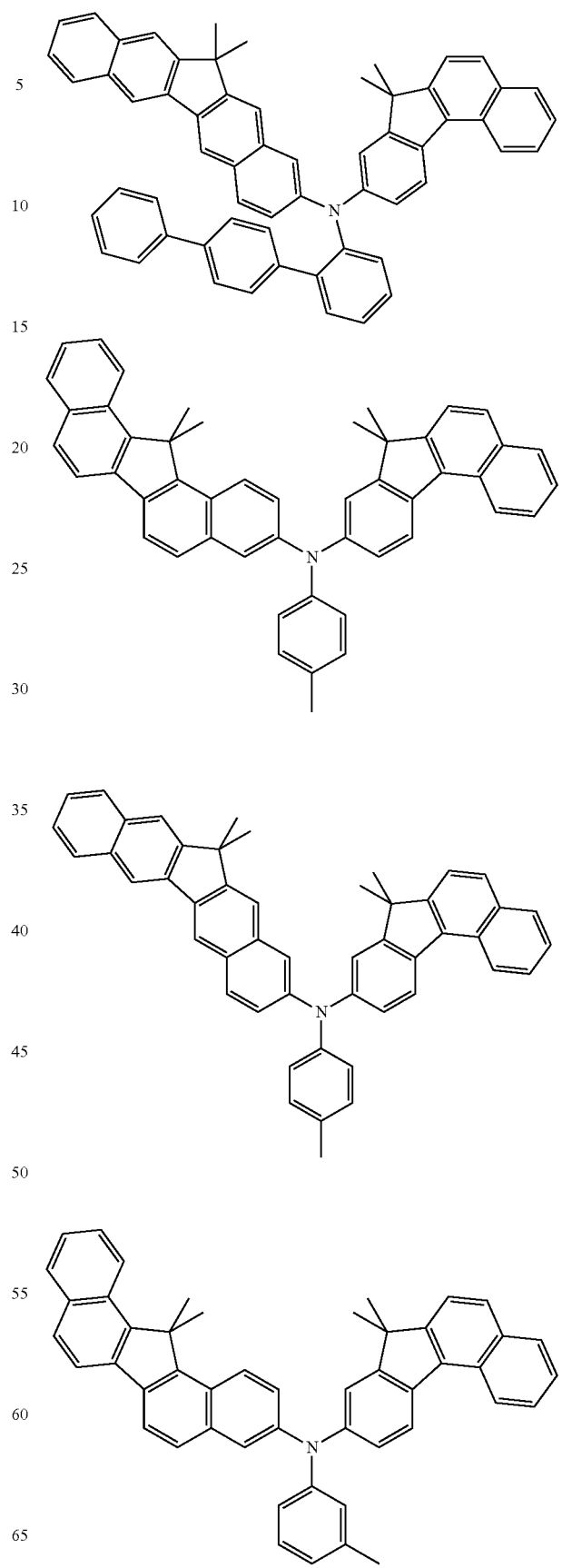

91
-continued
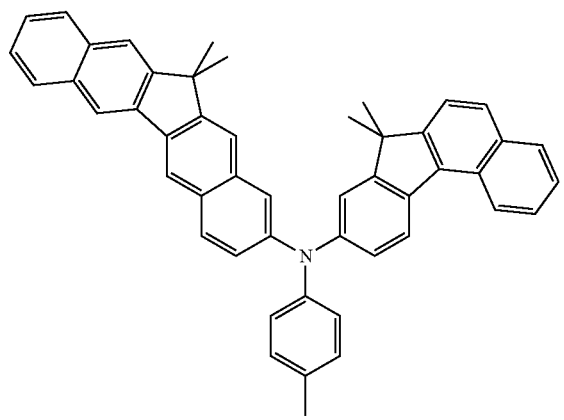
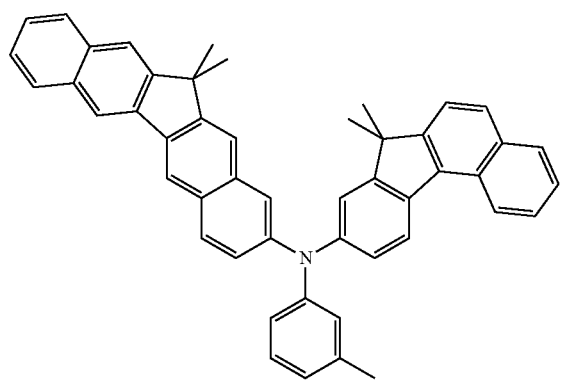
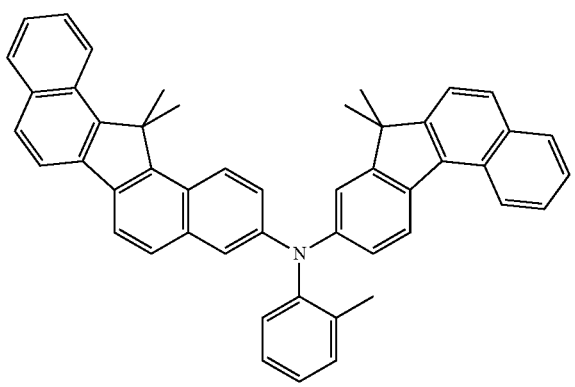
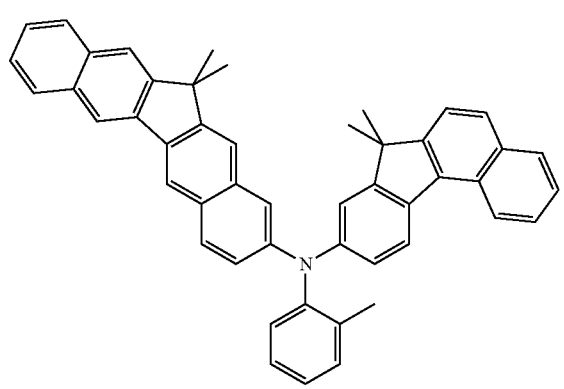
92
-continued
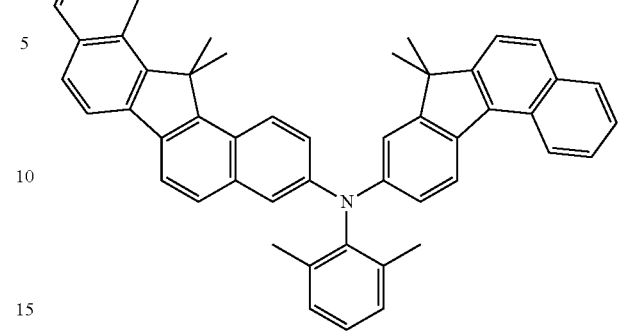
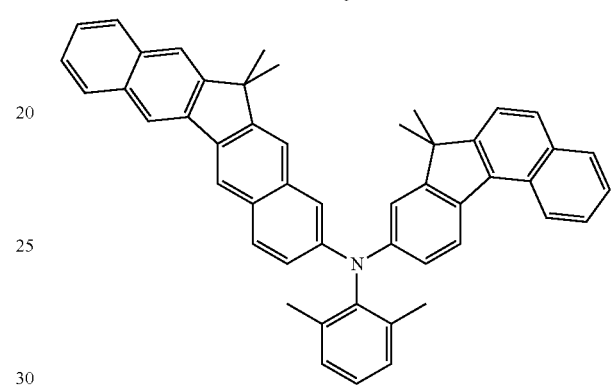
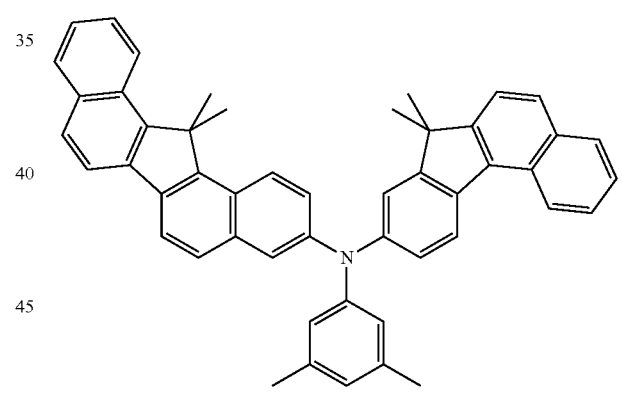
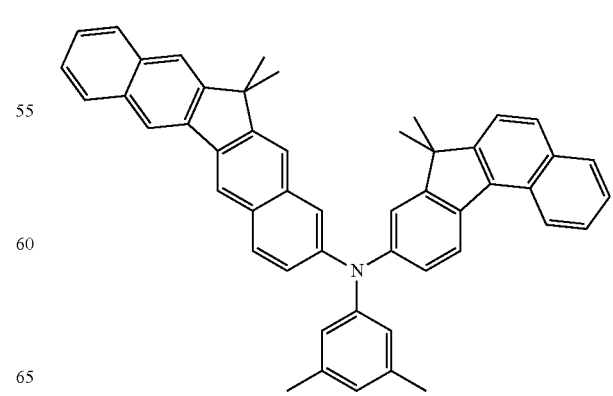

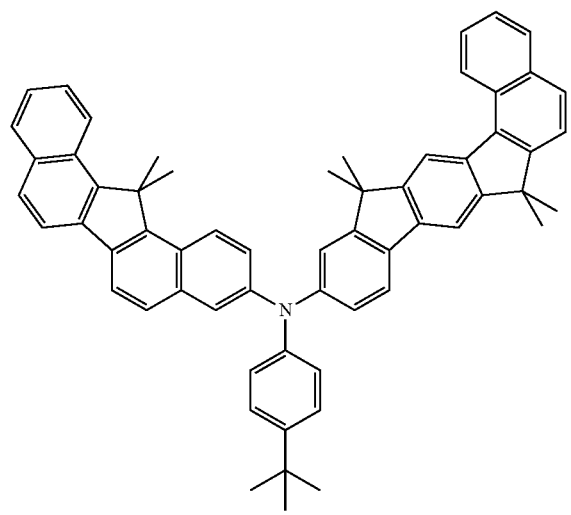
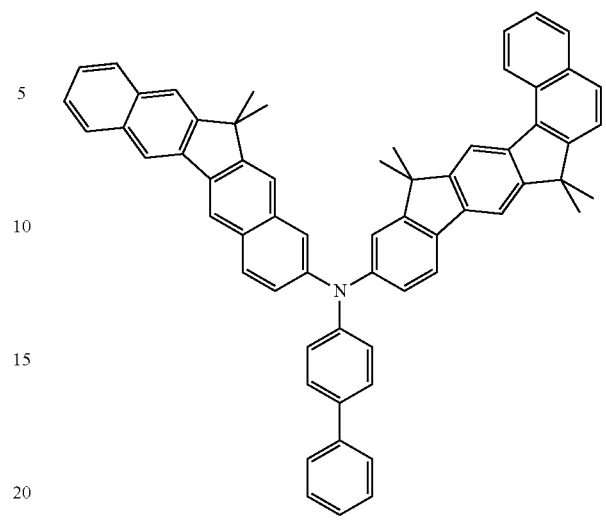
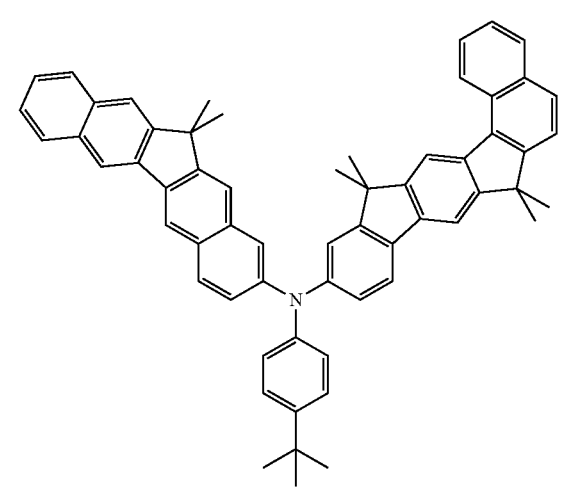
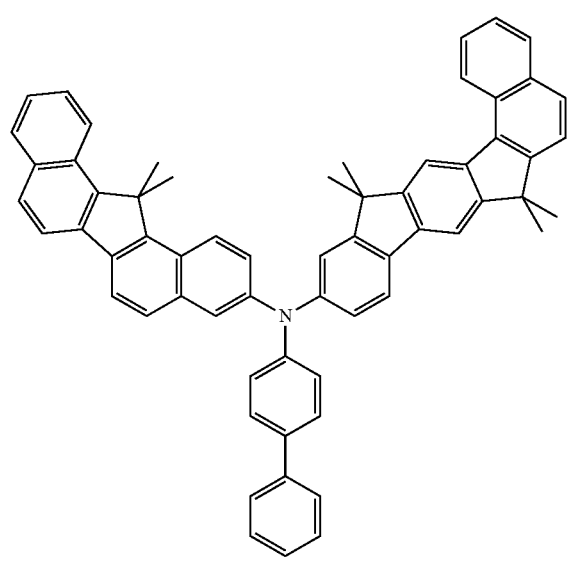
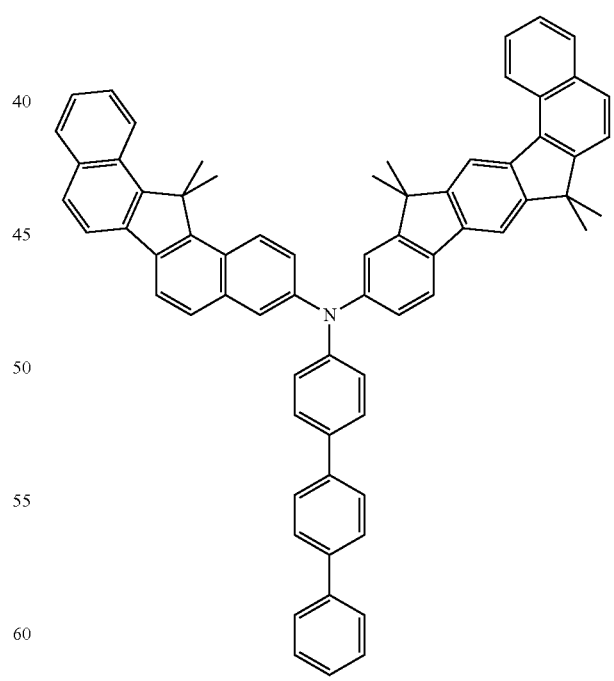

95
-continued
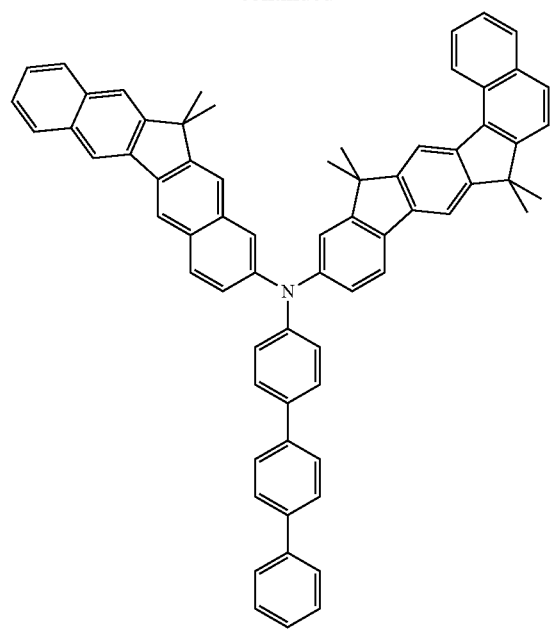
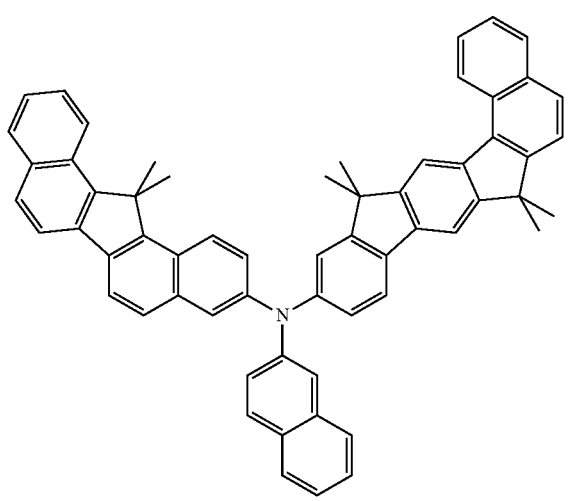
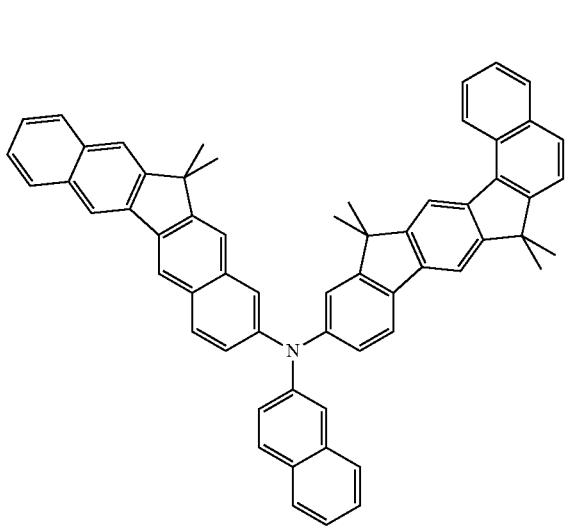
96
-continued
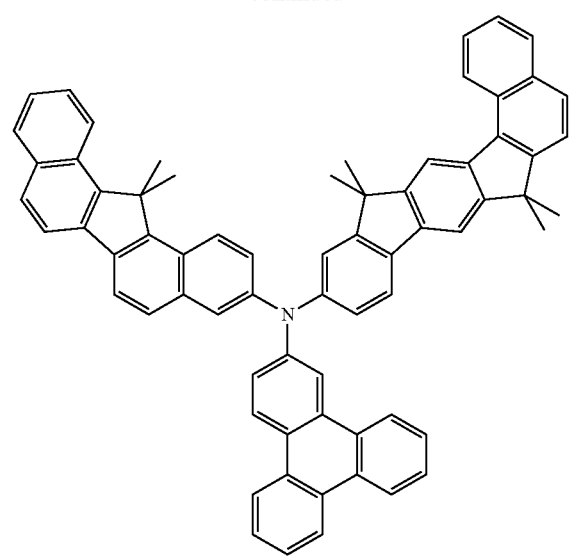
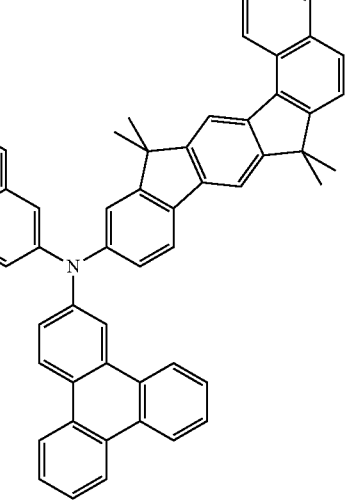

97
-continued
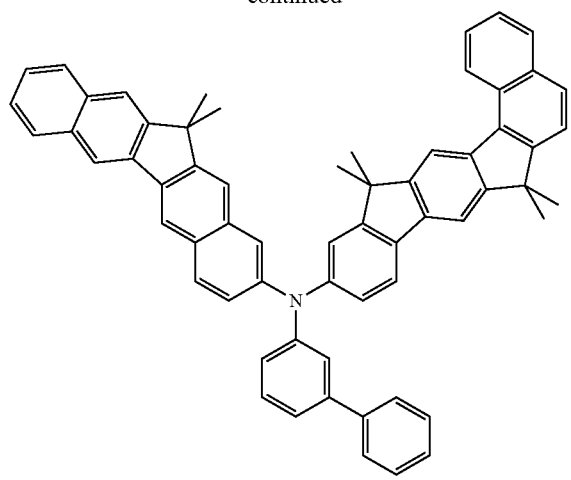
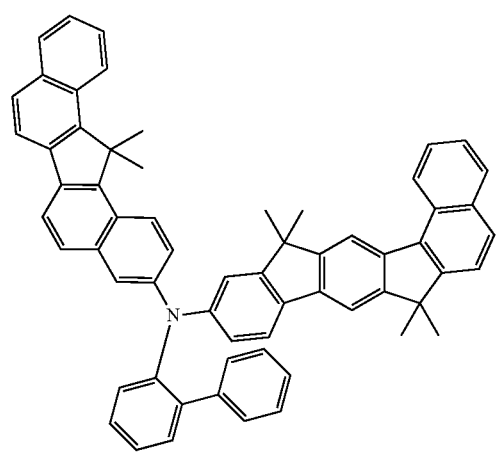
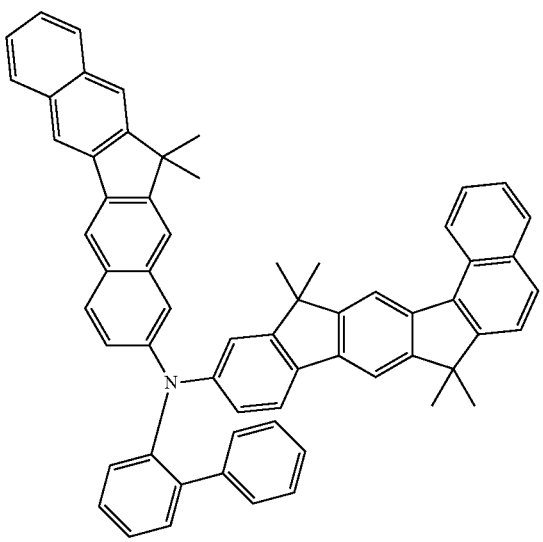
98
-continued
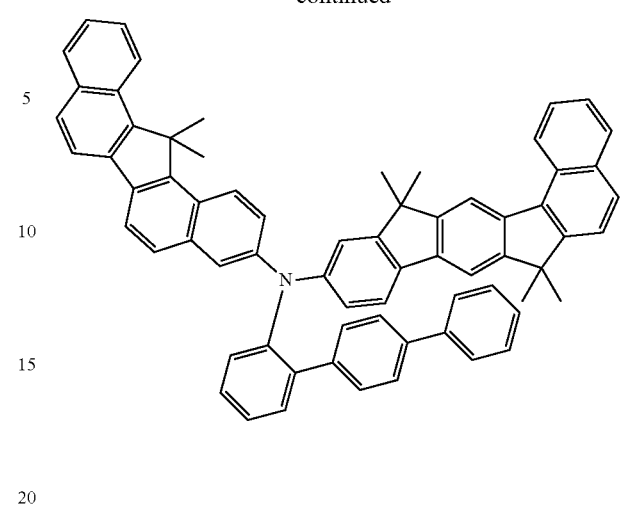
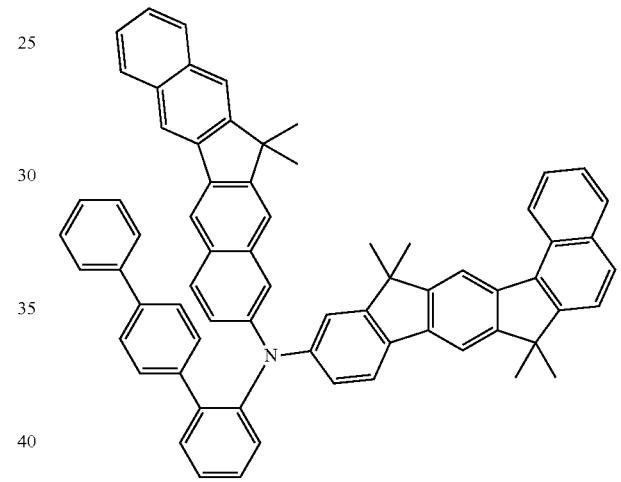
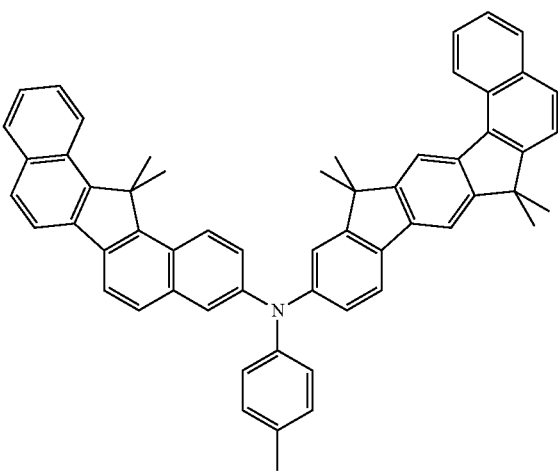

99
-continued
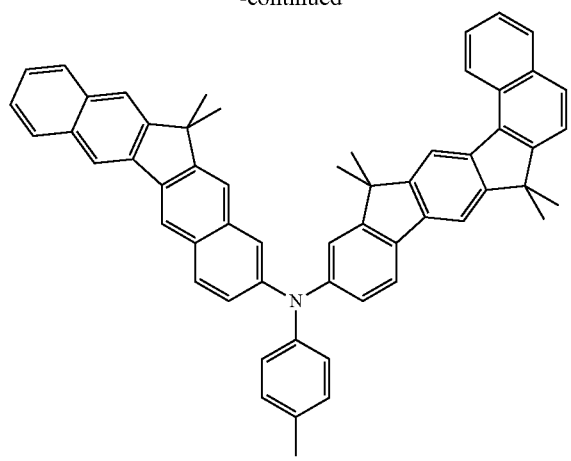
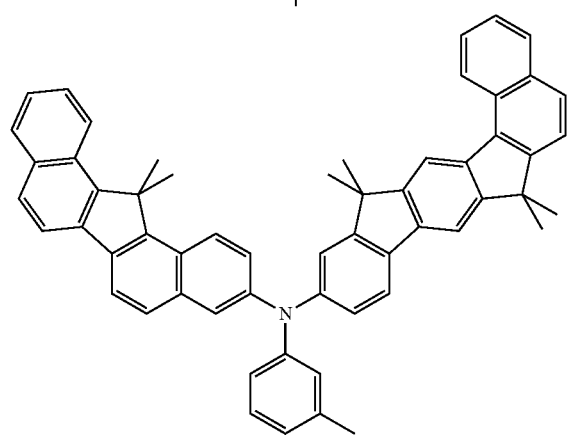
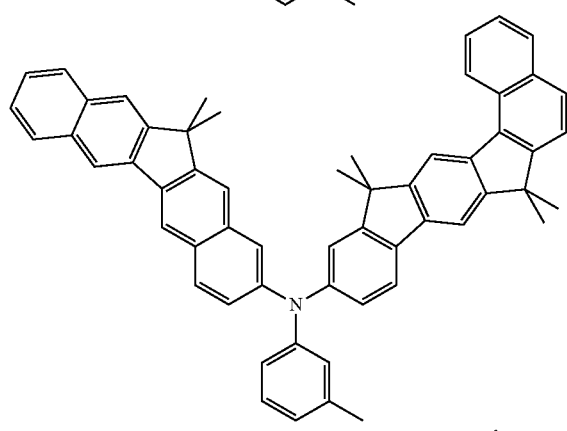
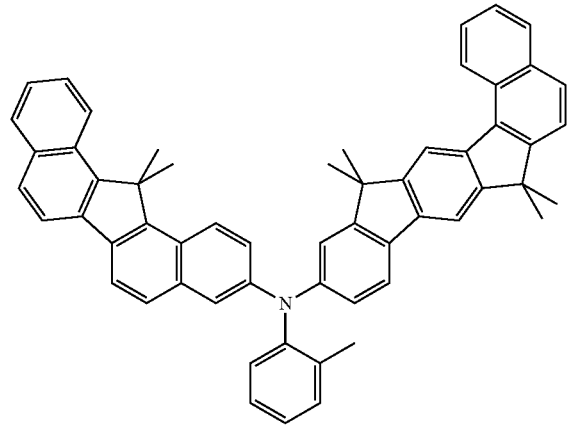
100
-continued
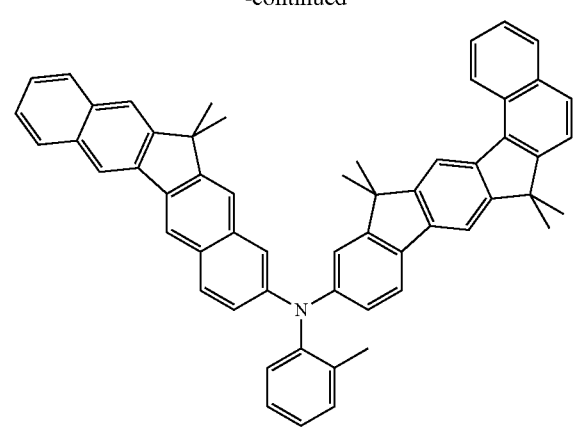
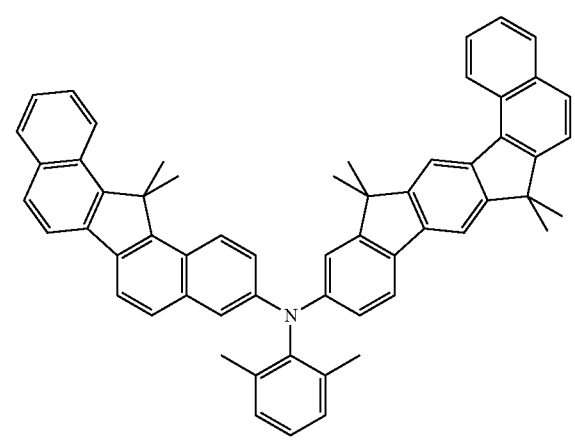
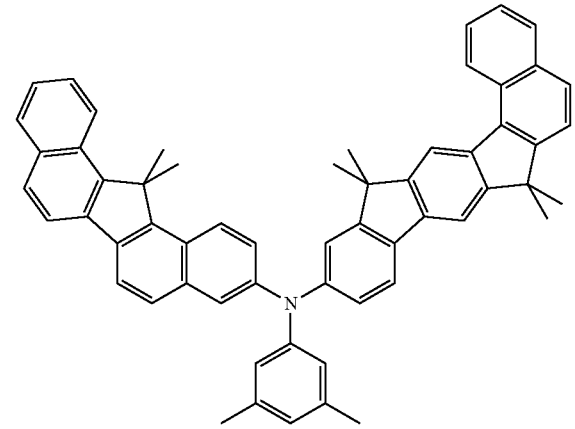

101
-continued
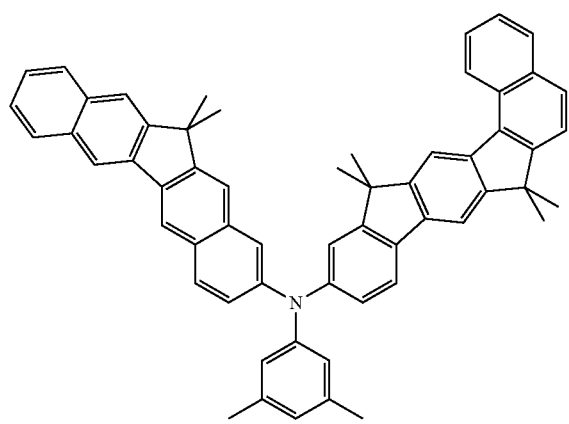
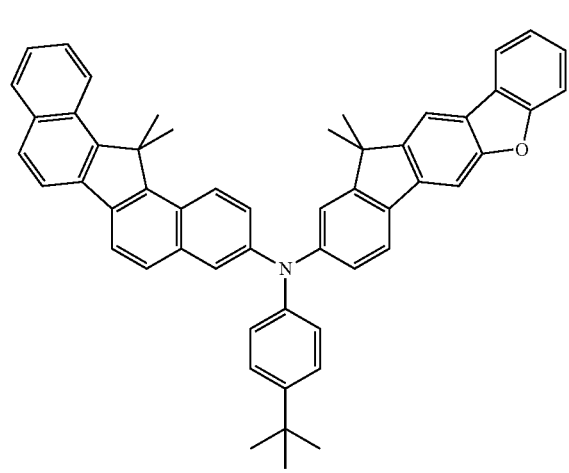
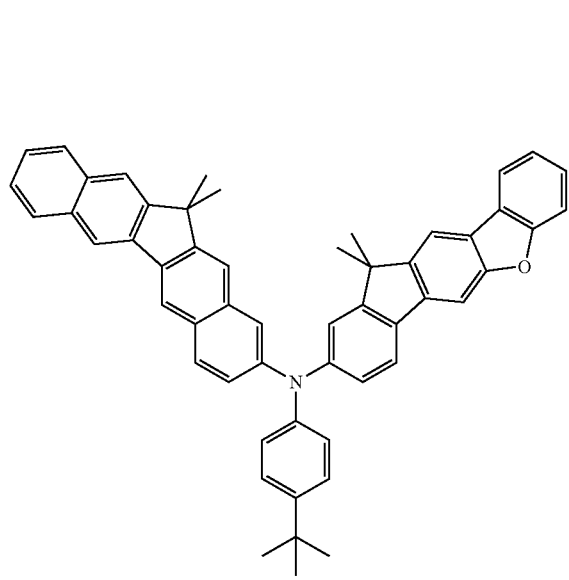
102
-continued
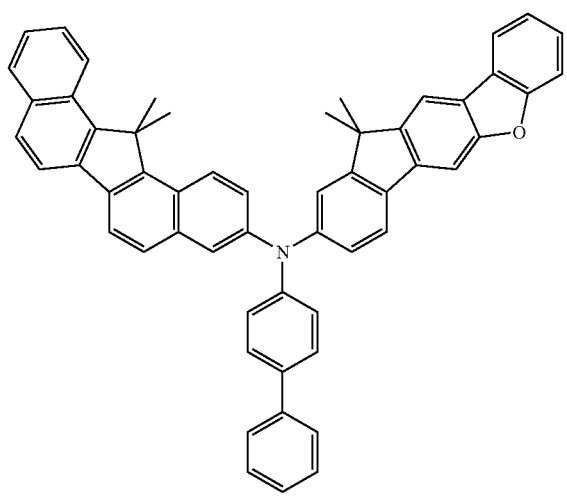
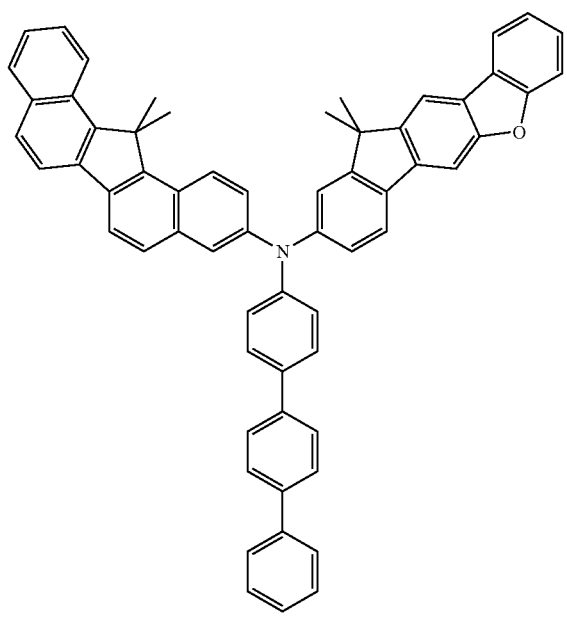

103
-continued
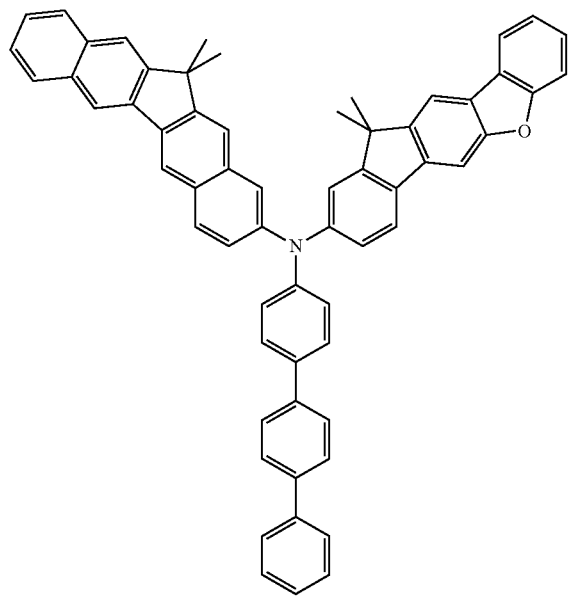
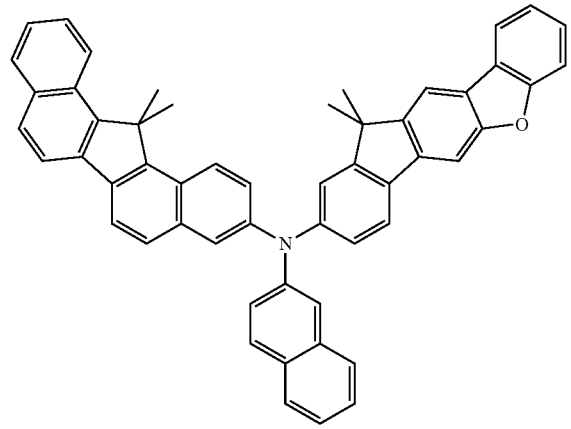
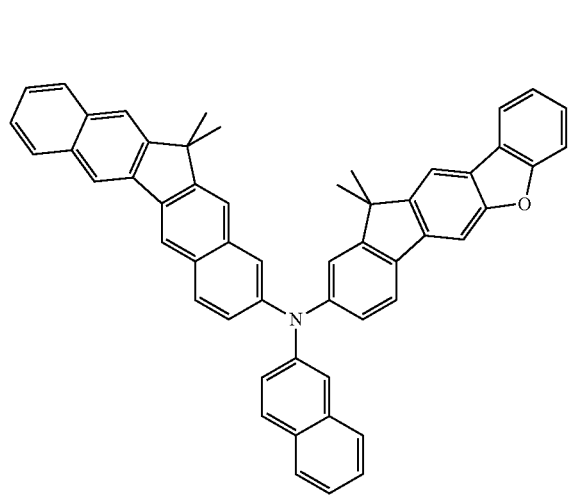
104
-continued
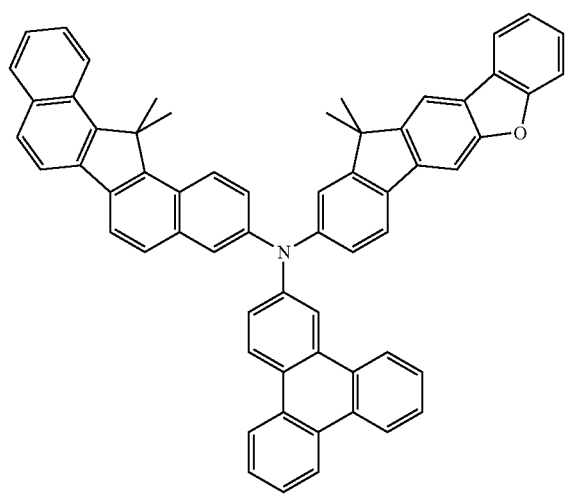
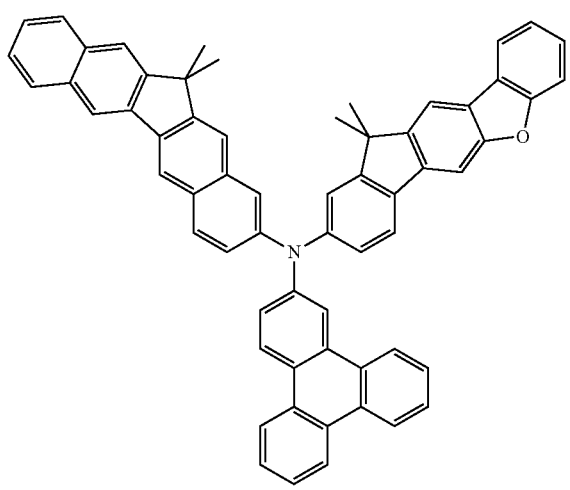
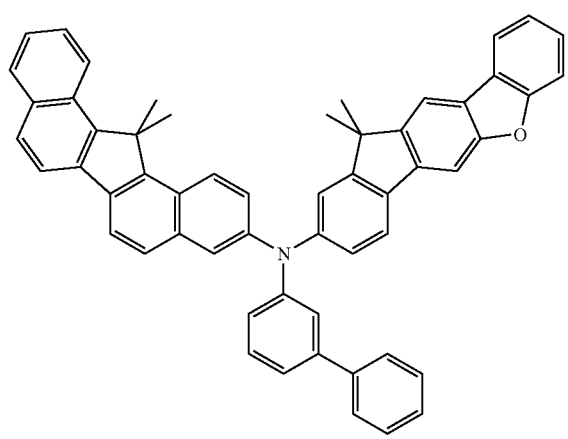

105
-continued
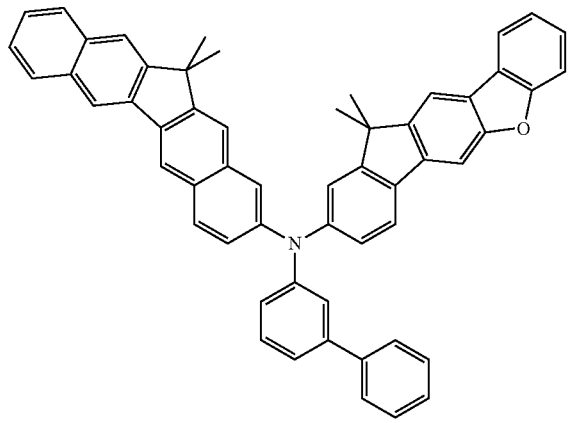
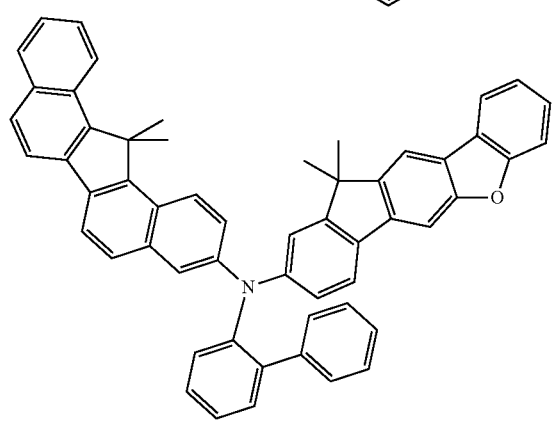
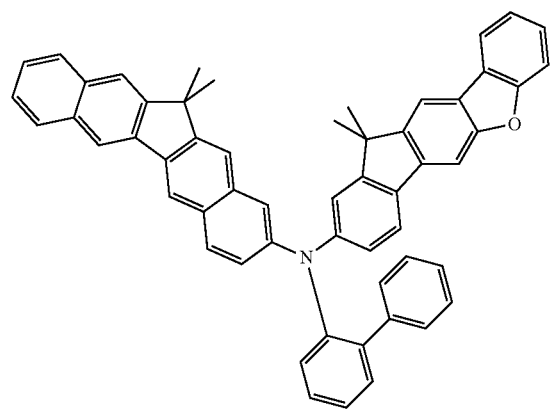
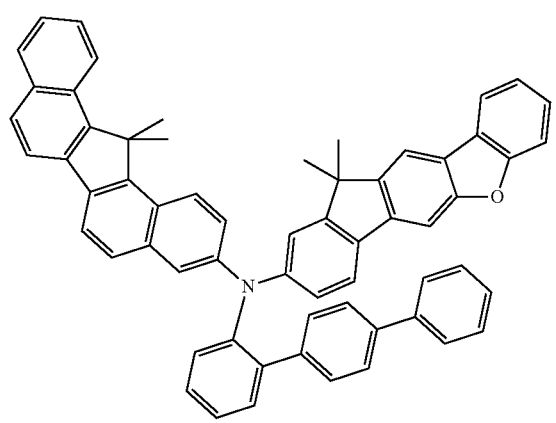
106
-continued
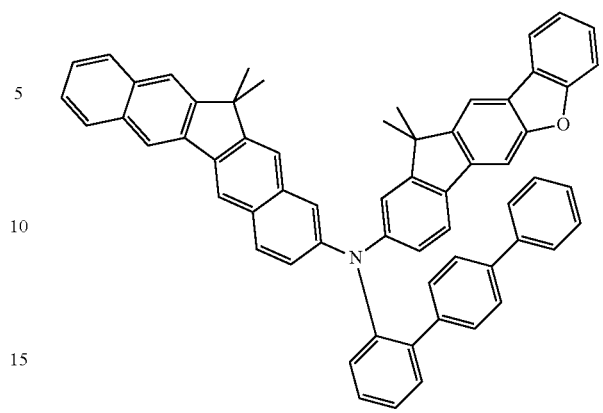
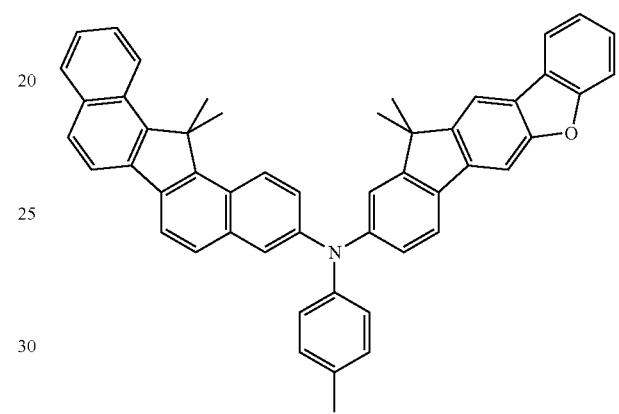
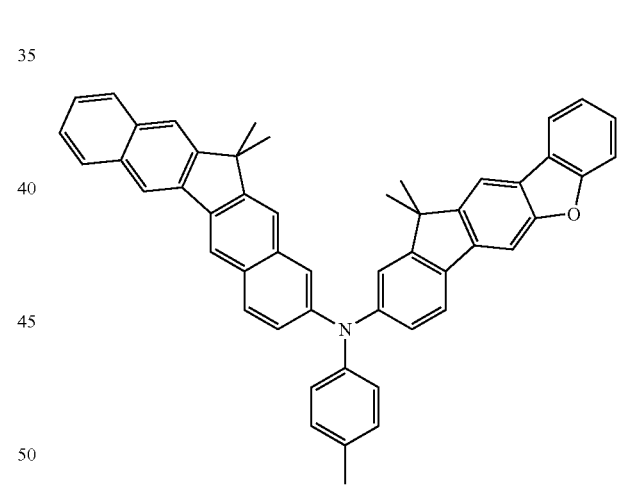
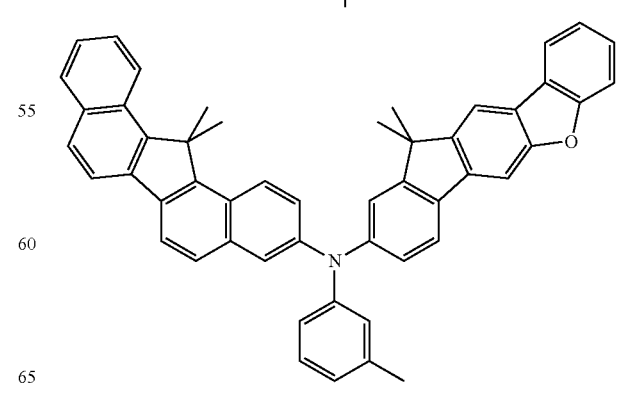

107
-continued
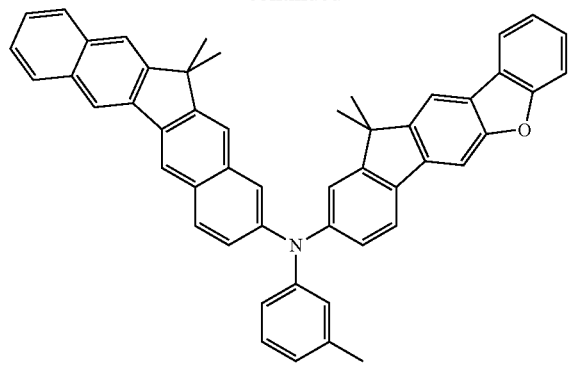
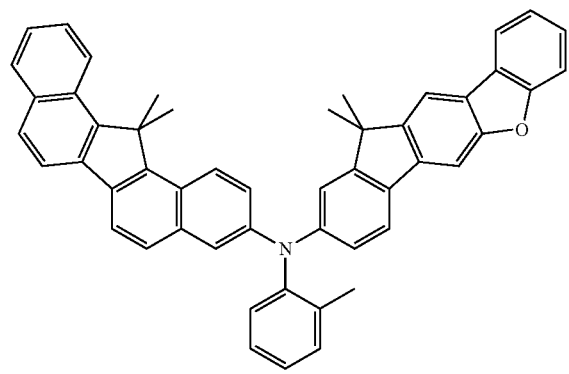
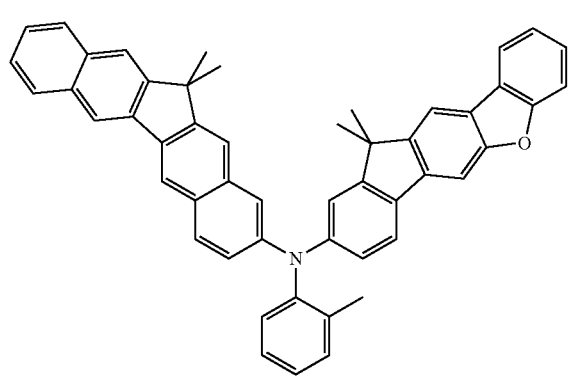
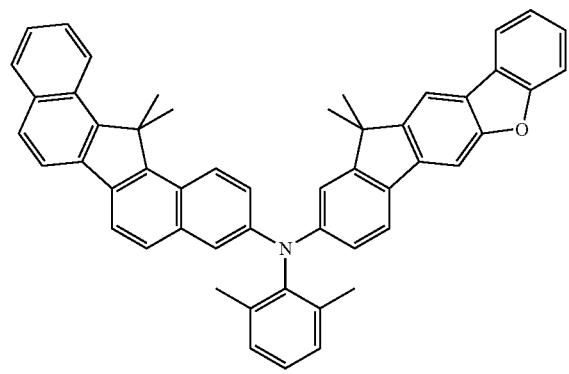
108
-continued
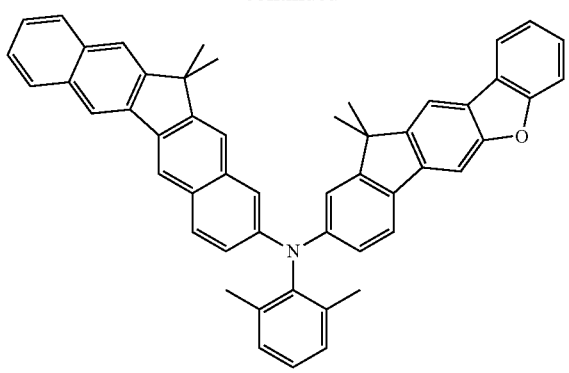
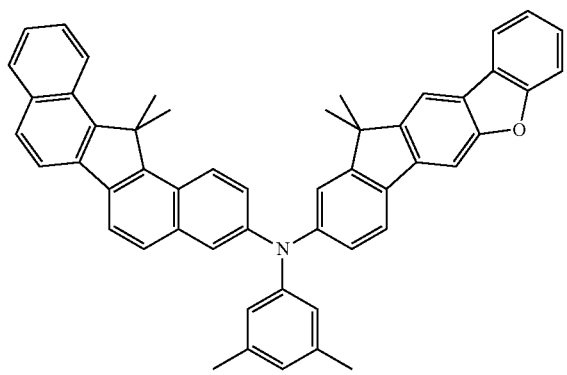
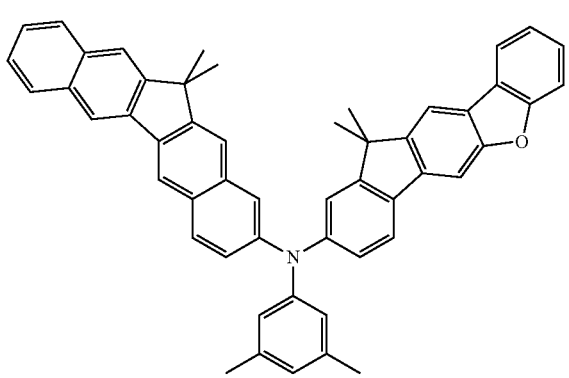
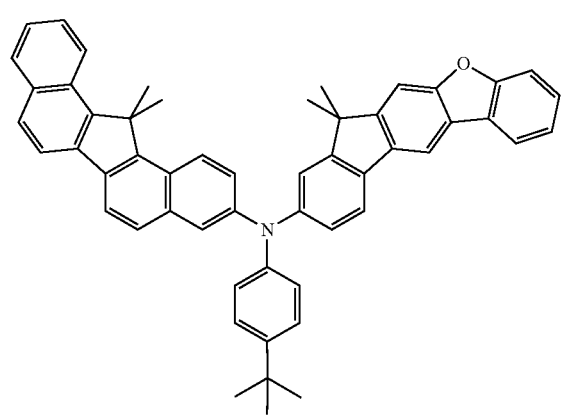

109
-continued
110
-continued
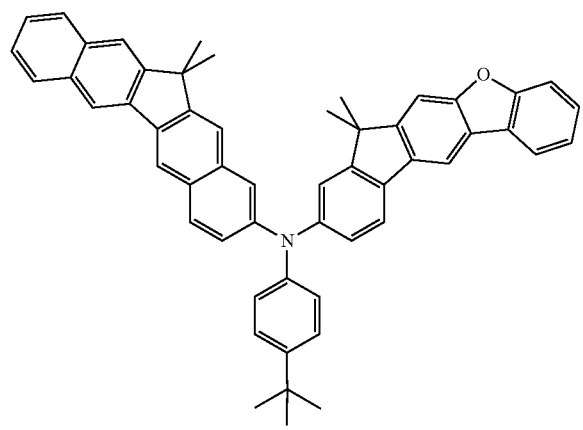
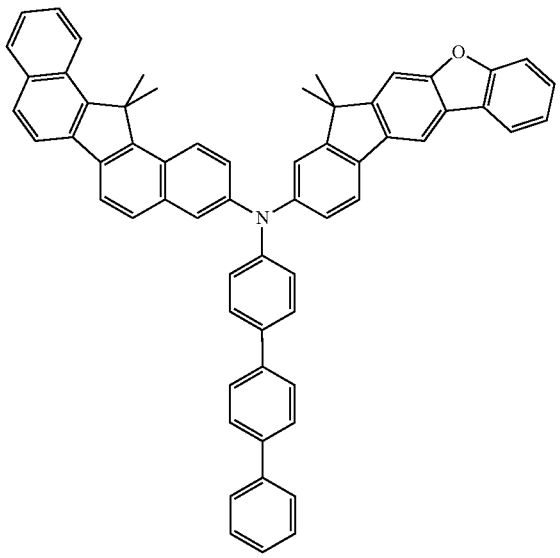
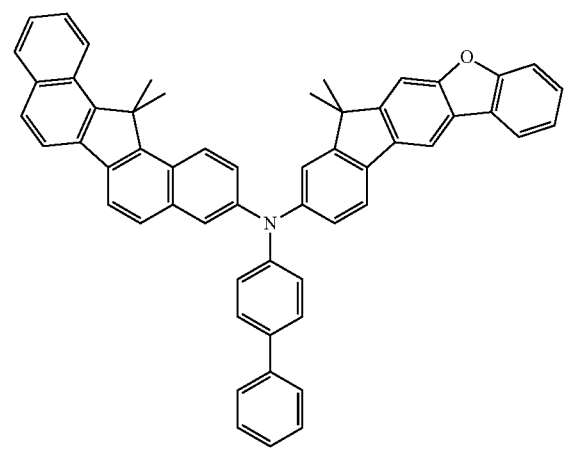
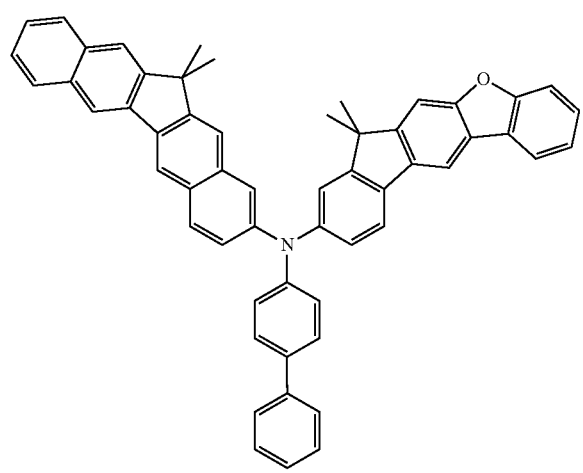

111
-continued
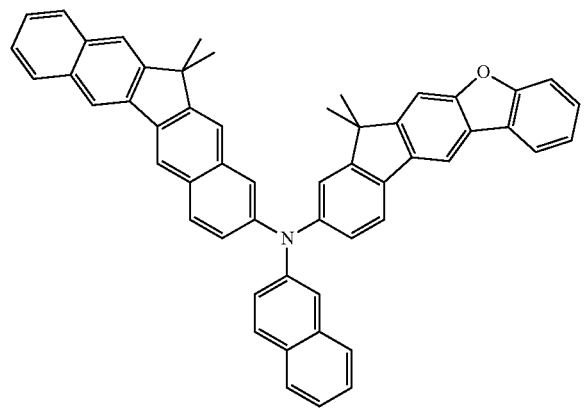
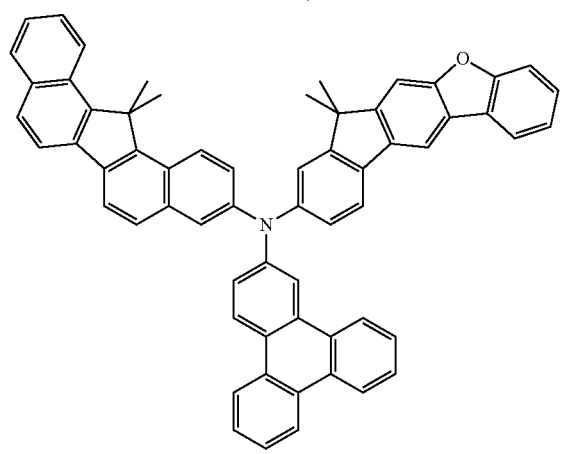
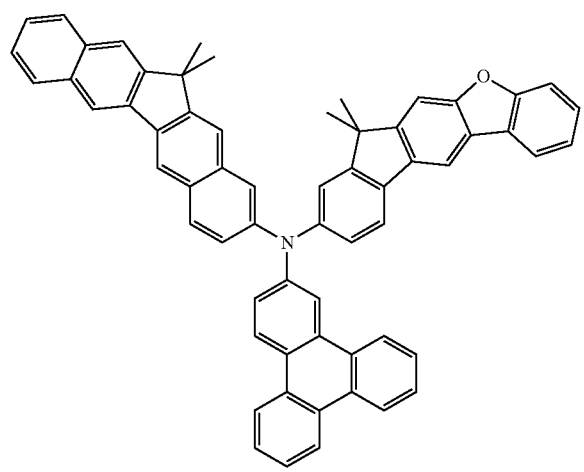
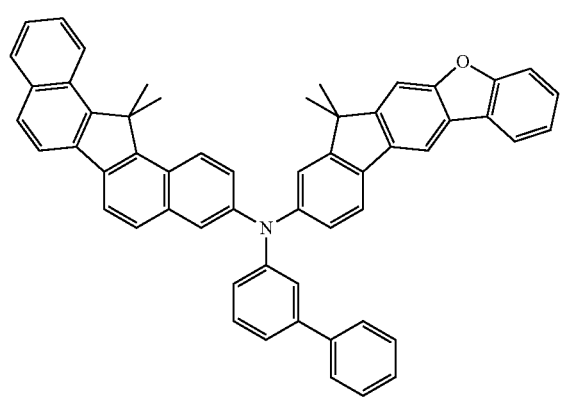
112
-continued
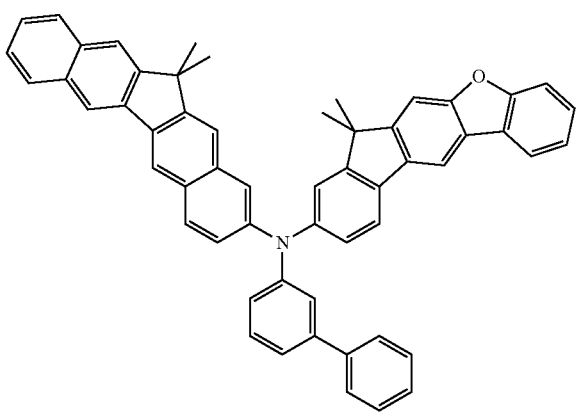
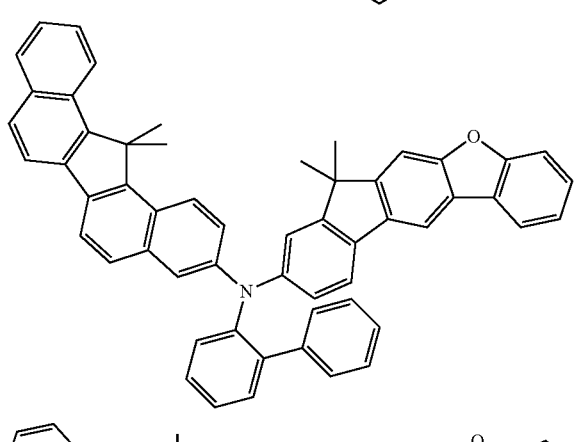
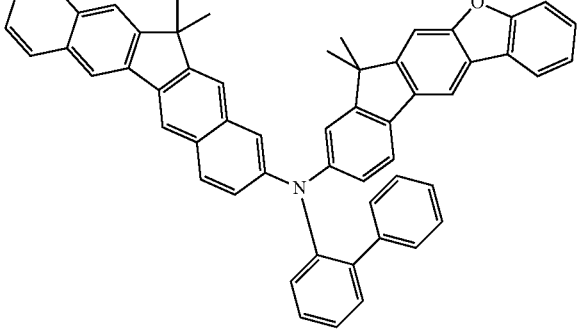

113
-continued
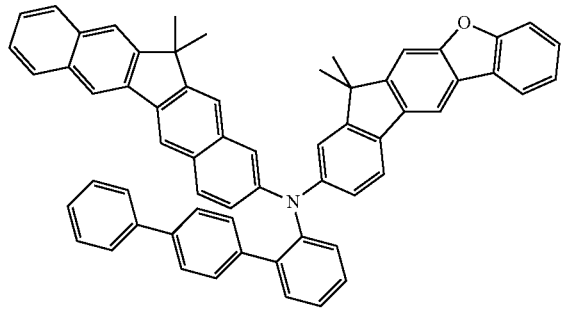
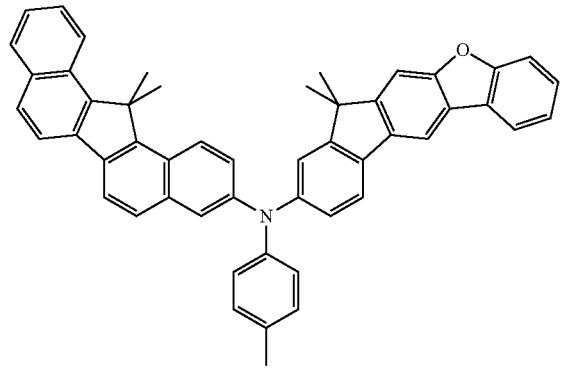
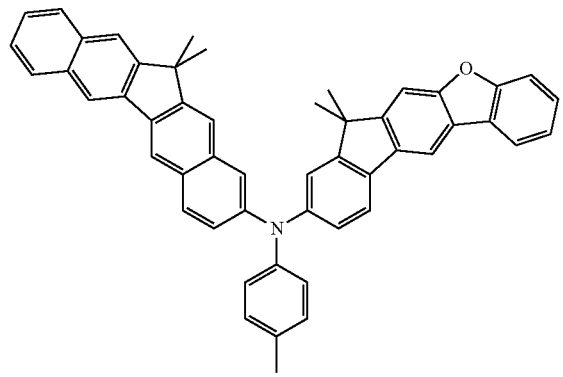
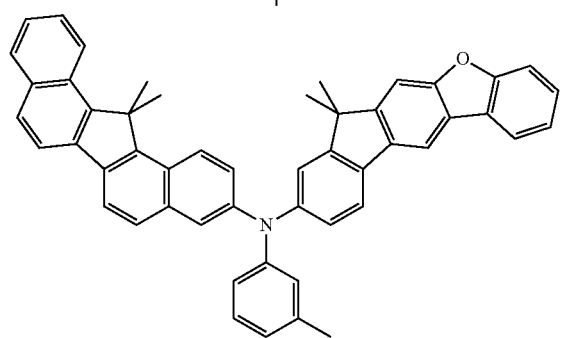
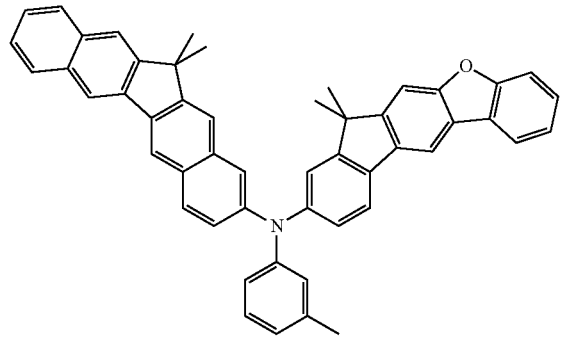
114
-continued
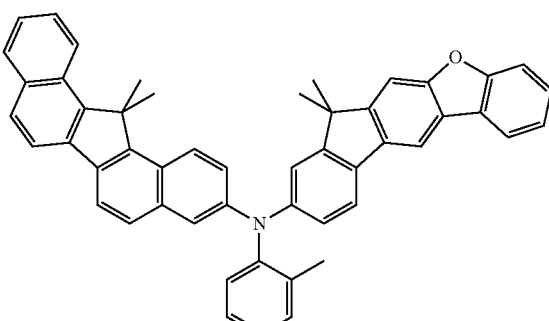
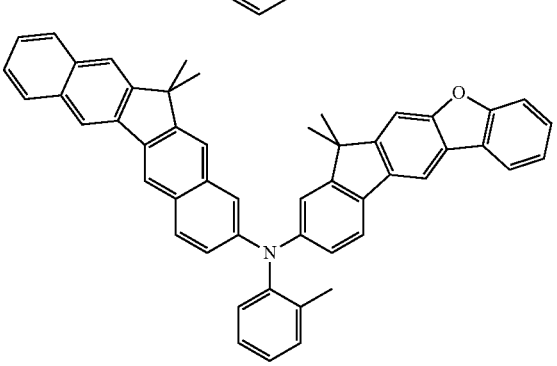
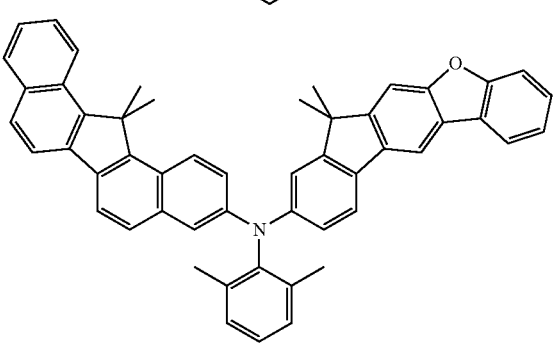
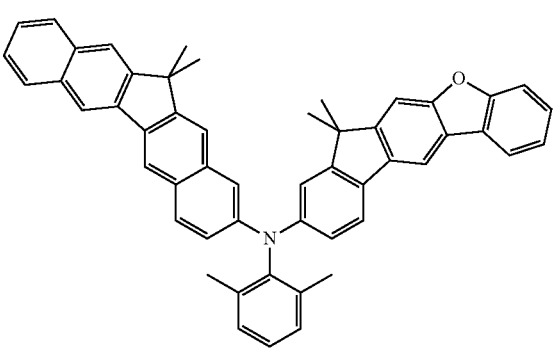
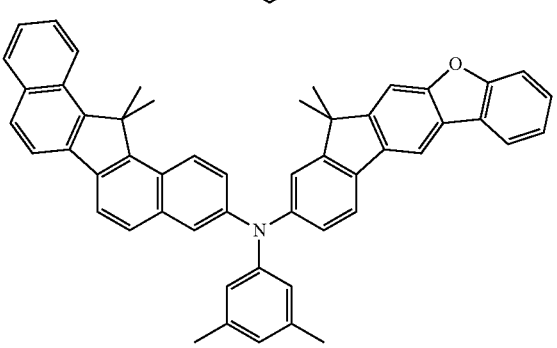

115
-continued
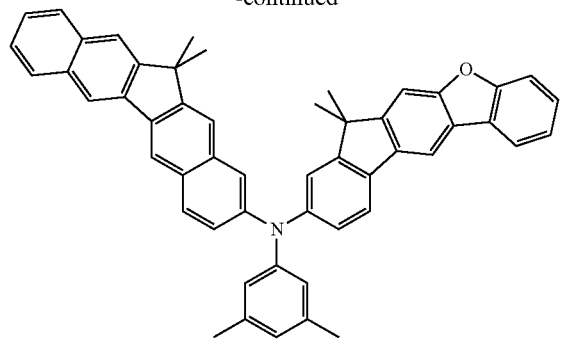
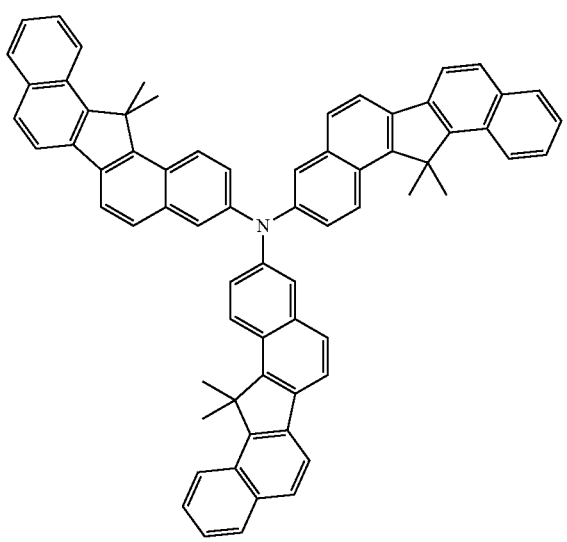
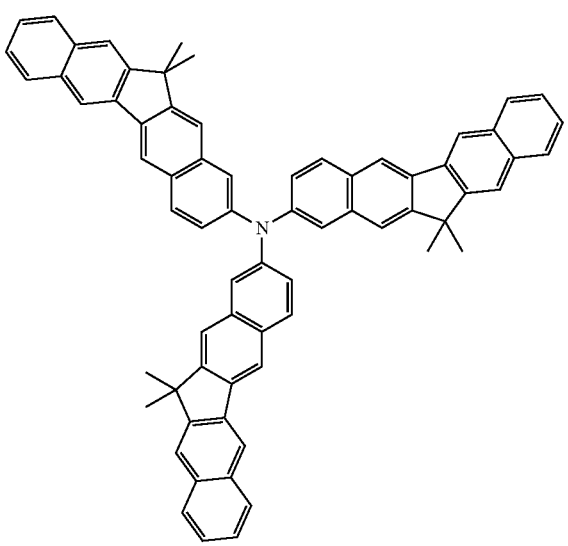
116
-continued
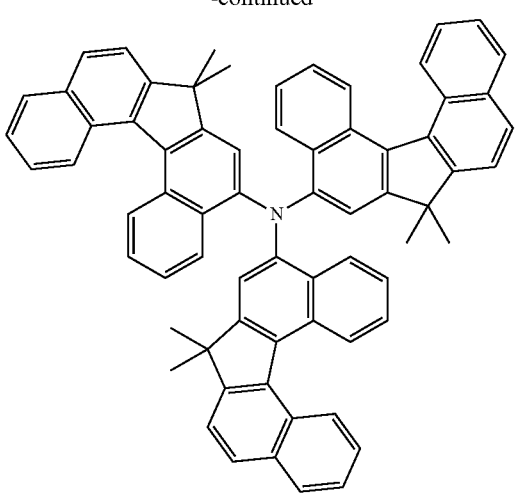
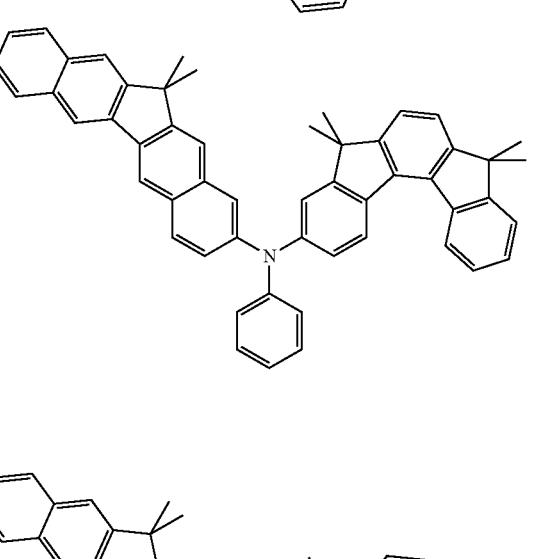
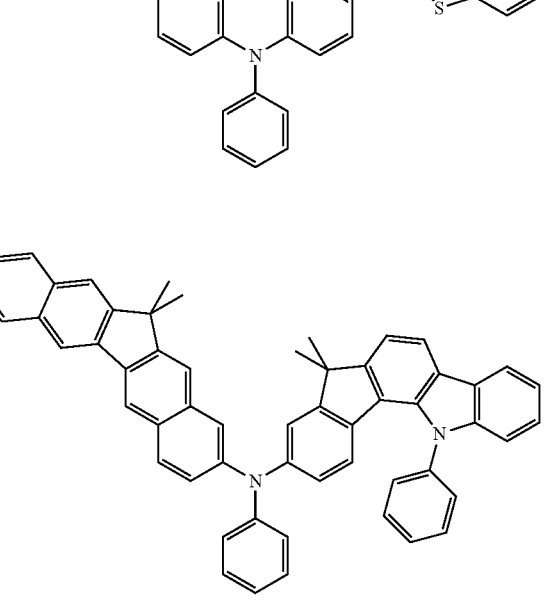

117
-continued
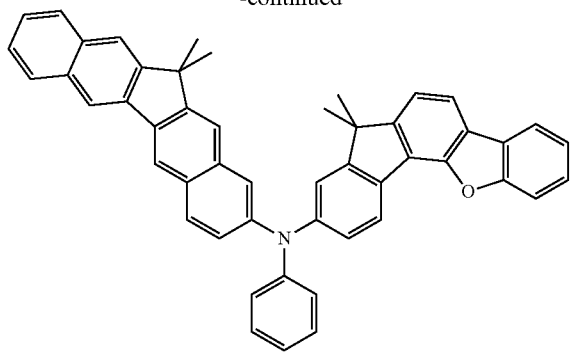
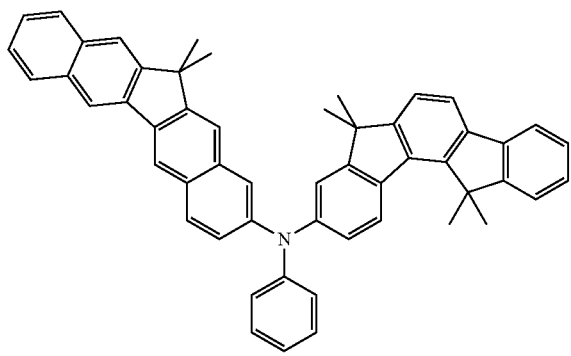
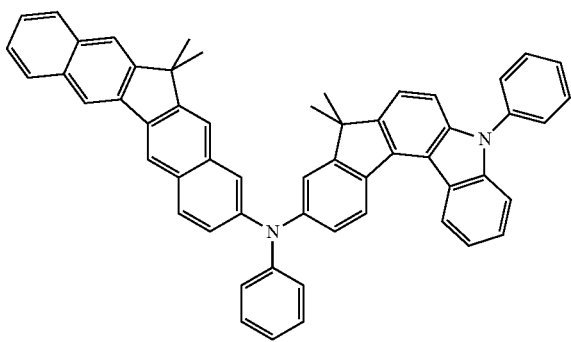
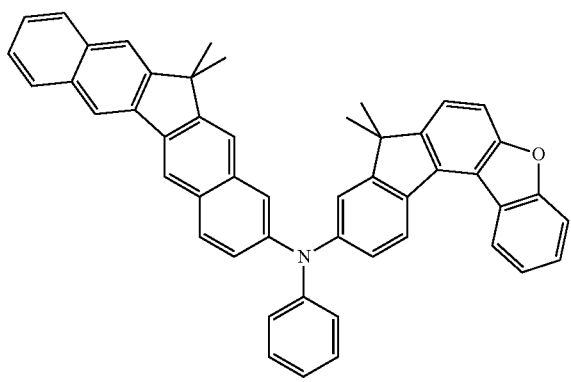
118
-continued
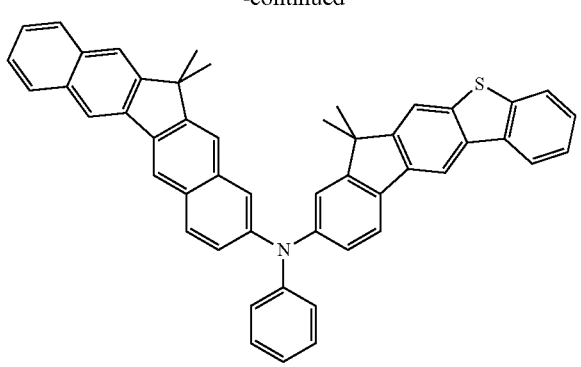
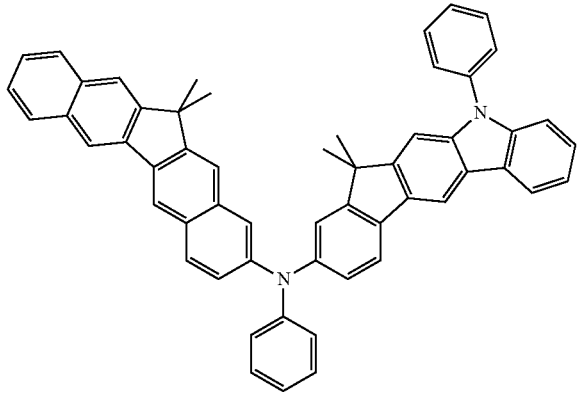
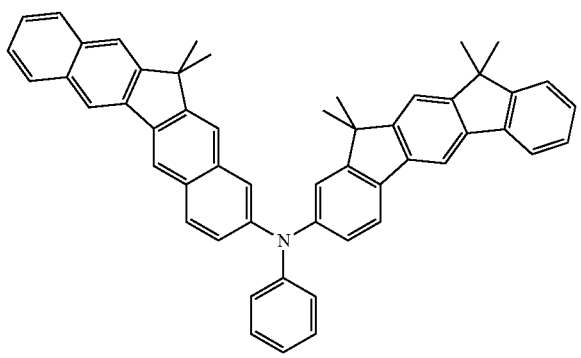
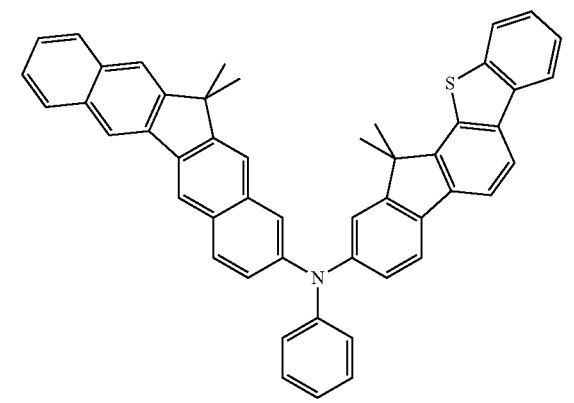

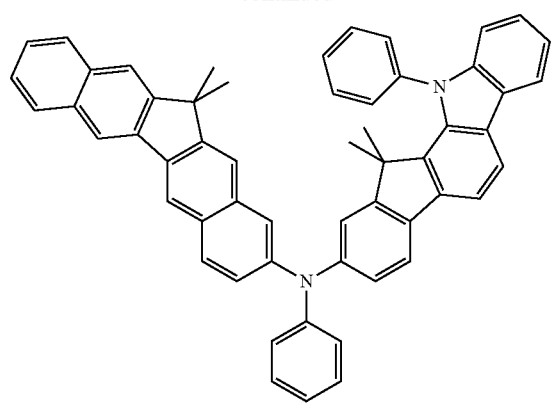
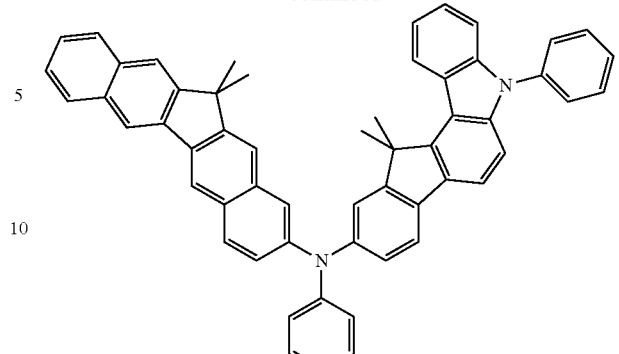
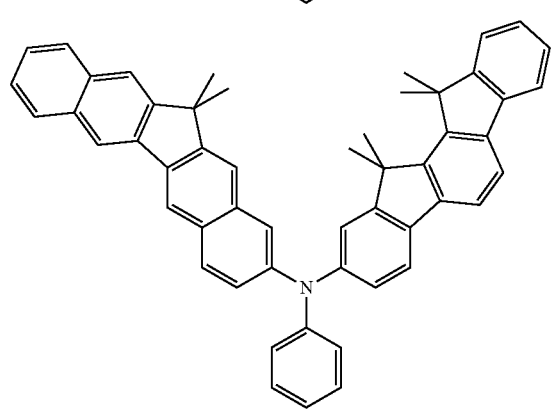
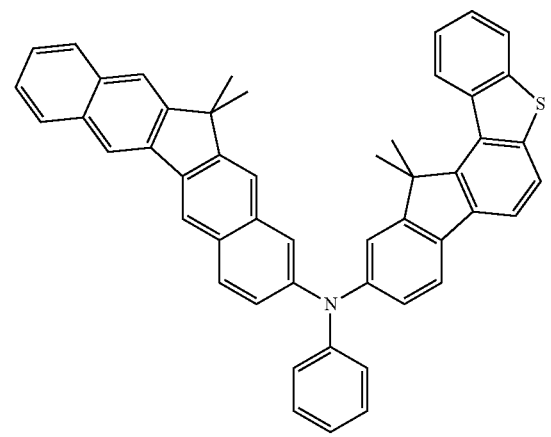
Organic Electroluminescence Device
The organic EL device in an aspect of the invention will be described below.

The organic EL device comprises at least one of organic thin film layer between a cathode and an anode. The at least one of organic thin film layer comprise a light emitting layer, and at least one layer of the at least one of organic thin film layer comprises the compound represented by formula (1) (compound (1)).

Examples of the organic thin film layer which comprises the compound (1) include an anode-side organic thin film layer formed between an anode and a light emitting layer (hole transporting layer, hole injecting layer, etc.), a light emitting layer, a cathode-side organic thin film layer formed between a cathode and a light emitting layer (electron transporting layer, electron injecting layer, etc.), a space layer, and a blocking layer, although not limited thereto. The compound (1) is usable as, for example, a host material or a dopant material for use in a light emitting layer of a fluorescent emission unit, a host material for use in a light emitting layer of a phosphorescent emission unit, and a hole transporting layer material or an electron transporting layer material in an emission unit, and preferably usable as a host material or a dopant material for use in a light emitting layer of a fluorescent emission unit, a host material for use in a light emitting layer of a phosphorescent emission unit, and a hole transporting layer material in an emission unit.

The organic EL device in an aspect of the invention may be any of a fluorescent or phosphorescent single color emitting device, a white-emitting device of fluorescent-phosphorescent hybrid type, a simple-type emitting device having a single emission unit, and a tandem emitting device having two or more emission units, with a fluorescent device being preferred. The "emission unit" referred to herein is the smallest unit for emitting light by the recombination of injected holes and injected electrons, which comprises one or more organic thin film layers wherein at least one layer is a light emitting layer.

Representative device structures of the simple-type organic EL device are shown below:
(1) Anode/Emission Unit/Cathode The emission unit may be a laminated unit comprising two or more layers selected from a phosphorescent light emitting layer and a fluorescent light emitting layer. A space layer may be disposed between the light emitting layers to prevent the diffusion of excitons generated in the phosphorescent light emitting layer into the fluorescent light emitting layer. Representative layered structures of the simple-type emission unit are shown below:
(a) hole transporting layer/fluorescent emitting layer (/electron transporting layer);
(b) hole transporting layer/first fluorescent emitting layer/second fluorescent emitting layer (/electron transporting layer);
(c) hole transporting layer/phosphorescent emitting layer/space layer/fluorescent emitting layer (/electron transporting layer);
(d) hole transporting layer/first phosphorescent emitting layer/second phosphorescent emitting layer/space layer/fluorescent emitting layer (/electron transporting layer);
(e) hole transporting layer/first phosphorescent emitting layer/space layer/second phosphorescent emitting layer/space layer/fluorescent emitting layer (/electron transporting layer);
(f) hole transporting layer/phosphorescent emitting layer/space layer/first fluorescent emitting layer/second fluorescent emitting layer (/electron transporting layer);
(g) hole transporting layer/electron blocking layer/fluorescent emitting layer (/electron transporting layer);
(h) hole transporting layer/fluorescent emitting layer/hole blocking layer (/electron transporting layer); and
(i) hole transporting layer/fluorescent emitting layer/triplet blocking layer (/electron transporting layer).

The emission color of the fluorescent emitting layer and that of the phosphorescent emitting layer may be different. For example, the layered structure of the laminated emission unit (d) may be hole transporting layer/first phosphorescent emitting layer (red emission)/second phosphorescent emitting layer (green emission)/space layer/fluorescent emitting layer (blue emission)/electron transporting layer.

An electron blocking layer may be disposed between the light emitting layer and the hole transporting layer or between the light emitting layer and the space layer, if necessary. Also, a hole blocking layer may be disposed between the light emitting layer and the electron transporting layer, if necessary. With such an electron blocking layer or a hole blocking layer, electrons and holes are confined in the light emitting layer to increase the charge recombination in the light emitting layer, thereby improving the emission efficiency.

Representative device structure of the tandem-type organic EL device is shown below:
(2) Anode/First Emission Unit/Intermediate Layer/Second Emission Unit/Cathode.

The layered structure of the first emission unit and the second emission unit may be selected from those described above with respect to the emission unit.

Generally, the intermediate layer is also called an intermediate electrode, an intermediate conductive layer, a charge generation layer, an electron withdrawing layer, a connecting layer, or an intermediate insulating layer. The intermediate layer may be formed by known materials which can supply electrons to the first emission unit and holes to the second emission unit.

A schematic structure of an example of the organic EL device is shown in FIG. 1, wherein the organic EL device 1 comprises a substrate 2, an anode 3, a cathode 4, and an emission unit 10 disposed between the anode 3 and the cathode 4. The emission unit 10 comprises a light emitting layer 5. A hole injecting/transporting layer 6 (anode-side organic thin film layer) may be disposed between the light emitting layer 5 and the anode 3, and an electron injecting/transporting layer 7 (cathode-side organic thin film layer) may be disposed between the light emitting layer 5 and the cathode 4. An electron blocking layer (not shown) may be disposed on the side of anode 3 of the light emitting layer 5, and a hole blocking layer (not shown) may be disposed on the side of cathode 4 of the light emitting layer 5. With these blocking layers, electrons and holes are confined in the light emitting layer 5 to increase the exciton generation in the light emitting layer 5.

In the present specification, a host is referred to as a fluorescent host when combinedly used with a fluorescent dopant (fluorescent emitting material) and as a phosphorescent host when combinedly used with a phosphorescent dopant. Therefore, the fluorescent host and the phosphorescent host are not distinguished from each other merely by the difference in their molecular structures. Namely, in the present invention, the term "phosphorescent host" means a material for constituting a phosphorescent emitting layer containing a phosphorescent dopant and does not mean a material that cannot be utilized as a material for a fluorescent emitting layer. The same applies to the fluorescent host.

Substrate

The substrate is a support for the emitting device and made of, for example, glass, quartz, and plastics. The substrate may be a flexible substrate, for example, a plastic substrate made of polycarbonate, polyarylate, polyether sulfone, polypropylene, polyester, polyvinyl fluoride, and polyvinyl chloride. An inorganic deposition film is also usable.

Anode

The anode is formed on the substrate preferably from a metal, an alloy, an electrically conductive compound, and a mixture thereof, each having a large work function, for example, 4.5 eV or more. Examples of the material for the anode include indium oxide-tin oxide (ITO: indium tin oxide), indium oxide-tin oxide doped with silicon or silicon oxide, indium oxide-zinc oxide, indium oxide doped with tungsten oxide and zinc oxide, and graphene. In addition, gold (Au), platinum (Pt), nickel (Ni), tungsten (W), chromium (Cr), molybdenum (Mo), iron (Fe), cobalt (Co), copper (Cu), palladium (Pd), titanium (Ti), and a nitride of the above metal (for example, titanium nitride) are also usable.

These materials are made into a film generally by a sputtering method. For example, a film of indium oxide-zinc oxide is formed by sputtering an indium oxide target doped with 1 to 10 wt % of zinc oxide, and a film of indium oxide doped with tungsten oxide and zinc oxide is formed by sputtering an indium oxide target doped with 0.5 to 5 wt % of tungsten oxide and 0.1 to 1 wt % of zinc oxide. In addition, a vacuum vapor deposition method, a coating method, an inkjet method, and a spin coating method are usable.

A hole injecting layer to be optionally formed in contact with the anode is formed from a composite material which is capable of easily injecting holes independently of the work function of the anode. Therefore, when a hole injecting layer is provided, the anode can be formed by a various kind of material which is usable as an electrode material, for example, a metal, an alloy, an electroconductive compound, a mixture thereof, and a group 1 element and a group 2 element of the periodic table.

A material having a small work function, for example, the group 1 element and the group 2 element of the periodic table, i.e., an alkali metal, such as lithium (Li) and cesium (Cs), an alkaline earth metal, such as magnesium (Mg), calcium (Ca), and strontium (Sr), and an alloy thereof, such as MgAg and AlLi, are also usable. In addition, a rare earth metal, such as europium (Eu) and ytterbium (Yb), and an alloy thereof are also usable. The alkali metal, the alkaline earth metal, and the alloy thereof can be made into the anode by a vacuum vapor deposition or a sputtering method. When a silver paste, etc. is used, a coating method and an inkjet method are usable.

Hole Injecting Layer

The hole injecting layer comprises a highly hole injecting material. Examples of the highly hole injecting material include molybdenum oxide, titanium oxide, vanadium oxide, rhenium oxide, ruthenium oxide, chromium oxide, zirconium oxide, hafnium oxide, tantalum oxide, silver oxide, tungsten oxide, and manganese oxide.

The following low molecular aromatic amine compound is also usable: 4,4',4"-tris(N,N-diphenylamino)triphenylamine (TDATA), 4,4',4"-tris[N-(3-methylphenyl)-N-phenylamino]triphenylamine (MTDATA), 4,4'-bis[N-(4-diphenylaminophenyl)-N-phenylamino]biphenyl (DPAB), 4,4'-bis(N-({4-[N'-(3-methylphenyl)-N'-phenylamino]phenyl}-N-phenylamino)biphenyl (DNTPD), 1,3,5-tris[N-(4-diphenylaminophenyl)-N-phenylamino]benzene (DPA3B), 3-[N-(9-phenylcarbazole-3-yl)-N-phenylamino]-9-phenylcarbazole (PCzPCA1), 3,6-bis[N-(9-phenylcarbazole-3-yl)-N-phenylamino]-9-phenylcarbazole (PCzPCA2), and 3-[N-(1-naphthyl)-N-(9-phenylcarbazole-3-yl)amino]-9-phenylcarbazole (PCzPCN1).

A macromolecular compound, such as an oligomer, a dendrimer, a polymer, is also usable. Examples thereof include poly(N-vinylcarbazole) (PVK), poly(4-vinyltriphenylamine) (PVTPA), poly[N-(4-{N'-[4-(4-diphenylamino)phenyl]phenyl-N'-phenylamino}phenyl)methacrylamide] (PTPDMA), and poly[N,N'-bis(4-butylphenyl)-N,N'-bis(phenyl)benzidine] (Poly-TPD). An acid-added macromolecular compound, such as poly(3,4-ethylenedioxythiophene)/poly(styrenesulfonic acid) (PEDOT/PSS) and polyaniline/poly(styrenesulfonic acid) (PAni/PSS), is also usable.

Hole Transporting Layer

The hole transporting layer comprises a highly hole-transporting material. The hole transporting layer may contain an aromatic amine compound, a carbazole derivative, an anthracene derivative, etc., for examples, an aromatic amine compound, such as 4,4'-bis[N-(1-naphthyl)-N-phenylamino] biphenyl (NPB), N,N'-bis(3-methylphenyl)-N,N'-diphenyl-[1,1'-biphenyl]-4,4'-diamine (TPD), 4-phenyl-4'-(9-phenylfluorene-9-yl)triphenylamine (BAFLP), 4,4'-bis[N-(9,9-dimethylfluorene-2-yl)-N-phenylamino]biphenyl (DFLDPBi), 4,4',4"-tris(N,N-diphenylamino)triphenylamine (TDATA), 4,4',4"-tris[N-(3-methylphenyl)-N-phenylamino]triphenylamine (MTDATA), and 4,4'-bis[N-(spiro-9,9'-bifluorene-2-yl)-N-phenylamino]biphenyl (BSPB). The above compounds have a hole mobility of mainly $10^{-6}$ cm$^2$/Vs or more.

The hole transporting layer may comprise a carbazole derivative, such as 4,4'-di(9-carbazolyl)biphenyl (CBP), 9-[4-(9-carbazolyl)phenyl]-10-phenylanthracene (CzPA), and 9-phenyl-3-[4-(10-phenyl-9-anthryl)phenyl]-9H-carbazole (PCzPA); an anthracene derivative, such as 2-t-butyl-9,10-di(2-naphthyl)anthracene (t-BuDNA), 9,10-di(2-naphthyl)anthracene (DNA), and 9,10-diphenylanthracene (DPAnth); and a macromolecular compound, such as poly (N-vinylcarbazole) (PVK) and poly(4-vinyltriphenylamine) (PVTPA).

Other materials are also usable if their hole transporting ability is higher than their electron transporting ability. The layer comprising a highly hole-transporting material may be a single layer or a laminate of two or more layers each comprising the material mentioned above.

Dopant Material of Light Emitting Layer

The light emitting layer comprises a highly light-emitting material and may be formed from a various kind of materials. For example, a fluorescent emitting compound and a phosphorescent emitting compound are usable as the highly light-emitting material. The fluorescent emitting compound is a compound capable of emitting light from a singlet excited state, and the phosphorescent emitting compound is a compound capable of emitting light from a triplet excited state.

In an embodiment of the invention, at least one light emitting layer of the organic EL device preferably comprises the compound (1), more preferably as a fluorescent dopant material. The following light emitting materials (dopant materials) other than the compound (1) are also usable in the light emitting layer.

Examples of blue fluorescent emitting material for use in the light emitting layer include a pyrene derivative, a styrylamine derivative, a chrysene derivative, a fluoranthene derivative, a fluorene derivative, a diamine derivative, and a triarylamine derivative, such as N,N'-bis[4-(9H-carbazole-9-yl)phenyl]-N,N'-diphenylstilbene-4,4'-diamine (YGA2S), 4-(9H-carbazole-9-yl)-4'-(10-phenyl-9-anthryl)triphenylamine (YGAPA), and 4-(10-phenyl-9-anthryl)-4'-(9-phenyl-9H-carb azole-3-yl)triphenylamine (PCBAPA).

Examples of green fluorescent emitting material for use in the light emitting layer include an aromatic amine derivative, such as N-(9,10-diphenyl-2-anthryl)-N,9-diphenyl-9H-carbazole-3-amine (2PCAPA), N-[9,10-bis(1,1'-biphenyl-2-yl)-2-anthryl]-N,9-diphenyl-9H-carbazole-3-amine (2PCABPhA), N-(9,10-diphenyl-2-anthryl)-N,N',N'-triphenyl-1,4-phenylenediamine (2DPAPA), N-[9,10-bis(1,1'-biphenyl-2-yl)-2-anthryl]-N,N',N'-triphenyl-1,4-phenylenediamine (2DPABPhA), N-[9,10-bis(1,1'-biphenyl-2-yl)]-N-[4-(9H-carbazole-9-yl)phenyl]-N-phenylanthracene-2-amine (2YGABPhA), and N,N,9-triphenylanthracene-9-amine (DPhAPhA).

Examples of red fluorescent emitting material for use in the light emitting layer include a tetracene derivative and a diamine derivative, such as N,N,N',N'-tetrakis(4-methylphenyl)tetracene-5,11-diamine (p-mPhTD) and 7,14-diphenyl-N,N,N',N'-tetrakis(4-methylphenyl)acenaphtho[1,2-a]fluoranthene-3,10-diamine (p-mPhAFD).

Examples of blue phosphorescent emitting material for use in the light emitting layer include a metal complex, such as an iridium complex, an osmium complex, and a platinum complex. Examples thereof include bis[2-(4',6'-difluorophenyl)pyridinato-N,C2']iridium(III) tetrakis(1-pyrazolyl)borato (FIr$_6$), bis[2-(4',6'-difluorophenyl)pyridinato-N,C2']iridium(III) picolinato (FIrpic), bis[2-(3',5'-bistrifluoromethylphenyl)pyridinato-N,C2']iridium(III) picolinato (Ir(CF$_3$ppy)$_2$(pic)), and bis[2-(4',6'-difluorophenyl)pyridinato-N,C2']iridium(III) acetylacetonato (FIracac).

Examples of green phosphorescent emitting material for use in the light emitting layer include an iridium complex, such as tris(2-phenylpyridinato-N,C2'(Ir(ppy)$_3$), bis(2-phenylpyridinato-N,C2')iridium(III) acetylacetonato (Ir(ppy)$_2$(acac)), bis(1,2-diphenyl-1H-benzimidazolato)iridium(III) acetylacetonato (Ir(pbi)$_2$(acac)), and bis(benzo[h]quinolinato)iridium(III) acetylacetonato (Ir(bzq)$_2$(acac)).

Examples of red phosphorescent emitting material for use in the light emitting layer include a metal complex, such as an iridium complex, a platinum complex, a terbium complex, and a europium complex. Examples thereof include an organometallic complex, such as bis[2-(2'-benzo[4,5-α]thienyl)pyridinato-N,C3']iridium(III) acetylacetonato (Ir(btp)$_2$(acac)), bis(1-phenylisoquinolinato-N,C2')iridium(III) acetylacetonato (Ir(piq)$_2$(acac)), (acetylacetonato)bis[2,3-bis(4-fluorophenyl)quinoxalinato]iridium(III) (Ir(Fdpq)$_2$(acac)), and 2,3,7,8,12,13,17,18-octaethyl-21H,23H-porphyrin platinum(II) (PtOEP).

A rare earth metal complex, such as tris(acetylacetonato)(monophenanthroline)terbium(III) (Tb(acac)$_3$(Phen)), tris(1,3-diphenyl-1,3-propanedionato)(monophenanthroline)europium(III) (Eu(DBM)$_3$(Phen)), and tris[1-(2-thenoyl)-3,3,3-trifluoroacetonato](monophenanthroline)europium(III) (Eu(TTA)$_3$(Phen)), emits light from the rare earth metal ion (electron transition between different multiple states), and therefore, usable as a phosphorescent emitting compound.

Host Material for Light Emitting Layer

The light emitting layer may be formed by dispersing the highly light-emitting material (dopant material) mentioned above in another material (host material). The host material may be selected from various kinds of materials and is preferably a material having a lowest unoccupied molecular orbital level (LUMO level) higher than that of the dopant material and a highest occupied molecular orbital level (HOMO level) lower than that of the dopant material.

The host material may include, for example, (1) a metal complex, such as an aluminum complex, a beryllium complex, and a zinc complex; (2) a heterocyclic compound, such as an oxadiazole derivative, a benzimidazole derivative, and a phenanthroline derivative; (3) a fused aromatic compound, such as a carbazole derivative, an anthracene derivative, a phenanthrene derivative, a pyrene derivative, and a chrysene derivative; and (4) an aromatic amine compound, such as a triarylamine derivative and a fused aromatic polycyclic amine derivative.

Examples thereof include a metal complex, such as tris(8-quinolinolato)aluminum(III) (Alq), tris(4-methyl-8-quinolinolato)aluminum(III) (Almq$_3$), bis(10-hydroxybenzo[h]quinolinato)beryllium(II) (BeBq$_2$), bis(2-methyl-8-quinolinolato)(4-phenylphenolato)aluminum(III) (BAlq), bis(8-quinolinolato)zinc(II) (Znq), bis[2-(2-benzoxazolyl)phenolato]zinc(II) (ZnPBO), and bis[2-(2-benzothiazolyl)phenolato]zinc(II) (ZnBTZ); a heterocyclic compound, such as 2-(4-biphenylyl)-5-(4-tert-butylphenyl)-1,3,4-oxadiazole (PBD), 1,3-bis[5-(p-tert-butylphenyl)-1,3,4-oxadiazole-2-yl]benzene (OXD-7), 3-(4-biphenylyl)-4-phenyl-5-(4-tert-butylphenyl)-1,2,4-triazole (TAZ), 2,2',2"-(1,3,5-benzenetriyl)tris(1-phenyl-1H-benzimidazole) (TPBI), bathophenanthroline (BPhen), and bathocuproin (BCP); a fused aromatic compound, such as 9-[4-(10-phenyl-9-anthryl)phenyl]-9H-carbazole (CzPA), 3,6-diphenyl-9-[4-(10-phenyl-9-anthryl)phenyl]-9H-carbazole (DPCzPA), 9,10-bis(3,5-diphenylphenyl)anthracene (DPPA), 9,10-di(2-naphthyl)anthracene (DNA), 2-tert-butyl-9,10-di(2-naphthyl)anthracene (t-BuDNA), 9,9'-bianthryl (BANT), 9,9'-(stilbene-3,3'-diyl)diphenanthrene (DPNS), 9,9'-(stilbene-4,4'-diyl)diphenanthrene (DPNS2), 3,3',3"-(benzene-1,3,5-triyl)tripyrene (TPB3), 9,10-diphenylanthracene (DPAnth), and 6,12-dimethoxy-5,11-diphenylchrysene; and an aromatic amine compound, such as N,N-diphenyl-9-[4-(10-phenyl-9-anthryl)phenyl]-9H-carbazole-3-amine (CzA1PA), 4-(10-phenyl-9-anthryl)triphenylamine (DPhPA), N,9-diphenyl-N-[4-(10-phenyl-9-anthryl)phenyl]-9H-carbazole-3-amine (PCAPA), N,9-diphenyl-N-{4-[4-(10-phenyl-9-anthryl)phenyl]phenyl}-9H-carbazole-3-amine (PCAPBA), N-(9,10-diphenyl-2-anthryl)-N,9-diphenyl-9H-carbazole-3-amine (2PCAPA), 4,4'-bis[N-(1-anthryl)-N-phenylamino]biphenyl (NPB or α-NPD), N,N'-bis(3-methylphenyl)-N,N'-diphenyl-[1,1'-biphenyl]-4,4'-diamine (TPD), 4,4'-bis[N-(9,9-dim-ethylfluorene-2-yl)-N-phenylamino]biphenyl (DFLDPBi), and 4,4'-bis[N-(spiro-9,9'-bifluorene-2-yl)-N-phenylamino]biphenyl (BSPB). The host material may be used alone or in combination of tow or more.

Electron Transporting Layer

The electron transporting layer comprises a highly electron-transporting material, for example, (1) a metal complex, such as an aluminum complex, a beryllium complex, and a zinc complex; (2) a heteroaromatic compound, such as an imidazole derivative, a benzimidazole derivative, an azine derivative, a carbazole derivative, and a phenanthroline derivative; and (3) a macromolecular compound. Examples of the metal complex include tris(8-quinolinolato)aluminum (III) (Alq), tris(4-methyl-8-quinolinolato)aluminum (Almq$_3$), bis(10-hydroxybenzo[h]quinolinato)beryllium (BeBq$_2$), bis(2-methyl-8-quinolinato)(4-phenylphenolato)aluminum (III)(BAlq), bis(8-quinolinato)zinc(II) (Znq), bis[2-(2-benzoxazolyl)phenolato]zinc (II) (ZnPBO), and bis[2-(2-benzothiazolyl)phenolato]zinc (II)(ZnBTZ). Examples of the heteroaromatic compound include 2-(4-biphenylyl)-5-(4-tert-butylphenyl)-1,3,4-oxadiazole (PBD), 1,3-bis[5-(ptert-butylphenyl)-1,3,4-oxadiazole-2-yl]benzene (OXD-7), 3-(4-tert-butylphenyl)-4-phenyl-5-(4-biphenylyl)-1,2,4-triazole (TAZ), 3-(4-tert-butylphenyl)-4-(4-ethylphenyl)-5-(4-biphenylyl)-1,2,4-triazole (p-EtTAZ), bathophenanthroline (BPhen), bathocuproine (BCP), and 4,4'-bis(5-methylbenzoxazole-2-yl)stilbene (BzOs). The above compounds have an electron mobility of mainly $10^{-6}$ cm$^2$/Vs or more. Examples of the macromolecular compound include poly[(9,9-dihexylfluorene-2,7-diyl)-co-(pyridine-3,5-diyl)] (PF-Py), and poly[(9,9-dioctylfluorene-2,7-diyl)-co-(2,2'-bipyridine-6,6'-diyl)] (PF-BPy).

Other materials are also usable in the electron transporting layer if their electron transporting ability is higher than their hole transporting ability. The electron transporting layer may be a single layer or a laminate of two or more layers each comprising the material mentioned above.

Electron Injecting Layer

The electron injecting layer comprises a highly electron-injecting material, for example, an alkali metal, an alkaline earth metal, and a compound of these metals, such as lithium (Li), cesium (Cs), calcium (Ca), lithium fluoride (LiF), cesium fluoride (CsF), calcium fluoride (CaF2), and lithium oxide (LiOx). In addition, an electron transporting material which is doped with an alkali metal, an alkaline earth metal or a compound thereof, for example, Alq doped with magnesium (Mg), is also usable. By using such a material, electrons are efficiently injected from the cathode.

A composite material obtained by mixing an organic compound and an electron donor is also usable in the electron injecting layer. Such a composite material is excellent in the electron injecting ability and the electron transporting ability, because the organic compound receives electrons from the electron donor. The organic compound is preferably a material excellent in transporting the received electrons. Examples thereof are the materials for the electron transporting layer mentioned above, such as the metal complex and the aromatic heterocyclic compound. Any material capable of giving its electron to another organic compound is usable as the electron donor. Preferred examples thereof are an alkali metal, an alkaline earth metal, and a rare earth metal, such as lithium, cesium, magnesium, calcium, erbium, and ytterbium; an alkali metal oxide and an alkaline earth metal oxide, such as, lithium oxide, calcium oxide, and barium oxide; a Lewis base, such as magnesium oxide; and an organic compound, such as tetrathiafulvalene (TTF).

Cathode

The cathode is formed preferably from a metal, an alloy, an electrically conductive compound, or a mixture thereof, each having a small work function, for example, a work function of 3.8 eV or less. Examples of the material for the cathode include a metal of the group 1 or 2 of the periodic table, for example, an alkali metal, such as lithium (Li) and cesium (Cs), an alkaline earth metal, such as magnesium (Mg), an alloy containing these metals (for example, MgAg and AlLi), a rare earth metal, such as europium (Eu) and ytterbium (Yb), and an alloy containing a rare earth metal.

The alkali metal, the alkaline earth metal, and the alloy thereof can be made into the cathode by a vacuum vapor deposition or a sputtering method. When a silver paste, etc. is used, a coating method and an inkjet method are usable.

When the electron injecting layer is formed, the material for the cathode can be selected independently from the work function and various electroconductive materials, such as Al, Ag, ITO, graphene, and indium oxide-tin oxide doped with silicon or silicon oxide, are usable. These electroconductive materials are made into films by a sputtering method, an inkjet method, and a spin coating method.

Each layer of the organic EL device in an aspect of the invention can be formed by a known method, such as a vapor deposition method and a coating method. For example, each layer can be formed by a known vapor deposition method, such as a vacuum vapor deposition method and a molecular beam evaporation method (MBE method), and a known coating method using a solution of the compound for forming the layer, such as a dipping method, a spin coating method, a casting method, a bar coating method, and a roll coating method.

The thickness of each organic thin film layer is not particularly limited and preferably several nanometers to 1 µm, because an excessively small thickness may cause defects such as pin holes and an excessively large thickness may require a high driving voltage.

In an aspect of the invention, the organic electroluminescence device can be used in an electronic device, for example, as display parts, such as organic EL panel module, display devices of television sets, mobile phones, personal computer, etc., and light emitting sources of lighting equipment and vehicle lighting equipment.

EXAMPLES

The invention will be described in more detail with reference to the examples and comparative examples. It should be noted that the scope of the invention is not limited to the following examples.

Synthesis Example 1: Synthesis of Intermediate 2

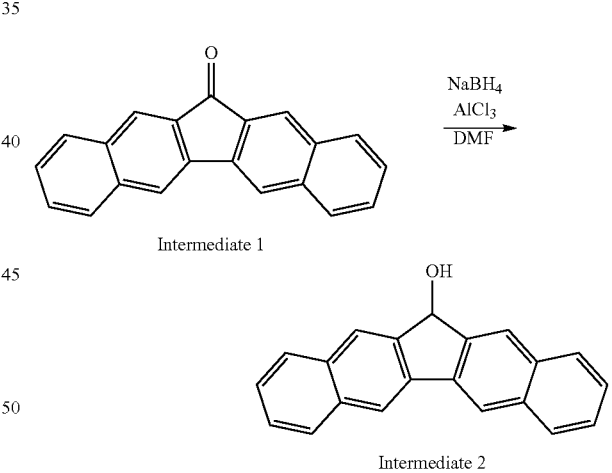

The intermediate 1 (24 g) synthesized by the method described in JP 2009-057323A was dissolved in dimethylformamide (500 mL), and sodium borohydride (12 g) and aluminum chloride (40 g) were added to the resultant solution little by little under cooling with ice. After stirring the mixture at room temperature for 2 h, a 1 M aqueous solution of sodium hydroxide was added under cooling with ice. The obtained mixture was filtered through Celite. The filtrate was washed with a saturated brine and then extracted with dichloromethane. The solvent was evaporated off under reduced pressure. The obtained residue was purified by a silica gel column chromatography to obtain the intermediate 2 (21.4 g, 89% yield).

Synthesis Example 2: Synthesis of Intermediate 3

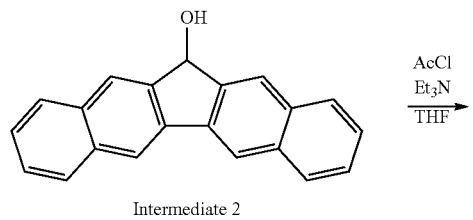

Intermediate 2

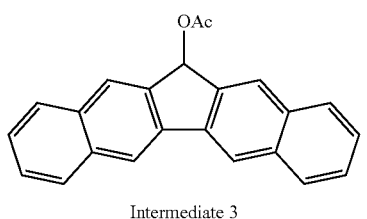

Intermediate 3

The intermediate 2 (21 g) obtained in Synthesis Example 2 was dissolved in tetrahydrofuran (500 mL), and triethylamine (18 g) was added to the resultant solution. The obtained mixture was stirred for 2 h while adding acetyl chloride (16 g) dropwise under cooling with ice. After adding water under cooling with ice, the mixture was washed with a saturated brine and then extracted with dichloromethane. The solvent was evaporated off under reduced pressure. The obtained residue was purified by a silica gel column chromatography to obtain the intermediate 3 (21.7 g, 90% yield).

Synthesis Example 3: Synthesis of Intermediate 4

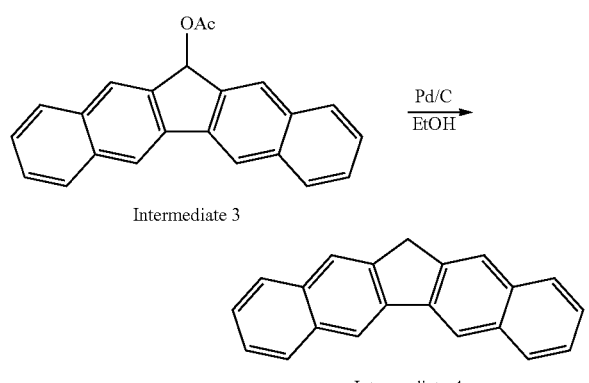

Under argon atmosphere, the intermediate 3 (21 g) obtained in Synthesis Example 2 was dissolved in ethanol (1 L), and a 10% palladium/carbon (10 g) was added to the resultant solution. After replacing the atmosphere with hydrogen gas, the mixture was vigorously stirred at room temperature for 8 h. The reaction mixture was filtered through Celite and the solvent was evaporated off under reduced pressure. The obtained residue was purified by a silica gel column chromatography to obtain the intermediate 4 (11.9 g, 69% yield).

Synthesis Example 4: Synthesis of Intermediate 5

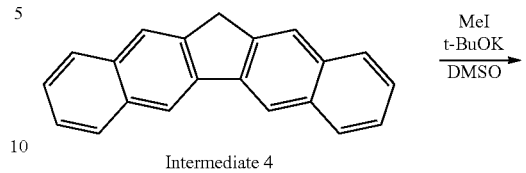

Intermediate 4

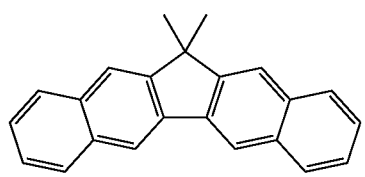

Intermediate 5

The intermediate 4 (11 g) obtained in Synthesis Example 3 was dissolved in dimethylsulfoxide (500 mL). After adding potassium t-butoxide (28 g) to the resultant solution under cooling with ice, methyl iodide (36 g) was added dropwise. After stirring at room temperature for 6 h, an aqueous solution of ammonium chloride was added under cooling with ice. The obtained mixture was extracted with dichloromethane and the solvent was evaporated off under reduced pressure. The obtained residue was purified by a silica gel column chromatography to obtain the intermediate 5 (8.8 g, 72% yield).

Synthesis Example 5: Synthesis of Intermediate 6

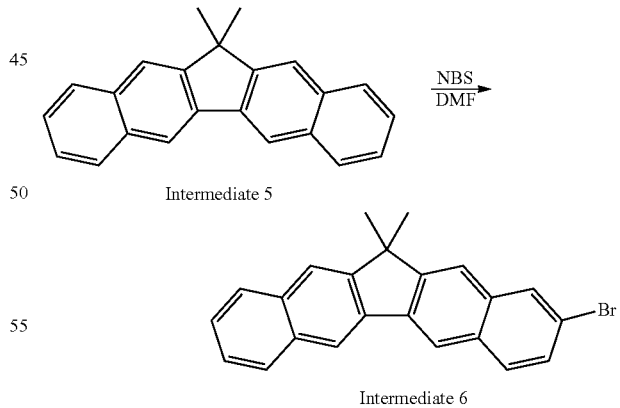

The intermediate 5 (150 mg) obtained in Synthesis Example 4 was dissolved in dimethylformamide (15 mL), and N-bromosuccinimide (181 mg) was added to the resultant solution at room temperature. After stirring at room temperature for one hour, the residue was purified by a silica gel column chromatography to obtain the intermediate 6 (146 mg, 77% yield).

Synthesis Example 6: Synthesis of Intermediate 10

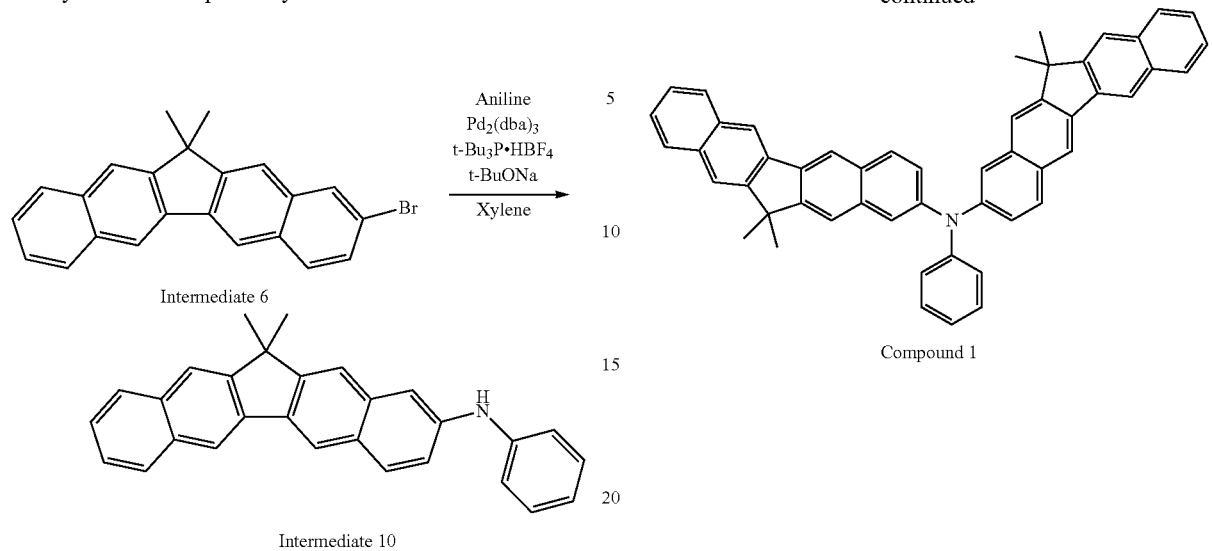

Under argon atmosphere, a mixture of aniline (27.3 L), the intermediate 6 (56.0 mg), tris(dibenzylideneacetone)dipalladium(0) (11.0 mg), tri-t-butylphosphonium tetrafluoroborate (7.0 mg), and sodium t-butoxide (43.3 mg) in dehydrated xylene (1 mL) was stirred for 9 h while refluxing under heating. After cooling to room temperature, the solvent was evaporated off. The obtained residue was purified by a silica gel column chromatography to obtain the intermediate 10 (40 mg, 70% yield).

Example 1: Synthesis of Compound 1

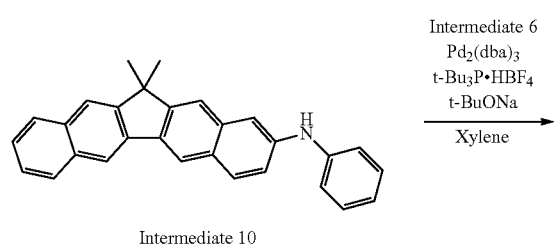

Under argon atmosphere, a mixture of the intermediate 6 (40 mg), the intermediate 10 (42.9 mg), tris(dibenzylideneacetone)dipalladium(0) (5.50 mg), tri-t-butylphosphonium tetrafluoroborate (3.5 mg), and sodium t-butoxide (29.8 mg) in dehydrated xylene (1 mL) was stirred for 7 h while refluxing under heating. After cooling to room temperature, the solvent was evaporated off. The obtained residue was purified by a silica gel column chromatography to obtain the compound 1 as a solid (20 mg, 28% yield). The obtained compound was identified by a mass spectrography which showed m/e=677 to the molecular weight of 677.31.

Example 2: Synthesis of Compound 2

The compound 2 was synthesized according to the following scheme.

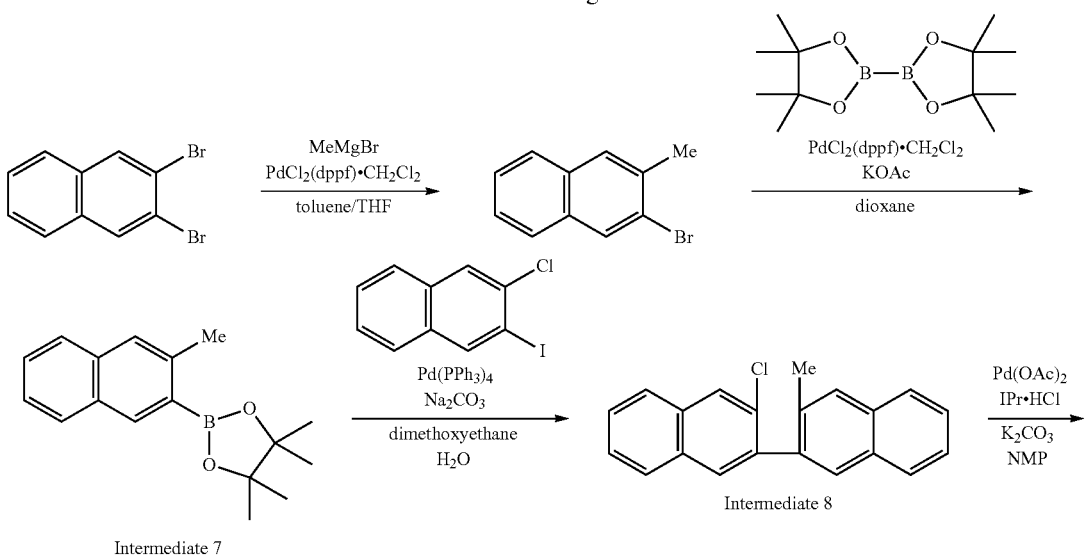

-continued

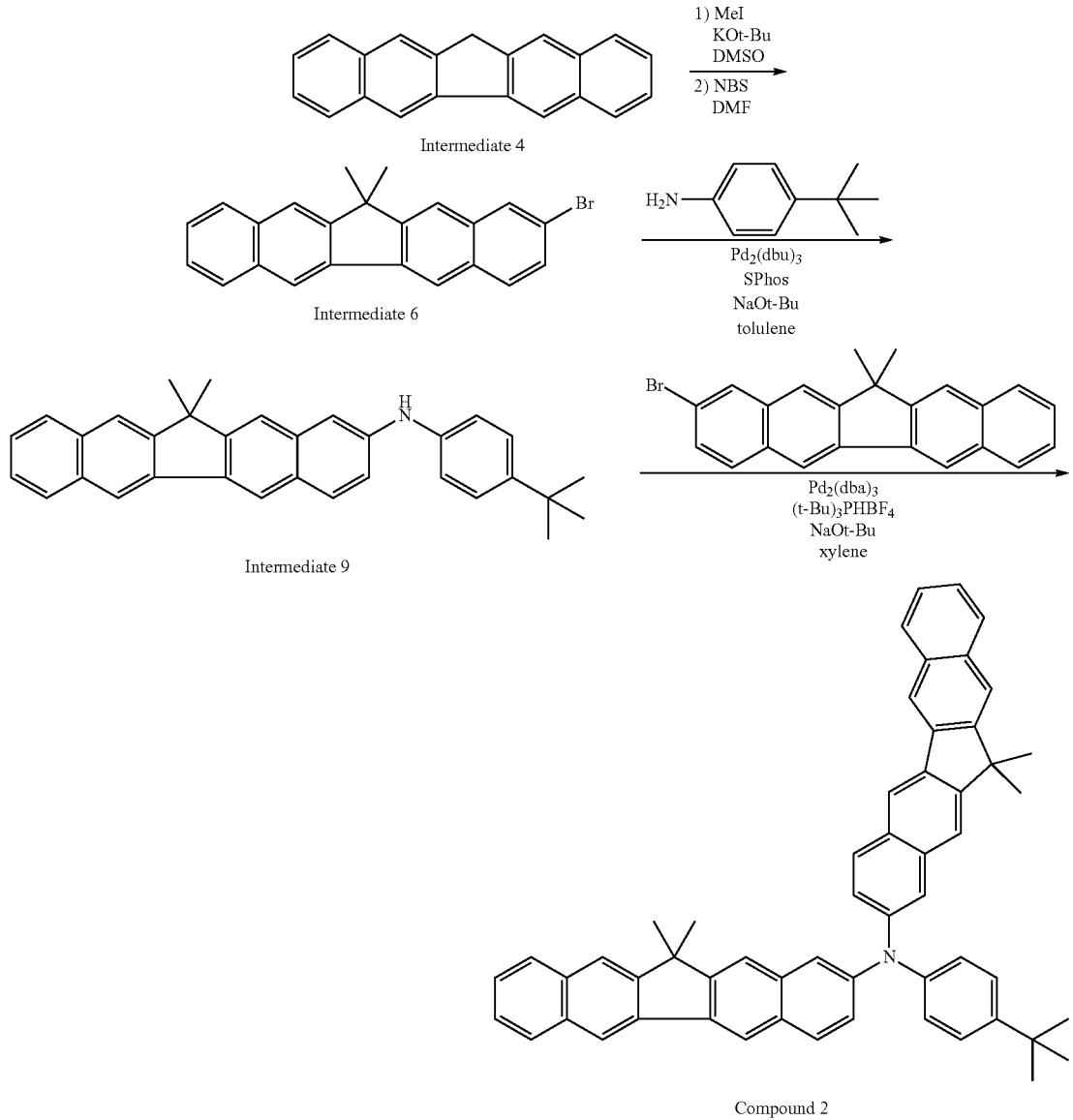

(2-1) Synthesis of 2-bromo-3-methylnaphthalene

Under argon atmosphere, 2,3-dibromonaphthalene (10.0 g), [1,1'-bis(diphenylphosphino)ferrocene]palladium(II) dichloride dichloromethane adduct (0.572 g), and toluene (300 mL) were charged in a flask. A 0.92 M tetrahydrofuran solution of methylmagnesium bromide (38 mL) was added to the resultant mixture under stirring and then the mixture was stirred for 2.5 h while refluxing under heating. After cooling to room temperature, water and ethyl acetate were added and the organic layer was collected. The organic layer was concentrated and the residue was purified by a silica gel column chromatography to obtain a white solid (6.04 g, 78% yield). The result of mass spectrometric analysis (m/e=221 to the molecular weight of 221.1) showed that the obtained compound was the target 2-bromo-3-methylnaphthalene.

(2-2) Synthesis of Intermediate 7

To 2-bromo-3-methylnaphthalene (4.00 g) in a flask, bis(pinacolato)diboron (5.5 g), [1,1'-bis(diphenylphosphino) ferrocene]palladium(II) dichloride dichloromethane adduct (0.443 g), and dioxane (90 mL) were added. Under argon atmosphere, the resultant mixture was stirred at 100° C. for 8 h under heating. After cooling to room temperature, a saturated aqueous solution of ammonium chloride and ethyl acetate were added, and the product was extracted into the organic layer. The collected organic layer was concentrated and the residue was purified by a silica gel column chromatography to obtain a white solid (3.81 g, 79% yield). The result of mass spectrometric analysis (m/e=268 to the molecular weight of 268.16) showed that the product was the target intermediate 7.

(2-3) Synthesis of Intermediate 8

Under argon atmosphere, 2-chloro-3-iodonaphthalene (2.13 g), the intermediate 7 (2.08 g), tetrakistriphenylphosphine palladium (0.17 g), sodium carbonate (2.35 g), dimethoxyethane (60 mL), and water (15 mL) were charged in a flask. The mixture was stirred at 80° C. for 7 h under heating.

After cooling to room temperature, water and ethyl acetate were added and then the organic layer was collected. The collected organic layer was concentrated and the residue was purified by a silica gel column chromatography to obtain a white solid (1.52 g, 63% yield). The result of mass spectrometric analysis (m/e=302 to the molecular weight of 302.80) showed that the product was the target intermediate 8.

(2-4) Synthesis of Intermediate 4

Under argon atmosphere, the intermediate 8 (1.52 g), palladium(II) acetate (0.023 g), 1,3-bis(2,6-diisopropylphenyl)imidazolium chloride (0.085 g), potassium carbonate (0.694 g), and N-methylpyrrolidone (15 mL) were charged in a flask. The mixture was stirred at 150° C. for 8 h while refluxing under heating. After cooling to room temperature, methanol was added and then the precipitate was collected by filtration. The collected solid was purified by a silica gel column chromatography to obtain a white solid (0.83 g, 62% yield). The result of mass spectrometric analysis (m/e=266 to the molecular weight of 266.34) showed that the product was the target intermediate 4.

(2-5) Synthesis of Intermediate 6

The intermediate 6 was obtained in the same manner as in Synthesis Example 4 and Synthesis Example 5.

(2-6) Synthesis of Intermediate 9

Under argon atmosphere, the intermediate 6 (0.38 g), tris(dibenzylideneacetone)dipalladium (0.018 g), 2-dicyclohexylphosphino-2',6'-dimethoxybiphenyl (SPhos) (0.033 g), sodium t-butoxide (0.134 g), and toluene (5 mL) were charged in a flask. After adding 4-t-butylaniline (0.31 mL), the resultant mixture was stirred at 100° C. for 6 h under heating. The reaction solution was cooled to room temperature and then purified by a silica gel column chromatography to obtain a yellow solid (0.33 g, 74% yield). The result of mass spectrometric analysis (m/e=441 to the molecular weight of 441.60) showed that the product was the target intermediate 9.

(2-7) Synthesis of Compound 2

Under argon atmosphere, the intermediate 9 (0.26 g), the intermediate 6 (0.22 g), tris(dibenzylideneacetone)dipalladium (0.011 g), tri-t-butylphosphonium tetrafluoroborate (0.014 g), sodium t-butoxide (0.113 g), and xylene (3 mL) were charged in a flask. The resultant mixture was stirred at 100° C. for 3 h under heating. The reaction solution was purified by a silica gel column chromatography and the obtained solid was washed with methanol to obtain a yellow solid (0.21 g, 49% solid). The result of mass spectrometric analysis (m/e=734 to the molecular weight of 733.98) showed that the product was the target compound 2.

Measurement of Emission Spectrum

Figure 2:
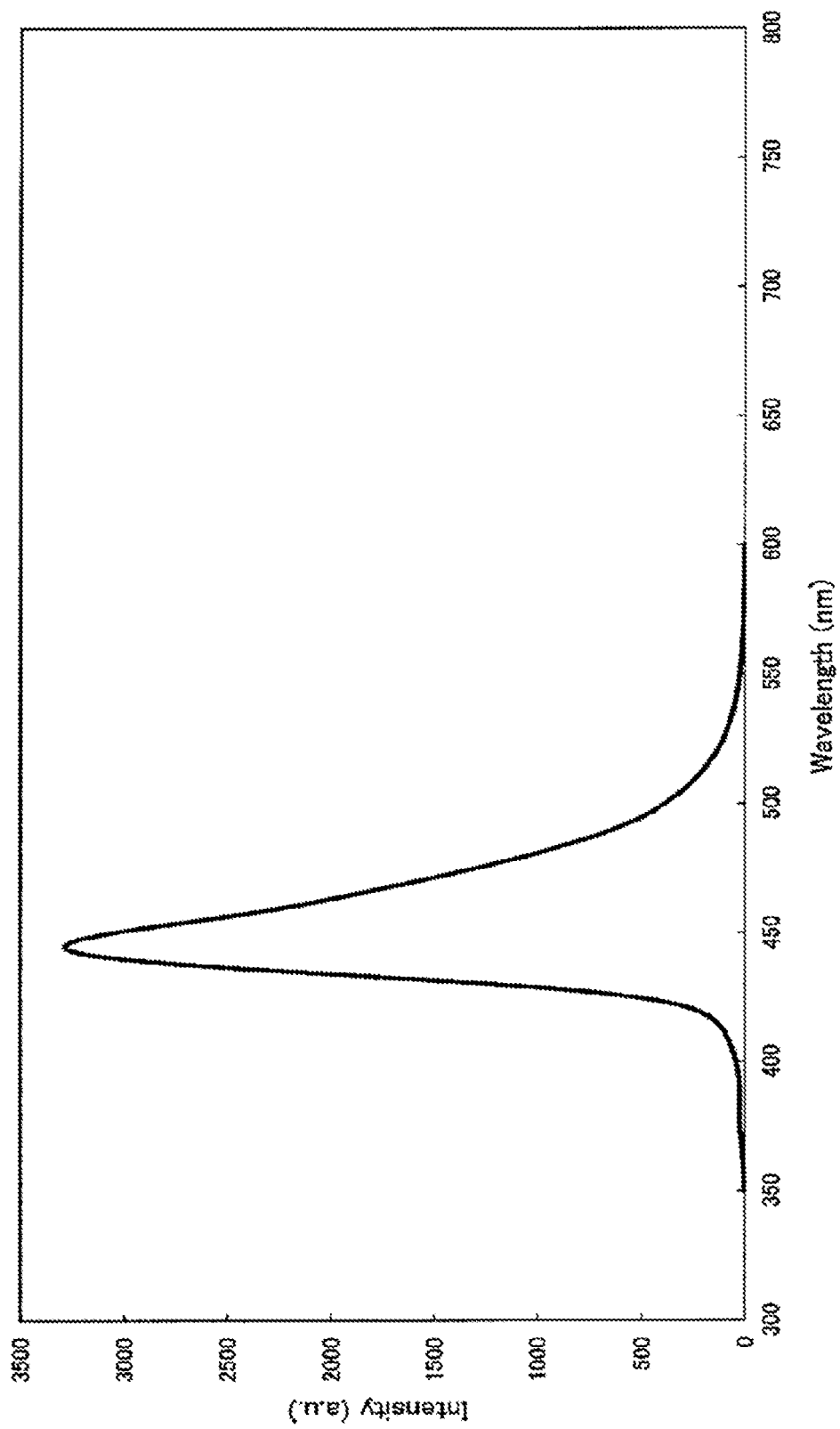
FIG. 2 is a chart showing an emission spectrum of the compound 1 synthesized in Example 1.
Figure 3:
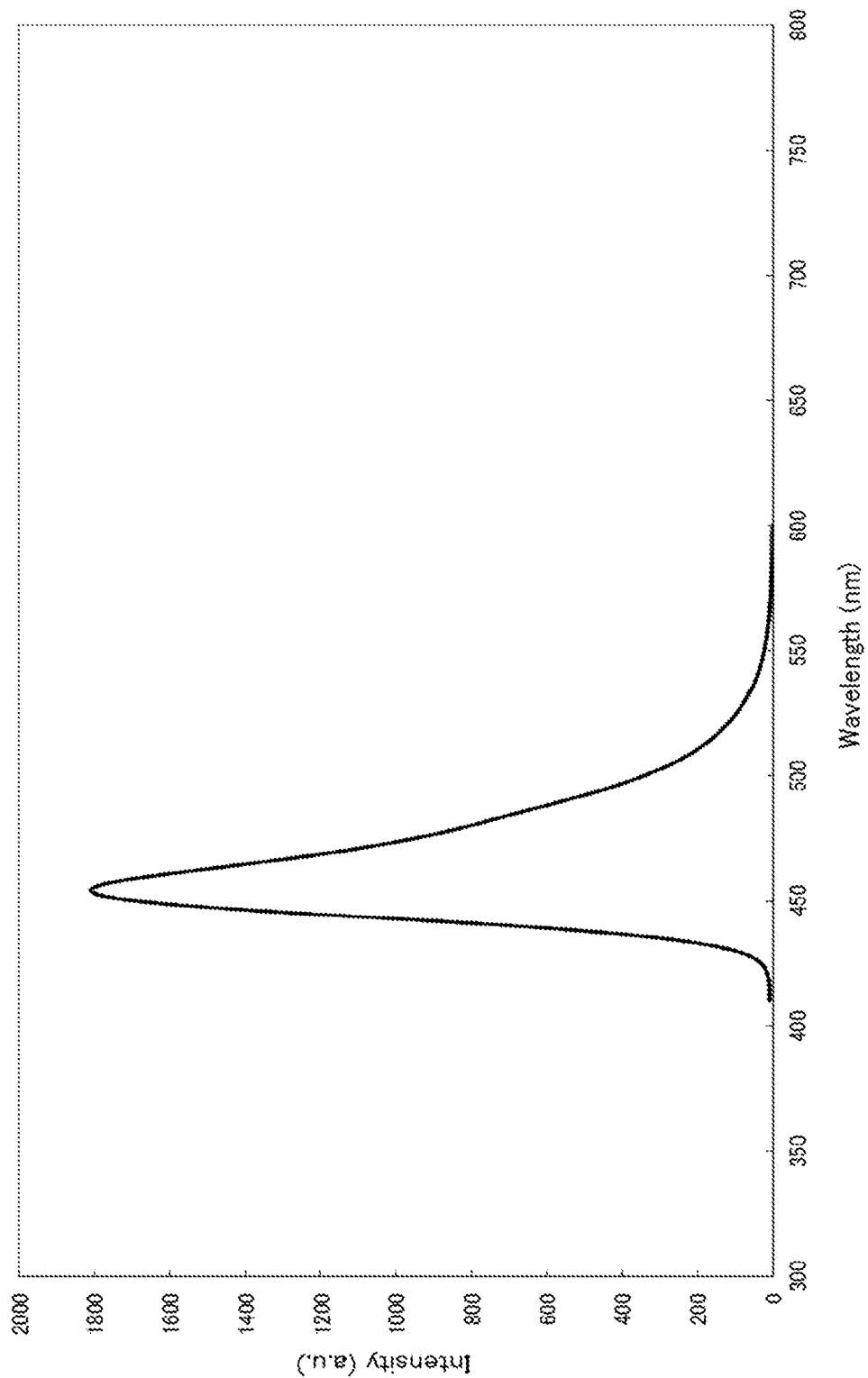
FIG. 3 is a chart showing an emission spectrum of the compound 2 synthesized in Example 2.

A toluene solution of the compound 1 ($10^{-5}$ mol/L) was used as a measuring sample. The emission spectrum of the sample was measured by using a fluorescence spectrophotometer F-7100 manufactured by Hitachi High-Technologies Corporation at a normal temperature (300 K). The result is shown in FIG. 2. The emission spectrum of the compound 2 was measured in the same manner. The result is shown in FIG. 3.

Comparative Examples 1 and 2

Figure 4:
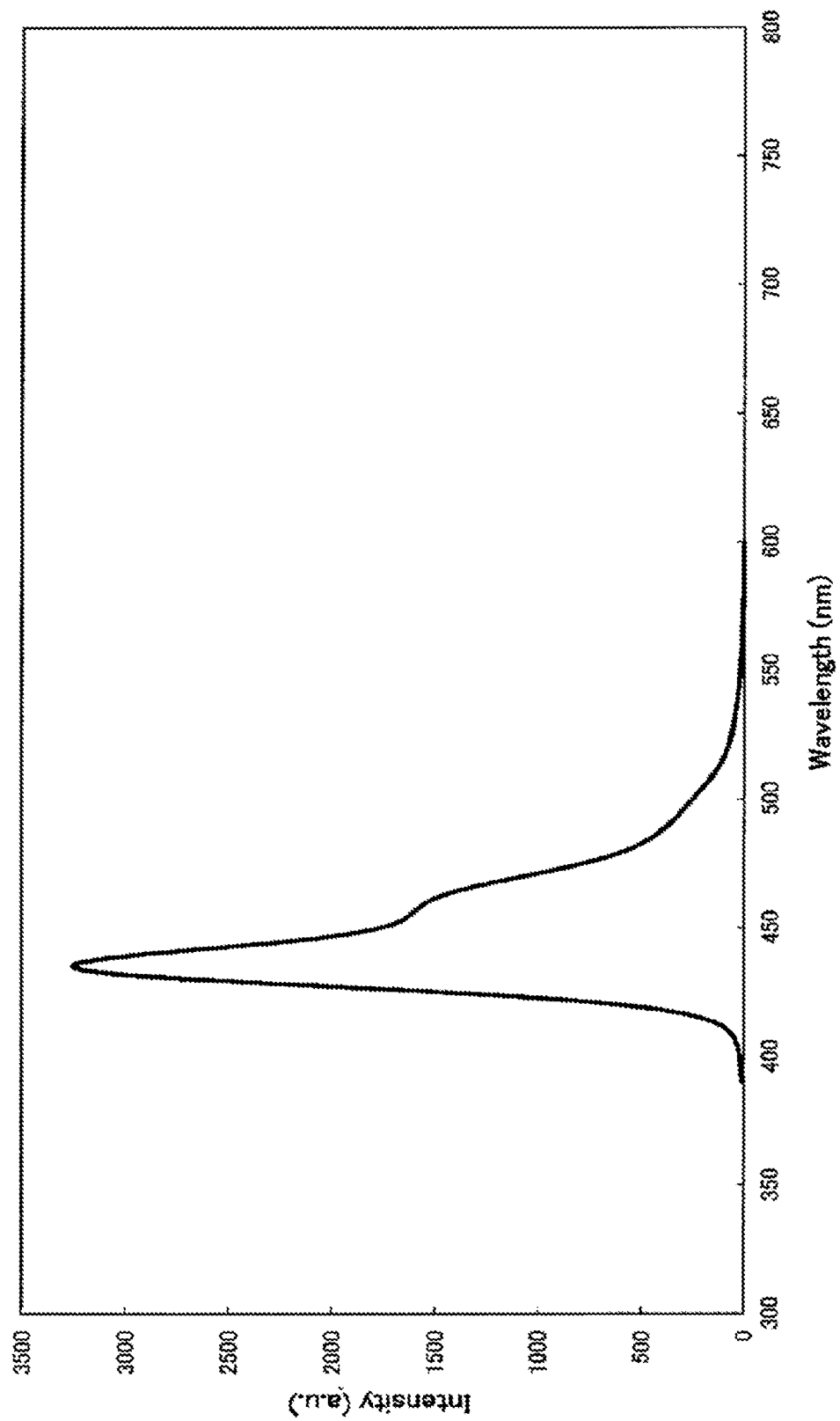
FIG. 4 is a chart showing an emission spectrum of the comparative compound 1.
Figure 5:
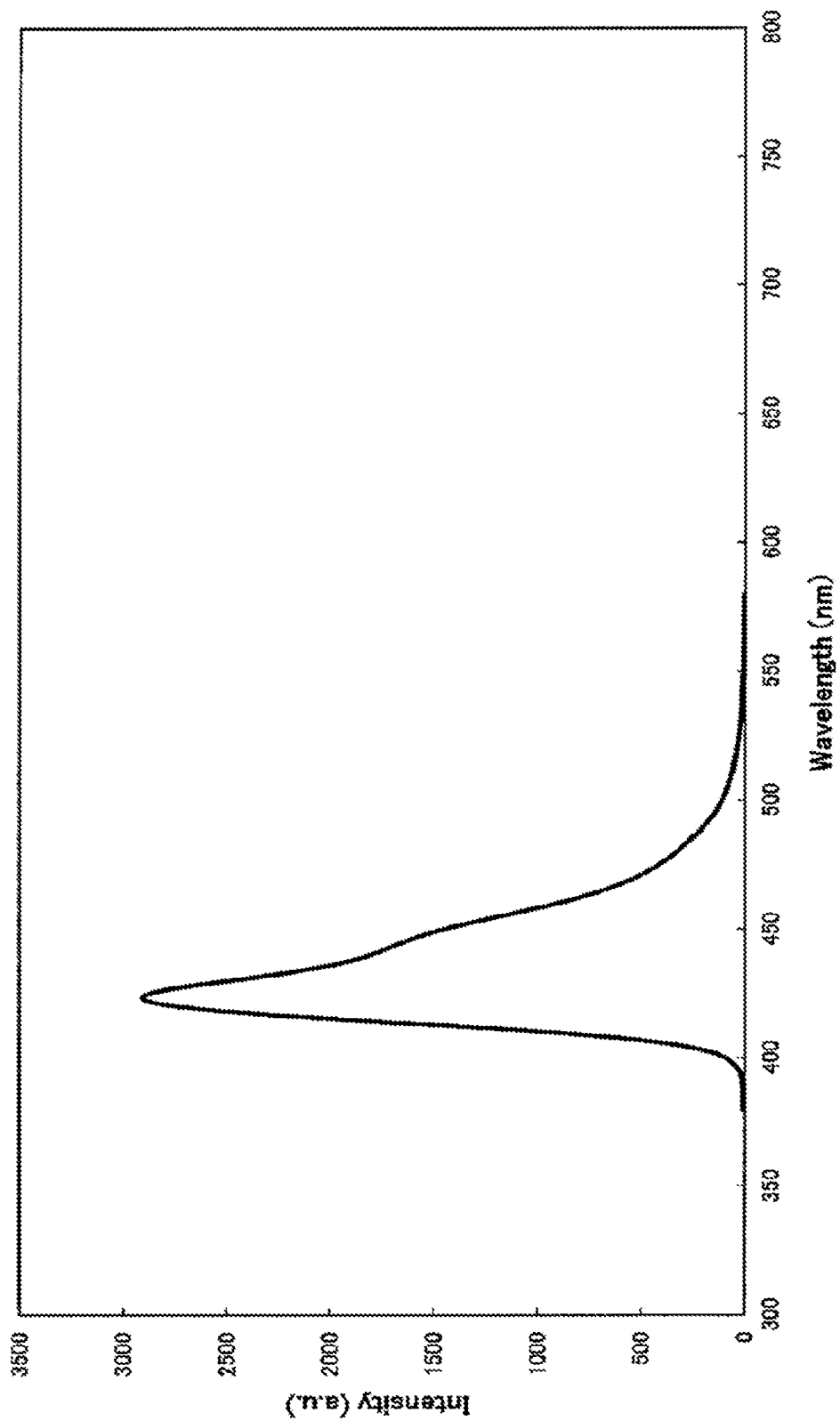
FIG. 5 is a chart showing an emission spectrum of the comparative compound 2.

The emission spectrum of each of the following comparative compounds 1 and 2 was measured in the same manner as above. The results are shown in FIGS. 4 and 5.

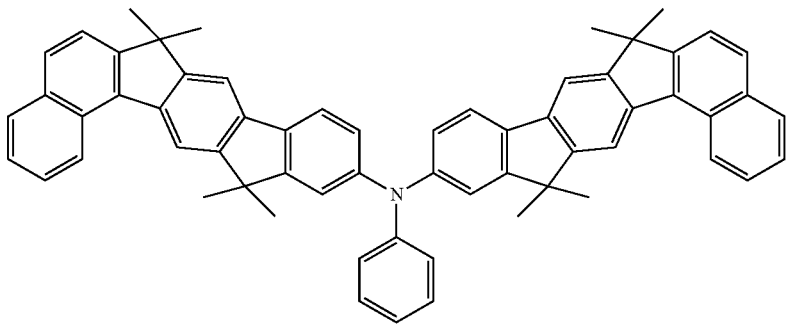

Comparative Compound 1

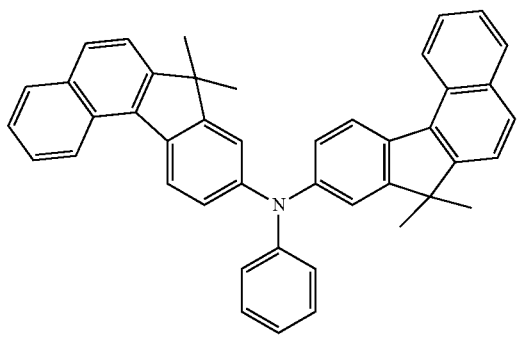

Comparative Compound 2

As seen from the emission spectra of FIGS. 2 to 5, each emission spectrum of the compounds 1 and 2 of the invention has an emission peak in the wavelength region suitable for a blue emitting device. The emission peak has a narrow half width and has no second peak, i.e., is a single peak. Therefore, a blue emitting organic EL device with a high color purity is obtained by using the compound of the invention which comprises a specific main skeleton, i.e., a fused fluorene structure, as a dopant material for the light emitting layer.

Example 3

Production of Organic EL Device

A glass substrate of 25 mm×75 mm×1.1 mm thickness having ITO transparent electrode (anode) (product of Geomatec Company) was cleaned by ultrasonic cleaning in isopropyl alcohol for 5 min and then UV ozone cleaning for 30 min.

The cleaned glass substrate having the transparent electrode lines was mounted to a substrate holder of a vacuum vapor deposition apparatus. The compound HI-1 was vapor-deposited on the surface on which the transparent electrode line was formed so as to cover the transparent electrode, thereby forming an HI-1 film of 10 nm thick. The HI-1 film works as a hole injecting layer.

Successively after forming the HI-1 film, the compound HT-1 was vapor deposited to form an HT-1 film of 80 nm thick on the HI-1 film. The HT-1 film works as a first hole transporting layer.

Successively after forming the HT-1 film, the compound HT-2 was vapor deposited to form an HT-2 film of 10 nm thick on the HT-1 film. The HT-2 film works as a second hole transporting layer.

On the HT-2 film, the compound BH-1 (host material) and the compound 2 (dopant material) were vapor co-deposited to form a light emitting layer of 25 nm thick. The concentration or the compound 2 was 4% by weight.

On the light emitting layer, the compounds ET-1 and the compound ET-2 were vapor deposited in a weight ratio of 1:1 to form an electron transporting layer of 25 nm thick.

On the electron transporting layer, the compound ET-2 was vapor deposited to form an electron injecting layer of 1 nm thick.

Then, a metallic Al was vapor deposited on the ET-2 layer to form a metal cathode of 80 nm thick.

The organic EL device was thus produced.

HI-1

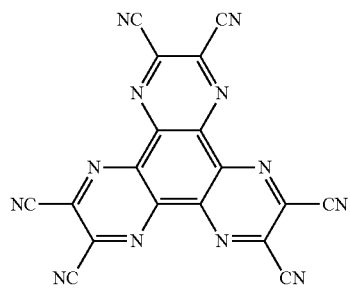

-continued

HT-1

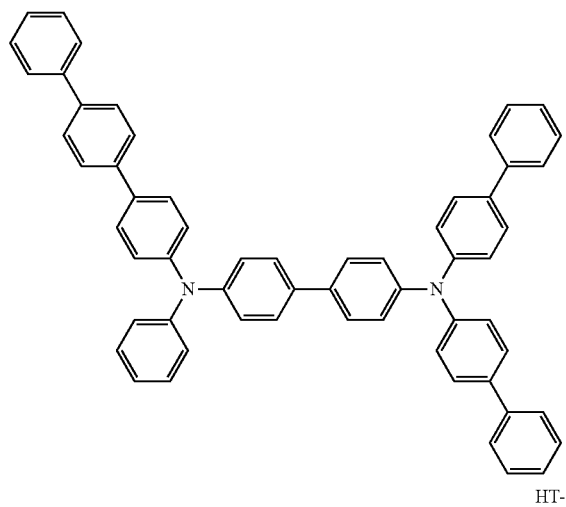

HT-2

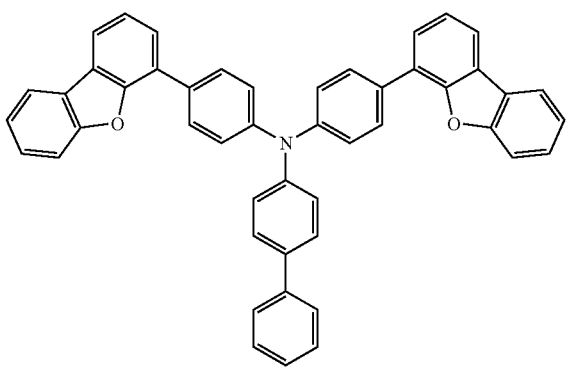

BH-1

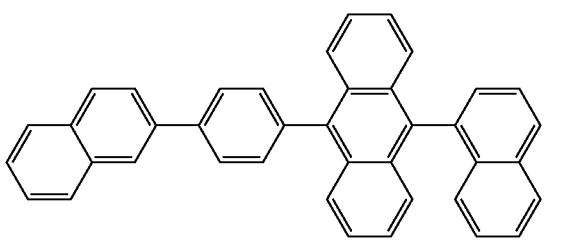

ET-1

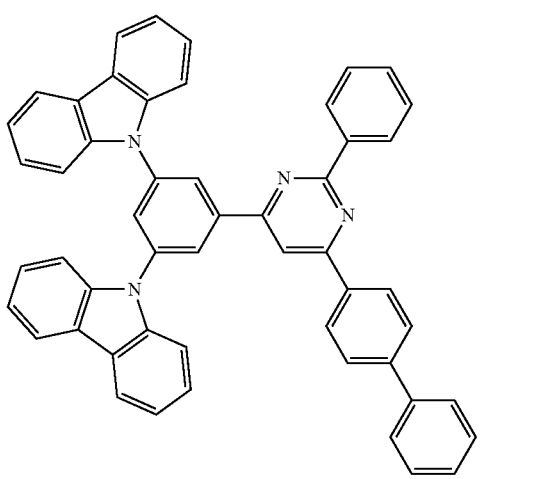

-continued

ET-2

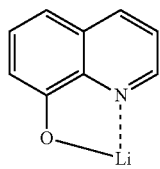

Evaluation of Organic EL Device

Figure 6:
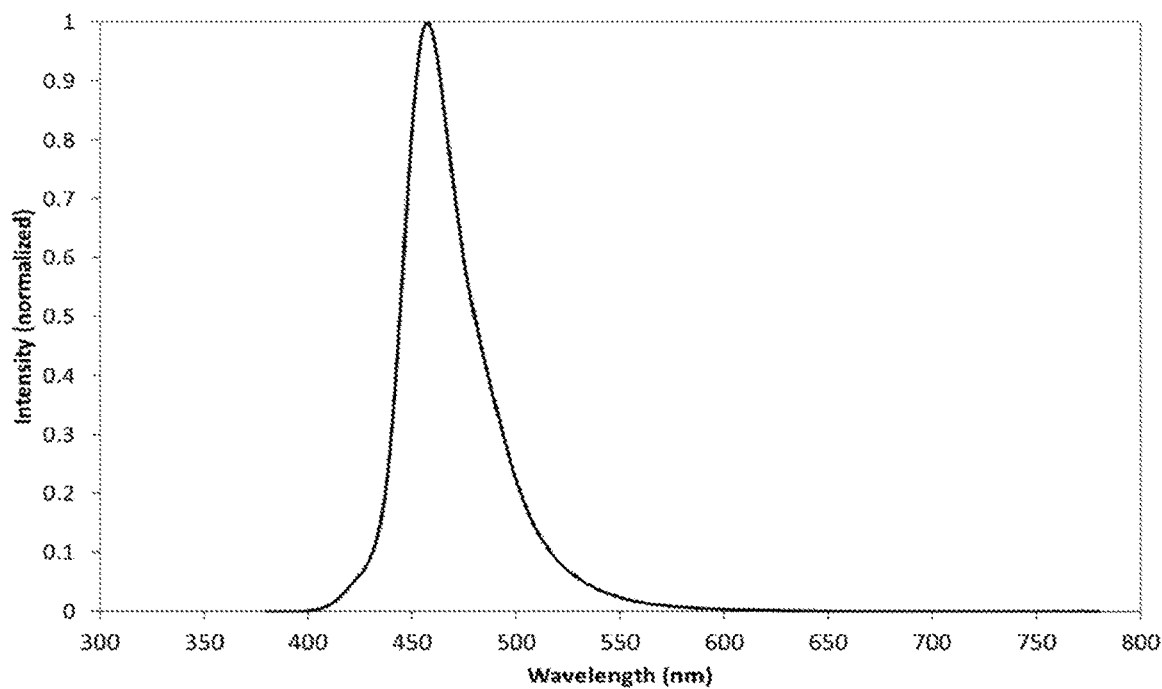
FIG. 6 is a chart showing an emission spectrum of the organic EL device produced in Example 3.

The emission spectrum of the organic EL device thus produced was measure by using a spectroradiometer "CS-1000" (manufactured by Konica Minolta, Inc.) by applying a voltage to the device so as to regulate the current density to 10 mA/cm$^2$. The result is shown in FIG. 6, wherein the maximum intensity of the measured spectroradiometric spectrum is taken as 1.0. The chromaticity of the light emitted from the device is shown in Table 1.

Comparative Example 3

Figure 7:
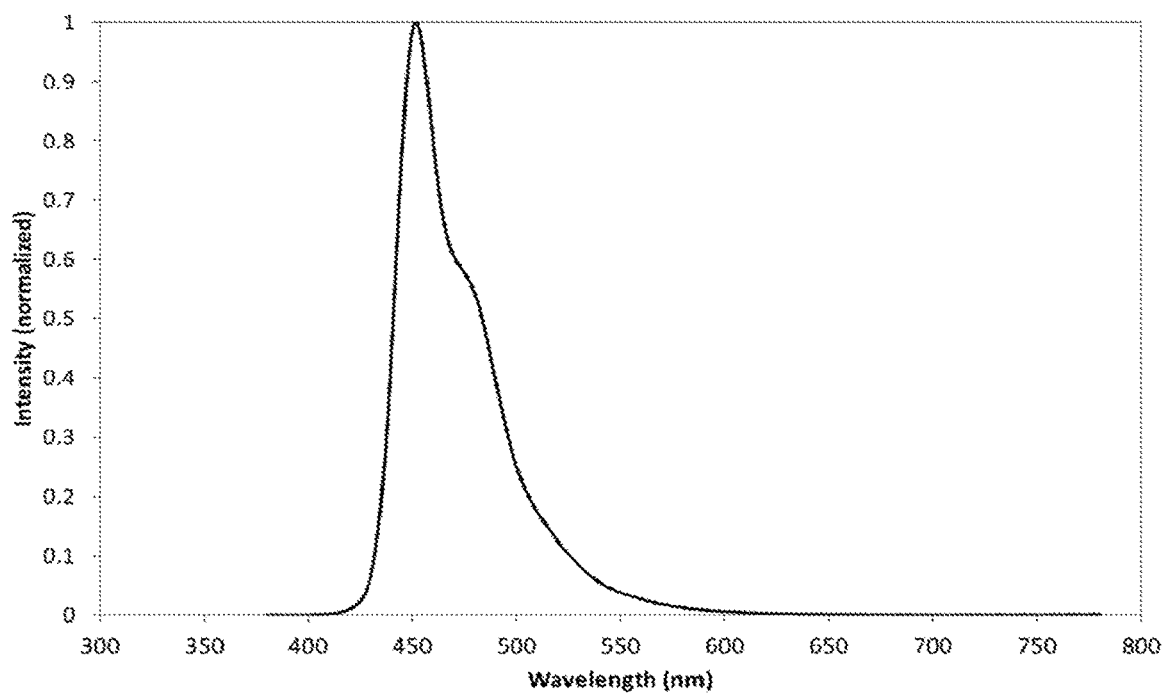
FIG. 7 is a chart showing an emission spectrum of the organic EL device produced in Comparative Example 3.

An organic EL device was produced in the same manner as in Example 3 except for using the comparative compound 3 in place of the compound 2. The device was evaluated in the same manner as in Example 3, the results of which are shown in FIG. 7 and Table 1.

Comparative Compound 3

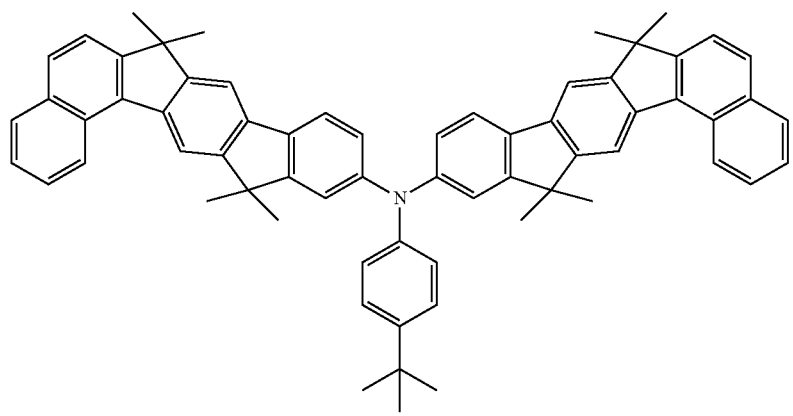

TABLE 1

|  |  | Chromaticity | |
|---|---|---|---|
|  |  | CIEx | CIEy |
| Example 3 | Compound 2 | 0.140 | 0.094 |
| Comparative Example 3 | Comparative compound 3 | 0.143 | 0.110 |

As compared with the emission spectrum of FIG. 7 for the EL device using the comparative compound 3, it can be found that the emission spectrum of FIG. 6 for the EL device using the compound 2 of the invention is a single peak spectrum having no second peak. This means that the emission component of the longer wavelength side is reduced in the emission from the EL device of the invention. As seen from Table 1, the CIEy value of the device using the compound of the invention is smaller, showing that a deeper blue emission with a good chromaticity is obtained.

Thus, the compound of the invention realizes an organic EL device with a good color purity, and therefore, is advantageous for optical design.

REFERENCE SIGNS LIST

1: Organic EL device
2: Substrate
3: Anode
4: Cathode
5: Light emitting layer
6: Anode-side organic thin film layer
7: Cathode-side organic thin film layer
10: Emission unit

The invention claimed is:

1. A compound represented by the formula (1):

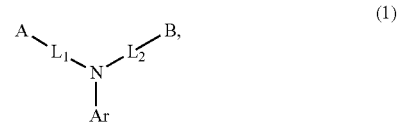

wherein:
Ar is a substituted or unsubstituted alkyl group having 1 to 20 carbon atoms, a substituted or unsubstituted aryl group having 6 to 30 ring carbon atoms, or a substituted or unsubstituted nitrogen-comprising heteroaryl group having 5 to 30 ring atoms;

each of $L_1$ and $L_2$ is independently a single bond, a substituted or unsubstituted arylene group having 6 to 30 ring carbon atoms, a substituted or unsubstituted heteroarylene group having 5 to 30 ring atoms, or a substituted or unsubstituted divalent linking group wherein 2 to 4 groups selected from an arylene group having 6 to 30 ring carbon atoms and a heteroarylene group having 5 to 30 ring atoms are bonded to each other via a single bond;

A is a monovalent group represented by the formula (2):

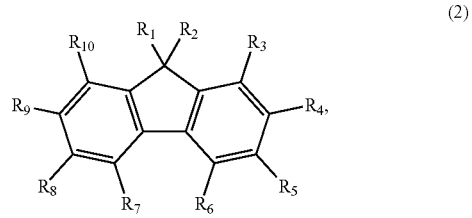

wherein:

each of $R_1$ and $R_2$ is independently a hydrogen atom, a substituted or unsubstituted alkyl group having 1 to 20 carbon atoms, a mono-, di-, or trialkylsilyl group each comprising a substituted or unsubstituted alkyl group having 1 to 20 carbon atoms, a substituted or unsubstituted aryl group having 6 to 30 ring carbon atoms, a mono-, di-, or triarylsilyl group each comprising a substituted or unsubstituted aryl group having 6 to 30 ring carbon atoms, or a substituted or unsubstituted heteroaryl group having 5 to 30 ring atoms, wherein $R_1$ and $R_2$ may be bonded to each other to form a ring;

adjacent two groups in one pair selected from $R_3$ and $R_4$, $R_4$ and $R_5$, and $R_5$ and $R_6$ are bonded to each other to form a divalent group represented by the formula (3);

adjacent two groups in one pair selected from $R_7$ and $R_8$, $R_8$ and $R_9$, and $R_9$ and $R_{10}$ are bonded to each other to form a divalent group represented by the formula (4);

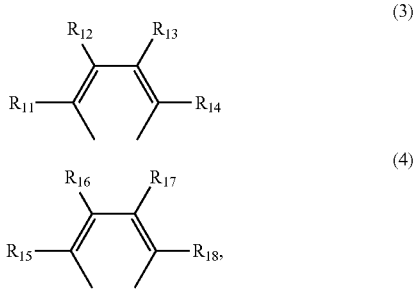

wherein:

each of $R_{11}$ to $R_{18}$ is independently a hydrogen atom, a substituted or unsubstituted alkyl group having 1 to 20 carbon atoms, a mono-, di-, or trialkylsilyl group each comprising a substituted or unsubstituted alkyl group having 1 to 20 carbon atoms, a substituted or unsubstituted aryl group having 6 to 30 ring carbon atoms, a mono-, di-, or triarylsilyl group each comprising a substituted or unsubstituted aryl group having 6 to 30 ring carbon atoms, or a substituted or unsubstituted heteroaryl group having 5 to 30 ring atoms;

provided that one selected from $R_3$ to $R_6$ which do not form the divalent group represented by formula (3), $R_7$ to $R_{10}$ which do not form the divalent group represented by the formula (4), and $R_{11}$ to $R_{18}$ is a single bond bonded to $L_1$;

each selected from $R_3$ to $R_6$ which do not form the divalent group represented by the formula (3) and is not a single bond bonded to $L_1$, and each selected from $R_7$ to $R_{10}$ which do not form the divalent group represented by the formula (4) and is not a single bond bonded to $L_1$ is independently a hydrogen atom, a substituted or unsubstituted alkyl group having 1 to 20 carbon atoms, a mono-, di-, or trialkylsilyl group each comprising a substituted or unsubstituted alkyl group having 1 to 20 carbon atoms, a substituted or unsubstituted aryl group having 6 to 30 ring carbon atoms, a mono-, di-, or triarylsilyl group each comprising a substituted or unsubstituted aryl group having 6 to 30 ring carbon atoms, or a substituted or unsubstituted heteroaryl group having 5 to 30 ring atoms;

B is a monovalent group represented by the formula (5):

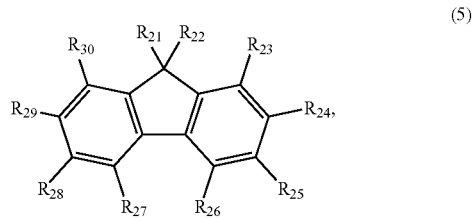

wherein:

each of $R_{21}$ and $R_{22}$ is independently a hydrogen atom, a substituted or unsubstituted alkyl group having 1 to 20 carbon atoms, a mono-, di-, or trialkylsilyl group each comprising a substituted or unsubstituted alkyl group having 1 to 20 carbon atoms, a substituted or unsubstituted aryl group having 6 to 30 ring carbon atoms, a mono-, di-, or triarylsilyl group each comprising a substituted or unsubstituted aryl group having 6 to 30 ring carbon atoms, or a substituted or unsubstituted heteroaryl group having 5 to 30 ring atoms, wherein $R_{21}$ and $R_{22}$ may be bonded to each other to form a ring;

each of $R_{23}$ to $R_{30}$ is independently a hydrogen atom, a substituted or unsubstituted alkyl group having 1 to 20 carbon atoms, a mono-, di-, or trialkylsilyl group each comprising a substituted or unsubstituted alkyl group having 1 to 20 carbon atoms, a substituted or unsubstituted aryl group having 6 to 30 ring carbon atoms, a mono-, di-, or triarylsilyl group each comprising a substituted or unsubstituted aryl group having 6 to 30 ring carbon atoms, or a substituted or unsubstituted heteroaryl group having 5 to 30 ring atoms;

adjacent groups in at least one pair selected from the group consisting of $R_{23}$ and $R_{24}$, $R_{24}$ and $R_{25}$, $R_{25}$ and $R_{26}$ are bonded to each other to form a ring; or adjacent groups in at least one pair selected from the group consisting of $R_{27}$ and $R_{28}$, $R_{28}$ and $R_{29}$, and $R_{29}$ and $R_{30}$ are bonded to each other to form a carbon ring;

provided that one selected from $R_{27}$ to $R_{30}$ which do not form a carbon ring is a single bond bonded to $L_2$, or one of ring carbon atoms of the carbon ring which is formed by the at least one pair selected from the group consisting of $R_{27}$ and $R_{28}$, $R_{28}$ and $R_{29}$, and $R_{29}$ and $R_{30}$ is bonded to $L_2$.

2. The compound according to claim 1, wherein A is a monovalent group represented by any of the formulae (6) to (11):

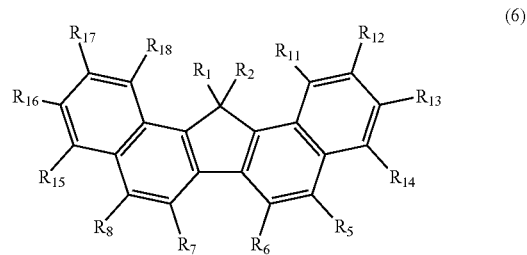

-continued

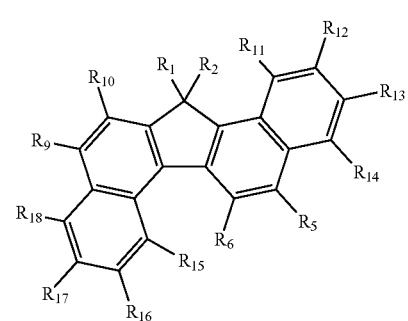
(7)

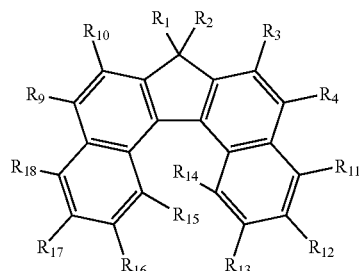
(8)

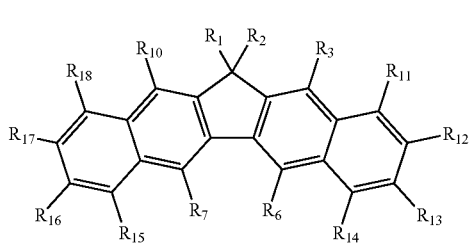
(9)

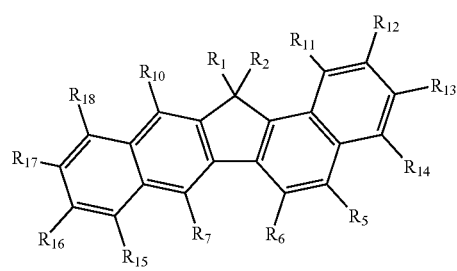
(10)

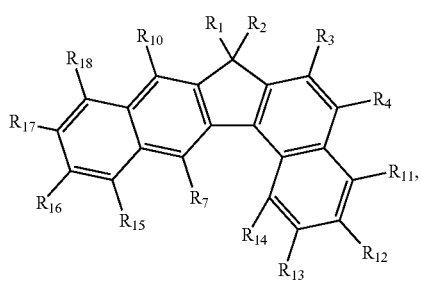
(11)

wherein $R_1$, $R_2$, $R_5$ to $R_8$, and $R_{11}$ to $R_{18}$ of the formula (6); $R_1$, $R_2$, $R_5$, $R_6$, and $R_9$ to $R_{18}$ of the formula (7); $R_1$ to $R_4$, $R_9$, $R_{10}$, and $R_{11}$ to $R_{18}$ of the formula (8); $R_1$ to $R_3$, $R_6$, $R_7$, and $R_{10}$ to $R_{18}$ of the formula (9); $R_1$, $R_2$, $R_5$ to $R_7$, and $R_{10}$ to $R_{18}$ of the formula (10); and $R_1$ to $R_4$, $R_7$, and $R_{10}$ to $R_{18}$ of the formula (11) are independently as defined above.

3. The compound according to claim 1, wherein one or two pairs selected from $R_{23}$ and $R_{24}$, $R_{24}$ and $R_{25}$, and $R_{25}$ and $R_{26}$ of the formula (5) form a divalent group represented by the formula (12) or (13), and one or two pairs selected from $R_{27}$ and $R_{28}$, $R_{28}$ and $R_{29}$, and $R_{29}$ and $R_{30}$ of formula (5) form a divalent group represented by the formula (14):

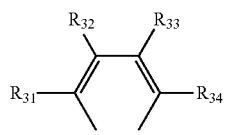
(12)

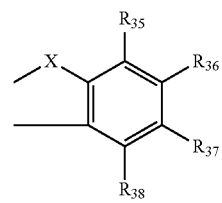
(13)

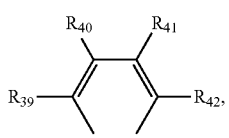
(14)

wherein:
each of $R_{31}$ to $R_{34}$ of the formula (12), $R_{35}$ to $R_{38}$ of the formula (13), and $R_{39}$ to $R_{42}$ of the formula (14) is independently a hydrogen atom, a substituted or unsubstituted alkyl group having 1 to 20 carbon atoms, a mono-, di-, or trialkylsilyl group each comprising a substituted or unsubstituted alkyl group having 1 to 20 carbon atoms, a substituted or unsubstituted aryl group having 6 to 30 ring carbon atoms, a mono-, di-, or triarylsilyl group each comprising a substituted or unsubstituted aryl group having 6 to 30 ring carbon atoms, or a substituted or unsubstituted heteroaryl group having 5 to 30 ring atoms;

adjacent two groups each selected from the group consisting of $R_{31}$ to $R_{34}$, $R_{35}$ to $R_{38}$, and $R_{39}$ to $R_{42}$ may be bonded to each other to form a ring;

one of $R_{39}$ to $R_{42}$ may be a single bond which is bonded to $L_2$;

X is $CR_{43}R_{44}$, $NR_{45}$, O, or S;

each of $R_{43}$ to $R_{45}$ is independently a hydrogen atom, a substituted or unsubstituted alkyl group having 1 to 20 carbon atoms, a mono-, di-, or trialkylsilyl group each comprising a substituted or unsubstituted alkyl group having 1 to 20 carbon atoms, a substituted or unsubstituted aryl group having 6 to 30 ring carbon atoms, a mono-, di-, or triarylsilyl group each comprising a substituted or unsubstituted aryl group having 6 to 30 ring carbon atoms, or a substituted or unsubstituted heteroaryl group having 5 to 30 ring atoms; and $R_{43}$ and $R_{44}$ may be bonded to each other to form a ring.

4. The compound according to claim 1, wherein B is a monovalent group represented by any of the formulae (15) to (23):

(15)
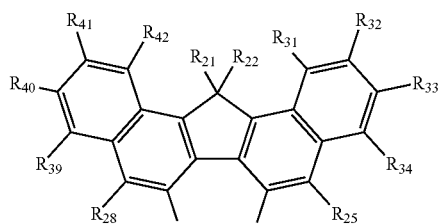

(16)
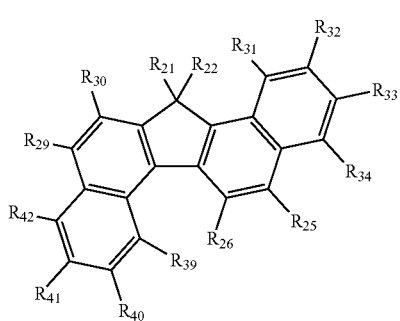

(17)
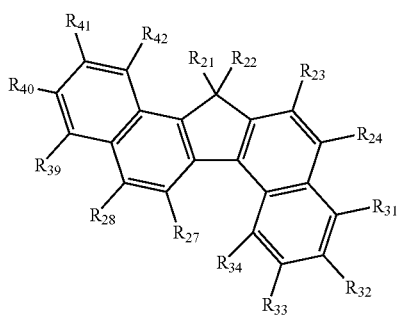

(18)
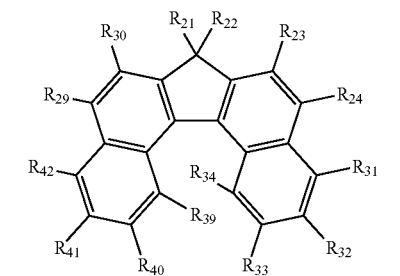

(19)
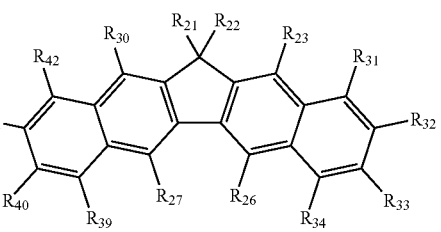

(20)
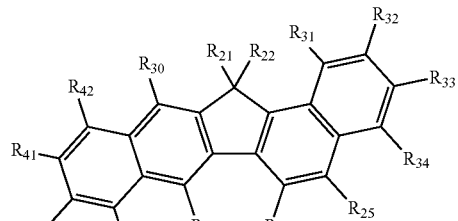

(21)
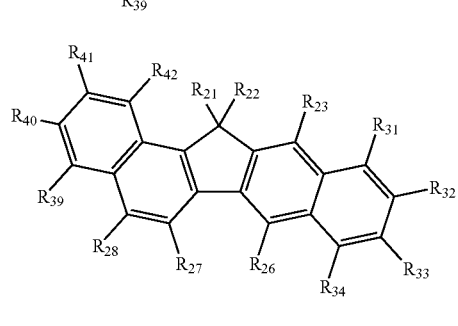

(22)
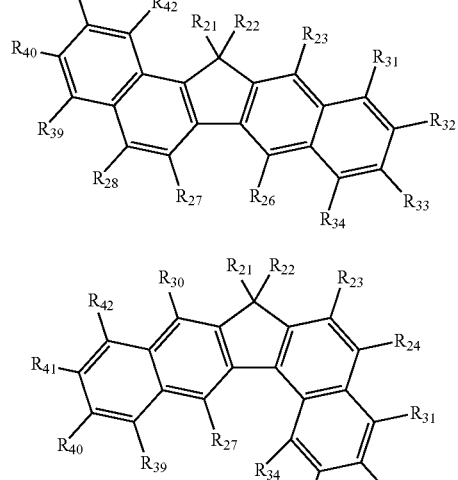

(23)
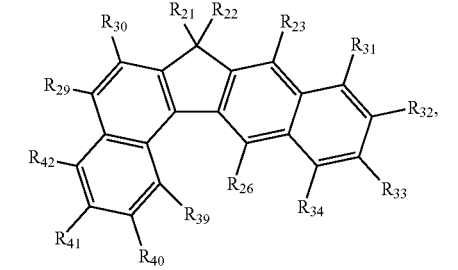

wherein:
$R_{21}$, $R_{22}$, and $R_{25}$ to $R_{28}$ of the formula (15), $R_{21}$, $R_{22}$, $R_{25}$, $R_{26}$, $R_{29}$, and $R_{30}$ of the formula (16), $R_{21}$ to $R_{24}$, $R_{27}$, and $R_{28}$ of the formula (17), $R_{21}$ to $R_{24}$, $R_{29}$, and $R_{30}$ of the formula (18), $R_{21}$ to $R_{23}$, $R_{26}$, $R_{27}$, and $R_{30}$ of the formula (19), $R_{21}$, $R_{22}$, $R_{25}$ to $R_{27}$, and $R_{30}$ of the formula (20), $R_{21}$ to $R_{23}$, and $R_{26}$ to $R_{28}$ of the formula (21), $R_{21}$ to $R_{24}$, $R_{27}$, and $R_{30}$ of formula (22), and $R_{21}$ to $R_{23}$, $R_{26}$, $R_{29}$, and $R_{30}$ of the formula (23) are independently as defined above;

each of $R_{31}$ to $R_{34}$ and $R_{39}$ to $R_{42}$ of the formulae (15) to (23) is independently a hydrogen atom, a substituted or unsubstituted alkyl group having 1 to 20 carbon atoms, a mono-, di-, or trialkylsilyl group each comprising a substituted or unsubstituted alkyl group having 1 to 20 carbon atoms, a substituted or unsubstituted aryl group having 6 to 30 ring carbon atoms, a mono-, di-, or triarylsilyl group each comprising a substituted or unsubstituted aryl group having 6 to 30 ring carbon atoms, or a substituted or unsubstituted heteroaryl group having 5 to 30 ring atoms;

adjacent two groups each selected from $R_{31}$ to $R_{34}$ and $R_{39}$ to $R_{42}$ may be bonded to each other to form a ring; and one of $R_{39}$ to $R_{42}$ may be a single bond which is bonded to $L_2$.

5. The compound according to claim 1, wherein B is represented by the formula (24) or (25):

(24)

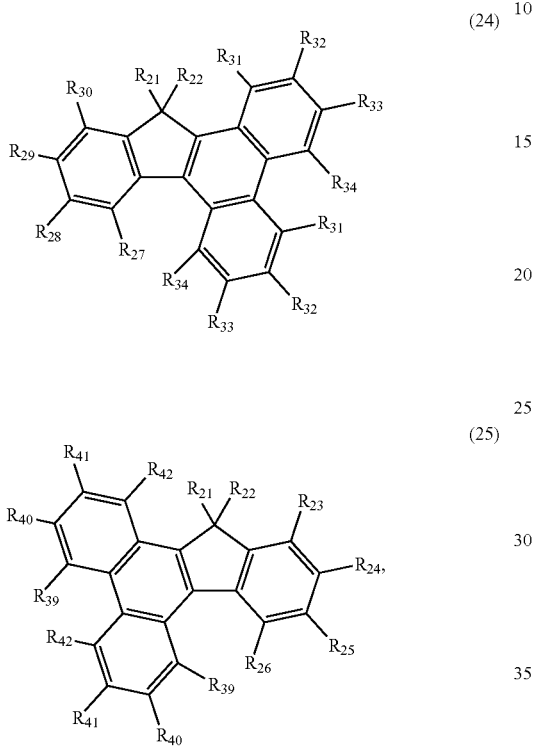

(25)

wherein:

$R_{22}$, $R_{27}$ to $R_{30}$ of the formula (24) and $R_{21}$ to $R_{26}$ of the formula (25) are independently as defined above;

each of $R_{31}$ to $R_{34}$ of the formula (24) and $R_{39}$ to $R_{42}$ of the formula (25) is independently a hydrogen atom, a substituted or unsubstituted alkyl group having 1 to 20 carbon atoms, a mono-, di-, or trialkylsilyl group each comprising a substituted or unsubstituted alkyl group having 1 to 20 carbon atoms, a substituted or unsubstituted aryl group having 6 to 30 ring carbon atoms, a mono-, di-, or triarylsilyl group each comprising a substituted or unsubstituted aryl group having 6 to 30 ring carbon atoms, or a substituted or unsubstituted heteroaryl group having 5 to 30 ring atoms;

adjacent two groups each selected from $R_{31}$ to $R_{34}$ and $R_{39}$ to $R_{42}$ may be bonded to each other to form a ring;

one of $R_{39}$ to $R_{42}$ may be a single bond which is bonded to $L_2$; and two groups $R_{31}$, two groups $R_{32}$, two groups $R_{33}$, and two groups $R_{34}$ each in the formula (24), and two groups $R_{39}$, two groups $R_{40}$, two groups $R_{41}$, and two groups $R_{42}$ each in the formula (25) may be the same or different, respectively.

6. The compound according to claim 1, wherein B is a monovalent group represented by any of the formulae (26) to (38):

(26)
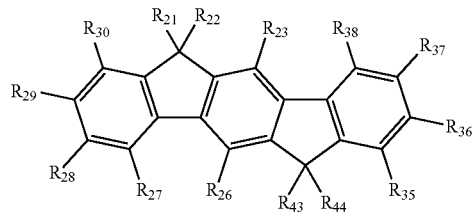

(27)
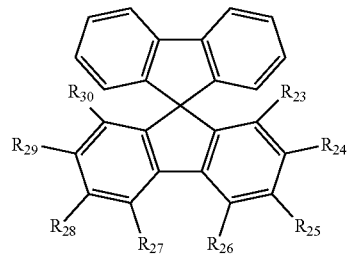

(28)
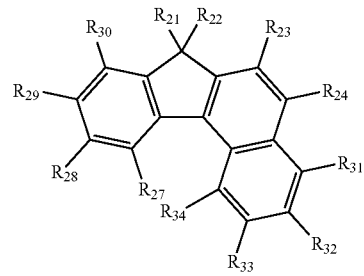

(29)
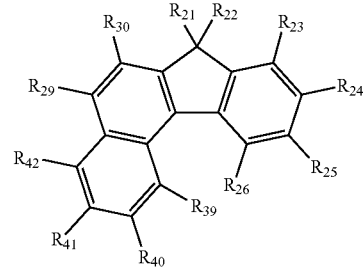

(30)
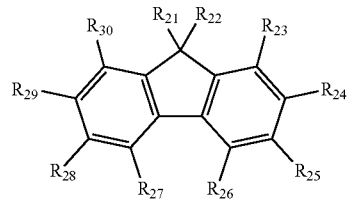

(31)
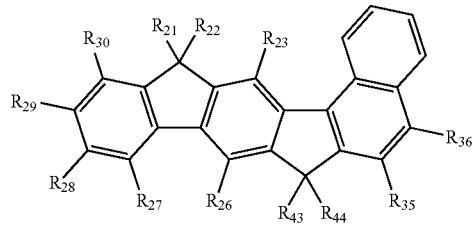

-continued

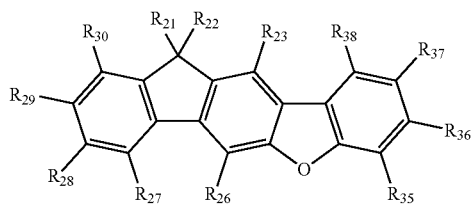
(32)

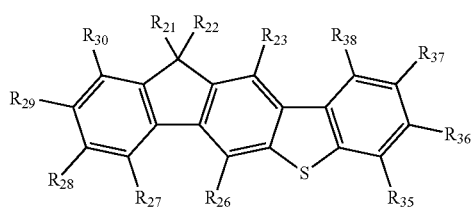
(33)

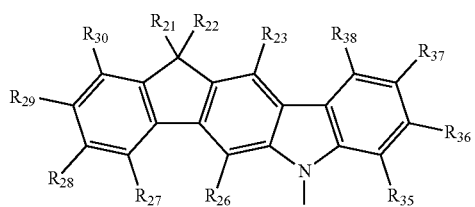
(34)

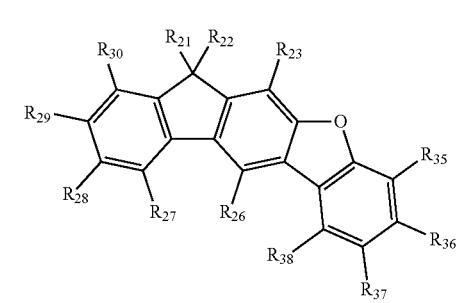
(35)

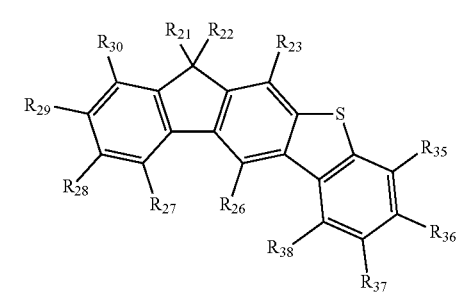
(36)

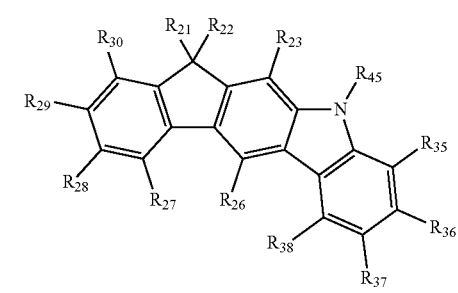
(37)

-continued

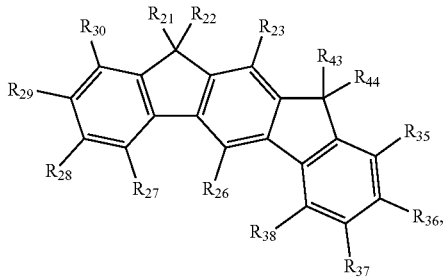
(38)

wherein:

$R_{21}$ to $R_{23}$ and $R_{26}$ to $R_{30}$ of the formulae (26) and (31) to (38), $R_{23}$ to $R_{30}$ of the formula (27), $R_{21}$ to $R_{24}$ and $R_{27}$ to $R_{30}$ of the formula (28), $R_{21}$ to $R_{26}$, $R_{29}$, and $R_{30}$ of the formula (29), and $R_{21}$ to $R_{30}$ of the formula (30) are independently as defined above;

each of $R_{35}$ to $R_{38}$ of the formula (26), $R_{31}$ to $R_{34}$ of the formula (28), $R_{39}$ to $R_{42}$ of the formula (29), $R_{35}$ and $R_{36}$ of the formula (31), and $R_{35}$ to $R_{38}$ of the formulae (32) to (38) is independently a hydrogen atom, a substituted or unsubstituted alkyl group having 1 to 20 carbon atoms, a mono-, di-, or trialkylsilyl group each comprising a substituted or unsubstituted alkyl group having 1 to 20 carbon atoms, a substituted or unsubstituted aryl group having 6 to 30 ring carbon atoms, a mono-, di-, or triarylsilyl group each comprising a substituted or unsubstituted aryl group having 6 to 30 ring carbon atoms, or a substituted or unsubstituted heteroaryl group having 5 to 30 ring atoms;

adjacent two groups each selected from $R_{31}$ to $R_{34}$, $R_{35}$ to $R_{38}$, and $R_{39}$ to $R_{42}$ may be bonded to each other to form a ring;

one of $R_{39}$ to $R_{42}$ may be a single bond which is bonded to $L_2$;

each of $R_{43}$ and $R_{44}$ of the formulae (26), (31), and (38) and $R_{45}$ of the formulae (34) and (37) is independently a hydrogen atom, a substituted or unsubstituted alkyl group having 1 to 20 carbon atoms, a mono-, di-, or trialkylsilyl group each comprising a substituted or unsubstituted alkyl group having 1 to 20 carbon atoms, a substituted or unsubstituted aryl group having 6 to 30 ring carbon atoms, a mono-, di-, or triarylsilyl group each comprising a substituted or unsubstituted aryl group having 6 to 30 ring carbon atoms, or a substituted or unsubstituted heteroaryl group having 5 to 30 ring atoms; and $R_{43}$ and $R_{44}$ may be bonded to each other to form a ring.

7. The compound according to claim 1, wherein Ar is represented by the formula (5).

8. The compound according to claim 7, wherein B and Ar are the same.

9. The compound according to claim 1, wherein A and B are the same.

10. The compound according to claim 9, wherein A is represented by any of the formulae (6) to (11):

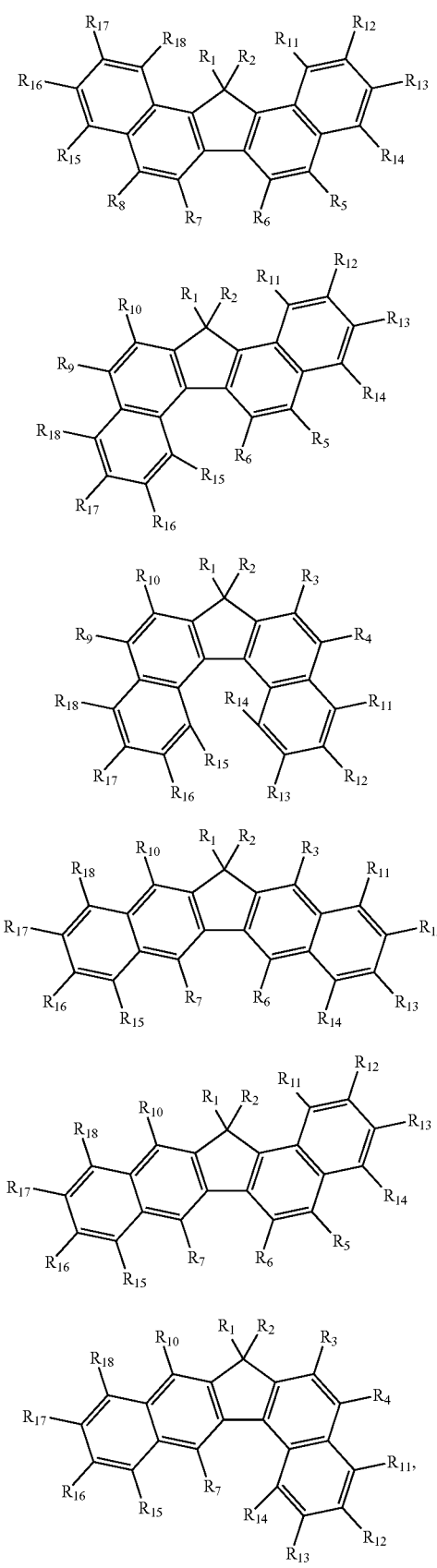
(6)
(7)
(8)
(9)
(10)
(11)
wherein $R_1$, $R_2$, $R_5$ to $R_8$, and $R_{11}$ to $R_{18}$ of the formula (6); $R_1$, $R_2$, $R_5$, $R_6$, and $R_9$ to $R_{18}$ of the formula (7); $R_1$ to $R_4$, $R_9$, $R_{10}$, and $R_{11}$ to $R_{18}$ of the formula (8); $R_1$ to $R_3$, $R_6$, $R_7$ and $R_{10}$ to $R_{18}$ of the formula (9); $R_1$, $R_2$, $R_5$ to $R_7$ and $R_{10}$ to $R_{18}$ of the formula (10); and $R_1$ to $R_4$, $R_7$ and $R_{10}$ to $R_{18}$ of the formula (11) are independently as defined above; and
B is represented by any of the formulae (15) to (23):
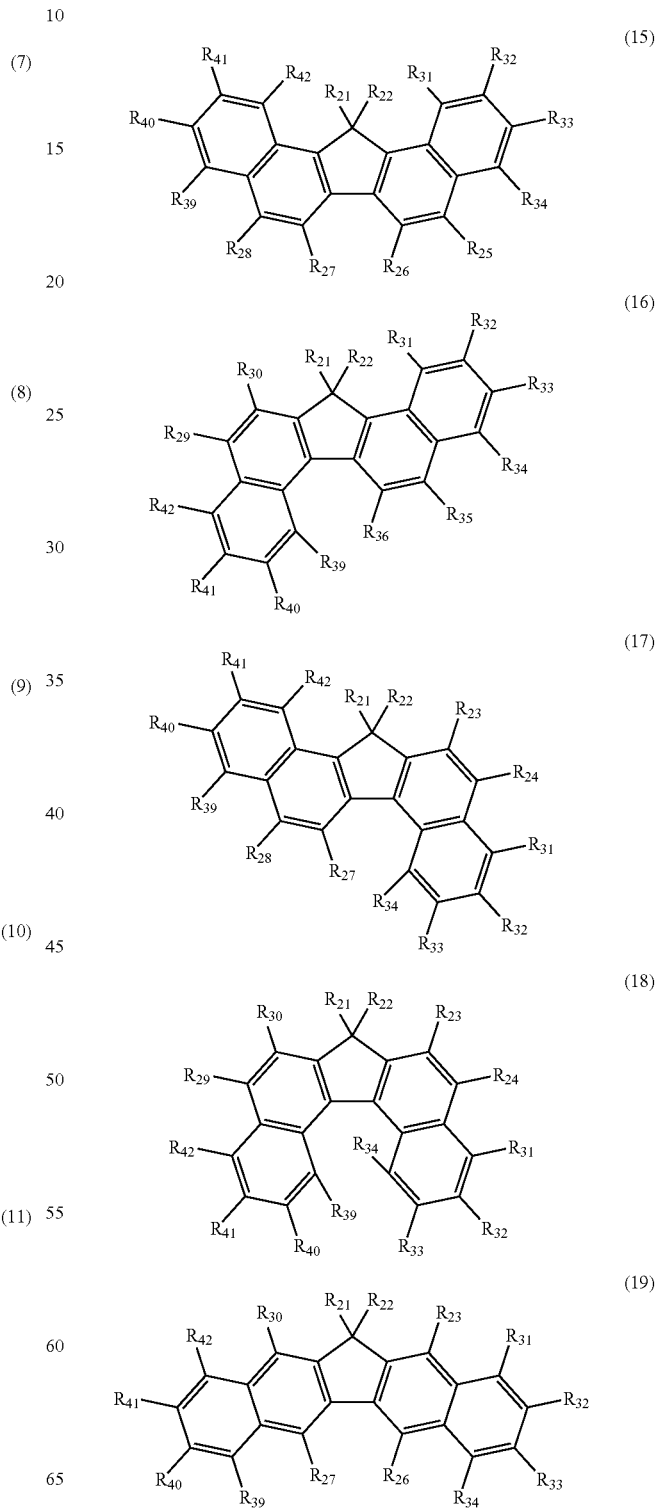
(15)
(16)
(17)
(18)
(19)

-continued

(20)
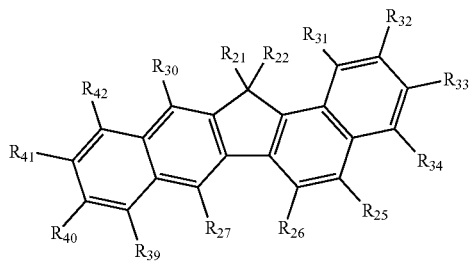

(21)
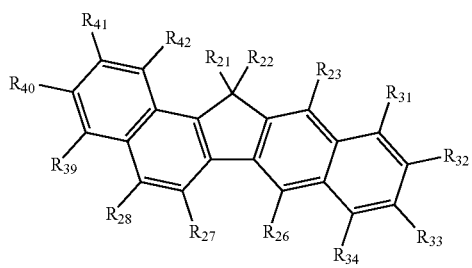

(22)
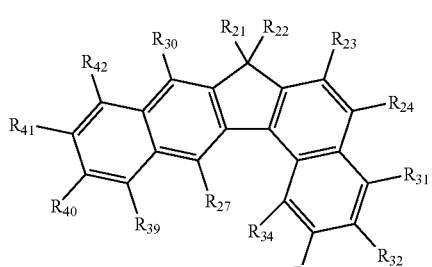

(23)
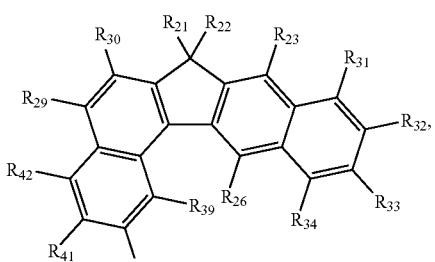

wherein:
$R_{21}$, $R_{22}$, and $R_{25}$ to $R_{28}$ of the formula (15), $R_{21}$, $R_{22}$, $R_{25}$, $R_{26}$, $R_{29}$ and $R_{30}$ of the formula (16), $R_{21}$ to $R_{24}$, $R_{27}$, and $R_{28}$ of the formula (17), $R_{21}$ to $R_{24}$, $R_{29}$ and $R_{30}$ of the formula (18), $R_{21}$ to $R_{23}$, $R_{26}$, $R_{27}$ and $R_{30}$ of the formula (19), $R_{21}$, $R_{22}$, $R_{25}$ to $R_{27}$, and $R_{30}$ of the formula (20), $R_{21}$ to $R_{23}$, and $R_{26}$ to $R_{28}$ of the formula (21), $R_{21}$ to $R_{24}$, $R_{27}$, and $R_{30}$ of formula (22), and $R_{21}$ to $R_{23}$, $R_{26}$, $R_{29}$ and $R_{30}$ of the formula (23) are independently as defined above;

each of $R_{31}$ to $R_{34}$ and $R_{39}$ to $R_{42}$ of the formulae (15) to (23) is independently a hydrogen atom a substituted or unsubstituted alkyl group having 1 to 20 carbon atoms, a mono-, di-, or trialkylsilyl group each comprising a substituted or unsubstituted alkyl group having 1 to 20 carbon atoms, a substituted or unsubstituted aryl group having 6 to 30 ring carbon atoms, a mono-, di-, or triarylsilyl group each comprising a substituted or unsubstituted aryl group having 6 to 30 ring carbon atoms, or a substituted or unsubstituted heteroaryl group having 5 to 30 ring atoms;

adjacent two groups each selected from $R_{31}$ to $R_{34}$ and $R_{39}$ to $R_{42}$ may be bonded to each other to form a ring; and one of $R_{39}$ to $R_{42}$ may be a single bond which is bonded to $L_2$.

11. The compound according to claim 1, wherein A, B, and Ar are the same.

12. The compound according to claim 11, wherein A is represented by any of the formulae (6) to (11):

(6)
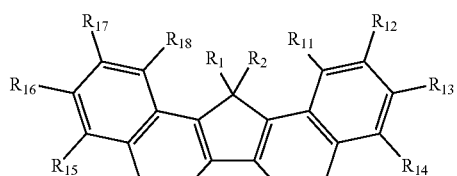

(7)
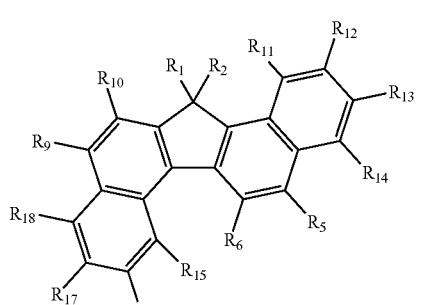

(8)
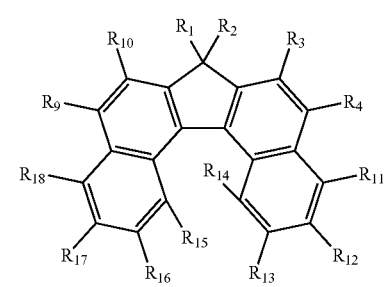

(9)
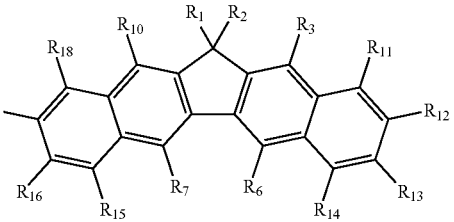

(10)
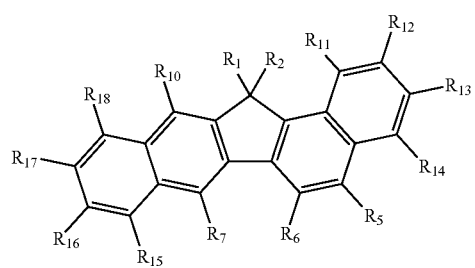

(11)
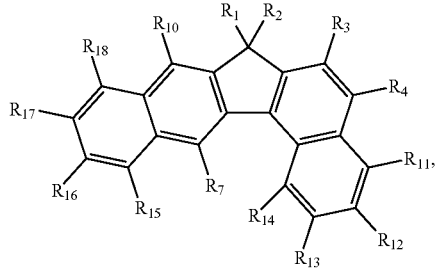
wherein $R_1$, $R_2$, $R_5$ to $R_8$, and $R_{11}$ to $R_{18}$ of the formula (6); $R_1$, $R_2$, $R_5$, $R_6$, and $R_9$ to $R_{18}$ of the formula (7); $R_1$ to $R_4$, $R_9$, $R_{10}$ and $R_{11}$ to $R_{18}$ of the formula (8); $R_1$ to $R_3$, $R_6$, $R_7$, and $R_{10}$ to $R_{18}$ of the formula (9); $R_1$, $R_2$, $R_5$ to $R_7$ and $R_{10}$ to $R_{18}$ of the formula (10); and $R_1$ to $R_4$, $R_7$, and $R_{10}$ to $R_{18}$ of the formula (11) are independently as defined above;
B is represented by any of the formulae (15) to (23):
(15)
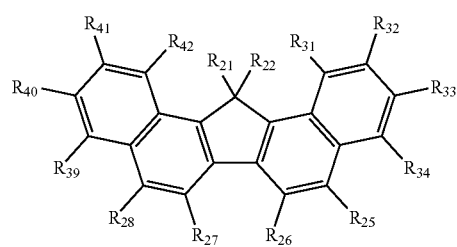
(16)
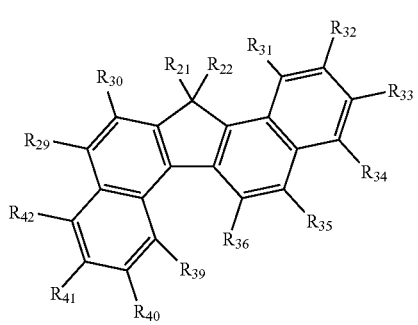
(17)
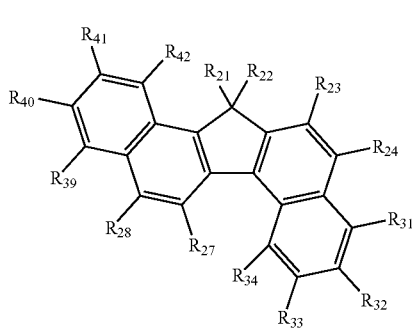
(18)
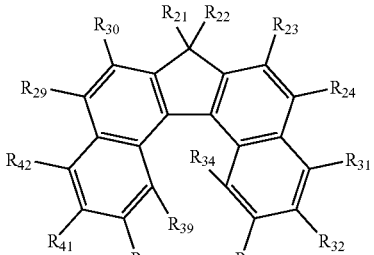
(19)
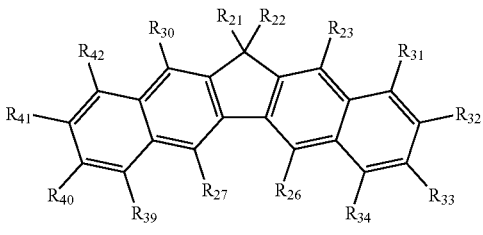
(20)
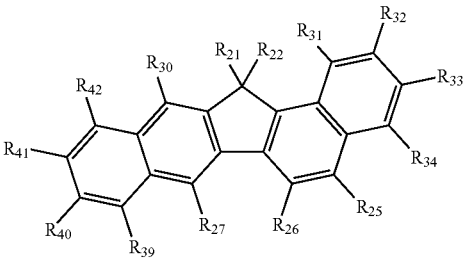
(21)
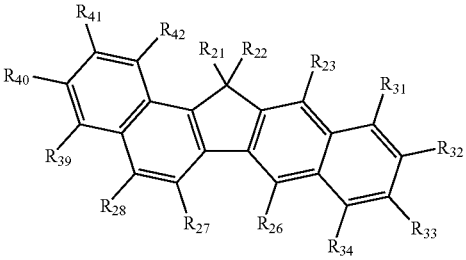
(22)
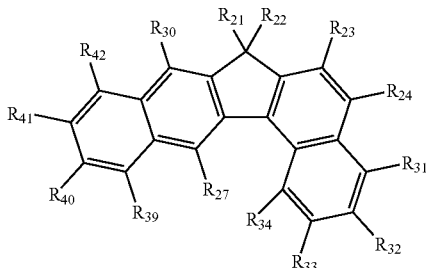
(23)
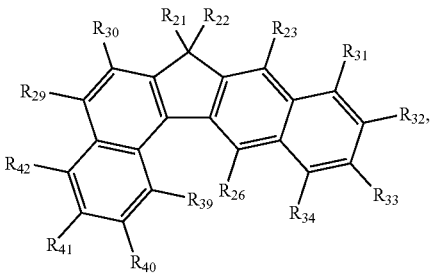

wherein:

$R_{21}$, $R_{22}$, and $R_{25}$ to $R_{28}$ of the formula (15), $R_{21}$, $R_{22}$, $R_{25}$, $R_{26}$, $R_{29}$, and $R_{30}$ of the formula (16), $R_{21}$ to $R_{24}$, $R_{27}$, and $R_{28}$ of the formula (17), $R_{21}$ to $R_{24}$, $R_{29}$ and $R_{30}$ of the formula (18), $R_{21}$ to $R_{23}$, $R_{26}$, $R_{27}$, and $R_{30}$ of the formula (19), $R_{21}$, $R_{22}$, $R_{25}$ to $R_{27}$, and $R_{30}$ of the formula (20), $R_{21}$ to $R_{23}$, and $R_{26}$ to $R_{28}$ of the formula (21), $R_{21}$ to $R_{24}$, $R_{27}$, and $R_{30}$ of formula (22), and $R_{21}$ to $R_{23}$, $R_{26}$, $R_{29}$, and $R_{30}$ of the formula (23) are independently as defined above;

each of $R_{31}$ to $R_{34}$ and $R_{39}$ to $R_{42}$ of the formulae (15) to (23) is independently a hydrogen atom, a substituted or unsubstituted alkyl group having 1 to 20 carbon atoms, a mono-, di-, or trialkylsilyl group each comprising a substituted or unsubstituted alkyl group having 1 to 20 carbon atoms, a substituted or unsubstituted aryl group having 6 to 30 ring carbon atoms, a mono-, di-, or triarylsilyl group each comprising a substituted or unsubstituted aryl group having 6 to 30 ring carbon atoms, or a substituted or unsubstituted heteroaryl group having 5 to 30 ring atoms;

adjacent two groups each selected from $R_{31}$ to $R_{34}$ and $R_{39}$ to $R_{42}$ may be bonded to each other to form a ring; and one of $R_{39}$ to $R_{42}$ may be a single bond which is bonded to $L_2$; and Ar is represented by any of the formulae (6) to (11).

13. The compound according to claim 1, wherein $L_1$ is a single bond.

14. The compound according to claim 1, wherein $L_2$ is a single bond.

15. The compound according to claim 1, wherein Ar is a substituted or unsubstituted aryl group having 6 to 30 ring carbon atoms.

16. A material for organic electroluminescence device comprising the compound according to claim 1.

17. An organic electroluminescence device comprising a cathode, an anode, and at least one organic thin film layer disposed between the cathode and the anode, wherein the at least one organic thin film layer comprises a light emitting layer and at least one layer of the at least one organic thin film layer comprises the compound according to claim 1.

18. The organic electroluminescence device according to claim 17, wherein the light emitting layer comprises the compound.

19. The organic electroluminescence device according to claim 18, wherein the compound is a dopant.

20. An electronic device comprising the organic electroluminescence device according to claim 17.

* * * * *

UNITED STATES PATENT AND TRADEMARK OFFICE
CERTIFICATE OF CORRECTION

PATENT NO. : 10,547,007 B2
APPLICATION NO. : 15/502401
DATED : January 28, 2020
INVENTOR(S) : Tasuku Haketa et al.

It is certified that error appears in the above-identified patent and that said Letters Patent is hereby corrected as shown below:

In the Claims

Column 140, Line 15, Claim 1, formula (1):

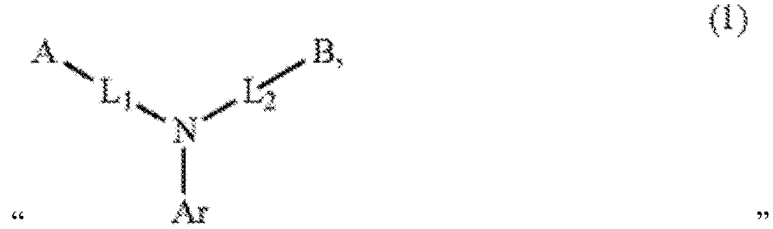

Should read:

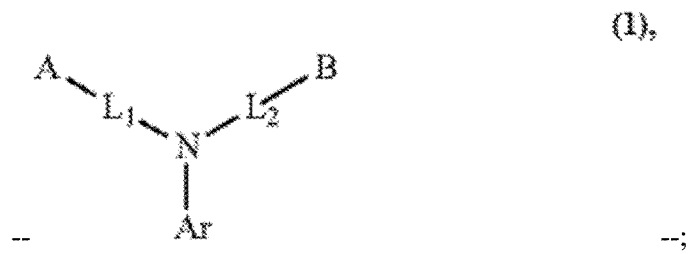

Column 140, Line 60, Claim 1, formula (2):

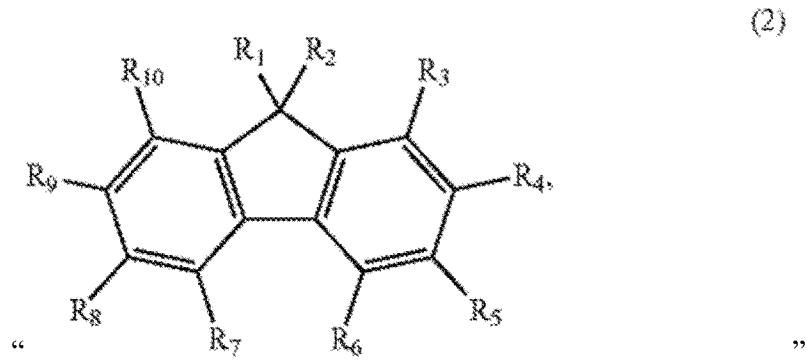

Signed and Sealed this
Eleventh Day of August, 2020

Andrei Iancu
*Director of the United States Patent and Trademark Office*

Should read:
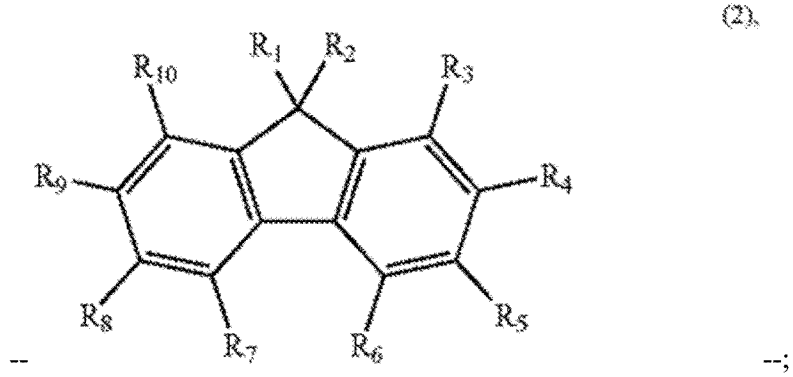
--;                                    (2),
Column 141, Line 30, Claim 1:
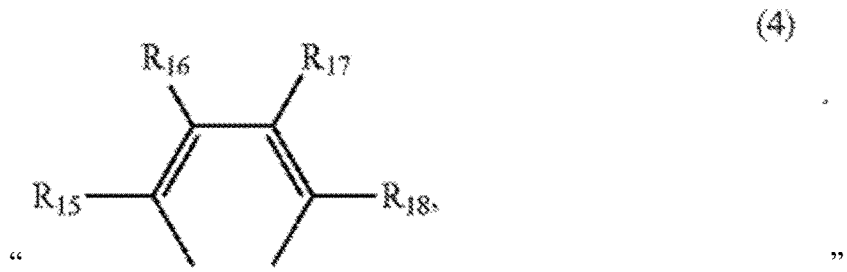
"                                        "      (4)
Should read:
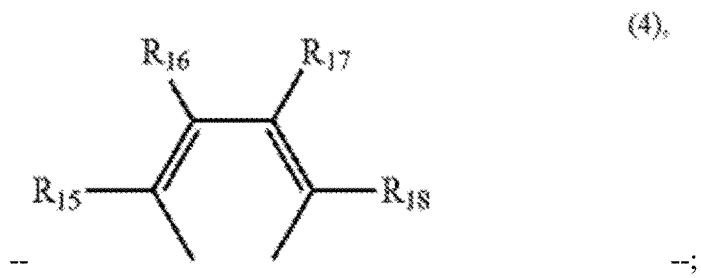
--                                      --;    (4),
Column 142, Line 5, Claim 1, formula (5):
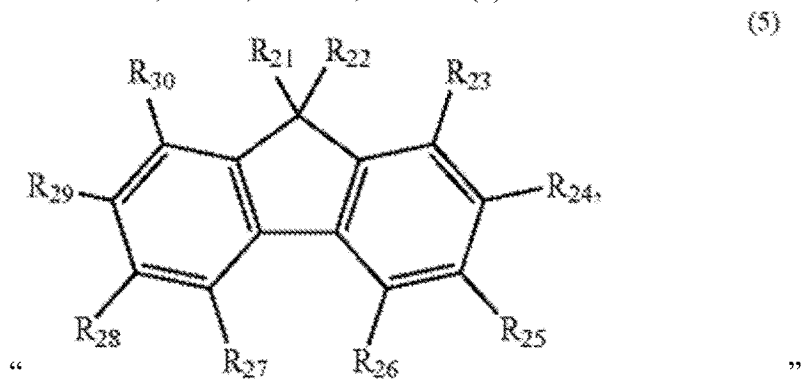
"                                         "     (5)

CERTIFICATE OF CORRECTION (continued)
U.S. Pat. No. 10,547,007 B2

Should read:

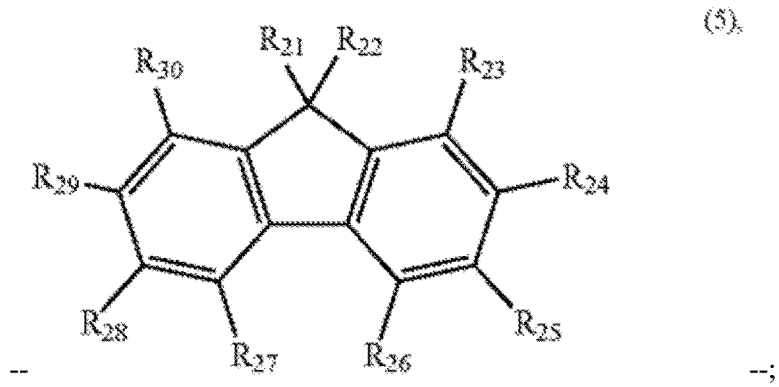

-- --;

Column 143, Line 50, Claim 2, formula (11):

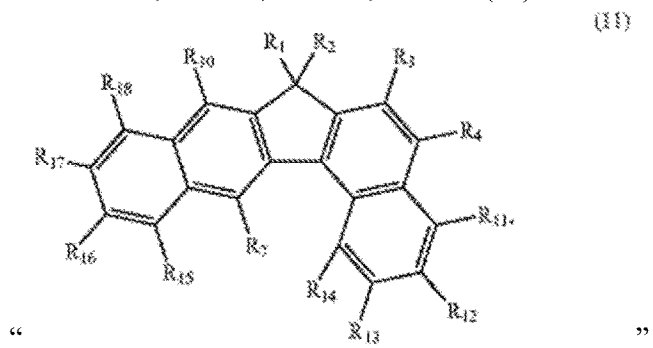

" "

Should read:

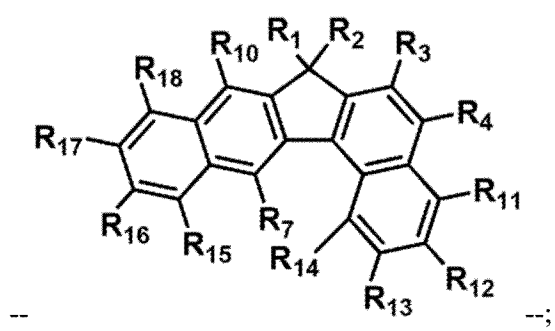

-- --;

Column 144, Claim 3, formula (14):

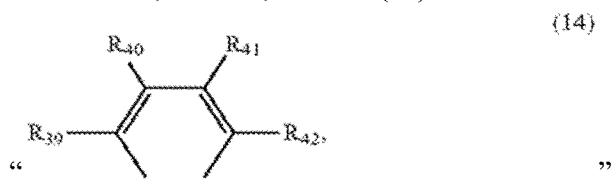

" "

Should read:
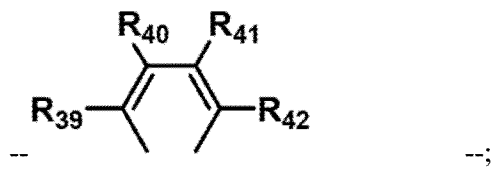
-- (14), --;
Column 145, Line 30, Claim 4, formula (17):
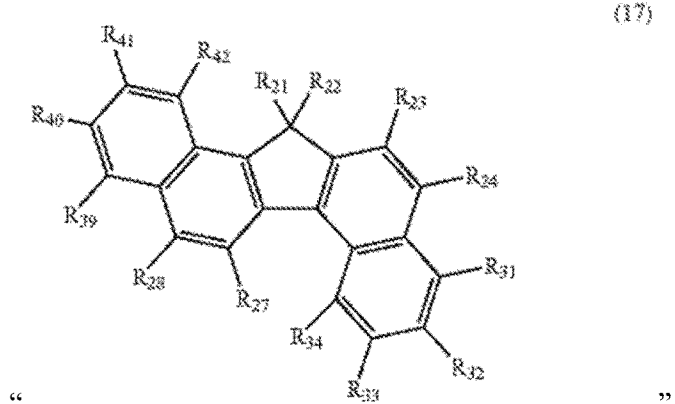
" (17) "
Should read:
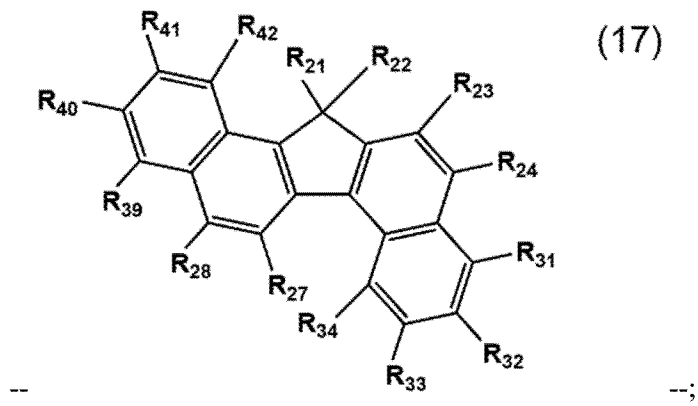
-- (17) --;
Column 146, Claim 4, formula (23):
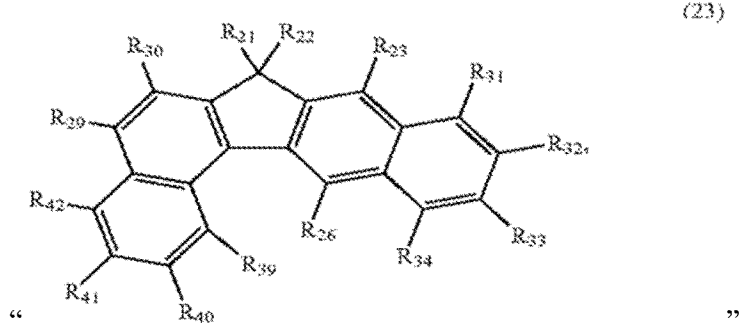
" (23) "

Should read:
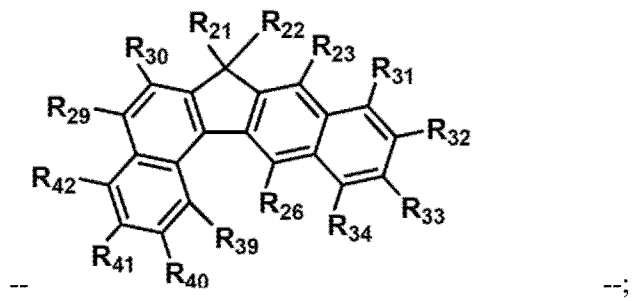
(23),
Column 147, Line 15, Claim 5, formula (24):
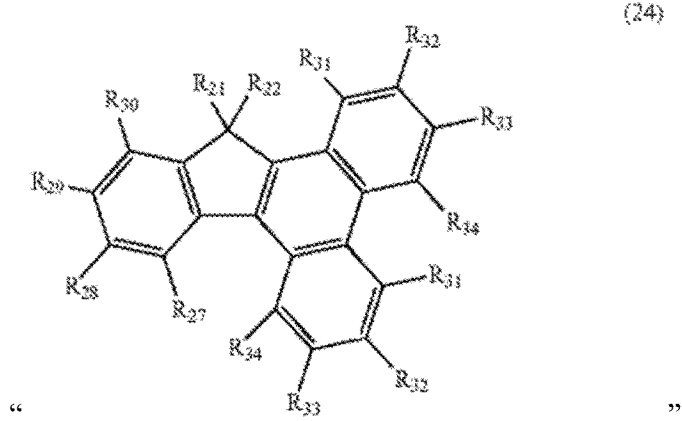
(24)
Should read:
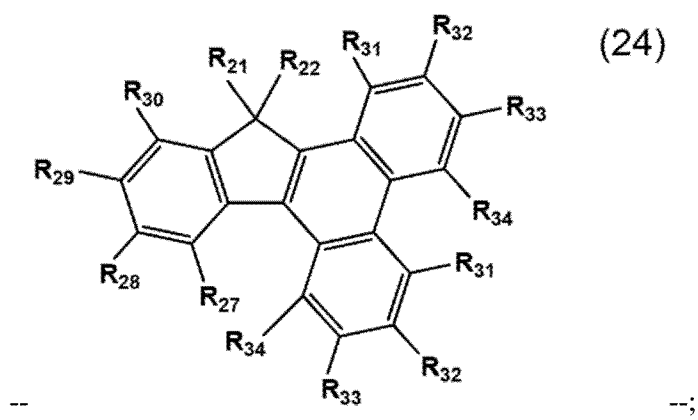
(24)

Column 147, Claim 5, formula (25):
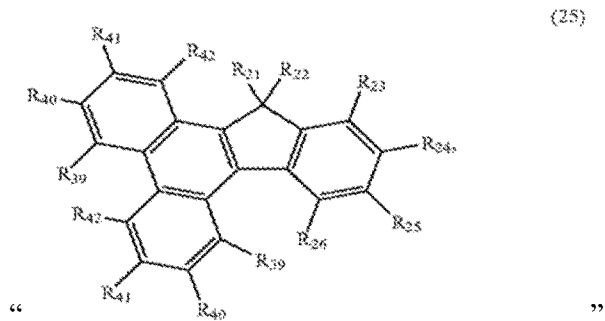
Should read:
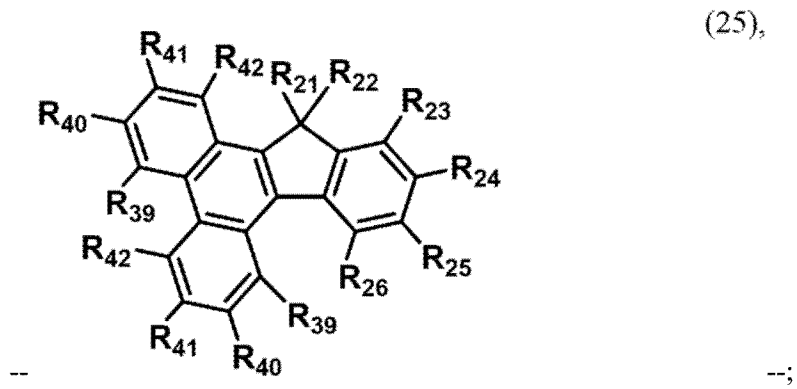
Column 147, Claim 5, Line 41:
"$R_{22}$, $R_{27}$ to $R_{30}$ of the formula (24) and $R_{21}$ to $R_{26}$ of the"
Should read:
-- $R_{21}$, $R_{22}$, $R_{27}$ to $R_{30}$ of the formula (24) and $R_{21}$ to $R_{26}$ of the --;
Column 150, Claim 6, formula (38):
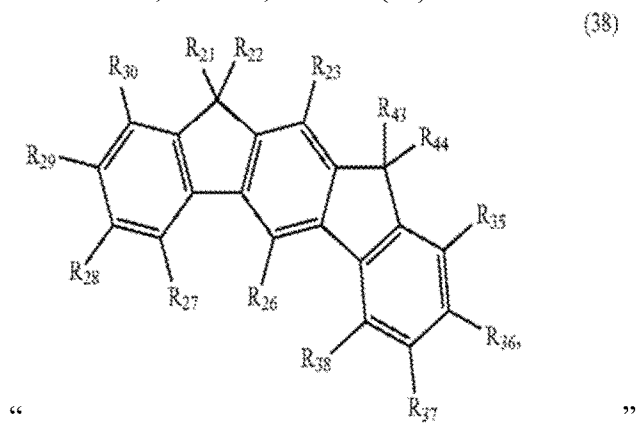

Should read:
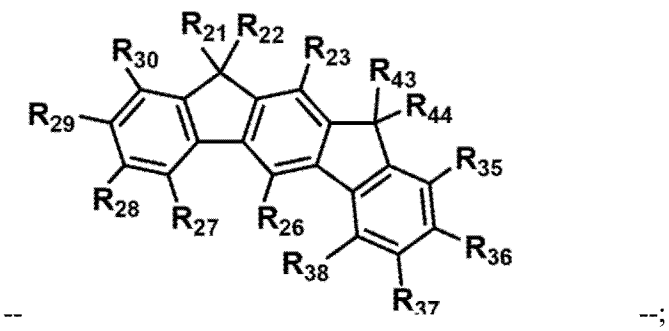
(38),
--;
Column 151, Claim 10, formula (11):
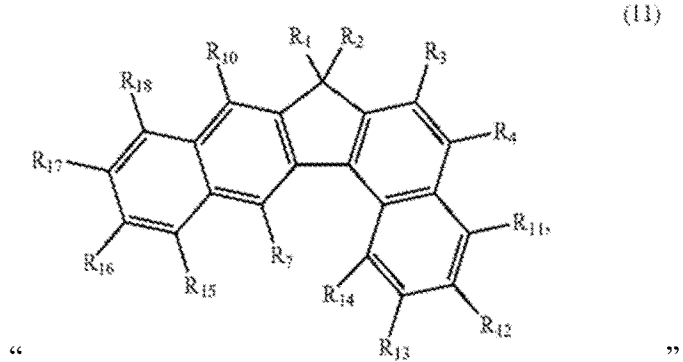
(11)
"  "
Should read:
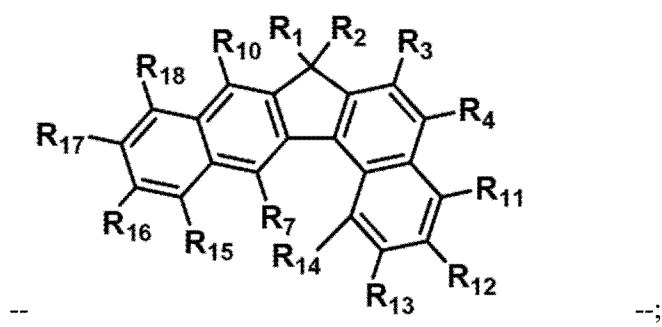
(11),
--;

Column 152, Claim 10, formula (16):
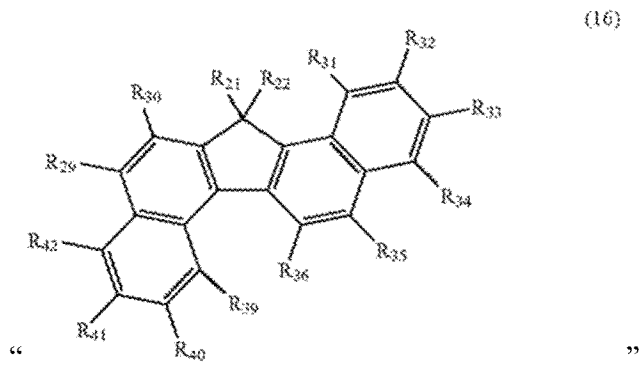
"
Should read:
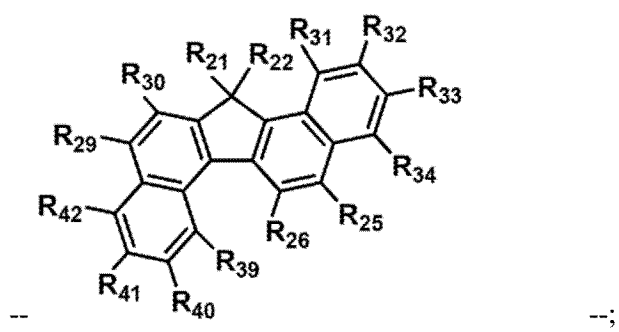
--;
Column 152, Line 40, Claim 10, formula (17):
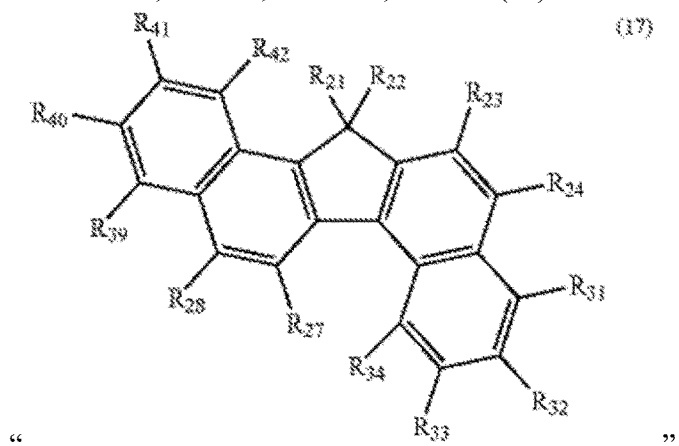
"

Should read:
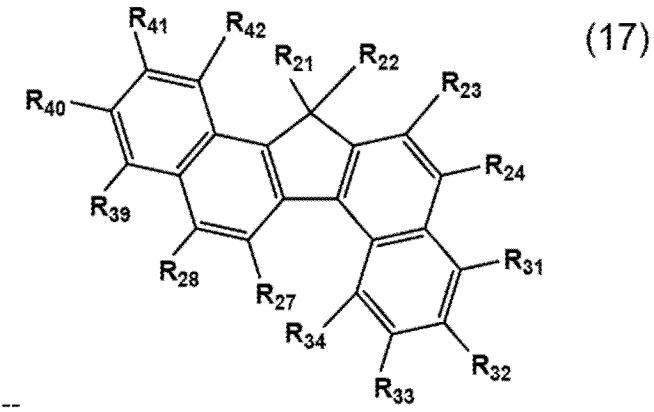
-- --;
Column 153, Claim 10, formula (23):
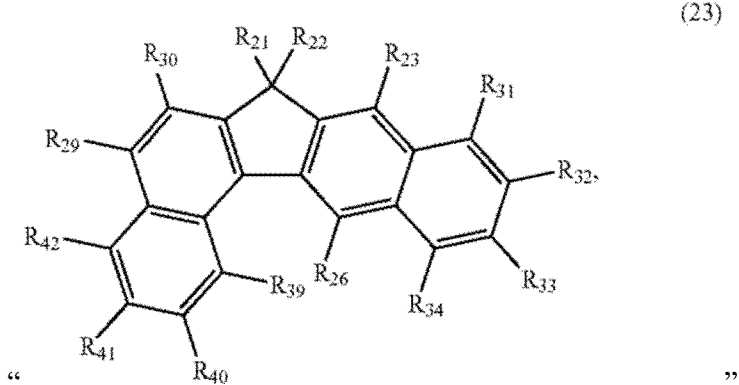
Should read:
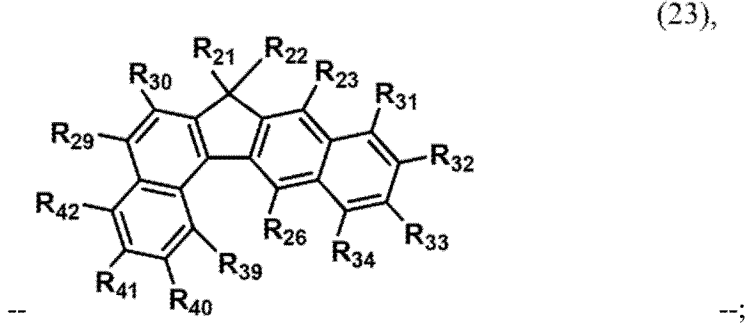
-- --;
Column 153, Claim 10, Line 49:
"$R_{25}$, $R_{26}$, $R_{29}$ and $R_{30}$ of the formula (16), $R_{21}$ to $R_{24}$,"
Should read:
-- $R_{25}$, $R_{26}$, $R_{29}$, and $R_{30}$ of the formula (16), $R_{21}$ to $R_{24}$, --;
Column 153, Claim 10, Line 50:
"$R_{27}$, and $R_{28}$ of the formula (17), $R_{21}$ to $R_{24}$, $R_{29}$ and"
Should read:
-- $R_{27}$, and $R_{28}$ of the formula (17), $R_{21}$ to $R_{24}$, $R_{29}$, and --;

CERTIFICATE OF CORRECTION (continued)
U.S. Pat. No. 10,547,007 B2

Column 153, Claim 10, Line 51:
"$R_{30}$ of the formula (18), $R_{21}$ to $R_{23}$, $R_{26}$, $R_{27}$ and $R_{30}$ of"
Should read:
-- $R_{30}$ of the formula (18), $R_{21}$ to $R_{23}$, $R_{26}$, $R_{27}$, and $R_{30}$ of --;

Column 153, Claim 10, Line 55:
"to $R_{23}$, $R_{26}$, $R_{29}$ and $R_{30}$ of the formula (23) are"
Should read:
-- to $R_{23}$, $R_{26}$, $R_{29}$, and $R_{30}$ of the formula (23) are --;

Column 153, Claim 10, Line 58:
"(23) is independently a hydrogen atom a substituted or"
Should read:
-- (23) is independently a hydrogen atom, a substituted or --;

Column 155, Claim 12, formula (11):

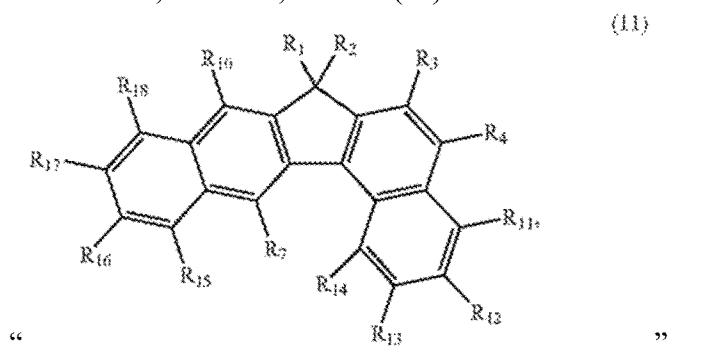

"

Should read:

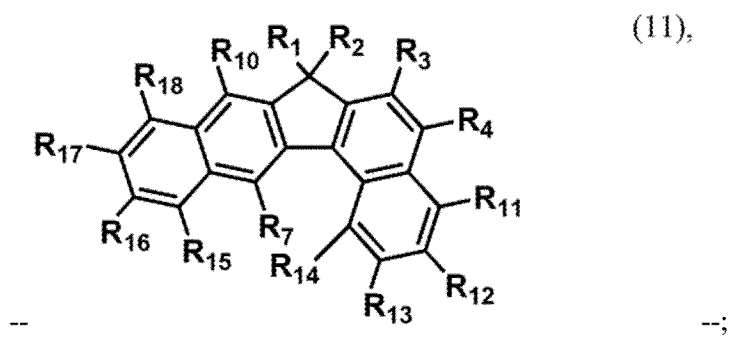

-- --;

Column 155, Claim 12, Line 17:
"$R_1$ to $R_4$, $R_9$, $R_{10}$ and $R_{11}$ to $R_{18}$ of the formula (8); $R_1$ to"
Should read:
-- $R_1$ to $R_4$, $R_9$, $R_{10}$, and $R_{11}$ to $R_{18}$ of the formula (8); $R_1$ to --;

Column 155, Claim 12, Line 19:
"$R_5$ to $R_7$ and $R_{10}$ to $R_{18}$ of the formula (10); and $R_1$ to"
Should read:
-- $R_5$ to $R_7$, and $R_{10}$ to $R_{18}$ of the formula (10); and R1 to --;

Column 155, Claim 12, formula (16):
" 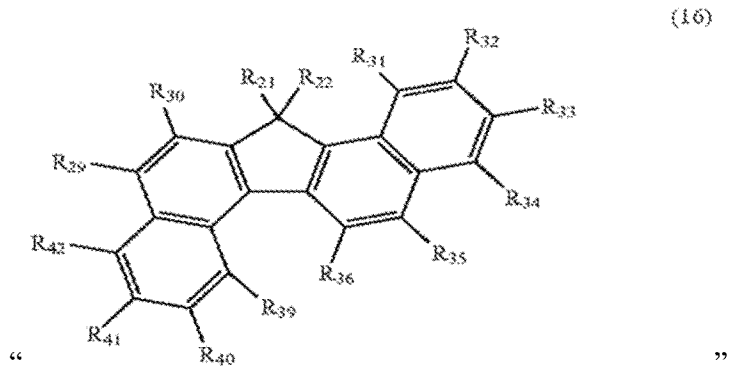 "
Should read:
-- 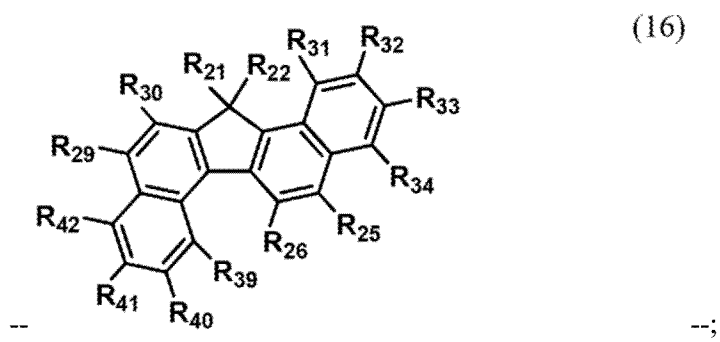 --;
Column 155, Line 60, Claim 12, formula (17):
" 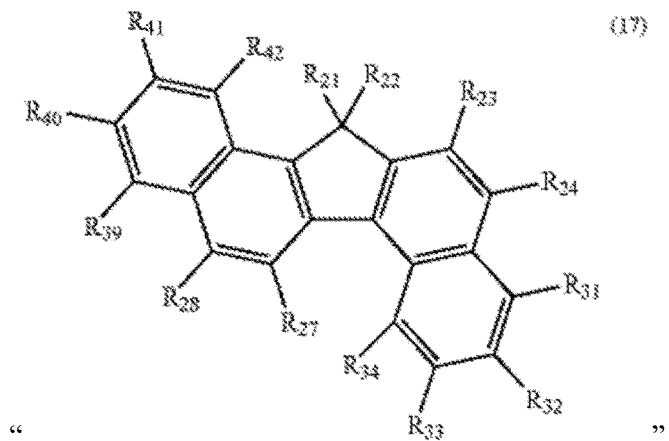 "

Should read:
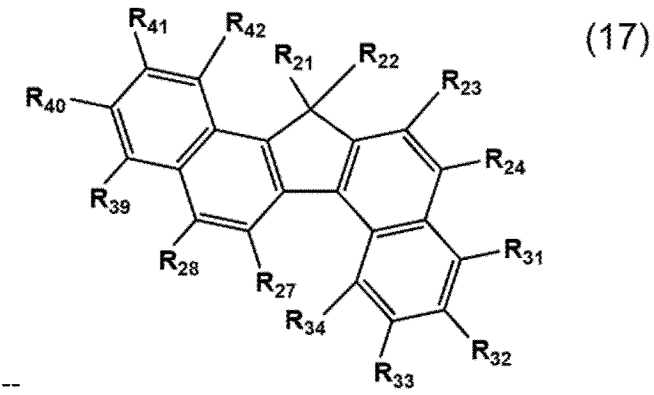
--;
Column 156, Claim 12, formula (23):
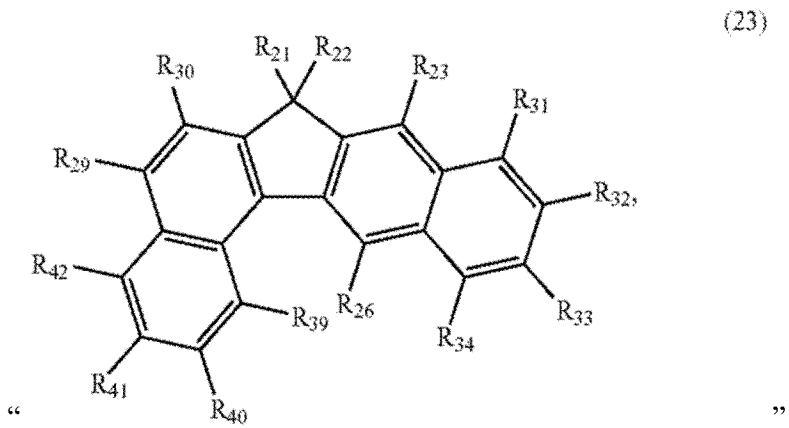
Should read:
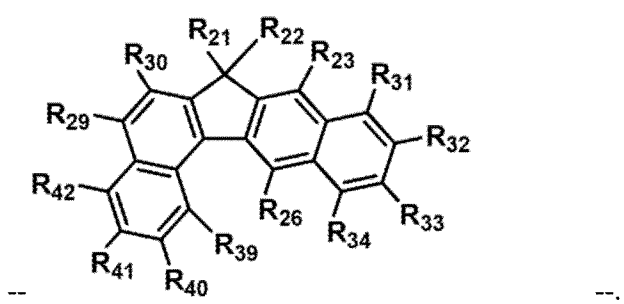
--.